United States Patent
Sun et al.

(10) Patent No.: US 7,737,148 B2
(45) Date of Patent: Jun. 15, 2010

(54) THERAPEUTIC AGENTS USEFUL FOR TREATING PAIN

(75) Inventors: Qun Sun, Princeton, NJ (US); Xiaoming Zhou, Plainsboro, NJ (US)

(73) Assignee: Purdue Pharma, L.P., Stamford, CT (US)

( * ) Notice: Subject to any disclaimer, the term of this patent is extended or adjusted under 35 U.S.C. 154(b) by 0 days.

(21) Appl. No.: 11/601,792

(22) Filed: Nov. 16, 2006

(65) Prior Publication Data

US 2007/0142360 A1 Jun. 21, 2007

Related U.S. Application Data

(63) Continuation of application No. 10/669,823, filed on Sep. 23, 2003, now Pat. No. 7,157,462.

(60) Provisional application No. 60/412,847, filed on Sep. 24, 2002.

(51) Int. Cl.
*A61K 31/44* (2006.01)
*A61K 31/496* (2006.01)
*A61K 31/497* (2006.01)
*A61K 31/506* (2006.01)
*A61P 19/02* (2006.01)
*A61P 25/02* (2006.01)
*A61P 29/02* (2006.01)
*C07D 401/04* (2006.01)
*C07D 401/14* (2006.01)
*C07D 403/04* (2006.01)
*C07D 403/14* (2006.01)
*C07D 417/04* (2006.01)
*C07D 417/14* (2006.01)

(52) U.S. Cl. .................. 514/252.18; 544/360
(58) Field of Classification Search ............ 514/252.18; 544/360
See application file for complete search history.

(56) References Cited

U.S. PATENT DOCUMENTS

| 4,439,606 A | 3/1984 | De et al. |
| 4,450,272 A | 5/1984 | Du et al. |

(Continued)

FOREIGN PATENT DOCUMENTS

| EP | 1 122 242 | 8/2001 |
| WO | WO 96/21648 | 7/1996 |
| WO | WO 98/00402 | 1/1998 |
| WO | WO 99/07672 | 1/1999 |
| WO | WO 00/52001 | 9/2000 |
| WO | WO 02/05819 | 1/2002 |
| WO | WO 02/16318 | 2/2002 |
| WO | WO 03/022809 | 3/2003 |
| WO | WO 03/062209 | 7/2003 |
| WO | WO 03/068749 | 8/2003 |

OTHER PUBLICATIONS

Valenzano et al. Curr. Med. Chem. 3185-3202, 2004.*
Szallasi et al, Journal of Medicinal Chemistry 47(20): 2717-2723, 2004.*

(Continued)

*Primary Examiner*—Venkataraman Balasubramanian
(74) *Attorney, Agent, or Firm*—Dechert LLP

(57) ABSTRACT

A compound of formula:

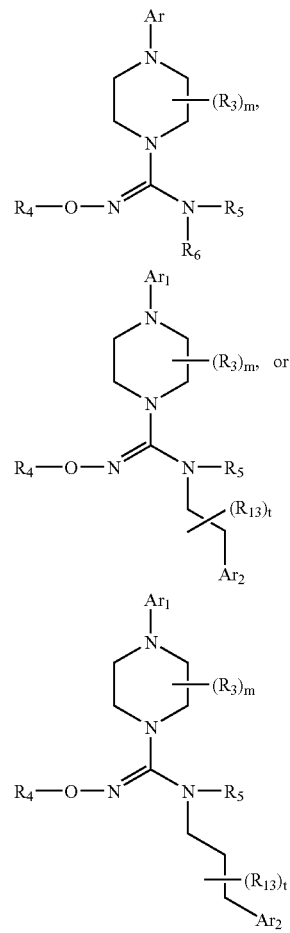

wherein Ar, $Ar_1$, $Ar_2$, $R_3$-$R_6$, $R_{13}$, m, and t are disclosed herein, or a pharmaceutically acceptable salt thereof (a "Hydroxyiminopiperazine Compound"); compositions comprising an effective amount of a Hydroxyiminopiperazine Compound; and methods for treating or preventing pain and other conditions in an animal comprising administering to an animal in need thereof an effective amount of a Hydroxyiminopiperazine Compound are disclosed.

49 Claims, No Drawings

U.S. PATENT DOCUMENTS

| | | | |
|---|---|---|---|
| 5,039,680 | A | 8/1991 | Imperato et al. |
| 5,075,341 | A | 12/1991 | Mendelson et al. |
| 5,198,459 | A | 3/1993 | Imperato et al. |
| 5,232,934 | A | 8/1993 | Downs |
| 5,430,033 | A | 7/1995 | Cliffe et al. |
| 5,442,064 | A | 8/1995 | Pieper et al. |
| 5,461,047 | A | 10/1995 | Hansen, Jr. et al. |
| 5,556,837 | A | 9/1996 | Nestler et al. |
| 5,556,838 | A | 9/1996 | Mayer et al. |
| 5,574,052 | A | 11/1996 | Rose et al. |
| 5,756,504 | A | 5/1998 | Bock et al. |
| 5,762,925 | A | 6/1998 | Sagen |
| 5,789,412 | A | 8/1998 | Halazy et al. |
| 5,792,768 | A | 8/1998 | Kulagowski et al. |
| 6,028,195 | A | 2/2000 | Cho et al. |
| 6,109,269 | A | 8/2000 | Rise et al. |
| 6,204,284 | B1 | 3/2001 | Beer et al. |
| 6,329,395 | B1 | 12/2001 | Dugar et al. |
| 6,423,716 | B1 | 7/2002 | Matsuno et al. |
| 7,157,462 | B2 | 1/2007 | Sun et al. |
| 7,279,493 | B2 | 10/2007 | Kyle et al. |
| 7,572,812 | B2 | 8/2009 | Sun et al. |
| 2003/0092910 | A1 | 5/2003 | Cho et al. |
| 2003/0153596 | A1 | 8/2003 | Suh et al. |
| 2003/0158188 | A1 | 8/2003 | Lee et al. |
| 2003/0158198 | A1 | 8/2003 | Lee et al. |
| 2006/0128717 | A1 | 6/2006 | Sun et al. |
| 2007/0032500 | A1 | 2/2007 | Sun et al. |
| 2008/0153835 | A1 | 6/2008 | Kyle et al. |
| 2009/0042902 | A1 | 2/2009 | Sun et al. |

OTHER PUBLICATIONS

Bartho et al., 1990, "Involvement of capsaicin-sensitive neurones in hyperalgesia and enhanced opiod antinociception in inflammation." Naunyn-Schmiedeberg's Arch Pharmacol. 342:666-670.
Berkow et al., The Merck Manual of Medical Information 1997; 525-526.
Berkow et al., The Merck Manual of Medical Information 1997; 528-530.
Berkow et al., The Merck Manual of Medical Information 1997; 530-532.
Berkow et al., The Merck Manual of Medical Information 1997; 631-634.
Berkow et al., The Merck Manual of Medical Information 1997;345-350.
Berkow et al., The Merck Manual of Medical Information 1997;352-355.
Berkow et al., The Merck Manual of Medical Information 1997;496-500.
Bevan et al., "Vanilloid Receptors: Pivotal Molecules in Noccicepion," Current Opinions in CPNS Investigational Drugs, 2(2):178-85 (2000).
Chiamulera et al., "Reinforcing and Locomotor Stimulant Effects of Cocaine are Absent in mGluR5 Null Mutant Mice," Nat Neuroscie 2001;4(9):873-874.
Cooke, "Glycopyrrolate in Bladder Dysfunction," S Afr Med J 1983;63:3.
D'Amour et al., 1941, "A method for Determining Loss of Pain Sensation." J. Pharamcol. Exp. Ther. 72:74-79.
Di Marzo et al., "Endovanilloid Signaling in Pain," Curr Opin Neurobiol 2002;12:372-379.
Dogrul et al., Peripheral and Spinal Antihyperalgesic Activity of SIB-1757, a Metabotropic Glutamate Receptor (mGluR$_5$) Antagonist, In Experimental Neuropathic Pain in Rats, Neurosci Lett 2000;292(2):115-118.
Foley, "Pain" Cecil Textbook of Medicine 1996;100-107.
Fundytus et al., "Antisense Oligonucleotide Knockdown of mGluR$_1$ Alleviates Hyperalgesia and Allodynia Associated with Chronic Inflammation," Pharmacol Biochem Behav 2002;73:401-410.
Fundytus et al., "In Vivo Antinociceptive Activity of Anti-rat mGluR$_1$ and mGluR$_5$ Antibodies in Rats," NeuroReport 1998;9:731-735.
Fundytus et al., "Knockdown of Spinal Metabotropic Glutamate Receptor 1 (mGluR$_1$) Alleviates Pain and Restores Opioid Efficacy After Nerve Injury in Rats," Br J Pharmacol 2001;132:354-367.
Fundytus, "Glutamate Receptors and Nociception Implications for the Drug-Treatment of Pain," CNS Drugs 2001;15:29-58.
Goodman and Gillman's The Pharmaceutical Basis of Therapeutics 506. 901-915 (J. Hardman and L. Limbird eds., $9^{th}$ ed. 1996).
Herzog et al., "Urinary Incontinence: Medical and Psychosocial Aspects," Annu Rev Gerontol Geriatr 1989;9:74-119.
Kwak et al., "A Capsaicin-Receptor Antagonist, Capsazepine Reduces Inflammation-Induced Hyperalgesic Responses in the Rat: Evidence for an Endogenous Capsaicin-Like Substance," Neuroscience 1998;84:619-626.
Levin et al., "Direct Measurement of the Anticholinergic Activity of a Series of Pharmacological Compounds on the Canine and Rabbit Urinary Bladder," J Urol 1982;128:396-398.
Lopez-Rodriquez et al., "VRI Receptor Modulators as Potential Drugs for Neuropathic Pain." Mini-Revs in Medicinal Chem. 3(7):729-48 (2003).
Mirakhur et al., "Glycopyrrolate: Pharmacology and Clinical Use," Anaesthesia 1983;38:1195-1204.
Ohkubo et al., "The Selective Capsaicin Antagonist Capsazepine Abolishes the Antinociceptive Action of Eugenol and Guaiacol," J. Dent Res Apr. 1997;76(4):848-851.
Ossowska et al., "Blockade of the Metabotropic Glutamate Receptor Subtype 5 (mGluR5) Produces Antiparkinsonian-like Effects in Rats," Neuropharmacology 2001;41:413-420.
Pan et al., "Soluble Polymer-Supported Synthesis of Arylpiperazines," Tett Lett 1998;39:9505-9508.
Pomonis et al., "N-(4-Tertiarybutylphenyl)-4-(3-chlorophyridin-2-yl)tetrahydropyrazine-1(2H)-carbox-amide (BCTC), a Novel, Orally Effective Vanilloid Receptor 1 Antagonist with Analgesic Properties: II. In Vivo Characterization in Rat Models of Inflammatory and Neuropathic Pain." J. Pharmacol. Exper. Therapeutics 306(1):387-393 (2003).
Resnick, "Urinary Incontinence," Lancet 1995;346:94-99.
Seltzer et al., 1990, "A novel behavioral model of neuropathic pain disorders produced in rats by partial sciatic nerve injury." Pain 43:210-215.
Spooren et al., "Novel Allosteric Antagonists Shed Light on mGluR$_5$ Receptors and CNS Disorders," Trends Pharmacol Sci 2001;22(7):331-337.
Szallasi et al., "The Cloned Rat Vanilloid Receptor VRI Mediates Both R-Type Binding and C-Type Calcium Response in Dorsal Root Ganglion Neurons," Molec. Pharmacol. 56:581-587 (1999).
Szallasi et al., "Vanilloid (Capsaicin) Receptors and Mechanisma." Pharmacol. Revs., 51(2):159-211 (1999).
Szallasi et al., 2004, "Vanilloid receptor TRPV1 antagonists as the next generation of painkillers. Are we putting the cart before the horse?" J. Med Chem. 47(20):2717-2723.
Tatarczynska et al., "Potential Anxiolytic- and Antidepressant-like Effects of MPEP, a Potent, Selective and Systemically Active mGlu5 Receptor Antagonist," Br J Pharmacol 2001;132(7):1423-1430.
Urban et al., "In Vivo Pharmacology of SDZ 249-665, A Novel, Non-pungent Capsaicin Analogue," Pain 2000;89:65-74.
Valenzano et al., 2004, "Current perspectives on the therapeutic utility of VRI antagonists." Curr. Med. Chem. 3185-3202.
Walker et al., "Metabotropic Glutamate Receptor Subtype 5 (mG1u5) and Nociceptive Function. 1. Selective Blockade of mGlu5 Receptors in Models of Acute, Persistent and Chronic Pain," Neuropharmacology 2000 40:1-9.
Wang et al., "High Affinity Antagonists of the Vanilloid Receptor," Mol. Pharmacol. 62(4):947-56 (2002).
Wein, "Pharmacology of Incontinence," Urol Clin North Am 1995;22(3):557-577.
Wrigglesworth et al., "Capsaicin-like Agonists." Drugs of the Future, 23(5):531-38 (1998).
Wu et al., "Multiple Sensory and Functional Effects of Non-phenolic Aminodimethylene Nonivamide: An Approach to Capsaicin Antagonist," Gen Pharmac 1996;27(1):151-158.

* cited by examiner

SEQUENCE LISTING

<160> NUMBER OF SEQ ID NOS: 2

<210> SEQ ID NO 1
<211> LENGTH: 31
<212> TYPE: DNA
<213> ORGANISM: Artificial Sequence
<220> FEATURE:
<223> OTHER INFORMATION: Human VR1 forward primer

<400> SEQUENCE: 1
aagatcttcg ctggttgcac actgggccac a                          31

<210> SEQ ID NO 2
<211> LENGTH: 32
<212> TYPE: DNA
<213> ORGANISM: Artificial Sequence
<220> FEATURE:
<223> OTHER INFORMATION: Human VR1 reverse primer

<400> SEQUENCE: 2
gaagatcttc ggggacagtg acggttggat gt                         32

THERAPEUTIC AGENTS USEFUL FOR TREATING PAIN

This application is a continuation of U.S. application Ser. No. 10/669,823, filed Sep. 23, 2003, now U.S. Pat. No. 7,157,462, which claims the benefit of U.S. Provisional Application No. 60/412,847, filed Sep. 24, 2002, the entire disclosure of each of which is incorporated herein by reference in its entirety.

1. FIELD OF THE INVENTION

The present invention relates to Hydroxyiminopiperazine Compounds, compositions comprising an effective amount of a Hydroxyiminopiperazine Compound and methods for treating or preventing a Condition, such as pain, comprising administering to an animal in need thereof an effective amount of a Hydroxyiminopiperazine Compound.

2. BACKGROUND OF THE INVENTION

Pain is the most common symptom for which patients seek medical advice and treatment. Pain can be acute or chronic. While acute pain is usually self-limited, chronic pain persists for 3 months or longer and can lead to significant changes in a patient's personality, lifestyle, functional ability and overall quality of life (K. M. Foley, *Pain, in Cecil Textbook of Medicine* 100-107 (J. C. Bennett and F. Plum eds., 20th ed. 1996)).

Pain has been traditionally managed by administering non-opioid analgesics, such as acetylsalicylic acid, choline magnesium trisalicylate, acetaminophen, ibuprofen, fenoprofen, diflusinal, and naproxen; or opioid analgesics, including morphine, hydromorphone, methadone, levorphanol, fentanyl, oxycodone, and oxymorphone. Id.

Urinary incontinence (UI) is uncontrollable urination, generally caused by bladder-detrusor-muscle instability. UI affects people of all ages and levels of physical health, both in health care settings and in the community at large. At present, UI afflicts 15-30% of elderly people living at home, one-third of those living in acute-care settings, and at least one-half of those living in long-term care institutions (R. M. Resnick, *Lancet* 346:94 (1995)). Persons having UI are predisposed to also having urinary-tract infections, pressure ulcers, perineal rashes and urosepsis. Psychosocially, UI is associated with embarrassment, social stigmatization, depression and a risk of institutionalization (Herzo et al., *Annu. Rev. Gerontol. Geriatr.* 9:74 (1989)). Economically, the costs of UI are great; in the United States alone, health-care costs associated with UI are over $15 billion per annum.

Physiologic bladder contraction results in large part from acetylcholine-induced stimulation of post-ganglionic muscarinic-receptor sites on bladder smooth muscle. Treatments for UI include the administration of drugs having bladder-relaxant properties, which help to control bladder-detrusor-muscle overactivity. For example, anticholinergics such as propantheline bromide and glycopyrrolate, and combinations of smooth-muscle relaxants such as a combination of racemic oxybutynin and dicyclomine or an anticholinergic, have been used to treat UI (See, e.g., A. J. Wein, *Urol. Clin. N. Am.* 22:557-577 (1995); Levin et al., *J. Urol.* 128:396-398 (1982); Cooke et al., *S. Afr. Med. J.* 63:3 (1983); R. K. Mirakhur et al., *Anaesthesia* 38:1195-1204 (1983)). These drugs are not effective, however, in all patients having uninhibited bladder contractions. Administration of anticholinergic medications represent the mainstay of this type of treatment.

None of the existing commercial drug treatments for UI, however, has achieved complete success in all classes of UI patients, nor has treatment occurred without significant adverse side effects. For example, drowsiness, dry mouth, constipation, blurred vision, headaches, tachycardia, and cardiac arrhythmia, which are related to the anticholinergic activity of traditional anti-UI drugs, can occur frequently and adversely affect patient compliance. Yet despite the prevalence of unwanted anticholinergic effects in many patients, anticholinergic drugs are currently prescribed for patients having UI. *The Merck Manual of Medical Information* 631-634 (R. Berkow ed., 1997).

About 1 in 10 people develop an ulcer. Ulcers develop as a result of an imbalance between acid-secretory factors, also known as "aggressive factors," such as stomach acid, pepsin, and *Helicobacter pylori* infection, and local mucosal-protective factors, such as secretion of bicarbonate, mucus, and prostaglandins.

Treatment of ulcers typically involves reducing or inhibiting the aggressive factors. For example, antacids such as aluminum hydroxide, magnesium hydroxide, sodium bicarbonate, and calcium bicarbonate can be used to neutralize stomach acids. Antacids, however, can cause alkalosis, leading to nausea, headache, and weakness. Antacids can also interfere with the absorption of other drugs into the blood stream and cause diarrhea.

$H_2$ antagonists, such as cimetidine, ranitidine, famotidine, and nizatidine, are also used to treat ulcers. $H_2$ antagonists promote ulcer healing by reducing gastric acid and digestive-enzyme secretion elicited by histamine and other $H_2$ agonists in the stomach and duodenum. $H_2$ antagonists, however, can cause breast enlargement and impotence in men, mental changes (especially in the elderly), headache, dizziness, nausea, myalgia, diarrhea, rash, and fever.

$H^+$, $K^+$-ATPase inhibitors such as omeprazole and lansoprazole are also used to treat ulcers. $H^+$, $K^+$-ATPase inhibitors inhibit the production of enzymes used by the stomach to secrete acid. Side effects associated with $H^+$, $K^+$-ATPase inhibitors include nausea, diarrhea, abdominal colic, headache, dizziness, somnolence, skin rashes, and transient elevations of plasma activities of aminotransferases.

Sucraflate is also used to treat ulcers. Sucraflate adheres to epithelial cells and is believed to form a protective coating at the base of an ulcer to promote healing. Sucraflate, however, can cause constipation, dry mouth, and interfere with the absorption of other drugs.

Antibiotics are used when *Helicobacter pylori* is the underlying cause of the ulcer. Often antibiotic therapy is coupled with the administration of bismuth compounds such as bismuth subsalicylate and colloidal bismuth citrate. The bismuth compounds are believed to enhance secretion of mucous and $HCO_3^-$, inhibit pepsin activity, and act as an antibacterial against *H. pylori*. Ingestion of bismuth compounds, however, can lead to elevated plasma concentrations of $Bi^{+3}$ and can interfere with the absorption of other drugs.

Prostaglandin analogues, such as misoprostal, inhibit secretion of acid and stimulate the secretion of mucous and bicarbonate and are also used to treat ulcers, especially ulcers in patients who require nonsteroidal anti-inflammatory drugs. Effective oral doses of prostaglandin analogues, however, can cause diarrhea and abdominal cramping. In addition, some prostaglandin analogues are abortifacients.

Carbenoxolone, a mineral corticoid, can also be used to treat ulcers. Carbenoxolone appears to alter the composition and quantity of mucous, thereby enhancing the mucosal barrier. Carbenoxolone, however, can lead to $Na^+$ and fluid retention, hypertension, hypokalemia, and impaired glucose tolerance.

Muscarinic cholinergic antagonists such as pirenzapine and telenzapine can also be used to reduce acid secretion and treat ulcers. Side effects of muscarinic cholinergic antagonists include dry mouth, blurred vision, and constipation. *The Merck Manual of Medical Information* 496-500 (R. Berkow ed., 1997) and *Goodman and Gilman's The Pharmacological Basis of Therapeutics* 901-915 (J. Hardman and L. Limbird eds., 9*th* ed. 1996).

Inflammatory-bowel disease (IBD) is a chronic disorder in which the bowel becomes inflamed, often causing recurring abdominal cramps and diarrhea. The two types of IBD are Crohn's disease and ulcerative colitis.

Crohn's disease, which can include regional enteritis, granulomatous ileitis, and ileocolitis, is a chronic inflammation of the intestinal wall. Crohn's disease occurs equally in both sexes and is more common in Jews of eastern-European ancestry. Most cases of Crohn's disease begin before age 30 and the majority start between the ages of 14 and 24. The disease typically affects the full thickness of the intestinal wall. Generally the disease affects the lowest portion of the small intestine (ileum) and the large intestine, but can occur in any part of the digestive tract.

Early symptoms of Crohn's disease are chronic diarrhea, crampy abdominal pain, fever, loss of appetite, and weight loss. Complications associated with Crohn's disease include the development of intestinal obstructions, abnormal connecting channels (fistulas), and abscesses. The risk of cancer of the large intestine is increased in people who have Crohn's disease. Often Crohn's disease is associated with other disorders such as gallstones, inadequate absorption of nutrients, amyloidosis, arthritis, episcleritis, aphthous stomatitis, erythema nodosum, pyoderma gangrenosum, ankylosing spondylitis, sacroilitis, uveitis, and primary sclerosing cholangitis. There is no known cure for Crohn's disease.

Cramps and diarrhea, side effects associated with Crohn's disease, can be relieved by anticholinergic drugs, diphenoxylate, loperamide, deodorized opium tincture, or codeine. Generally, the drug is taken orally before a meal.

Broad-spectrum antibiotics are often administered to treat the symptoms of Crohn's disease. The antibiotic metronidazole is often administered when the disease affects the large intestine or causes abscesses and fistulas around the anus. Long-term use of metronidazole, however, can damage nerves, resulting in pins-and-needles sensations in the arms and legs. Sulfasalazine and chemically related drugs can suppress mild inflammation, especially in the large intestine. These drugs, however, are less effective in sudden, severe flare-ups. Corticosteroids, such as prednisone, reduce fever and diarrhea and relieve abdominal pain and tenderness. Long-term corticosteroid therapy, however, invariably results in serious side effects such as high blood-sugar levels, increased risk of infection, osteoporosis, water retention, and fragility of the skin. Drugs such as azathioprine and mercaptourine can compromise the immune system and are often effective for Crohn's disease in patients that do not respond to other drugs. These drugs, however, usually need 3 to 6 months before they produce benefits and can cause serious side effects such as allergy, pancreatitis, and low white-blood-cell count.

When Crohn's disease causes the intestine to be obstructed or when abscesses or fistulas do not heal, surgery can be necessary to remove diseased sections of the intestine. Surgery, however, does not cure the disease, and inflammation tends to recur where the intestine is rejoined. In almost half of the cases a second operation is needed. *The Merck Manual of Medical Information* 528-530 (R. Berkow ed., 1997).

Ulcerative colitis is a chronic disease in which the large intestine becomes inflamed and ulcerated, leading to episodes of bloody diarrhea, abdominal cramps, and fever. Ulcerative colitis usually begins between ages 15 and 30, however, a small group of people have their first attack between ages 50 and 70. Unlike Crohn's disease, ulcerative colitis never affects the small intestine and does not affect the full thickness of the intestine. The disease usually begins in the rectum and the sigmoid colon and eventually spreads partially or completely through out the large intestine. The cause of ulcerative colitis is unknown. Treatment of ulcerative colitis is directed to controlling inflammation, reducing symptoms, and replacing lost fluids and nutrients.

Irritable-bowel syndrome (IBS) is a disorder of motility of the entire gastrointestinal tract, causing abdominal pain, constipation, and/or diarrhea. IBS affects three-times more women than men.

There are two major types of IBS. The first type, spastic-colon type, is commonly triggered by eating, and usually produces periodic constipation and diarrhea with pain. Mucous often appears in the stool. The pain can come in bouts of continuous dull aching pain or cramps, usually in the lower abdomen. The person suffering from spastic-colon type EBS can also experience bloating, gas, nausea, headache, fatigue, depression, anxiety, and difficulty concentrating. The second type of IBS usually produces painless diarrhea or constipation. The diarrhea can begin suddenly and with extreme urgency. Often the diarrhea occurs soon after a meal and can sometimes occur immediately upon awakening.

Treatment of EBS typically involves modification of an IBS-patient's diet. Often it is recommended that an EBS patient avoid beans, cabbage, sorbitol, and fructose. A low-fat, high-fiber diet can also help some IBS patients. Regular physical activity can also help keep the gastrointestinal tract functioning properly. Drugs such as propantheline that slow the function of the gastrointestinal tract are generally not effective for treating IBS. Antidiarrheal drugs, such as diphenoxylate and loperamide, help with diarrhea. *The Merck Manual of Medical Information* 525-526 (R. Berkow ed., 1997).

Certain pharmaceutical agents have been administered for treating addiction. U.S. Pat. No. 5,556,838 to Mayer et al. discloses the use of nontoxic NMDA-blocking agents co-administered with an addictive substance to prevent the development of tolerance or withdrawal symptoms. U.S. Pat. No. 5,574,052 to Rose et al. discloses co-administration of an addictive substance with an antagonist to partially block the pharmacological effects of the substance. U.S. Pat. No. 5,075,341 to Mendelson et al. discloses the use of a mixed opiate agonist/antagonist to treat cocaine and opiate addiction. U.S. Pat. No. 5,232,934 to Downs discloses administration of 3-phenoxypyridine to treat addiction. U.S. Pat. Nos. 5,039,680 and 5,198,459 to Imperato et al. disclose using a serotonin antagonist to treat chemical addiction. U.S. Pat. No. 5,556,837 to Nestler et. al. discloses infusing BDNF or NT-4 growth factors to inhibit or reverse neurological adaptive changes that correlate with behavioral changes in an addicted individual. U.S. Pat. No. 5,762,925 to Sagan discloses implanting encapsulated adrenal medullary cells into an animal's central nervous system to inhibit the development of opioid intolerance. U.S. Pat. No. 6,204,284 to Beer et al. discloses racemic (±)-1-(3,4-dichlorophenyl)-3-azabicyclo [3.1.0]hexane for use in the prevention or relief of a withdrawal syndrome resulting from addiction to drugs and for the treatment of chemical dependencies.

Parkinson's disease is a clinical syndrome comprising bradykinesia (slowness and poverty of movement), muscular rigidity, resting tremor (which usually abates during voluntary movement), and an impairment of postural balance leading to disturbance of gait and falling. The features of Parkinson's disease are a loss of pigmented, dopaminergic neurons of the substantia nigra pars compacta and the appearance of intracellular inclusions known as Lewy bodies (*Goodman* and Gillman's *The Pharmaceutical Basis of Therapeutics* 506 (9th ed. 1996)). Without treatment, Parkinson's disease progresses to a rigid akinetic state in which patients are incapable of caring for themselves. Death frequently results from complications of immobility, including aspiration pneumonia or pulmonary embolism. Drugs commonly used for the treatment of Parkinson's disease include carbidopa/levodopa, pergolide, bromocriptine, selegiline, amantadine, and trihexyphenidyl hydrochloride. There remains, however, a need for drugs useful for the treatment of Parkinson's disease and having an improved therapeutic profile.

Anxiety is a fear, apprehension, or dread of impending danger often accompanied by restlessness, tension, tachycardia, and dyspnea. Currently, benzodiazepines are the most commonly used anti-anxiety agents for generalized anxiety disorder. Benzodiazepines, however, carry the risk of producing impairment of cognition and skilled motor functions, particularly in the elderly, which can result in confusion, delerium, and falls with fractures. Sedatives are also commonly prescribed for treating anxiety. The azapirones, such as buspirone, are also used to treat moderate anxiety. The azapirones, however, are less useful for treating severe anxiety accompanied with panic attacks.

Epilepsy is a disorder characterized by the tendency to have recurring seizures. Examples of drugs for treating a seizure and epilepsy include carbamazepine, ethosuximide, gabapentin, lamotrignine, phenobarbital, phenytoin, primidone, valproic acid, trimethadione, bemzodiaepines, gabapentin, lamotrigine, γ-vinyl GABA, acetazolamide, and felbamate. Anti-seizure drugs, however, can have side effects such as drowsiness; hyperactivity; hallucinations; inability to concentrate; central and peripheral nervous system toxicity, such as nystagmus, ataxia, diplopia, and vertigo; gingival hyperplasia; gastrointestinal disturbances such as nausea, vomiting, epigastric pain, and anorexia; endocrine effects such as inhibition of antidiuretic hormone, hyperglycemia, glycosuria, osteomalacia; and hypersensitivity such as scarlatiniform rash, morbilliform rash, Stevens-Johnson syndrome, systemic lupus erythematosus, and hepatic necrosis; and hematological reactions such as red-cell aplasia, agranulocytosis, thrombocytopenia, aplastic anemia, and megaloblastic anemia. *The Merck Manual of Medical Information* 345-350 (R. Berkow ed., 1997).

A stroke or cerebrovascular accident, is the death of brain tissue (cerebral infarction) resulting from the lack of blood flow and insufficient oxygen to the brain. A stroke can be either ischemic or hemorrhagic. Examples of drugs for treating strokes include anticoagulants such as heparin, drugs that break up clots such as streptokinase or tissue plasminogen activator, and drugs that reduce swelling such as mnannitol or corticosteroids. *The Merck Manual of Medical Information* 352-355 (R. Berkow ed., 1997).

Pruritus is an unpleasant sensation that prompts scratching. Pruritus can be attributed to dry skin, scabies, dermatitis, herpetiformis, atopic dermatitis, pruritus vulvae et ani, miliaria, insect bites, pediculosis, contact dermatitis, drug reactions, urticaria, urticarial eruptions of pregnancy, psoriasis, lichen planus, lichen simplex chronicus, exfoliative dermatitis, folliculitis, bullous pemphigoid, and fiberglass dermatitis. Conventionally, pruritus is treated by phototherapy with ultraviolet B or PUVA or with therapeutic agents such as naltrexone, nalmefene, danazol, tricyclics, and antidepressants.

Selective antagonists of the metabotropic glutamate receptor 5 ("mGluR5") have been shown to exert analgesic activity in in vivo animal models (K. Walker et al., *Neuropharmacology* 40:1-9 (2000) and A. Dogrul et al., *Neuroscience Letters*, 292(2):115-118 (2000)).

Selective antagonists of the mGluR5 receptor have also been shown to exert anxiolytic and anti-depressant activity in in vivo animal models (E. Tatarczynska et al., *Br. J. Pharmacol.* 132(7):1423-1430 (2001) and P. J. M. Will et al., *Trends in Pharmacological Sciences* 22(7):331-37 (2001)).

Selective antagonists of the mGluR5 receptor have also been shown to exert anti-Parkinson activity in vivo (K. J. Ossowska et al., *Neuropharmacology* 41(4):413-20 (2001) and P. J. M. Will et al., *Trends in Pharmacological Sciences* 22(7):331-37 (2001)).

Selective antagonists of the mGluR5 receptor have also been shown to exert anti-dependence activity in vivo (C. Chiamulera et al., *Nature Neuroscience* 4(9):873-74 (2001)).

There remains, however, a clear need in the art for new drugs useful for treating or preventing pain, UI, an ulcer, IBD, IBS, an addictive disorder, Parkinson's disease, parkinsonism, anxiety, epilepsy, stroke, a seizure, a pruritic condition, psychosis, a cognitive disorder, a memory deficit, restricted brain function, Huntington's chorea, amyotrophic lateral sclerosis ("ALS"), dementia, retinopathy, a muscle spasm, a migraine, vomiting, dyskinesia, or depression.

Citation of any reference in Section 2 of this application is not to be construed as an admission that such reference is prior art to the present application.

3. SUMMARY OF THE INVENTION

The present invention encompasses compounds having the formula (I):

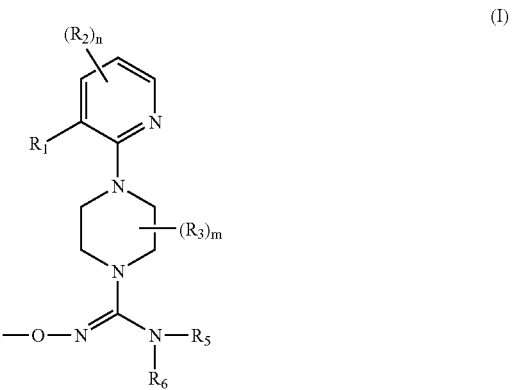

and pharmaceutically acceptable salts thereof, wherein:

$R_1$ is -halo, —$CH_3$, —$NO_2$, —CN, —OH, —$OCH_3$, —$NH_2$, —C(halo)$_3$, —CH(halo)$_2$, or —$CH_2$(halo);

each $R_2$ is independently:
(a) -halo, —CN, —OH, $NO_2$, —O($C_1$-$C_6$)alkyl, or —$NH_2$;
(b) —($C_1$-$C_{10}$)akyl, —($C_2$-$C_{10}$)alkenyl, —($C_2$-$C_{10}$)alkynyl, —($C_3$-$C_{10}$)cycloalkyl, —($C_8$-$C_{14}$)bicycloalkyl, —($C_8$-$C_{14}$)tricycloalkyl, —($C_5$-$C_{10}$)cycloalkenyl, —($C_8$-$C_{14}$)bicycloalkenyl, —($C_8$-$C_{14}$)tricycloalkenyl, -(3- to 7-membered)heterocycle, or -(7- to 10-membered)bicycloheterocycle, each of which is unsubstituted or substituted with one or more $R_7$ groups; or
(c) -phenyl, -naphthyl, —($C_{14}$)aryl, or -(5- to 10-membered)heteroaryl, each of which is unsubstituted or substituted with one or more $R_8$ groups;

each $R_3$ is independently:
(a) -halo, —CN, —OH, $NO_2$, —O($C_1$-$C_6$)alkyl, or —$NH_2$;
(b) —($C_1$-$C_{10}$)alkyl, —($C_2$-$C_{10}$)alkenyl, —($C_2$-$C_{10}$)alkynyl, —($C_3$-$C_{10}$)cycloalkyl, —($C_8$-$C_{14}$)bicycloalkyl, —($C_8$-$C_{14}$)tricycloalkyl, —($C_5$-$C_{10}$)cycloalkenyl, —($C_8$-$C_{14}$)bicycloalkenyl, —($C_8$-$C_{14}$)tricycloalkenyl, -(3- to 7-membered)heterocycle, or -(7- to 10-membered)bicycloheterocycle, each of which is unsubstituted or substituted with one or more $R_7$ groups; or
(c) -phenyl, -naphthyl, —($C_{14}$)aryl, or -(5- to 10-membered)heteroaryl, each of which is unsubstituted or substituted with one or more $R_8$ groups;

$R_4$ is —H, —($C_1$-$C_{10}$)alkyl, —C(O)$R_9$, or —C(O)NH$R_9$;
$R_5$ is —H or —($C_1$-$C_{10}$)alkyl;
$R_6$ is:
(a) —($C_1$-$C_{10}$)alkyl, —($C_2$-$C_{10}$)alkenyl, —($C_2$-$C_{10}$)alkynyl, —($C_3$-$C_{10}$)cycloalkyl, —($C_8$-$C_{14}$)bicycloalkyl, —($C_8$-$C_{14}$)tricycloalkyl, —($C_5$-$C_{10}$)cycloalkenyl, —($C_8$-$C_{14}$)bicycloalkenyl, —($C_8$-$C_{14}$)tricycloalkenyl, -(3- to 7-membered)heterocycle, or -(7- to 10-membered)bicycloheterocycle, each of which is unsubstituted or substituted with one or more $R_7$ groups; or
(b) -phenyl, -naphthyl, —($C_{14}$)aryl, or -(5- to 10-membered)heteroaryl, each of which is unsubstituted or substituted with one or more $R_8$ groups;

each $R_7$ and $R_8$ is independently —($C_1$-$C_6$)alkyl, —($C_2$-$C_6$)alkenyl, —($C_2$-$C_6$)alkynyl, —($C_3$-$C_8$)cycloalkyl, —($C_5$-$C_8$)cycloalkenyl, -phenyl, -(3- to 5-membered)heterocycle, —C(halo)$_3$, —CH(halo)$_2$, —CH$_2$(halo), —CN, —OH, -halo, —$N_3$, —$NO_2$, —N($R_{10}$)$_2$, —CH=N$R_{10}$, —N$R_{10}$OH, —O$R_{10}$, —CO$R_{10}$, —C(O)O$R_{10}$, —OC(O)$R_{10}$, —OC(O)O$R_{10}$, —S$R_{10}$, —S(O)$R_{10}$, or —S(O)$_2R_{10}$;

each $R_9$ is —H, —($C_1$-$C_6$)alkyl, —($C_2$-$C_6$)alkenyl, —($C_2$-$C_6$)alkynyl, —($C_3$-$C_8$)cycloalkyl, —($C_5$-$C_8$)cycloalkenyl, -phenyl, -(3- to 5-membered)heterocycle, —C(halo)$_3$, —CH(halo)$_2$, —CH$_2$(halo), —OH, —N($R_{10}$)$_2$, —CH=N$R_{10}$, —N$R_{10}$OH, —O$R_{10}$, or —S$R_{10}$;

each $R_{10}$ is independently —H, —($C_1$-$C_6$)alkyl, —($C_2$-$C_6$)alkenyl, —($C_2$-$C_6$)alkynyl, —($C_3$-$C_8$)cycloalkyl, —($C_5$-$C_8$)cycloalkenyl, -phenyl, -(3- to 5-membered)heterocycle, —C(halo)$_3$, —CH(halo)$_2$, or —CH$_2$(halo);

each halo is independently —F, —Cl, —Br, or —I;
n is an integer ranging from 0 to 3; and
m is an integer ranging from 0 to 2.

The present invention encompasses compounds having the formula (II):

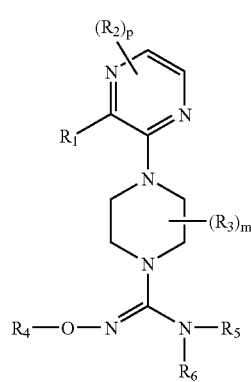

(II)

and pharmaceutically acceptable salts thereof, wherein:
$R_1$ is -halo, —CH$_3$, —NO$_2$, —CN, —OH, —OCH$_3$, —NH$_2$, —C(halo)$_3$, —CH(halo)$_2$, or —CH$_2$(halo);
each $R_2$ is independently:
(a) -halo, —CN, —OH, NO$_2$, —O($C_1$-$C_6$)alkyl, or —NH$_2$;
(b) —($C_1$-$C_{10}$)alkyl, —($C_2$-$C_{10}$)alkenyl, —($C_2$-$C_{10}$)alkynyl, —($C_3$-$C_{10}$)cycloalkyl, —($C_8$-$C_{14}$)bicycloalkyl, —($C_8$-$C_{14}$)tricycloalkyl, —($C_5$-$C_{10}$)cycloalkenyl, —($C_8$-$C_{14}$)bicycloalkenyl, —($C_8$-$C_{14}$)tricycloalkenyl, -(3- to 7-membered)heterocycle, or -(7- to 10-membered)bicycloheterocycle, each of which is unsubstituted or substituted with one or more $R_7$ groups; or
(c) -phenyl, -naphthyl, —($C_{14}$)aryl, or -(5- to 10-membered)heteroaryl, each of which is unsubstituted or substituted with one or more $R_8$ groups;

each $R_3$ is independently:
(a) -halo, —CN, —OH, NO$_2$, —O($C_1$-$C_6$)alkyl, or —NH$_2$;
(b) —($C_1$-$C_{10}$)alkyl, —($C_2$-$C_{10}$)alkenyl, —($C_2$-$C_{10}$)alkynyl, —($C_3$-$C_{10}$)cycloalkyl, —($C_8$-$C_{14}$)bicycloalkyl, —($C_8$-$C_{14}$)tricycloalkyl, —($C_5$-$C_{10}$)cycloalkenyl, —($C_8$-$C_{14}$)bicycloalkenyl, —($C_8$-$C_{14}$)tricycloalkenyl, -(3- to 7-membered)heterocycle, or -(7- to 10-membered)bicycloheterocycle, each of which is unsubstituted or substituted with one or more $R_7$ groups; or
(c) -phenyl, -naphthyl, —($C_{14}$)aryl, or -(5- to 10-membered)heteroaryl, each of which is unsubstituted or substituted with one or more $R_8$ groups;

$R_4$ is —H, —($C_1$-$C_{10}$)alkyl, —C(O)$R_9$, or —C(O)NH$R_9$;
$R_5$ is —H or —($C_1$-$C_{10}$)alkyl;
$R_6$ is:
(a) —($C_1$-$C_{10}$)alkyl, —($C_2$-$C_{10}$)alkenyl, —($C_2$-$C_{10}$)alkynyl, —($C_3$-$C_{10}$)cycloalkyl, —($C_8$-$C_{14}$)bicycloalkyl, —($C_8$-$C_{14}$)tricycloalkyl, —($C_5$-$C_{10}$)cycloalkenyl, —($C_8$-$C_{14}$)bicycloalkenyl, —($C_8$-$C_{14}$)tricycloalkenyl, -(3- to 7-membered)heterocycle, or -(7- to 10-membered)bicycloheterocycle, each of which is unsubstituted or substituted with one or more $R_7$ groups; or
(b) -phenyl, -naphthyl, —($C_{14}$)aryl, or -(5- to 10-membered)heteroaryl, each of which is unsubstituted or substituted with one or more $R_8$ groups;

each $R_7$ and $R_8$ is independently —($C_1$-$C_6$)alkyl, —($C_2$-$C_6$)alkenyl, —($C_2$-$C_6$)alkynyl, —($C_3$-$C_8$)cycloalkyl, —($C_5$-$C_8$)cycloalkenyl, -phenyl, -(3- to 5-membered)heterocycle, —C(halo)$_3$, —CH(halo)$_2$, —CH$_2$(halo), —CN, —OH, -halo, —$N_3$, —$NO_2$, —N($R_{10}$)$_2$, —CH=N$R_{10}$, —N$R_{10}$OH, —O$R_{10}$, —CO$R_{10}$, —C(O)O$R_{10}$, —OC(O)$R_{10}$, —OC(O)O$R_{10}$, —S$R_{10}$, —S(O)$R_{10}$, or —S(O)$_2R_{10}$;

each $R_9$ is —H, —($C_1$-$C_6$)alkyl, —($C_2$-$C_6$)alkenyl, —($C_2$-$C_6$)alkynyl, —($C_3$-$C_8$)cycloalkyl, —($C_5$-$C_8$)cycloalkenyl, -phenyl, -(3- to 5-membered)heterocycle, —C(halo)$_3$, —CH(halo)$_2$, —CH$_2$(halo), —OH, —N($R_{10}$)$_2$, —CH=N$R_{10}$, —N$R_{10}$OH, —O$R_{10}$, or —S$R_{10}$;

each $R_{10}$ is independently —H, —($C_1$-$C_6$)alkyl, —($C_2$-$C_6$)alkenyl, —($C_2$-$C_6$)alkynyl, —($C_3$-$C_8$)cycloalkyl, —($C_5$-$C_8$)cycloalkenyl, -phenyl, -(3- to 5-membered)heterocycle, —C(halo)$_3$, —CH(halo)$_2$, or —CH$_2$(halo);

each halo is independently —F, —Cl, —Br, or —I;
p is an integer ranging from 0 to 2; and
m is an integer ranging from 0 to 2.

The present invention also encompasses compounds having the formula (III):

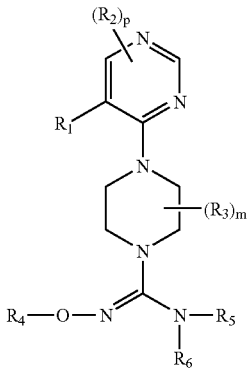

(III)

and pharmaceutically acceptable salts thereof, wherein:
R$_1$ is -halo, —CH$_3$, —NO$_2$, —CN, —OH, —OCH$_3$, —NH$_2$, —C(halo)$_3$, —CH(halo)$_2$, or —CH$_2$(halo);
each R$_2$ is independently:
(a) -halo, —CN, —OH, NO$_2$, —O(C$_1$-C$_6$)alkyl, or —NH$_2$;
(b) —(C$_1$-C$_{10}$)alkyl, —(C$_2$-C$_{10}$)alkenyl, —(C$_2$-C$_{10}$)alkynyl, —(C$_3$-C$_{10}$)cycloalkyl, —(C$_8$-C$_{14}$)bicycloalkyl, —(C$_8$-C$_{14}$)tricycloalkyl, —(C$_5$-C$_{10}$)cycloalkenyl, —(C$_8$-C$_{14}$)bicycloalkenyl, —(C$_8$-C$_{14}$)tricycloalkenyl, -(3- to 7-membered)heterocycle, or -(7- to 10-membered)bicycloheterocycle, each of which is unsubstituted or substituted with one or more R$_7$ groups; or
(c) -phenyl, -naphthyl, —(C$_{14}$)aryl, or -(5- to 10-membered)heteroaryl, each of which is unsubstituted or substituted with one or more R$_8$ groups;
each R$_3$ is independently:
(a) -halo, —CN, —OH, NO$_2$, —O(C$_1$-C$_6$)alkyl, or —NH$_2$;
(b) —(C$_1$-C$_{10}$)alkyl, —(C$_2$-C$_{10}$)alkenyl, —(C$_2$-C$_{10}$)alkynyl, —(C$_3$-C$_{10}$)cycloalkyl, —(C$_8$-C$_{14}$)bicycloalkyl, —(C$_8$-C$_{14}$)tricycloalkyl, —(C$_5$-C$_{10}$)cycloalkenyl, —(C$_8$-C$_{14}$)bicycloalkenyl, —(C$_8$-C$_{14}$)tricycloalkenyl, -(3- to 7-membered)heterocycle, or -(7- to 10-membered)bicycloheterocycle, each of which is unsubstituted or substituted with one or more R$_7$ groups; or
(c) -phenyl, -naphthyl, —(C$_{14}$)aryl, or -(5- to 10-membered)heteroaryl, each of which is unsubstituted or substituted with one or more R$_8$ groups;
R$_4$ is —H, —(C$_1$-C$_{10}$)alkyl, —C(O)R$_9$, or —C(O)NHR$_9$;
R$_5$ is —H or —(C$_1$-C$_{10}$)alkyl;
R$_6$ is:
(a) —(C$_1$-C$_{10}$)alkyl, —(C$_2$-C$_{10}$)alkenyl, —(C$_2$-C$_{10}$)alkynyl, —(C$_3$-C$_{10}$)cycloalkyl, —(C$_8$-C$_{14}$)bicycloalkyl, —(C$_8$-C$_{14}$)tricycloalkyl, —(C$_5$-C$_{10}$)cycloalkenyl, —(C$_8$-C$_{14}$)bicycloalkenyl, —(C$_8$-C$_{14}$)tricycloalkenyl, -(3- to 7-membered)heterocycle, or -(7- to 10-membered)bicycloheterocycle, each of which is unsubstituted or substituted with one or more R$_7$ groups; or
(b) -phenyl, -naphthyl, —(C$_{14}$)aryl, or -(5- to 10-membered)heteroaryl, each of which is unsubstituted or substituted with one or more R$_8$ groups;
each R$_7$ and R$_8$ is independently —(C$_1$-C$_6$)alkyl, —(C$_2$-C$_6$)alkenyl, —(C$_2$-C$_6$)alkynyl, —(C$_3$-C$_8$)cycloalkyl, —(C$_5$-C$_8$)cycloalkenyl, -phenyl, -(3- to 5-membered)heterocycle, —C(halo)$_3$, —CH(halo)$_2$, —CH$_2$(halo), —CN, —OH, -halo, —N$_3$, —NO$_2$, —N(R$_{10}$)$_2$, —CH=NR$_{10}$, —NR$_{10}$OH, —OR$_{10}$, —COR$_{10}$, —C(O)OR$_{10}$, —OC(O)R$_{10}$, —OC(O)OR$_{10}$, —SR$_{10}$, —S(O)R$_{10}$, or —S(O)$_2$R$_{10}$;
each R$_9$ is —H, —(C$_1$-C$_6$)alkyl, —(C$_2$-C$_6$)alkenyl, —(C$_2$-C$_6$)alkynyl, —(C$_3$-C$_8$)cycloalkyl, —(C$_5$-C$_8$)cycloalkenyl, -phenyl, -(3- to 5-membered)heterocycle, —C(halo)$_3$, —CH(halo)$_2$, —CH$_2$(halo), —OH, —N(R$_{10}$)$_2$, —CH=NR$_{10}$, —NR$_{10}$OH, —OR$_{10}$, or —SR$_{10}$;
each R$_{10}$ is independently —H, —(C$_1$-C$_6$)alkyl, —(C$_2$-C$_6$)alkenyl, —(C$_2$-C$_6$)alkynyl, —(C$_3$-C$_8$)cycloalkyl, —(C$_5$-C$_8$)cycloalkenyl, -phenyl, -(3- to 5-membered)heterocycle, —C(halo)$_3$, —CH(halo)$_2$, or —CH$_2$(halo);
each halo is independently —F, —Cl, —Br, or —I;
p is an integer ranging from 0 to 2; and
m is an integer ranging from 0 to 2.

The present invention also encompasses compounds having the formula (IV):

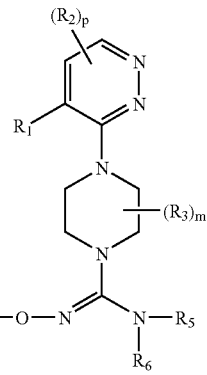

(IV)

and pharmaceutically acceptable salts thereof, wherein:
R$_1$ is -halo, —CH$_3$, —NO$_2$, —CN, —OH, —OCH$_3$, —NH$_2$, —C(halo)$_3$, —CH(halo)$_2$, or —CH$_2$(halo);
each R$_2$ is independently:
(a) -halo, —CN, —OH, NO$_2$, —O(C$_1$-C$_6$)alkyl, or —NH$_2$;
(b) —(C$_1$-C$_{10}$)alkyl, —(C$_2$-C$_{10}$)alkenyl, —(C$_2$-C$_{10}$)alkynyl, —(C$_3$-C$_{10}$)cycloalkyl, —(C$_8$-C$_{14}$)bicycloalkyl, —(C$_8$-C$_{14}$)tricycloalkyl, —(C$_5$-C$_{10}$)cycloalkenyl, —(C$_8$-C$_{14}$)bicycloalkenyl, —(C$_8$-C$_{14}$)tricycloalkenyl, -(3- to 7-membered)heterocycle, or -(7- to 10-membered)bicycloheterocycle, each of which is unsubstituted or substituted with one or more R$_7$ groups; or
(c) -phenyl, -naphthyl, —(C$_{14}$)aryl, or -(5- to 10-membered)heteroaryl, each of which is unsubstituted or substituted with one or more R$_8$ groups;
each R$_3$ is independently:
(a) -halo, —CN, —OH, NO$_2$, —O(C$_1$-C$_6$)alkyl, or —NH$_2$;
(b) —(C$_1$-C$_{10}$)alkyl, —(C$_2$-C$_{10}$)alkenyl, —(C$_2$-C$_{10}$)alkynyl, —(C$_3$-C$_{10}$)cycloalkyl, —(C$_8$-C$_{14}$)bicycloalkyl, —(C$_8$-C$_{14}$)tricycloalkyl, —(C$_5$-C$_{10}$)cycloalkenyl, —(C$_8$-C$_{14}$)bicycloalkenyl, —(C$_8$-C$_{14}$)tricycloalkenyl, -(3- to 7-membered)heterocycle, or -(7- to 10-membered)bicycloheterocycle, each of which is unsubstituted or substituted with one or more R$_7$ groups; or
(c) -phenyl, -naphthyl, —(C$_{14}$)aryl, or -(5- to 10-membered)heteroaryl, each of which is unsubstituted or substituted with one or more R$_8$ groups;
R$_4$ is —H, —(C$_1$-C$_{10}$)alkyl, —C(O)R$_9$, or —C(O)NHR$_9$;
R$_5$ is —H or —(C$_1$-C$_{10}$)alkyl;
R$_6$ is:
(a) —(C$_1$-C$_{10}$)alkyl, —(C$_2$-C$_{10}$)alkenyl, —(C$_2$-C$_{10}$)alkynyl, —(C$_3$-C$_{10}$)cycloalkyl, —(C$_8$-C$_{14}$)bicycloalkyl, —(C₈-C₁₄)tricycloalkyl, —(C₅-C₁₀)cycloalkenyl, —(C₈-C₁₄)bicycloalkenyl, —(C₈-C₁₄)tricycloalkenyl, -(3- to 7-membered)heterocycle, or -(7- to 10-membered)bicycloheterocycle, each of which is unsubstituted or substituted with one or more $R_7$ groups; or (b) -phenyl, -naphthyl, —(C₁₄)aryl, or -(5- to 10-membered)heteroaryl, each of which is unsubstituted or substituted with one or more $R_8$ groups;

each $R_7$ and $R_8$ is independently —(C₁-C₆)alkyl, —(C₂-C₆)alkenyl, —(C₂-C₆)alkynyl, —(C₃-C₈)cycloalkyl, —(C₅-C₈)cycloalkenyl, -phenyl, -(3- to 5-membered)heterocycle, —C(halo)₃, —CH(halo)₂, —CH₂(halo), —CN, —OH, -halo, —N₃, —NO₂, —N($R_{10}$)₂, —CH=N$R_{10}$, —N$R_{10}$OH, —O$R_{10}$, —CO$R_{10}$, —C(O)O$R_{10}$, —OC(O)$R_{10}$, —OC(O)O$R_{10}$, —S$R_{10}$, —S(O)$R_{10}$, or —S(O)₂$R_{10}$;

each $R_9$ is —H, —(C₁-C₆)alkyl, —(C₂-C₆)alkenyl, —(C₂-C₆)alkynyl, —(C₃-C₈)cycloalkyl, —(C₅-C₈)cycloalkenyl, -phenyl, -(3- to 5-membered)heterocycle, —C(halo)₃, —CH(halo)₂, —CH₂(halo), —OH, —N($R_{10}$)₂, —CH=N$R_{10}$, —N$R_{10}$OH, —O$R_{10}$, or —S$R_{10}$;

each $R_{10}$ is independently —H, —(C₁-C₆)alkyl, —(C₂-C₆)alkenyl, —(C₂-C₆)alkynyl, —(C₃-C₈)cycloalkyl, —(C₅-C₈)cycloalkenyl, -phenyl, -(3- to 5-membered)heterocycle, —C(halo)₃, —CH(halo)₂, or —CH₂(halo);

each halo is independently —F, —Cl, —Br, or —I;

p is an integer ranging from 0 to 2; and m is an integer ranging from 0 to 2.

The present invention also encompasses compounds having the formula (V):

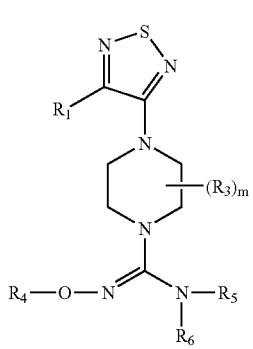

(V)

and pharmaceutically acceptable salts thereof, wherein:

$R_1$ is -halo, —CH₃, —NO₂, —CN, —OH, —OCH₃, —NH₂, —C(halo)₃, —CH(halo)₂, or —CH₂(halo);

each $R_2$ is independently:

(a) -halo, —CN, —OH, NO₂, or —NH₂;

(b) —(C₁-C₁₀)alkyl, —(C₂-C₁₀)alkenyl, —(C₂-C₁₀)alkynyl, —(C₃-C₁₀)cycloalkyl, —(C₈-C₁₄)bicycloalkyl, —(C₈-C₁₄)tricycloalkyl, —(C₅-C₁₀)cycloalkenyl, —(C₈-C₁₄)bicycloalkenyl, —(C₈-C₁₄)tricycloalkenyl, -(3- to 7-membered)heterocycle, or -(7- to 10-membered)bicycloheterocycle, each of which is unsubstituted or substituted with one or more $R_7$ groups; or (c) -phenyl, -naphthyl, —(C₁₄)aryl, or -(5- to 10-membered)heteroaryl, each of which is unsubstituted or substituted with one or more $R_8$ groups;

$R_4$ is —H, —(C₁-C₁₀)alkyl, —C(O)$R_9$, or —C(O)NH$R_9$;

$R_5$ is —H or —(C₁-C₁₀)alkyl;

$R_6$ is:

(a) —(C₁-C₁₀)alkyl, —(C₂-C₁₀)alkenyl, —(C₂-C₁₀)alkynyl, —(C₃-C₁₀)cycloalkyl, —(C₈-C₁₄)bicycloalkyl, —(C₈-C₁₄)tricycloalkyl, —(C₅-C₁₀)cycloalkenyl, —(C₈-C₁₄)bicycloalkenyl, —(C₈-C₁₄)tricycloalkenyl, -(3- to 7-membered)heterocycle, or -(7- to 10-membered)bicycloheterocycle, each of which is unsubstituted or substituted with one or more $R_7$ groups; or (b) -phenyl, -naphthyl, —(C₁₄)aryl, or -(5- to 10-membered)heteroaryl, each of which is unsubstituted or substituted with one or more $R_8$ groups;

each $R_7$ and $R_8$ is independently —(C₁-C₆)alkyl, —(C₂-C₆)alkenyl, —(C₂-C₆)alkynyl, —(C₃-C₈)cycloalkyl, —(C₅-C₈)cycloalkenyl, -phenyl, -(3- to 5-membered)heterocycle, —C(halo)₃, —CH(halo)₂, —CH₂(halo), —CN, —OH, -halo, —N₃, —NO₂, —N($R_{10}$)₂, —CH=N$R_{10}$, —N$R_{10}$OH, —O$R_{10}$, —CO$R_{10}$, —C(O)O$R_{10}$, —OC(O)$R_{10}$, —OC(O)O$R_{10}$, —S$R_{10}$, —S(O)$R_{10}$, or —S(O)₂$R_{10}$;

each $R_9$ is —H, —(C₁-C₆)alkyl, —(C₂-C₆)alkenyl, —(C₂-C₆)alkynyl, —(C₃-C₈)cycloalkyl, —(C₅-C₈)cycloalkenyl, -phenyl, -(3- to 5-membered)heterocycle, —C(halo)₃, —CH(halo)₂, —CH₂(halo), —OH, —N($R_{10}$)₂, —CH=N$R_{10}$, —N$R_{10}$OH, —O$R_{10}$, or —S$R_{10}$;

each $R_{10}$ is independently —H, —(C₁-C₆)alkyl, —(C₂-C₆)alkenyl, —(C₂-C₆)alkynyl, —(C₃-C₈)cycloalkyl, —(C₅-C₈)cycloalkenyl, -phenyl, -(3- to 5-membered)heterocycle, —C(halo)₃, —CH(halo)₂, or —CH₂(halo);

each halo is independently —F, —Cl, —Br, or —I; and m is an integer ranging from 0 to 2.

The present invention also encompasses compounds having the formula (VI):

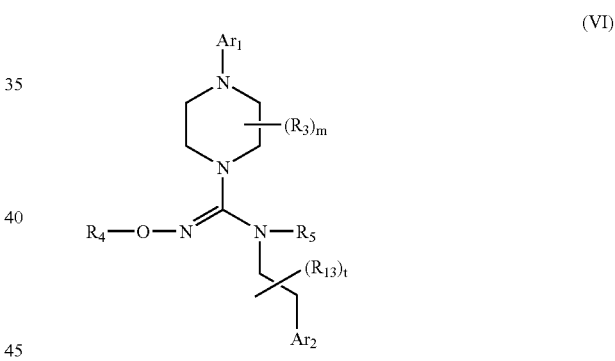

(VI)

and pharmaceutically acceptable salts thereof, wherein:

$Ar_1$ is

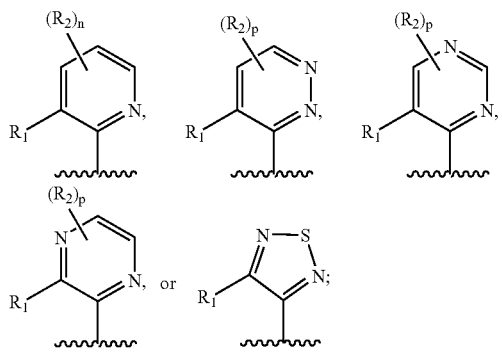

Ar$_2$ is

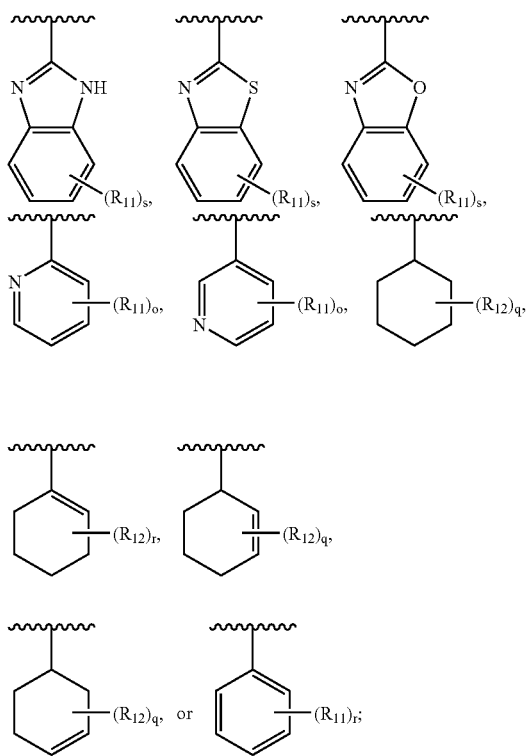

R$_1$ is —H, -halo, —CH$_3$, —NO$_2$, —CN, —OH, —OCH$_3$, —NH$_2$, —C(halo)$_3$, —CH(halo)$_2$, or —CH$_2$(halo);

each R$_2$ is independently:
(a) -halo, —CN, —OH, NO$_2$, —O(C$_1$-C$_6$)alkyl, or —NH$_2$;
(b) —(C$_1$-C$_{10}$)alkyl, —(C$_2$-C$_{10}$)alkenyl, —(C$_2$-C$_{10}$)alkynyl, —(C$_3$-C$_{10}$)cycloalkyl, —(C$_8$-C$_{14}$)bicycloalkyl, —(C$_8$-C$_{14}$)tricycloalkyl, —(C$_5$-C$_{10}$)cycloalkenyl, —(C$_8$-C$_{14}$)bicycloalkenyl, —(C$_8$-C$_{14}$)tricycloalkenyl, -(3- to 7-membered)heterocycle, or -(7- to 10-membered)bicycloheterocycle, each of which is unsubstituted or substituted with one or more R$_7$ groups; or
(c) -phenyl, -naphthyl, —(C$_{14}$)aryl, or -(5- to 10-membered)heteroaryl, each of which is unsubstituted or substituted with one or more R$_8$ groups;

each R$_3$ is independently:
(a) -halo, —CN, —OH, NO$_2$, —O(C$_1$-C$_6$)alkyl, or —NH$_2$;
(b) —(C$_1$-C$_{10}$)alkyl, —(C$_2$-C$_{10}$)alkenyl, —(C$_2$-C$_{10}$)alkynyl, —(C$_3$-C$_{10}$)cycloalkyl, —(C$_8$-C$_{14}$)bicycloalkyl, —(C$_8$-C$_{14}$)tricycloalkyl, —(C$_5$-C$_{10}$)cycloalkenyl, —(C$_8$-C$_{14}$)bicycloalkenyl, —(C$_8$-C$_{14}$)tricycloalkenyl, -(3- to 7-membered)heterocycle, or -(7- to 10-membered)bicycloheterocycle, each of which is unsubstituted or substituted with one or more R$_7$ groups; or
(c) -phenyl, -naphthyl, —(C$_{14}$)aryl, or -(5- to 10-membered)heteroaryl, each of which is unsubstituted or substituted with one or more R$_8$ groups;

R$_4$ is —H, —(C$_1$-C$_{10}$)alkyl, —C(O)R$_9$, or —C(O)NHR$_9$;
R$_5$ is —H or —(C$_1$-C$_{10}$)alkyl;

each R$_7$ and R$_8$ is independently —(C$_1$-C$_6$)alkyl, —(C$_2$-C$_6$)alkenyl, —(C$_2$-C$_6$)alkynyl, —(C$_3$-C$_8$)cycloalkyl, —(C$_5$-C$_8$)cycloalkenyl, -phenyl, -(3- to 5-membered)heterocycle, —C(halo)$_3$, —CH(halo)$_2$, —CH$_2$(halo), —CN, —OH, -halo, —N$_3$, —NO$_2$, —N(R$_{10}$)$_2$, —CH=NR$_{10}$, —NR$_{10}$OH, —OR$_{10}$, —COR$_{10}$, —C(O)OR$_{10}$, —OC(O)R$_{10}$, —OC(O)OR$_{10}$, —SR$_{10}$, —S(O)R$_{10}$, or —S(O)$_2$R$_{10}$;

each R$_9$ is —H, —(C$_1$-C$_6$)alkyl, —(C$_2$-C$_6$)alkenyl, —(C$_2$-C$_6$)alkynyl, —(C$_3$-C$_8$)cycloalkyl, —(C$_5$-C$_8$)cycloalkenyl, -phenyl, -(3- to 5-membered)heterocycle, —C(halo)$_3$, —CH(halo)$_2$, —CH$_2$(halo), —OH, —N(R$_{10}$)$_2$, —CH=NR$_{10}$, —NR$_{10}$OH, —OR$_{10}$, or —SR$_{10}$;

each R$_{10}$ is independently —H, —(C$_1$-C$_6$)alkyl, —(C$_2$-C$_6$)alkenyl, —(C$_2$-C$_6$)alkynyl, —(C$_3$-C$_8$)cycloalkyl, —(C$_5$-C$_8$)cycloalkenyl, -phenyl, -(3- to 5-membered)heterocycle, —C(halo)$_3$, —CH(halo)$_2$, or —CH$_2$(halo);

each R$_{11}$ and R$_{12}$ is independently —(C$_1$-C$_6$)alkyl, —(C$_2$-C$_6$)alkenyl, —(C$_2$-C$_6$)alkynyl, —(C$_3$-C$_8$)cycloalkyl, —(C$_5$-C$_8$)cycloalkenyl, -phenyl, —C(halo)$_3$, —CH(halo)$_2$, —CH$_2$(halo), —CN, —OH, -halo, —N$_3$, —NO$_2$, —N(R$_7$)$_2$, —CH=NR$_7$, —NR$_7$OH, —OR$_7$, —COR$_7$, —C(O)OR$_7$, —OC(O)R$_7$, —OC(O)OR$_7$, —SR$_7$, —S(O)R$_7$, or —S(O)$_2$R$_7$;

each R$_{13}$ is independently —(C$_1$-C$_6$)alkyl, —(C$_2$-C$_6$)alkenyl, —(C$_2$-C$_6$)alkynyl, —(C$_3$-C$_8$)cycloalkyl, —(C$_5$-C$_8$)cycloalkenyl, -phenyl, -(3- to 5-membered)heterocycle, —C(halo)$_3$, —CH(halo)$_2$, CH$_2$(halo), or -halo;

each halo is independently —F, —Cl, —Br, or —I;
s is an integer ranging from 0 to 4;
o is an integer ranging from 0 to 4;
q is an integer ranging from 0 to 6;
r is an integer ranging from 0 to 5;
t is an integer ranging from 0 to 2;
p is an integer ranging from 0 to 2;
n is an integer ranging from 0 to 3; and
m is an integer ranging from 0 to 2.

The present invention also encompasses compounds having the formula (VII):

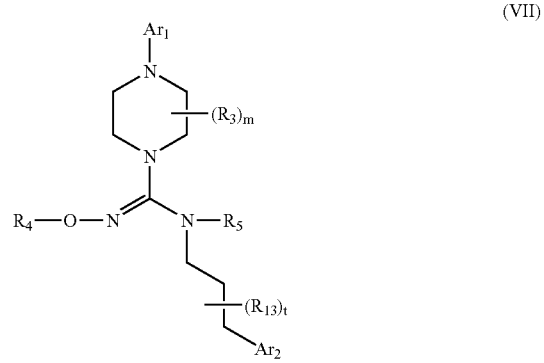

(VII)

and pharmaceutically acceptable salts thereof, wherein:
Ar$_1$ is

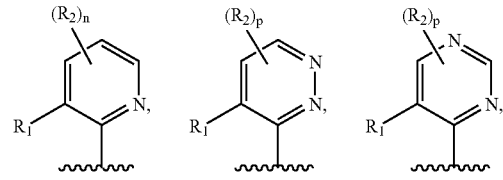

-continued

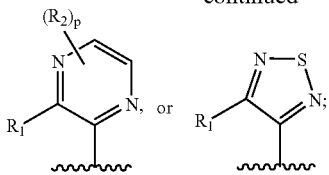

Ar$_2$ is

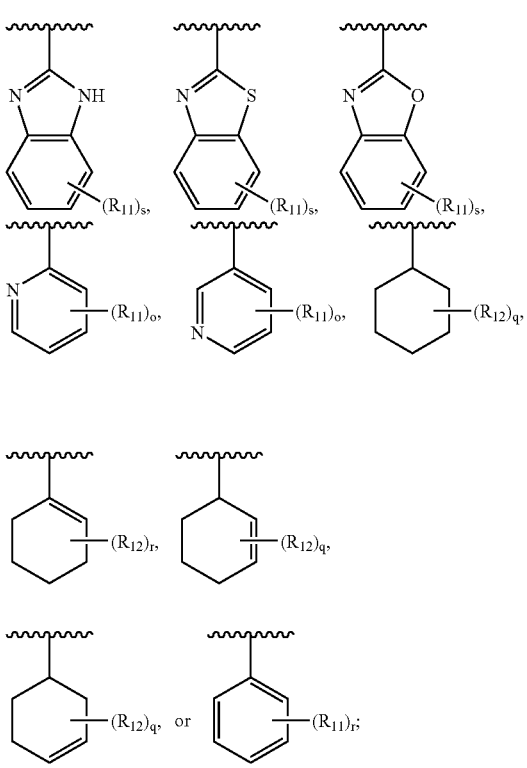

R$_1$ is -halo, —CH$_3$, —NO$_2$, —CN, —OH, —OCH$_3$, —NH$_2$, —C(halo)$_3$, —CH(halo)$_2$, or —CH$_2$(halo);

each R$_2$ is independently:
(a) -halo, —CN, —OH, NO$_2$, —O(C$_1$-C$_6$)alkyl, or —NH$_2$;
(b) —(C$_1$-C$_{10}$)alkyl, —(C$_2$-C$_{10}$)alkenyl, —(C$_2$-C$_{10}$)alkynyl, —(C$_3$-C$_{10}$)cycloalkyl, —(C$_8$-C$_{14}$)bicycloalkyl, —(C$_8$-C$_{14}$)tricycloalkyl, —(C$_5$-C$_{10}$)cycloalkenyl, —(C$_8$-C$_{14}$)bicycloalkenyl, —(C$_8$-C$_{14}$)tricycloalkenyl, -(3- to 7-membered)heterocycle, or -(7- to 10-membered)bicycloheterocycle, each of which is unsubstituted or substituted with one or more R$_7$ groups; or
(c) -phenyl, -naphthyl, —(C$_{14}$)aryl, or -(5- to 10-membered)heteroaryl, each of which is unsubstituted or substituted with one or more R$_8$ groups;

each R$_3$ is independently:
(a) -halo, —CN, —OH, NO$_2$, —O(C$_1$-C$_6$)alkyl, or —NH$_2$;
(b) —(C$_1$-C$_{10}$)alkyl, —(C$_2$-C$_{10}$)alkenyl, —(C$_2$-C$_{10}$)alkynyl, —(C$_3$-C$_{10}$)cycloalkyl, —(C$_8$-C$_{14}$)bicycloalkyl, —(C$_8$-C$_{14}$)tricycloalkyl, —(C$_5$-C$_{10}$)cycloalkenyl, —(C$_8$-C$_{14}$)bicycloalkenyl, —(C$_8$-C$_{14}$)tricycloalkenyl, -(3- to 7-membered)heterocycle, or -(7- to 10-membered)bicycloheterocycle, each of which is unsubstituted or substituted with one or more R$_7$ groups; or
(c) -phenyl, -naphthyl, —(C$_{14}$)aryl, or -(5- to 10-membered)heteroaryl, each of which is unsubstituted or substituted with one or more R$_8$ groups;

R$_4$ is —H, —(C$_1$-C$_{10}$)alkyl, —C(O)R$_9$, or —C(O)NHR$_9$;
R$_5$ is —H or —(C$_1$-C$_{10}$)alkyl;
each R$_7$ and R$_8$ is independently —(C$_1$-C$_6$)alkyl, —(C$_2$-C$_6$)alkenyl, —(C$_2$-C$_6$)alkynyl, —(C$_3$-C$_8$)cycloalkyl, —(C$_5$-C$_8$)cycloalkenyl, -phenyl, -(3- to 5-membered)heterocycle, —C(halo)$_3$, —CH(halo)$_2$, —CH$_2$(halo), —CN, —OH, -halo, —N$_3$, —NO$_2$, —N(R$_{10}$)$_2$, —CH=NR$_{10}$, —NR$_{10}$OH, —OR$_{10}$, —COR$_{10}$, —C(O)OR$_{10}$, —OC(O)R$_{10}$, —OC(O)OR$_{10}$, —SR$_{10}$, —S(O)R$_{10}$, or —S(O)$_2$R$_{10}$;

each R$_9$ is —H, —(C$_1$-C$_6$)alkyl, —(C$_2$-C$_6$)alkenyl, —(C$_2$-C$_6$)alkynyl, —(C$_3$-C$_8$)cycloalkyl, —(C$_5$-C$_8$)cycloalkenyl, -phenyl, -(3- to 5-membered)heterocycle, —C(halo)$_3$, —CH(halo)$_2$, —CH$_2$(halo), —OH, —N(R$_{10}$)$_2$, —CH=NR$_{10}$, —NR$_{10}$OH, —OR$_{10}$, or —SR$_{10}$;

each R$_{10}$ is independently —H, —(C$_1$-C$_6$)alkyl, —(C$_2$-C$_6$)alkenyl, —(C$_2$-C$_6$)alkynyl, —(C$_3$-C$_8$)cycloalkyl, —(C$_5$-C$_8$)cycloalkenyl, -phenyl, -(3- to 5-membered)heterocycle, —C(halo)$_3$, —CH(halo)$_2$, or —CH$_2$(halo);

each R$_{11}$ and R$_{12}$ is independently —(C$_1$-C$_6$)alkyl, —(C$_2$-C$_6$)alkenyl, —(C$_2$-C$_6$)alkynyl, —(C$_3$-C$_8$)cycloalkyl, —(C$_5$-C$_8$)cycloalkenyl, -phenyl, —C(halo)$_3$, —CH(halo)$_2$, —CH$_2$(halo), —CN, —OH, -halo, —N$_3$, —NO$_2$, —N(R$_7$)$_2$, —CH=NR$_7$, —NR$_7$OH, —OR$_7$, —COR$_7$, —C(O)OR$_7$, —OC(O)R$_7$, —OC(O)OR$_7$, —SR$_7$, —S(O)R$_7$, or —S(O)$_2$R$_7$;

each R$_{13}$ is independently —(C$_1$-C$_6$)alkyl, —(C$_2$-C$_6$)alkenyl, —(C$_2$-C$_6$)alkynyl, —(C$_3$-C$_8$)cycloalkyl, —(C$_5$-C$_8$)cycloalkenyl, -phenyl, -(3- to 5-membered)heterocycle, —C(halo)$_3$, —CH(halo)$_2$, CH$_2$(halo), or -halo;

each halo is independently —F, —Cl, —Br, or —I;
s is an integer ranging from 0 to 4;
o is an integer ranging from 0 to 4;
q is an integer ranging from 0 to 6;
r is an integer ranging from 0 to 5;
t is an integer ranging from 0 to 2;
p is an integer ranging from 0 to 2;
n is an integer ranging from 0 to 3; and
m is an integer ranging from 0 to 2.

A compound of formula (I)-(VII) or a pharmaceutically acceptable salt thereof (a "Hydroxyiminopiperazine Compound") is useful for treating or preventing pain, UI, an ulcer, IBD, IBS, an addictive disorder, Parkinson's disease, parkinsonism, anxiety, epilepsy, stroke, a seizure, a pruritic condition, psychosis, a cognitive disorder, a memory deficit, restricted brain function, Huntington's chorea, ALS, dementia, retinopathy, a muscle spasm, a migraine, vomiting, dyskinesia, or depression (each being a "Condition") in an animal.

The invention also relates to compositions comprising an effective amount of a Hydroxyiminopiperazine Compound and a pharmaceutically acceptable carrier or excipient. The compositions are useful for treating or preventing a Condition in an animal.

The invention further relates to methods for treating a Condition, comprising administering to an animal in need thereof an effective amount of a Hydroxyiminopiperazine Compound.

The invention further relates to methods for preventing a Condition, comprising administering to an animal in need thereof an effective amount of a Hydroxyiminopiperazine Compound.

The invention still further relates to methods for inhibiting Vanilloid Receptor 1 ("VR1") function in a cell, comprising contacting a cell capable of expressing VR1 with an effective amount of a Hydroxyiminopiperazine Compound.

The invention still further relates to methods for inhibiting mGluR5 function in a cell, comprising contacting a cell capable of expressing mGluR5 with an effective amount of a Hydroxyiminopiperazine Compound.

The invention still further relates to methods for inhibiting metabotropic glutamate receptor 1 ("mGluR1") function in a cell, comprising contacting a cell capable of expressing mGluR1 with an effective amount of a Hydroxyiminopiperazine Compound.

The invention still further relates to a method for preparing a composition, comprising the step of admixing a Hydroxyiminopiperazine Compound and a pharmaceutically acceptable carrier or excipient.

The invention still further relates to a kit comprising a container containing an effective amount of a Hydroxyiminopiperazine Compound.

The present invention can be understood more fully by reference to the following detailed description and illustrative examples, which are intended to exemplify non-limiting embodiments of the invention.

4. DETAILED DESCRIPTION OF THE INVENTION

4.1 The Hydroxyiminopiperazine Compounds of Formula (I)

As stated above, the present invention encompasses compounds of Formula (I)

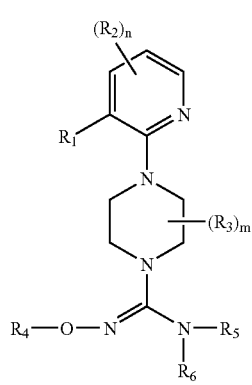

(I)

and pharmaceutically acceptable salts thereof, where $R_1$-$R_6$, n, and m are defined above for the Hydroxyiminopiperazine Compounds of formula (I).

In one embodiment, n is 0.
In another embodiment n is 1.
In another embodiment, n is 2.
In another embodiment, n is 3.
In another embodiment, n is an integer ranging from 0 to 3.
In another embodiment, m is 0.
In another embodiment, m is 1.
In another embodiment, m is 2.
In another embodiment, $R_1$ is -halo.
In another embodiment, $R_1$ is —Cl.
In another embodiment, $R_1$ is —Br.
In another embodiment, $R_1$ is —I.
In another embodiment, $R_1$ is —F.
In another embodiment, $R_1$ is —CH$_3$.

In another embodiment, $R_1$ is —NO$_2$.
In another embodiment, $R_1$ is —OH.
In another embodiment, $R_1$ is —OCH$_3$.
In another embodiment, $R_1$ is —NH$_2$.
In another embodiment, $R_1$ is —C(halo)$_3$.
In another embodiment, $R_1$ is —CH(halo)$_2$.
In another embodiment, $R_1$ is —CH$_2$(halo).
In another embodiment, n is 1 and $R_2$ is -halo, —CN, —OH, NO$_2$, —O(C$_1$-C$_6$)alkyl, or —NH$_2$.
In another embodiment, n is 1 and $R_2$ is —(C$_1$-C$_{10}$)alkyl, —(C$_2$-C$_{10}$)alkenyl, —(C$_2$-C$_{10}$)alkynyl, —(C$_3$-C$_{10}$)cycloalkyl, —(C$_8$-C$_{14}$)bicycloalkyl, —(C$_8$-C$_{14}$)tricycloalkyl, —(C$_5$-C$_{10}$)cycloalkenyl, —(C$_8$-C$_{14}$)bicycloalkenyl, —(C$_8$-C$_{14}$)tricycloalkenyl, -(3- to 7-membered)heterocycle, or -(7- to 10-membered)bicycloheterocycle, each of which is unsubstituted or substituted with one or more $R_7$ groups.
In another embodiment, n is 1 and $R_2$ is -phenyl, -naphthyl, —(C$_{14}$)aryl, or -(5- to 10-membered)heteroaryl, each of which is unsubstituted or substituted with one or more $R_8$ groups.
In another embodiment, m is 1 and $R_3$ is -halo, —CN, —OH, NO$_2$, —O(C$_1$-C$_6$)alkyl, or —NH$_2$.
In another embodiment, m is 1 and $R_3$ is —(C$_1$-C$_{10}$)alkyl, —(C$_2$-C$_{10}$)alkenyl, —(C$_2$-C$_{10}$)alkynyl, —(C$_3$-C$_{10}$)cycloalkyl, —(C$_8$-C$_{14}$)bicycloalkyl, —(C$_8$-C$_{14}$)tricycloalkyl, —(C$_5$-C$_{10}$)cycloalkenyl, —(C$_8$-C$_{14}$)bicycloalkenyl, —(C$_8$-C$_{14}$)tricycloalkenyl, -(3- to 7-membered)heterocycle, or -(7- to 10-membered)bicycloheterocycle, each of which is unsubstituted or substituted with one or more $R_7$ groups.
In another embodiment, m is 1 and $R_3$ is -phenyl, -naphthyl, —(C$_{14}$)aryl, or -(5- to 10-membered)heteroaryl, each of which is unsubstituted or substituted with one or more $R_8$ groups.
In another embodiment, m is 1 and $R_3$ is a —(C$_1$-C$_{10}$)alkyl.
In another embodiment, m is 1, $R_3$ is a —(C$_1$-C$_{10}$)alkyl, and the carbon to which the $R_3$ group is attached is in the (R)-configuration.
In another embodiment, m is 1, $R_3$ is a —(C$_1$-C$_{10}$)alkyl, and the carbon to which the $R_3$ group is attached is in the (S)-configuration.
In another embodiment, m is 1 and $R_3$ is methyl.
In another embodiment, m is 1, $R_3$ is methyl, and the carbon to which the $R_3$ group is attached is in the (R)-configuration.
In another embodiment, m is 1, $R_3$ is methyl, and the carbon to which the $R_3$ group is attached is in the (S)-configuration.
In another embodiment, $R_4$ is —H.
In another embodiment, $R_4$ is —(C$_1$-C$_{10}$)alkyl.
In another embodiment, $R_4$ is —C(O)$R_9$.
In another embodiment, $R_5$ is —C(O)NHR$_9$.
In another embodiment, $R_5$ is —H.
In another embodiment, $R_5$ is —(C$_1$-C$_{10}$)alkyl.
In another embodiment, $R_6$ is —(C$_1$-C$_{10}$)alkyl, —(C$_2$-C$_{10}$)alkenyl, —(C$_2$-C$_{10}$)alkynyl, —(C$_3$-C$_{10}$)cycloalkyl, —(C$_8$-C$_{14}$)bicycloalkyl, —(C$_8$-C$_{14}$)tricycloalkyl, —(C$_5$-C$_{10}$)cycloalkenyl, —(C$_8$-C$_{14}$)bicycloalkenyl, —(C$_8$-C$_{14}$)tricycloalkenyl, —(3- to 7-membered)heterocycle, or -(7- to 1-membered)bicycloheterocycle, each of which is unsubstituted or substituted with one or more $R_7$ groups.
In another embodiment, $R_6$ is -phenyl, -naphthyl, —(C$_{14}$)aryl, or -(5- to 10-membered)heteroaryl, each of which is unsubstituted or substituted with one or more $R_8$ groups.
In another embodiment $R_6$ is -phenyl.
In another embodiment, n and m are 0, $R_1$ is —CH$_3$, $R_4$ is —H, $R_5$ is —H, and $R_6$ is -phenyl. In another embodiment, the $R_6$-phenyl is substituted with a —(C$_1$-C$_6$)alkyl group. In another embodiment, the —($C_1$-$C_6$)alkyl group is substituted at the para-position of the $R_6$-phenyl. In another embodiment, the —($C_1$-$C_6$)alkyl group is a t-butyl group substituted at the para-position of the $R_6$-phenyl. In another embodiment, the —($C_1$-$C_6$)alkyl group is an iso-propyl group substituted at the para-position of the $R_6$-phenyl.

In another embodiment, n and m are 0, $R_1$ is —$CF_3$, $R_4$ is —H, $R_5$ is —H, and $R_6$ is -phenyl. In another embodiment, the $R_6$-phenyl is substituted with a —($C_1$-$C_6$)alkyl group. In another embodiment, the —($C_1$-$C_6$)alkyl group is substituted at the para-position of the $R_6$-phenyl. In another embodiment, the —($C_1$-$C_6$)alkyl group is a t-butyl group substituted at the para-position of the $R_6$-phenyl. In another embodiment, the —($C_1$-$C_6$)alkyl group is an iso-propyl group substituted at the para-position of the $R_6$-phenyl.

In another embodiment, n and m are 0, $R_1$ is —Cl, $R_4$ is —H, $R_5$ is —H, and $R_6$ is -phenyl. In another embodiment, the $R_6$-phenyl is substituted with a —($C_1$-$C_6$)alkyl group. In another embodiment, the —($C_1$-$C_6$)alkyl group is substituted at the para-position of the $R_6$-phenyl. In another embodiment, the —($C_1$-$C_6$)alkyl group is a t-butyl group substituted at the para-position of the $R_6$-phenyl. In another embodiment, the —($C_1$-$C_6$)alkyl group is an iso-propyl group substituted at the para-position of the $R_6$-phenyl.

In another embodiment, n and m are 0, $R_1$ is —$CH_3$, $R_4$ is —$CH_3$, $R_5$ is —H, and $R_6$ is -phenyl. In another embodiment, the $R_6$-phenyl is substituted with a —($C_1$-$C_6$)alkyl group. In another embodiment, the —($C_1$-$C_6$)alkyl group is substituted at the para-position of the $R_6$-phenyl. In another embodiment, the —($C_1$-$C_6$)alkyl group is a t-butyl group substituted at the para-position of the $R_6$-phenyl. In another embodiment, the —($C_1$-$C_6$)alkyl group is an iso-propyl group substituted at the para-position of the $R_6$-phenyl.

In another embodiment, n and m are 0, $R_1$ is —$CF_3$, $R_4$ is —$CH_3$, $R_5$ is —H, and $R_6$ is -phenyl. In another embodiment, the $R_6$-phenyl is substituted with a —($C_1$-$C_6$)alkyl group. In another embodiment, the —($C_1$-$C_6$)alkyl group is substituted at the para-position of the $R_6$-phenyl. In another embodiment, the —($C_1$-$C_6$)alkyl group is a t-butyl group substituted at the para-position of the $R_6$-phenyl. In another embodiment, the —($C_1$-$C_6$)alkyl group is an iso-propyl group substituted at the para-position of the $R_6$-phenyl.

In another embodiment, n and m are 0, $R_1$ is —Cl, $R_4$ is —$CH_3$, $R_5$ is —H, and $R_6$ is -phenyl. In another embodiment, the $R_6$-phenyl is substituted with a —($C_1$-$C_6$)alkyl group. In another embodiment, the —($C_1$-$C_6$)alkyl group is substituted at the para-position of the $R_6$-phenyl. In another embodiment, the —($C_1$-$C_6$)alkyl group is a t-butyl group substituted at the para-position of the $R_6$-phenyl. In another embodiment, the —($C_1$-$C_6$)alkyl group is an iso-propyl group substituted at the para-position of the $R_6$-phenyl.

In another embodiment, n is 0, m is 1, $R_1$ is —$CH_3$, $R_3$ is —$CH_3$, $R_4$ is —H, $R_5$ is —H, and $R_6$ is -phenyl. In another embodiment, the $R_6$-phenyl is substituted with a —($C_1$-$C_6$) alkyl group. In another embodiment, the —($C_1$-$C_6$)alkyl group is substituted at the para-position of the $R_6$-phenyl. In another embodiment, the —($C_1$-$C_6$)alkyl group is a t-butyl group substituted at the para-position of the $R_6$-phenyl. In another embodiment, the —($C_1$-$C_6$)alkyl group is an iso-propyl group substituted at the para-position of the $R_6$-phenyl.

In another embodiment, n is 0, m is 1, $R_1$ is —$CF_3$, $R_3$ is —$CH_3$, $R_4$ is —H, $R_5$ is —H, and $R_6$ is -phenyl. In another embodiment, the $R_6$-phenyl is substituted with a —($C_1$-$C_6$) alkyl group. In another embodiment, the —($C_1$-$C_6$)alkyl group is substituted at the para-position of the $R_6$-phenyl. In another embodiment, the —($C_1$-$C_6$)alkyl group is a t-butyl group substituted at the para-position of the $R_6$-phenyl. In another embodiment, the —($C_1$-$C_6$)alkyl group is an iso-propyl group substituted at the para-position of the $R_6$-phenyl.

In another embodiment, n is 0, m is 1, $R_1$ is —Cl, $R_3$ is —$CH_3$, $R_4$ is —H, $R_5$ is —H, and $R_6$ is -phenyl. In another embodiment, the $R_6$-phenyl is substituted with a —($C_1$-$C_6$) alkyl group. In another embodiment, the —($C_1$-$C_6$)alkyl group is substituted at the para-position of the $R_6$-phenyl. In another embodiment, the —($C_1$-$C_6$)alkyl group is a t-butyl group substituted at the para-position of the $R_6$-phenyl. In another embodiment, the —($C_1$-$C_6$)alkyl group is an iso-propyl group substituted at the para-position of the $R_6$-phenyl.

In another embodiment, n is 0, m is 1, $R_1$ is —$CH_3$, $R_3$ is —$CH_3$, $R_4$ is —$CH_3$, $R_5$ is —H, and $R_6$ is -phenyl. In another embodiment, the $R_6$-phenyl is substituted with a —($C_1$-$C_6$) alkyl group. In another embodiment, the —($C_1$-$C_6$)alkyl group is substituted at the para-position of the $R_6$-phenyl. In another embodiment, the —($C_1$-$C_6$)alkyl group is a t-butyl group substituted at the para-position of the $R_6$-phenyl. In another embodiment, the —($C_1$-$C_6$)alkyl group is an iso-propyl group substituted at the para-position of the $R_6$ phenyl.

In another embodiment, n is 0, m is 1, $R_1$ is —$CF_3$, $R_3$ is —$CH_3$, $R_4$ is —$CH_3$, $R_5$ is —H, and $R_6$ is -phenyl. In another embodiment, the $R_6$-phenyl is substituted with a —($C_1$-$C_6$) alkyl group. In another embodiment, the —($C_1$-$C_6$)alkyl group is substituted at the para-position of the $R_6$-phenyl. In another embodiment, the —($C_1$-$C_6$)alkyl group is a t-butyl group substituted at the para-position of the $R_6$-phenyl. In another embodiment, the —($C_1$-$C_6$)alkyl group is an iso-propyl group substituted at the para-position of the $R_6$-phenyl.

In another embodiment, n is 0, m is 1, $R_1$ is —Cl, $R_3$ is —$CH_3$, $R_4$ is —$CH_3$, $R_5$ is —H, and $R_6$ is -phenyl. In another embodiment, the $R_6$-phenyl is substituted with a —($C_1$-$C_6$) alkyl group. In another embodiment, the —($C_1$-$C_6$)alkyl group is substituted at the para-position of the $R_6$-phenyl. In another embodiment, the —($C_1$-$C_6$)alkyl group is a t-butyl group substituted at the para-position of the $R_6$-phenyl. In another embodiment, the —($C_1$-$C_6$)alkyl group is an iso-propyl group substituted at the para-position of the $R_6$-phenyl.

In another embodiment, n and m are 0, $R_1$ is —$CH_3$, $R_4$ is —H, $R_5$ is —H, and $R_6$ is -phenyl substituted at its para-position with a —$CF_3$.

In another embodiment, n and m are 0, $R_1$ is —$CF_3$, $R_4$ is —H, $R_5$ is —H, and $R_6$ is -phenyl substituted at its para-position with a —$CF_3$.

In another embodiment, n and m are 0, $R_1$ is —Cl, $R_4$ is —H, $R_5$ is —H, and $R_6$ is -phenyl substituted at its para-position with a —$CF_3$.

In another embodiment, n and m are 0, $R_1$ is —$CH_3$, $R_4$ is —$CH_3$, $R_5$ is —H, and $R_6$ is -phenyl substituted at its para-position with a —$CF_3$.

In another embodiment, n and m are 0, $R_1$ is —$CF_3$, $R_4$ is —$CH_3$, $R_5$ is —H, and $R_6$ is -phenyl substituted at its para-position with a —$CF_3$.

In another embodiment, n and m are 0, $R_1$ is —Cl, $R_4$ is —$CH_3$, $R_5$ is —H, and $R_6$ is -phenyl substituted at its para-position with a —$CF_3$.

In another embodiment, n is 0, m is 1, $R_1$ is —$CH_3$, $R_3$ is —$CH_3$, $R_4$ is —H, $R_5$ is —H, and $R_6$ is -phenyl substituted at its para-position with a —$CF_3$.

In another embodiment, n is 0, m is 1, $R_1$ is —$CF_3$, $R_3$ is —$CH_3$, $R_4$ is —H, $R_5$ is —H, and $R_6$ is -phenyl substituted at its para-position with a —$CF_3$.

In another embodiment, n is 0, m is 1, $R_1$ is —Cl, $R_3$ is —$CH_3$, $R_4$ is —H, $R_5$ is —H, and $R_6$ is -phenyl substituted at its para-position with a —$CF_3$.

In another embodiment, n is 0, m is 1, $R_1$ is —$CH_3$, $R_3$ is —$CH_3$, $R_4$ is —$CH_3$, $R_5$ is —H, and $R_6$ is -phenyl substituted at its para-position with a —$CF_3$.

In another embodiment, n is 0, m is 1, $R_1$ is —$CF_3$, $R_3$ is —$CH_3$, $R_4$ is —$CH_3$, $R_5$ is —H, and $R_6$ is -phenyl substituted at its para-position with a —$CF_3$.

In another embodiment, n is 0, m is 1, $R_1$ is —Cl, $R_3$ is —$CH_3$, $R_4$ is —$CH_3$, $R_5$ is —H, and $R_6$ is -phenyl substituted at its para-position with a —$CF_3$.

4.2 The Hydroxyiminopiperazine Compounds of Formula (I)

The present invention also encompasses compounds of formula (II):

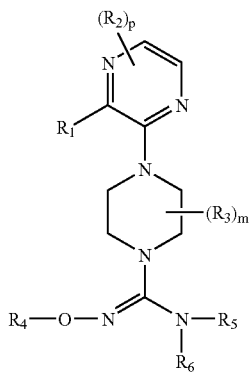

(II)

and pharmaceutically acceptable salts thereof, where $R_1$-$R_6$, p, and m are defined above for the Hydroxyiminopiperazine Compounds of formula (II).

In one embodiment, p is 0.
In another embodiment p is 1.
In another embodiment, p is 2.
In another embodiment, m is 0.
In another embodiment, m is 1.
In another embodiment, m is 2.
In another embodiment, $R_1$ is -halo.
In another embodiment, $R_1$ is —Cl.
In another embodiment, $R_1$ is —Br.
In another embodiment, $R_1$ is —I.
In another embodiment, $R_1$ is —F.
In another embodiment, $R_1$ is —$CH_3$.
In another embodiment, $R_1$ is —$NO_2$.
In another embodiment, $R_1$ is —OH.
In another embodiment, $R_1$ is —$OCH_3$.
In another embodiment, $R_1$ is —$NH_2$.
In another embodiment, $R_1$ is —C(halo)$_3$.
In another embodiment, $R_1$ is —CH(halo)$_2$.
In another embodiment, $R_1$ is —$CH_2$(halo).

In another embodiment, p is 1 and $R_2$ is -halo, —CN, —OH, $NO_2$, —O($C_1$-$C_6$)alkyl, or —$NH_2$.

In another embodiment, p is 1 and $R_2$ is —($C_1$-$C_{10}$)alkyl, —($C_2$-$C_{10}$)alkenyl, —($C_2$-$C_{10}$)alkynl, —($C_3$-$C_{10}$)cycloalkyl, —($C_8$-$C_{14}$)bicycloalkyl, —($C_8$-$C_{14}$)tricycloalkyl, —($C_5$-$C_{10}$)cycloalkenyl, —($C_8$-$C_{14}$)bicycloalkenyl, —($C_8$-$C_{14}$)tricycloalkenyl, -(3- to 7-membered)heterocycle, or -(7- to 10-membered)bicycloheterocycle, each of which is unsubstituted or substituted with one or more $R_7$ groups.

In another embodiment, p is 1 and $R_2$ is -phenyl, -naphthyl, —($C_{14}$)aryl, or -(5- to 10-membered)heteroaryl, each of which is unsubstituted or substituted with one or more $R_8$ groups.

In another embodiment, m is 1 and $R_3$ is -halo, —CN, —OH, $NO_2$, —O($C_1$-$C_6$)alkyl, or —$NH_2$.

In another embodiment, m is 1 and $R_3$ is —($C_1$-$C_{10}$)alkyl, —($C_2$-$C_{10}$)alkenyl, —($C_2$-$C_{10}$)alkynyl, —($C_3$-$C_{10}$)cycloalkyl, —($C_8$-$C_{14}$)bicycloalkyl, —($C_8$-$C_{14}$)tricycloalkyl, —($C_5$-$C_{10}$)cycloalkenyl, —($C_8$-$C_{14}$)bicycloalkenyl, —($C_8$-$C_{14}$)tricycloalkenyl, -(3- to 7-membered)heterocycle, or -(7- to 10-membered)bicycloheterocycle, each of which is unsubstituted or substituted with one or more $R_7$ groups.

In another embodiment, m is 1 and $R_3$ is -phenyl, -naphthyl, —($C_{14}$)aryl, or —(5- to 10-membered)heteroaryl, each of which is unsubstituted or substituted with one or more $R_8$ groups.

In another embodiment, m is 1 and $R_3$ is a —($C_1$-$C_{10}$)alkyl.

In another embodiment, m is 1, $R_3$ is a —($C_1$-$C_{10}$)alkyl, and the carbon to which the $R_3$ group is attached is in the (R)-configuration.

In another embodiment, m is 1, $R_3$ is a —($C_1$-$C_{10}$)alkyl, and the carbon to which the $R_3$ group is attached is in the (S)-configuration.

In another embodiment, m is 1 and $R_3$ is —$CH_3$.

In another embodiment, m is 1, $R_3$ is —$CH_3$, and the carbon to which the $R_3$ group is attached is in the (R)-configuration.

In another embodiment, m is 1, $R_3$ is —$CH_3$, and the carbon to which the $R_3$ group is attached is in the (S)-configuration.

In another embodiment, $R_4$ is —H.
In another embodiment, $R_4$ is —($C_1$-$C_{10}$)alkyl.
In another embodiment, $R_4$ is —C(O)$R_9$.
In another embodiment, $R_4$ is —C(O)NHR$_9$.
In another embodiment, $R_5$ is —H.
In another embodiment, $R_5$ is —($C_1$-$C_{10}$)alkyl.

In another embodiment, $R_6$ is —($C_1$-$C_{10}$)alkyl, —($C_2$-$C_{10}$)alkenyl, —($C_2$-$C_{10}$)alkynyl, —($C_3$-$C_{10}$)cycloalkyl, —($C_8$-$C_{14}$)bicycloalkyl, —($C_8$-$C_{14}$)tricycloalkyl, —($C_5$-$C_{10}$)cycloalkenyl, —($C_8$-$C_{14}$)bicycloalkenyl, —($C_8$-$C_{14}$)tricycloalkenyl, -(3- to 7-membered)heterocycle, or -(7- to 1-membered)bicycloheterocycle, each of which is unsubstituted or substituted with one or more $R_7$ groups.

In another embodiment, $R_6$ is -phenyl, -naphthyl, —($C_{14}$)aryl, or -(5- to 10-membered)heteroaryl, each of which is unsubstituted or substituted with one or more $R_8$ groups.

In another embodiment, $R_6$ is -phenyl.

In another embodiment, p and m are 0, $R_1$ is —$CH_3$, $R_4$ is —H, $R_5$ is —H, and $R_6$ is -phenyl. In another embodiment, the $R_6$-phenyl is substituted with a —($C_1$-$C_6$)alkyl group. In another embodiment, the —($C_1$-$C_6$)alkyl group is substituted at the para-position of the $R_6$-phenyl. In another embodiment, the —($C_1$-$C_6$)alkyl group is a t-butyl group substituted at the para-position of the $R_6$-phenyl. In another embodiment, the —($C_1$-$C_6$)alkyl group is an iso-propyl group substituted at the para-position of the $R_6$-phenyl.

In another embodiment, p and m are 0, $R_1$ is —$CF_3$, $R_4$ is —H, $R_5$ is —H, and $R_6$ is -phenyl. In another embodiment, the $R_6$-phenyl is substituted with a —($C_1$-$C_6$)alkyl group. In another embodiment, the —($C_1$-$C_6$)alkyl group is substituted at the para-position of the $R_6$-phenyl. In another embodiment, the —($C_1$-$C_6$)alkyl group is a t-butyl group substituted at the para-position of the $R_6$-phenyl. In another embodiment, the —(C$_1$-C$_6$)alkyl group is an iso-propyl group substituted at the para-position of the R$_6$-phenyl.

In another embodiment, p and m are 0, R$_1$ is —Cl, R$_4$ is —H, R$_5$ is —H, and R$_6$ is -phenyl. In another embodiment, the R$_6$-phenyl is substituted with a —(C$_1$-C$_6$)alkyl group. In another embodiment, the —(C$_1$-C$_6$)alkyl group is substituted at the para-position of the R$_6$-phenyl. In another embodiment, the —(C$_1$-C$_6$)alkyl group is a t-butyl group substituted at the para-position of the R$_6$-phenyl. In another embodiment, the —(C$_1$-C$_6$)alkyl group is an iso-propyl group substituted at the para-position of the R$_6$-phenyl.

In another embodiment, p and m are 0, R$_1$ is —CH$_3$, R$_4$ is —CH$_3$, R$_5$ is —H, and R$_6$ is -phenyl. In another embodiment, the R$_6$-phenyl is substituted with a —(C$_1$-C$_6$)alkyl group. In another embodiment, the —(C$_1$-C$_6$)alkyl group is substituted at the para-position of the R$_6$-phenyl. In another embodiment, the —(C$_1$-C$_6$)alkyl group is a t-butyl group substituted at the para-position of the R$_6$-phenyl. In another embodiment, the —(C$_1$-C$_6$)alkyl group is an iso-propyl group substituted at the para-position of the R$_6$-phenyl.

In another embodiment, p and m are 0, R$_1$ is —CF$_3$, R$_4$ is —CH$_3$, R$_5$ is —H, and R$_6$ is -phenyl. In another embodiment, the R$_6$-phenyl is substituted with a —(C$_1$-C$_6$)alkyl group. In another embodiment, the —(C$_1$-C$_6$)alkyl group is substituted at the para-position of the R$_6$-phenyl. In another embodiment, the —(C$_1$-C$_6$)alkyl group is a t-butyl group substituted at the para-position of the R$_6$-phenyl. In another embodiment, the —(C$_1$-C$_6$)alkyl group is an iso-propyl group substituted at the para-position of the R$_6$-phenyl.

In another embodiment, p and m are 0, R$_1$ is —Cl, R$_4$ is —CH$_3$, R$_5$ is —H, and R$_6$ is -phenyl. In another embodiment, the R$_6$-phenyl is substituted with a —(C$_1$-C$_6$)alkyl group. In another embodiment, the —(C$_1$-C$_6$)alkyl group is substituted at the para-position of the R$_6$-phenyl. In another embodiment, the —(C$_1$-C$_6$)alkyl group is a t-butyl group substituted at the para-position of the R$_6$-phenyl. In another embodiment, the —(C$_1$-C$_6$)alkyl group is an iso-propyl group substituted at the para-position of the R$_6$-phenyl.

In another embodiment, p is 0, m is 1, R$_1$ is —CH$_3$, R$_3$ is —CH$_3$, R$_4$ is —H, R$_5$ is —H, and R$_6$ is -phenyl. In another embodiment, the R$_6$-phenyl is substituted with a —(C$_1$-C$_6$)alkyl group. In another embodiment, the —(C$_1$-C$_6$)alkyl group is substituted at the para-position of the R$_6$-phenyl. In another embodiment, the —(C$_1$-C$_6$)alkyl group is a t-butyl group substituted at the para-position of the R$_6$-phenyl. In another embodiment, the —(C$_1$-C$_6$)alkyl group is an iso-propyl group substituted at the para-position of the R$_6$-phenyl.

In another embodiment, p is 0, m is 1, R$_1$ is —CF$_3$, R$_3$ is —CH$_3$, R$_4$ is —H, R$_5$ is —H, and R$_6$ is -phenyl. In another embodiment, the R$_6$-phenyl is substituted with a —(C$_1$-C$_6$)alkyl group. In another embodiment, the —(C$_1$-C$_6$)alkyl group is substituted at the para-position of the R$_6$-phenyl. In another embodiment, the —(C$_1$-C$_6$)alkyl group is a t-butyl group substituted at the para-position of the R$_6$-phenyl. In another embodiment, the —(C$_1$-C$_6$)alkyl group is an iso-propyl group substituted at the para-position of the R$_6$-phenyl.

In another embodiment, p is 0, m is 1, R$_1$ is —Cl, R$_3$ is —CH$_3$, R$_4$ is —H, R$_5$ is —H, and R$_6$ is -phenyl. In another embodiment, the R$_6$-phenyl is substituted with a —(C$_1$-C$_6$)alkyl group. In another embodiment, the —(C$_1$-C$_6$)alkyl group is substituted at the para-position of the R$_6$-phenyl. In another embodiment, the —(C$_1$-C$_6$)alkyl group is a t-butyl group substituted at the para-position of the R$_6$-phenyl. In another embodiment, the —(C$_1$-C$_6$)alkyl group is an iso-propyl group substituted at the para-position of the R$_6$-phenyl.

In another embodiment, p is 0, m is 1, R$_1$ is —CH$_3$, R$_3$ is —CH$_3$, R$_4$ is —CH$_3$, R$_5$ is —H, and R$_6$ is -phenyl. In another embodiment, the R$_6$-phenyl is substituted with a —(C$_1$-C$_6$)alkyl group. In another embodiment, the —(C$_1$-C$_6$)alkyl group is substituted at the para-position of the R$_6$-phenyl. In another embodiment, the —(C$_1$-C$_6$)alkyl group is a t-butyl group substituted at the para-position of the R$_6$-phenyl. In another embodiment, the —(C$_1$-C$_6$)alkyl group is an iso-propyl group substituted at the para-position of the R$_6$-phenyl.

In another embodiment, p is 0, m is 1, R$_1$ is —CF$_3$, R$_3$ is —CH$_3$, R$_4$ is —CH$_3$, R$_5$ is —H, and R$_6$ is -phenyl. In another embodiment, the R$_6$-phenyl is substituted with a —(C$_1$-C$_6$)alkyl group. In another embodiment, the —(C$_1$-C$_6$)alkyl group is substituted at the para-position of the R$_6$-phenyl. In another embodiment, the —(C$_1$-C$_6$)alkyl group is a t-butyl group substituted at the para-position of the R$_6$-phenyl. In another embodiment, the —(C$_1$-C$_6$)alkyl group is an iso-propyl group substituted at the para-position of the R$_6$-phenyl.

In another embodiment, p is 0, m is 1, R$_1$ is —Cl, R$_3$ is —CH$_3$, R$_4$ is —CH$_3$, R$_5$ is —H, and R$_6$ is -phenyl. In another embodiment, the R$_6$-phenyl is substituted with a —(C$_1$-C$_6$)alkyl group. In another embodiment, the —(C$_1$-C$_6$)alkyl group is substituted at the para-position of the R$_6$-phenyl. In another embodiment, the —(C$_1$-C$_6$)alkyl group is a t-butyl group substituted at the para-position of the R$_6$-phenyl. In another embodiment, the —(C$_1$-C$_6$)alkyl group is an iso-propyl group substituted at the para-position of the R$_6$-phenyl.

In another embodiment, p and m are 0, R$_1$ is —CH$_3$, R$_4$ is —H, R$_5$ is —H, and R$_6$ is -phenyl substituted at its para-position with a —CF$_3$.

In another embodiment, p and m are 0, R$_1$ is —CF$_3$, R$_4$ is —H, R$_5$ is —H, and R$_6$ is -phenyl substituted at its para-position with a —CF$_3$.

In another embodiment, p and m are 0, R$_1$ is —Cl, R$_4$ is —H, R$_5$ is —H, and R$_6$ is -phenyl substituted at its para-position with a —CF$_3$.

In another embodiment, p and m are 0, R$_1$ is —CH$_3$, R$_4$ is —CH$_3$, R$_5$ is —H, and R$_6$ is -phenyl substituted at its para-position with a —CF$_3$.

In another embodiment, p and m are 0, R$_1$ is —CF$_3$, R$_4$ is —CH$_3$, R$_5$ is —H, and R$_6$ is -phenyl substituted at its para-position with a —CF$_3$.

In another embodiment, p and m are 0, R$_1$ is —Cl, R$_4$ is —CH$_3$, R$_5$ is —H, and R$_6$ is -phenyl substituted at its para-position with a —CF$_3$.

In another embodiment, p is 0, m is 1, R$_1$ is —CH$_3$, R$_3$ is —CH$_3$, R$_4$ is —H, R$_5$ is —H, and R$_6$ is -phenyl substituted at its para-position with a —CF$_3$.

In another embodiment, p is 0, m is 1, R$_1$ is —CF$_3$, R$_3$ is —CH$_3$, R$_4$ is —H, R$_5$ is —H, and R$_6$ is -phenyl substituted at its para-position with a —CF$_3$.

In another embodiment, p is 0, m is 1, R$_1$ is —Cl, R$_3$ is —CH$_3$, R$_4$ is —H, R$_5$ is —H, and R$_6$ is -phenyl substituted at its para-position with a —CF$_3$.

In another embodiment, p is 0, m is 1, R$_1$ is —CH$_3$, R$_3$ is —CH$_3$, R$_4$ is —CH$_3$, R$_5$ is —H, and R$_6$ is -phenyl substituted at its para-position with a —CF$_3$.

In another embodiment, p is 0, m is 1, R$_1$ is —CF$_3$, R$_3$ is —CH$_3$, R$_4$ is —CH$_3$, R$_5$ is —H, and R$_6$ is -phenyl substituted at its para-position with a —CF$_3$.

In another embodiment, p is 0, m is 1, $R_1$ is —Cl, $R_3$ is —CH$_3$, $R_4$ is —CH$_3$, $R_5$ is —H, and $R_6$ is -phenyl substituted at its para-position with a —CF$_3$.

4.3 The Hydroxyiminopiperazine Compounds of Formula (III)

The present invention also encompasses compounds of formula (III):

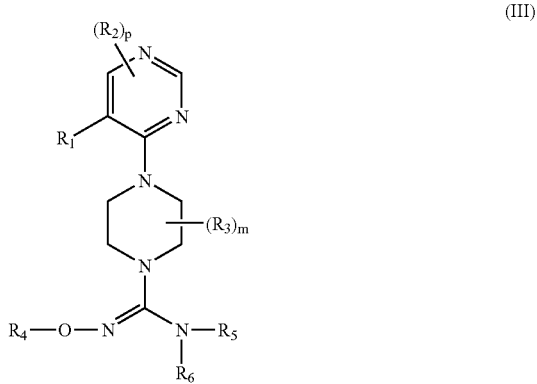

and pharmaceutically acceptable salts thereof, where $R_1$-$R_6$, p, and m are defined above for the Hydroxyiminopiperazine Compounds of formula (III).

In one embodiment, p is 0.
In another embodiment p is 1.
In another embodiment, p is 2.
In another embodiment, m is 0.
In another embodiment, m is 1.
In another embodiment, m is 2.
In another embodiment, $R_1$ is -halo.
In another embodiment, $R_1$ is —Cl.
In another embodiment, $R_1$ is —Br.
In another embodiment, $R_1$ is —I.
In another embodiment, $R_1$ is —F.
In another embodiment, $R_1$ is —CH$_3$.
In another embodiment, $R_1$ is —NO$_2$.
In another embodiment, $R_1$ is —OH.
In another embodiment, $R_1$ is —OCH$_3$.
In another embodiment, $R_1$ is —NH$_2$.
In another embodiment, $R_1$ is —C(halo)$_3$.
In another embodiment, $R_1$ is —CH(halo)$_2$.
In another embodiment, $R_1$ is —CH$_2$(halo).
In another embodiment, p is 1 and $R_2$ is -halo, —CN, —OH, NO$_2$, —O(C$_1$-C$_6$)alkyl, or —NH$_2$.
In another embodiment, p is 1 and $R_2$ is —(C$_1$-C$_{10}$)alkyl, —(C$_2$-C$_{10}$)alkenyl, —(C$_2$-C$_{10}$)alkynyl, —(C$_3$-C$_{10}$)cycloalkyl, —(C$_8$-C$_{14}$)bicycloalkyl, —(C$_8$-C$_{14}$)tricycloalkyl, —(C$_5$-C$_{10}$)cycloalkenyl, —(C$_8$-C$_{14}$)bicycloalkenyl, —(C$_8$-C$_{14}$)tricycloalkenyl, -(3- to 7-membered)heterocycle, or -(7- to 10-membered)bicycloheterocycle, each of which is unsubstituted or substituted with one or more $R_7$ groups.
In another embodiment, p is 1 and $R_2$ is -phenyl, -naphthyl, —(C$_{14}$)aryl, or -(5- to 10-membered)heteroaryl, each of which is unsubstituted or substituted with one or more $R_8$ groups.
In another embodiment, m is 1 and $R_3$ is -halo, —CN, —OH, NO$_2$, —O(C$_1$-C$_6$)alkyl, or —NH$_2$.
In another embodiment, m is 1 and $R_3$ is —(C$_1$-C$_{10}$)alkyl, —(C$_2$-C$_{10}$)alkenyl, —(C$_2$-C$_{10}$)alkynyl, —(C$_3$-C$_{10}$)cycloalkyl, —(C$_8$-C$_{14}$)bicycloalkyl, —(C$_8$-C$_{14}$)tricycloalkyl, —(C$_5$-C$_{10}$)cycloalkenyl, —(C$_8$-C$_{14}$)bicycloalkenyl, —(C$_8$-C$_{14}$)tricycloalkenyl, -(3- to 7-membered)heterocycle, or -(7- to 10-membered)bicycloheterocycle, each of which is unsubstituted or substituted with one or more $R_7$ groups.

In another embodiment, m is 1 and $R_3$ is -phenyl, -naphthyl, —(C$_{14}$)aryl, or -(5- to 10-membered)heteroaryl, each of which is unsubstituted or substituted with one or more $R_8$ groups.

In another embodiment, m is 1 and $R_3$ is a —(C$_1$-C$_{10}$)alkyl.
In another embodiment, m is 1, $R_3$ is a —(C$_1$-C$_{10}$)alkyl, and the carbon to which the $R_3$ group is attached is in the (R)-configuration.
In another embodiment, m is 1, $R_3$ is a —(C$_1$-C$_{10}$)alkyl, and the carbon to which the $R_3$ group is attached is in the (S)-configuration.
In another embodiment, m is 1 and $R_3$ is —CH$_3$.
In another embodiment, m is 1, $R_3$ is —CH$_3$, and the carbon to which the $R_3$ group is attached is in the (R)-configuration.
In another embodiment, m is 1, $R_3$ is —CH$_3$, and the carbon to which the $R_3$ group is attached is in the (S)-configuration.
In another embodiment, $R_4$ is —H.
In another embodiment, $R_4$ is —(C$_1$-C$_{10}$)alkyl.
In another embodiment, $R_4$ is —C(O)R$_9$.
In another embodiment, $R_4$ is —C(O)NHR$_9$.
In another embodiment, $R_5$ is —H.
In another embodiment, $R_5$ is —(C$_1$-C$_{10}$)alkyl.
In another embodiment, $R_6$ is —(C$_1$-C$_{10}$)alkyl, —(C$_2$-C$_{10}$)alkenyl, —(C$_2$-C$_{10}$)alkynyl, —(C$_3$-C$_{10}$)cycloalkyl, —(C$_8$-C$_{14}$)bicycloalkyl, —(C$_8$-C$_{14}$)tricycloalkyl, —(C$_5$-C$_{10}$)cycloalkenyl, —(C$_8$-C$_{14}$)bicycloalkenyl, —(C$_8$-C$_{14}$)tricycloalkenyl, -(3- to 7-membered)heterocycle, or -(7- to 1-membered)bicycloheterocycle, each of which is unsubstituted or substituted with one or more $R_7$ groups.

In another embodiment, $R_6$ is -phenyl.
In another embodiment, $R_6$ is -phenyl, -naphthyl, —(C$_{14}$)aryl, or -(5- to 10-membered)heteroaryl, each of which is unsubstituted or substituted with one or more $R_8$ groups.

In another embodiment, p and m are 0, $R_1$ is —CH$_3$, $R_4$ is —H, $R_5$ is —H, and $R_6$ is -phenyl. In another embodiment, the $R_6$-phenyl is substituted with a —(C$_1$-C$_6$)alkyl group. In another embodiment, the —(C$_1$-C$_6$)alkyl group is substituted at the para-position of the $R_6$-phenyl. In another embodiment, the —(C$_1$-C$_6$)alkyl group is a t-butyl group substituted at the para-position of the $R_6$-phenyl. In another embodiment, the —(C$_1$-C$_6$)alkyl group is an iso-propyl group substituted at the para-position of the $R_6$-phenyl.

In another embodiment, p and m are 0, $R_1$ is —CF$_3$, $R_4$ is —H, $R_5$ is —H, and $R_6$ is -phenyl. In another embodiment, the $R_6$-phenyl is substituted with a —(C$_1$-C$_6$)alkyl group. In another embodiment, the —(C$_1$-C$_6$)alkyl group is substituted at the para-position of the $R_6$-phenyl. In another embodiment, the —(C$_1$-C$_6$)alkyl group is a t-butyl group substituted at the para-position of the $R_6$-phenyl. In another embodiment, the —(C$_1$-C$_6$)alkyl group is an iso-propyl group substituted at the para-position of the $R_6$-phenyl.

In another embodiment, p and m are 0, $R_1$ is —Cl, $R_4$ is —H, $R_5$ is —H, and $R_6$ is -phenyl. In another embodiment, the $R_6$-phenyl is substituted with a —(C$_1$-C$_6$)alkyl group. In another embodiment, the —(C$_1$-C$_6$)alkyl group is substituted at the para-position of the $R_6$-phenyl. In another embodiment, the —(C$_1$-C$_6$)alkyl group is a t-butyl group substituted at the para-position of the $R_6$-phenyl. In another embodiment, the —(C$_1$-C$_6$)alkyl group is an iso-propyl group substituted at the para-position of the $R_6$-phenyl.

In another embodiment, p and m are 0, $R_1$ is —$CH_3$, $R_4$ is —$CH_3$, $R_5$ is —H, and $R_6$ is -phenyl. In another embodiment, the $R_6$-phenyl is substituted with a —($C_1$-$C_6$)alkyl group. In another embodiment, the —($C_1$-$C_6$)alkyl group is substituted at the para-position of the $R_6$-phenyl. In another embodiment, the —($C_1$-$C_6$)alkyl group is a t-butyl group substituted at the para-position of the $R_6$-phenyl. In another embodiment, the —($C_1$-$C_6$)alkyl group is an iso-propyl group substituted at the para-position of the $R_6$-phenyl.

In another embodiment, p and m are 0, $R_1$ is —$CF_3$, $R_4$ is —$CH_3$, $R_5$ is —H, and $R_6$ is -phenyl. In another embodiment, the $R_6$-phenyl is substituted with a —($C_1$-$C_6$)alkyl group. In another embodiment, the —($C_1$-$C_6$)alkyl group is substituted at the para-position of the $R_6$-phenyl. In another embodiment, the —($C_1$-$C_6$)alkyl group is a t-butyl group substituted at the para-position of the $R_6$-phenyl. In another embodiment, the —($C_1$-$C_6$)alkyl group is an iso-propyl group substituted at the para-position of the $R_6$-phenyl.

In another embodiment, p and m are 0, $R_1$ is —Cl, $R_4$ is —$CH_3$, $R_5$ is —H, and $R_6$ is -phenyl. In another embodiment, the $R_6$-phenyl is substituted with a —($C_1$-$C_6$)alkyl group. In another embodiment, the —($C_1$-$C_6$)alkyl group is substituted at the para-position of the $R_6$-phenyl. In another embodiment, the —($C_1$-$C_6$)alkyl group is a t-butyl group substituted at the para-position of the $R_6$-phenyl. In another embodiment, the —($C_1$-$C_6$)alkyl group is an iso-propyl group substituted at the para-position of the $R_6$-phenyl.

In another embodiment, p is 0, m is 1, $R_1$ is —$CH_3$, $R_3$ is —$CH_3$, $R_4$ is —H, $R_5$ is —H, and $R_6$ is -phenyl. In another embodiment, the $R_6$-phenyl is substituted with a —($C_1$-$C_6$)alkyl group. In another embodiment, the —($C_1$-$C_6$)alkyl group is substituted at the para-position of the $R_6$-phenyl. In another embodiment, the —($C_1$-$C_6$)alkyl group is a t-butyl group substituted at the para-position of the $R_6$-phenyl. In another embodiment, the —($C_1$-$C_6$)alkyl group is an iso-propyl group substituted at the para-position of the $R_6$-phenyl.

In another embodiment, p is 0, m is 1, $R_1$ is —$CF_3$, $R_3$ is —$CH_3$, $R_4$ is —H, $R_5$ is —H, and $R_6$ is -phenyl. In another embodiment, the -phenyl is substituted with a —($C_1$-$C_6$)alkyl group. In another embodiment, the —($C_1$-$C_6$)alkyl group is substituted at the para-position of the $R_6$-phenyl. In another embodiment, the —($C_1$-$C_6$)alkyl group is a t-butyl group substituted at the para-position of the $R_6$-phenyl. In another embodiment, the —($C_1$-$C_6$)alkyl group is an iso-propyl group substituted at the para-position of the $R_6$-phenyl.

In another embodiment, p is 0, m is 1, $R_1$ is —Cl, $R_3$ is —$CH_3$, $R_4$ is —H, $R_5$ is —H, and $R_6$ is -phenyl. In another embodiment, the $R_6$-phenyl is substituted with a —($C_1$-$C_6$)alkyl group. In another embodiment, the —($C_1$-$C_6$)alkyl group is substituted at the para-position of the $R_6$-phenyl. In another embodiment, the —($C_1$-$C_6$)alkyl group is a t-butyl group substituted at the para-position of the $R_6$-phenyl. In another embodiment, the —($C_1$-$C_6$)alkyl group is an iso-propyl group substituted at the para-position of the $R_6$-phenyl.

In another embodiment, p is 0, m is 1, $R_1$ is —$CH_3$, $R_3$ is —$CH_3$, $R_4$ is —$CH_3$, $R_5$ is —H, and $R_6$ is -phenyl. In another embodiment, the $R_6$-phenyl is substituted with a —($C_1$-$C_6$)alkyl group. In another embodiment, the —($C_1$-$C_6$)alkyl group is substituted at the para-position of the $R_6$-phenyl. In another embodiment, the —($C_1$-$C_6$)alkyl group is a t-butyl group substituted at the para-position of the $R_6$-phenyl. In another embodiment, the —($C_1$-$C_6$)alkyl group is an iso-propyl group substituted at the para-position of the $R_6$-phenyl.

In another embodiment, p is 0, m is 1, $R_1$ is —$CF_3$, $R_3$ is —$CH_3$, $R_4$ is —$CH_3$, $R_5$ is —H, and $R_6$ is -phenyl. In another embodiment, the $R_6$-phenyl is substituted with a —($C_1$-$C_6$)alkyl group. In another embodiment, the —($C_1$-$C_6$)alkyl group is substituted at the para-position of the $R_6$-phenyl. In another embodiment, the —($C_1$-$C_6$)alkyl group is a t-butyl group substituted at the para-position of the $R_6$-phenyl. In another embodiment, the —($C_1$-$C_6$)alkyl group is an iso-propyl group substituted at the para-position of the $R_6$-phenyl.

In another embodiment, p is 0, m is 1, $R_1$ is —Cl, $R_3$ is —$CH_3$, $R_4$ is —$CH_3$, $R_5$ is —H, and $R_6$ is -phenyl. In another embodiment, the $R_6$-phenyl is substituted with a —($C_1$-$C_6$) alkyl group. In another embodiment, the —($C_1$-$C_6$)alkyl group is substituted at the para-position of the $R_6$-phenyl. In another embodiment, the —($C_1$-$C_6$)alkyl group is a t-butyl group substituted at the para-position of the $R_6$-phenyl. In another embodiment, the —($C_1$-$C_6$)alkyl group is an iso-propyl group substituted at the para-position of the $R_6$-phenyl.

In another embodiment, p and m are 0, $R_1$ is —$CH_3$, $R_4$ is —H, $R_5$ is —H, and $R_6$ is -phenyl substituted at its para-position with a —$CF_3$.

In another embodiment, p and m are 0, $R_1$ is —$CF_3$, $R_4$ is —H, $R_5$ is —H, and $R_6$ is -phenyl substituted at its para-position with a —$CF_3$.

In another embodiment, p and m are 0, $R_1$ is —Cl, $R_4$ is —H, $R_5$ is —H, and $R_6$ is -phenyl substituted at its para-position with a —$CF_3$.

In another embodiment, p and m are 0, $R_1$ is —$CH_3$, $R_4$ is —$CH_3$, $R_5$ is —H, and $R_6$ is -phenyl substituted at its para-position with a —$CF_3$.

In another embodiment, p and m are 0, $R_1$ is —$CF_3$, $R_4$ is —$CH_3$, $R_5$ is —H, and $R_6$ is -phenyl substituted at its para-position with a —$CF_3$.

In another embodiment, p and m are 0, $R_1$ is —Cl, $R_4$ is —$CH_3$, $R_5$ is —H, and $R_6$ is -phenyl substituted at its para-position with a —$CF_3$.

In another embodiment, p is 0, m is 1, $R_1$ is —$CH_3$, $R_3$ is —$CH_3$, $R_4$ is —H, $R_5$ is —H, and $R_6$ is -phenyl substituted at its para-position with a —$CF_3$.

In another embodiment, p is 0, m is 1, $R_1$ is —$CF_3$, $R_3$ is —$CH_3$, $R_4$ is —H, $R_5$ is —H, and $R_6$ is -phenyl substituted at its para-position with a —$CF_3$.

In another embodiment, p is 0, m is 1, $R_1$ is —Cl, $R_3$ is —$CH_3$, $R_4$ is —H, $R_5$ is —H, and $R_6$ is -phenyl substituted at its para-position with a —$CF_3$.

In another embodiment, p is 0, m is 1, $R_1$ is —$CH_3$, $R_3$ is —$CH_3$, $R_4$ is —$CH_3$, $R_5$ is —H, and $R_6$ is -phenyl substituted at its para-position with a —$CF_3$.

In another embodiment, p is 0, m is 1, $R_1$ is —$CF_3$, $R_3$ is —$CH_3$, $R_4$ is —$CH_3$, $R_5$ is —H, and $R_6$ is -phenyl substituted at its para-position with a —$CF_3$.

In another embodiment, p is 0, m is 1, $R_1$ is —Cl, $R_3$ is —$CH_3$, $R_4$ is —$CH_3$, $R_5$ is —H, and $R_6$ is -phenyl substituted at its para-position with a —$CF_3$.

4.4 The Hydroxyiminopiperazine Compounds of Formula (IV)

The present invention also encompasses compounds of formula (IV):

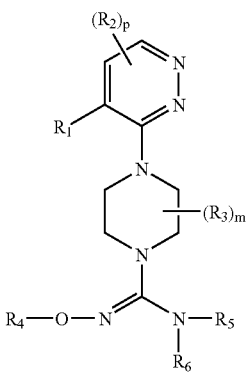

(IV)

and pharmaceutically acceptable salts thereof, where $R_1$-$R_6$, p, and m are defined above for the Hydroxyiminopiperazine Compounds of formula (IV).

In one embodiment, p is 0.
In another embodiment p is 1.
In another embodiment, p is 2.
In another embodiment, m is 0.
In another embodiment, m is 1.
In another embodiment, m is 2.
In another embodiment, $R_1$ is -halo.
In another embodiment, $R_1$ is —Cl.
In another embodiment, $R_1$ is —Br.
In another embodiment, $R_1$ is —I.
In another embodiment, $R_1$ is —F.
In another embodiment, $R_1$ is —$CH_3$.
In another embodiment, $R_1$ is —$NO_2$.
In another embodiment, $R_1$ is —OH.
In another embodiment, $R_1$ is —$OCH_3$.
In another embodiment, $R_1$ is —$NH_2$.
In another embodiment, $R_1$ is —C(halo)$_3$.
In another embodiment, $R_1$ is —CH(halo)$_2$.
In another embodiment, $R_1$ is —$CH_2$(halo).
In another embodiment, p is 1 and $R_2$ is -halo, —CN, —OH, $NO_2$, —O($C_1$-$C_6$)alkyl, or —$NH_2$.
In another embodiment, p is 1 and $R_2$ is —($C_1$-$C_{10}$)alkyl, —($C_2$-$C_{10}$)alkenyl, —($C_2$-$C_{10}$)alkynyl, —($C_3$-$C_{10}$)cycloalkyl, —($C_8$-$C_{14}$)bicycloalkyl, —($C_8$-$C_{14}$)tricycloalkyl, —($C_5$-$C_{10}$)cycloalkenyl, —($C_8$-$C_{14}$)bicycloalkenyl, —($C_8$-$C_{14}$)tricycloalkenyl, -(3- to 7-membered)heterocycle, or -(7- to 10-membered)bicycloheterocycle, each of which is unsubstituted or substituted with one or more $R_7$ groups.

In another embodiment, p is 1 and $R_2$ is -phenyl, -naphthyl, —($C_{14}$)aryl, or -(5- to 10-membered)heteroaryl, each of which is unsubstituted or substituted with one or more $R_8$ groups.

In another embodiment, m is 1 and $R_3$ is -halo, —CN, —OH, $NO_2$, —O($C_1$-$C_6$)alkyl, or —$NH_2$.
In another embodiment, m is 1 and $R_3$ is —($C_1$-$C_{10}$)alkyl, —($C_2$-$C_{10}$)alkenyl, —($C_2$-$C_{10}$)alkynyl, —($C_3$-$C_{10}$)cycloalkyl, —($C_8$-$C_{14}$)bicycloalkyl, —($C_8$-$C_{14}$)tricycloalkyl, —($C_5$-$C_{10}$)cycloalkenyl, —($C_8$-$C_{14}$)bicycloalkenyl, —($C_8$-$C_{14}$)tricycloalkenyl, -(3- to 7-membered)heterocycle, or -(7- to 10-membered)bicycloheterocycle, each of which is unsubstituted or substituted with one or more $R_7$ groups.

In another embodiment, m is 1 and $R_3$ is -phenyl, -naphthyl, —($C_{14}$)aryl, or -(5- to 10-membered)heteroaryl, each of which is unsubstituted or substituted with one or more $R_8$ groups.

In another embodiment, m is 1 and $R_3$ is a —($C_1$-$C_{10}$)alkyl.

In another embodiment, m is 1, $R_3$ is a —($C_1$-$C_{10}$)alkyl, and the carbon to which the $R_3$ group is attached is in the (R)-configuration.

In another embodiment, m is 1, $R_3$ is a —($C_1$-$C_{10}$)alkyl, and the carbon to which the $R_3$ group is attached is in the (S)-configuration.

In another embodiment, m is 1 and $R_3$ is —$CH_3$.
In another embodiment, m is 1, $R_3$ is —$CH_3$, and the carbon to which the $R_3$ group is attached is in the (R)-configuration.

In another embodiment, m is 1, $R_3$ is —$CH_3$, and the carbon to which the $R_3$ group is attached is in the (S)-configuration.

In another embodiment, $R_4$ is —H.
In another embodiment, $R_4$ is —($C_1$-$C_{10}$)alkyl.
In another embodiment, $R_4$ is —C(O)$R_9$.
In another embodiment, $R_4$ is —C(O)NH$R_9$.
In another embodiment, $R_5$ is —H.
In another embodiment, $R_5$ is —($C_1$-$C_{10}$)alkyl.
In another embodiment, $R_6$ is —($C_1$-$C_{10}$)alkyl, —($C_2$-$C_{10}$)alkenyl, —($C_2$-$C_{10}$)alkynyl, —($C_3$-$C_{10}$)cycloalkyl, —($C_8$-$C_{14}$)bicycloalkyl, —($C_8$-$C_{14}$)tricycloalkyl, —($C_5$-$C_{10}$)cycloalkenyl, —($C_8$-$C_{14}$)bicycloalkenyl, —($C_8$-$C_{14}$)tricycloalkenyl, -(3- to 7-membered)heterocycle, or -(7- to 1-membered)bicycloheterocycle, each of which is unsubstituted or substituted with one or more $R_7$ groups.

In another embodiment, $R_6$ is -phenyl, -naphthyl, —($C_{14}$)aryl, or -(5- to 10-membered)heteroaryl, each of which is unsubstituted or substituted with one or more $R_8$ groups.

In another embodiment, $R_6$ is -phenyl.

In one embodiment, p and m are 0, $R_1$ is —$CH_3$, $R_4$ is —H, $R_5$ is —H, and $R_6$ is -phenyl. In another embodiment, the $R_6$-phenyl is substituted with a —($C_1$-$C_6$)alkyl group. In another embodiment, the —($C_1$-$C_6$)alkyl group is substituted at the para-position of the $R_6$-phenyl. In another embodiment, the —($C_1$-$C_6$)alkyl group is a t-butyl group substituted at the para-position of the $R_6$-phenyl. In another embodiment, the —($C_1$-$C_6$)alkyl group is an iso-propyl group substituted at the para-position of the $R_6$-phenyl.

In another embodiment, p and m are 0, $R_1$ is —$CF_3$, $R_4$ is —H, $R_5$ is —H, and $R_6$ is -phenyl. In another embodiment, the $R_6$-phenyl is substituted with a —($C_1$-$C_6$)alkyl group. In another embodiment, the —($C_1$-$C_6$)alkyl group is substituted at the para-position of the $R_6$-phenyl. In another embodiment, the —($C_1$-$C_6$)alkyl group is a t-butyl group substituted at the para-position of the $R_6$-phenyl. In another embodiment, the —($C_1$-$C_6$)alkyl group is an iso-propyl group substituted at the para-position of the $R_6$-phenyl.

In another embodiment, p and m are 0, $R_1$ is —Cl, $R_4$ is —H, $R_5$ is —H, and $R_6$ is -phenyl. In another embodiment, the $R_6$-phenyl is substituted with a —($C_1$-$C_6$)alkyl group. In another embodiment, the —($C_1$-$C_6$)alkyl group is substituted at the para-position of the $R_6$-phenyl. In another embodiment, the —($C_1$-$C_6$)alkyl group is a t-butyl group substituted at the para-position of the $R_6$-phenyl. In another embodiment, the —($C_1$-$C_6$)alkyl group is an iso-propyl group substituted at the para-position of the $R_6$-phenyl.

In another embodiment, p and m are 0, $R_1$ is —$CH_3$, $R_4$ is —$CH_3$, $R_5$ is —H, and $R_6$ is -phenyl. In another embodiment, the $R_6$-phenyl is substituted with a —($C_1$-$C_6$)alkyl group. In another embodiment, the —($C_1$-$C_6$)alkyl group is substituted at the para-position of the $R_6$-phenyl. In another embodiment, the —($C_1$-$C_6$)alkyl group is a t-butyl group substituted at the para-position of the $R_6$-phenyl. In another embodiment, the —($C_1$-$C_6$)alkyl group is an iso-propyl group substituted at the para-position of the $R_6$-phenyl.

In another embodiment, p and m are 0, $R_1$ is —$CF_3$, $R_4$ is —$CH_3$, $R_5$ is —H, and $R_6$ is -phenyl. In another embodiment, the $R_6$-phenyl is substituted with a —($C_1$-$C_6$)alkyl group. In another embodiment, the —($C_1$-$C_6$)alkyl group is substituted at the para-position of the $R_6$-phenyl. In another embodiment, the —($C_1$-$C_6$)alkyl group is a t-butyl group substituted at the para-position of the $R_6$-phenyl. In another embodiment, the —($C_1$-$C_6$)alkyl group is an iso-propyl group substituted at the para-position of the $R_6$-phenyl.

In another embodiment, p and m are 0, $R_1$ is —Cl, $R_4$ is —$CH_3$, $R_5$ is —H, and $R_6$ is -phenyl. In another embodiment, the $R_6$-phenyl is substituted with a —($C_1$-$C_6$)alkyl group. In another embodiment, the —($C_1$-$C_6$)alkyl group is substituted at the para-position of the $R_6$-phenyl. In another embodiment, the —($C_1$-$C_6$)alkyl group is a t-butyl group substituted at the para-position of the $R_6$-phenyl. In another embodiment, the —($C_1$-$C_6$)alkyl group is an iso-propyl group substituted at the para-position of the $R_6$-phenyl.

In another embodiment, p is 0, m is 1, $R_1$ is —$CH_3$, $R_3$ is —$CH_3$, $R_4$ is —H, $R_5$ is —H, and $R_6$ is -phenyl. In another embodiment, the $R_6$-phenyl is substituted with a —($C_1$-$C_6$) alkyl group. In another embodiment, the —($C_1$-$C_6$)alkyl group is substituted at the para-position of the $R_6$-phenyl. In another embodiment, the —($C_2$-$C_6$)alkyl group is a t-butyl group substituted at the para-position of the $R_6$-phenyl. In another embodiment, the —($C_1$-$C_6$)alkyl group is an iso-propyl group substituted at the para-position of the $R_6$-phenyl.

In another embodiment, p is 0, m is 1, $R_1$ is —$CF_3$, $R_3$ is —$CH_3$, $R_4$ is —H, $R_5$ is —H, and $R_6$ is -phenyl. In another embodiment, the $R_6$-phenyl is substituted with a —($C_1$-$C_6$) alkyl group. In another embodiment, the —($C_1$-$C_6$)alkyl group is substituted at the para-position of the $R_6$-phenyl. In another embodiment, the —($C_1$-$C_6$)alkyl group is a t-butyl group substituted at the para-position of the $R_6$-phenyl. In another embodiment, the —($C_1$-$C_6$)alkyl group is an iso-propyl group substituted at the para-position of the $R_6$-phenyl.

In another embodiment, p is 0, m is 1, $R_1$ is —Cl, $R_3$ is —$CH_3$, $R_4$ is —H, $R_5$ is —H, and $R_6$ is -phenyl. In another embodiment, the $R_6$-phenyl is substituted with a —($C_1$-$C_6$) alkyl group. In another embodiment, the —($C_1$-$C_6$)alkyl group is substituted at the para-position of the $R_6$-phenyl. In another embodiment, the —($C_1$-$C_6$)alkyl group is a t-butyl group substituted at the para-position of the $R_6$-phenyl. In another embodiment, the —($C_1$-$C_6$)alkyl group is an iso-propyl group substituted at the para-position of the $R_6$-phenyl.

In another embodiment, p is 0, m is 1, $R_1$ is —$CH_3$, $R_3$ is —$CH_3$, $R_4$ is —$CH_3$, $R_5$ is —H, and $R_6$ is -phenyl. In another embodiment, the $R_6$-phenyl is substituted with a —($C_1$-$C_6$) alkyl group. In another embodiment, the —($C_1$-$C_6$)alkyl group is substituted at the para-position of the $R_6$-phenyl. In another embodiment, the —($C_1$-$C_6$)alkyl group is a t-butyl group substituted at the para-position of the $R_6$-phenyl. In another embodiment, the —($C_1$-$C_6$)alkyl group is an iso-propyl group substituted at the para-position of the $R_6$-phenyl.

In another embodiment, p is 0, m is 1, $R_1$ is —$CF_3$, $R_3$ is —$CH_3$, $R_4$ is —$CH_3$, $R_5$ is —H, and $R_6$ is -phenyl. In another embodiment, the $R_6$-phenyl is substituted with a —($C_1$-$C_6$) alkyl group. In another embodiment, the —($C_1$-$C_6$)alkyl group is substituted at the para-position of the $R_6$-phenyl. In another embodiment, the —($C_1$-$C_6$)alkyl group is a t-butyl group substituted at the para-position of the $R_6$-phenyl. In another embodiment, the —($C_1$-$C_6$)alkyl group is an iso-propyl group substituted at the para-position of the $R_6$-phenyl.

In another embodiment, p is 0, m is 1, $R_1$ is —Cl, $R_3$ is —$CH_3$, $R$ is —$CH_3$, $R_5$ is —H, and $R_6$ is -phenyl. In another embodiment, the $R_6$-phenyl is substituted with a —($C_1$-$C_6$) alkyl group. In another embodiment, the —($C_1$-$C_6$)alkyl group is substituted at the para-position of the $R_6$-phenyl. In another embodiment, the —($C_1$-$C_6$)alkyl group is a t-butyl group substituted at the para-position of the $R_6$-phenyl. In another embodiment, the —($C_1$-$C_6$)alkyl group is an iso-propyl group substituted at the para-position of the $R_6$-phenyl.

In another embodiment, p and m are 0, $R_1$ is —$CH_3$, $R_4$ is —H, $R_5$ is —H, and $R_6$ is -phenyl substituted at its para-position with a —$CF_3$.

In another embodiment, p and m are 0, $R_1$ is —$CF_3$, $R_4$ is —H, $R_5$ is —H, and $R_6$ is -phenyl substituted at its para-position with a —$CF_3$.

In another embodiment, p and m are 0, $R_1$ is —Cl, $R_4$ is —H, $R_5$ is —H, and $R_6$ is -phenyl substituted at its para-position with a —$CF_3$.

In another embodiment, p and m are 0, $R_1$ is —$CH_3$, $R_4$ is —$CH_3$, $R_5$ is —H, and $R_6$ is -phenyl substituted at its para-position with a —$CF_3$.

In another embodiment, p and m are 0, $R_1$ is —$CF_3$, $R_4$ is —$CH_3$, $R_5$ is —H, and $R_6$ is -phenyl substituted at its para-position with a —$CF_3$.

In another embodiment, p and m are 0, $R_1$ is —Cl, $R_4$ is —$CH_3$, $R_5$ is —H, and $R_6$ is -phenyl substituted at its para-position with a —$CF_3$.

In another embodiment, p is 0, m is 1, $R_1$ is —$CH_3$, $R_3$ is —$CH_3$, $R_4$ is —H, $R_5$ is —H, and $R_6$ is -phenyl substituted at its para-position with a —$CF_3$.

In another embodiment, p is 0, m is 1, $R_1$ is —$CF_3$, $R_3$ is —$CH_3$, $R_4$ is —H, $R_5$ is —H, and $R_6$ is -phenyl substituted at its para-position with a —$CF_3$.

In another embodiment, p is 0, m is 1, $R_1$ is —Cl, $R_3$ is —$CH_3$, $R_4$ is —H, $R_5$ is —H, and $R_6$ is -phenyl substituted at its para-position with a —$CF_3$.

In another embodiment, p is 0, m is 1, $R_1$ is —$CH_3$, $R_3$ is —$CH_3$, $R_4$ is —$CH_3$, $R_5$ is —H, and $R_6$ is -phenyl substituted at its para-position with a —$CF_3$.

In another embodiment, p is 0, m is 1, $R_1$ is —$CF_3$, $R_3$ is —$CH_3$, $R_4$ is —$CH_3$, $R_5$ is —H, and $R_6$ is -phenyl substituted at its para-position with a —$CF_3$.

In another embodiment, p is 0, m is 1, $R_1$ is —Cl, $R_3$ is —$CH_3$, $R_4$ is —$CH_3$, $R_5$ is —H, and $R_6$ is -phenyl substituted at its para-position with a —$CF_3$.

4.5 The Hydroxyiminopiperazine Compounds of Formula (V)

The present invention also encompasses compounds of formula (V):

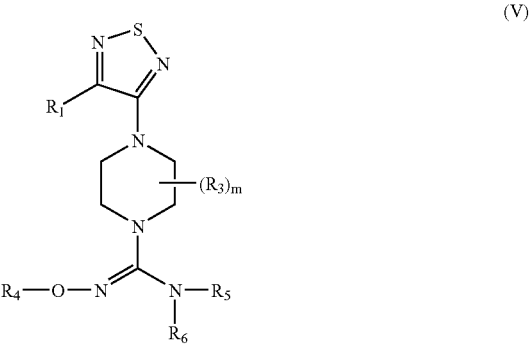

and pharmaceutically acceptable salts thereof, where $R_1$, $R_3$-$R_6$, and m are defined above for the Hydroxyiminopiperazine Compounds of formula (V).

In one embodiment, m is 0.

In another embodiment, m is 1.

In another embodiment, m is 2.

In another embodiment, $R_1$ is -halo.

In another embodiment, $R_1$ is —Cl.

In another embodiment, $R_1$ is —Br.

In another embodiment, $R_1$ is —I.

In another embodiment, $R_1$ is —F.

In another embodiment, $R_1$ is —$CH_3$.

In another embodiment, $R_1$ is —$NO_2$.

In another embodiment, $R_1$ is —OH.

In another embodiment, $R_1$ is —$OCH_3$.

In another embodiment, $R_1$ is —$NH_2$.

In another embodiment, $R_1$ is —C(halo)$_3$.

In another embodiment, $R_1$ is —CH(halo)$_2$.

In another embodiment, $R_1$ is —$CH_2$(halo).

In another embodiment, m is 1 and $R_3$ is -halo, —CN, —OH, $NO_2$, or —$NH_2$.

In another embodiment, m is 1 and $R_3$ is —($C_1$-$C_{10}$)alkyl, —($C_2$-$C_{10}$)alkenyl, —($C_2$-$C_{10}$)alkynyl, —($C_3$-$C_{10}$)cycloalkyl, —($C_8$-$C_{14}$)bicycloalkyl, —($C_8$-$C_{14}$)tricycloalkyl, —($C_5$-$C_{10}$)cycloalkenyl, —($C_8$-$C_{14}$)bicycloalkenyl, —($C_8$-$C_{14}$)tricycloalkenyl, -(3- to 7-membered)heterocycle, or -(7- to 10-membered)bicycloheterocycle, each of which is unsubstituted or substituted with one or more $R_7$ groups.

In another embodiment, m is 1 and $R_3$ is -phenyl, -naphthyl, —($C_{14}$)aryl, or -(5- to 10-membered)heteroaryl, each of which is unsubstituted or substituted with one or more $R_8$ groups.

In another embodiment, m is 1 and $R_3$ is a —($C_1$-$C_{10}$)alkyl.

In another embodiment, m is 1, $R_3$ is a —($C_1$-$C_{10}$)alkyl, and the carbon to which the $R_3$ group is attached is in the (R)-configuration.

In another embodiment, m is 1, $R_3$ is a —($C_1$-$C_{10}$)alkyl, and the carbon to which the $R_3$ group is attached is in the (S)-configuration.

In another embodiment, m is 1 and $R_3$ is —$CH_3$.

In another embodiment, m is 1, $R_3$ is —$CH_3$, and the carbon to which the $R_3$ group is attached is in the (R)-configuration.

In another embodiment, m is 1, $R_3$ is —$CH_3$, and the carbon to which the $R_3$ group is attached is in the (S)-configuration.

In another embodiment, $R_4$ is —H.

In another embodiment, $R_4$ is —($C_1$-$C_{10}$)alkyl.

In another embodiment, $R_4$ is —(O)$R_9$.

In another embodiment, $R_4$ is —(O)NH$R_9$.

In another embodiment, $R_5$ is —H.

In another embodiment, $R_5$ is —($C_1$-$C_{10}$)alkyl.

In another embodiment, $R_6$ is —($C_1$-$C_{10}$)alkyl, —($C_2$-$C_{10}$)alkenyl, —($C_2$-$C_{10}$)alkynyl, —($C_3$-$C_{10}$)cycloalkyl, —($C_8$-$C_{14}$)bicycloalkyl, —($C_8$-$C_{14}$)tricycloalkyl, —($C_5$-$C_{10}$)cycloalkenyl, —($C_8$-$C_{14}$)bicycloalkenyl, —($C_8$-$C_{14}$)tricycloalkenyl, -(3- to 7-membered)heterocycle, or -(7- to 1-membered)bicycloheterocycle, each of which is unsubstituted or substituted with one or more $R_7$ groups.

In another embodiment, $R_6$ is -phenyl, -naphthyl, —($C_{14}$)aryl, or -(5- to 10-membered)heteroaryl, each of which is unsubstituted or substituted with one or more $R_8$ groups.

In another embodiment, $R_6$ is -phenyl.

In another embodiment, m is 0, $R_1$ is —$CH_3$, $R_4$ is —H, $R_5$ is —H, and $R_6$ is -phenyl. In another embodiment, the $R_6$-phenyl is substituted with a —($C_1$-$C_6$)alkyl group. In another embodiment, the —($C_1$-$C_6$)alkyl group is substituted at the para-position of the $R_6$-phenyl. In another embodiment, the —($C_1$-$C_6$)alkyl group is a t-butyl group substituted at the para-position of the $R_6$-phenyl. In another embodiment, the —($C_1$-$C_6$)alkyl group is an iso-propyl group substituted at the para-position of the $R_6$-phenyl.

In another embodiment, m is 0, $R_1$ is —$CF_3$, $R_4$ is —H, $R_5$ is —H, and $R_6$ is -phenyl. In another embodiment, the $R_6$-phenyl is substituted with a —($C_1$-$C_6$)alkyl group. In another embodiment, the —($C_1$-$C_6$)alkyl group is substituted at the para-position of the $R_6$-phenyl. In another embodiment, the —($C_1$-$C_6$)alkyl group is a t-butyl group substituted at the para-position of the $R_6$-phenyl. In another embodiment, the —($C_1$-$C_6$)alkyl group is an iso-propyl group substituted at the para-position of the $R_6$-phenyl.

In another embodiment, m is 0, $R_1$ is —Cl, $R_4$ is —H, $R_5$ is —H, and $R_6$ is -phenyl. In another embodiment, the $R_6$-phenyl is substituted with a —($C_1$-$C_6$)alkyl group. In another embodiment, the —($C_1$-$C_6$)alkyl group is substituted at the para-position of the $R_6$-phenyl. In another embodiment, the —($C_1$-$C_6$)alkyl group is a t-butyl group substituted at the para-position of the $R_6$-phenyl. In another embodiment, the —($C_1$-$C_6$)alkyl group is an iso-propyl group substituted at the para-position of the $R_6$-phenyl.

In another embodiment, m is 0, $R_1$ is —$CH_3$, $R_4$ is —$CH_3$, $R_5$ is —H, and $R_6$ is -phenyl. In another embodiment, the $R_6$-phenyl is substituted with a —($C_1$-$C_6$)alkyl group. In another embodiment, the —($C_1$-$C_6$)alkyl group is substituted at the para-position of the $R_6$-phenyl. In another embodiment, the —($C_1$-$C_6$)alkyl group is a t-butyl group substituted at the para-position of the $R_6$-phenyl. In another embodiment, the —($C_1$-$C_6$)alkyl group is an iso-propyl group substituted at the para-position of the $R_6$-phenyl.

In another embodiment, m is 0, $R_1$ is —$CF_3$, $R_4$ is —$CH_3$, $R_5$ is —H, and $R_6$ is -phenyl. In another embodiment, the $R_6$-phenyl is substituted with a —($C_1$-$C_6$)alkyl group. In another embodiment, the —($C_1$-$C_6$)alkyl group is substituted at the para-position of the $R_6$-phenyl. In another embodiment, the —($C_1$-$C_6$)alkyl group is a t-butyl group substituted at the para-position of the $R_6$-phenyl. In another embodiment, the —($C_1$-$C_6$)alkyl group is an iso-propyl group substituted at the para-position of the $R_6$-phenyl.

In another embodiment, m is 0, $R_1$ is —Cl, $R_4$ is —$CH_3$, $R_5$ is —H, and $R_6$ is -phenyl. In another embodiment, the $R_6$-phenyl is substituted with a —($C_1$-$C_6$)alkyl group. In another embodiment, the —($C_1$-$C_6$)alkyl group is substituted at the para-position of the $R_6$-phenyl. In another embodiment, the —($C_1$-$C_6$)alkyl group is a t-butyl group substituted at the para-position of the $R_6$-phenyl. In another embodiment, the —($C_1$-$C_6$)alkyl group is an iso-propyl group substituted at the para-position of the $R_6$-phenyl.

In another embodiment, m is 1, $R_1$ is —$CH_3$, $R_3$ is —$CH_3$, $R_4$ is —H, $R_5$ is —H, and $R_6$ is -phenyl. In another embodiment, the $R_6$-phenyl is substituted with a —($C_1$-$C_6$)alkyl group. In another embodiment, the —($C_1$-$C_6$)alkyl group is substituted at the para-position of the $R_6$-phenyl. In another embodiment, the —($C_1$-$C_6$)alkyl group is a t-butyl group substituted at the para-position of the $R_6$-phenyl. In another embodiment, the —($C_1$-$C_6$)alkyl group is an iso-propyl group substituted at the para-position of the $R_6$-phenyl.

In another embodiment, m is 1, $R_1$ is —$CF_3$, $R_3$ is —$CH_3$, $R_4$ is —H, $R_5$ is —H, and $R_6$ is -phenyl. In another embodiment, the $R_6$-phenyl is substituted with a —($C_1$-$C_6$)alkyl group. In another embodiment, the —($C_1$-$C_6$)alkyl group is substituted at the para-position of the $R_6$-phenyl. In another embodiment, the —($C_1$-$C_6$)alkyl group is a t-butyl group substituted at the para-position of the $R_6$-phenyl. In another embodiment, the —($C_1$-$C_6$)alkyl group is an iso-propyl group substituted at the para-position of the $R_6$-phenyl.

In another embodiment, m is 1, $R_1$ is —Cl, $R_3$ is —$CH_3$, $R_4$ is —H, $R_5$ is —H, and $R_6$ is -phenyl. In another embodiment, the $R_6$-phenyl is substituted with a —($C_1$-$C_6$)alkyl group. In another embodiment, the —($C_1$-$C_6$)alkyl group is substituted at the para-position of the $R_6$-phenyl. In another embodiment, the —($C_1$-$C_6$)alkyl group is a t-butyl group substituted at the para-position of the $R_6$-phenyl. In another embodiment, the —($C_1$-$C_6$)alkyl group is an iso-propyl group substituted at the para-position of the $R_6$-phenyl.

In another embodiment, m is 1, $R_1$ is —$CH_3$, $R_3$ is —$CH_3$, $R_4$ is —$CH_3$, $R_5$ is —H, and $R_6$ is -phenyl. In another embodiment, the $R_6$-phenyl is substituted with a —($C_1$-$C_6$) alkyl group. In another embodiment, the —($C_1$-$C_6$)alkyl group is substituted at the para-position of the $R_6$-phenyl. In another embodiment, the —($C_1$-$C_6$)alkyl group is a t-butyl group substituted at the para-position of the $R_6$-phenyl. In another embodiment, the —($C_1$-$C_6$)alkyl group is an iso-propyl group substituted at the para-position of the $R_6$-phenyl.

In another embodiment, m is 1, $R_1$ is —$CF_3$, $R_3$ is —$CH_3$, $R_4$ is —$CH_3$, $R_5$ is —H, and $R_6$ is -phenyl. In another embodiment, the $R_6$-phenyl is substituted with a —($C_1$-$C_6$) alkyl group. In another embodiment, the —($C_1$-$C_6$)alkyl group is substituted at the para-position of the $R_6$-phenyl. In another embodiment, the —($C_1$-$C_6$)alkyl group is a t-butyl group substituted at the para-position of the $R_6$-phenyl. In another embodiment, the —($C_1$-$C_6$)alkyl group is an iso-propyl group substituted at the para-position of the $R_6$-phenyl.

In another embodiment, m is 1, $R_1$ is —Cl, $R_3$ is —$CH_3$, $R_4$ is —$CH_3$, $R_5$ is —H, and $R_6$ is -phenyl. In another embodiment, the $R_6$-phenyl is substituted with a —($C_1$-$C_6$) alkyl group. In another embodiment, the —($C_1$-$C_6$)alkyl group is substituted at the para-position of the $R_6$-phenyl. In another embodiment, the —($C_1$-$C_6$)alkyl group is a t-butyl group substituted at the para-position of the $R_6$-phenyl. In another embodiment, the —($C_1$-$C_6$)alkyl group is an iso-propyl group substituted at the para-position of the $R_6$-phenyl.

In another embodiment, m is 0, $R_1$ is —$CH_3$, $R_4$ is —H, $R_5$ is —H, and $R_6$ is -phenyl substituted at its para-position with a —$CF_3$.

In another embodiment, m is 0, $R_1$ is —$CF_3$, $R_4$ is —H, $R_5$ is —H, and $R_6$ is -phenyl substituted at its para-position with a —$CF_3$.

In another embodiment, m is 0, $R_1$ is —Cl, $R_4$ is —H, $R_5$ is —H, and $R_6$ is -phenyl substituted at its para-position with a —$CF_3$.

In another embodiment, m is 0, $R_1$ is —$CH_3$, $R_4$ is —$CH_3$, $R_5$ is —H, and $R_6$ is -phenyl substituted at its para-position with a —$CF_3$.

In another embodiment, m is 0, $R_1$ is —$CF_3$, $R_4$ is —$CH_3$, $R_5$ is —H, and $R_6$ is -phenyl substituted at its para-position with a —$CF_3$.

In another embodiment, m is 0, $R_1$ is —Cl, $R_4$ is —$CH_3$, $R_5$ is —H, and $R_6$ is -phenyl substituted at its para-position with a —$CF_3$.

In another embodiment, m is 1, $R_1$ is —$CH_3$, $R_3$ is —$CH_3$, $R_4$ is —H, $R_5$ is —H, and $R_6$ is -phenyl substituted at its para-position with a —$CF_3$.

In another embodiment, m is 1, $R_1$ is —$CF_3$, $R_3$ is —$CH_3$, $R_4$ is —H, $R_5$ is —H, and $R_6$ is -phenyl substituted at its para-position with a —$CF_3$.

In another embodiment, m is 1, $R_1$ is —Cl, $R_3$ is —$CH_3$, $R_4$ is —H, $R_5$ is —H, and $R_6$ is -phenyl substituted at its para-position with a —$CF_3$.

In another embodiment, m is 1, $R_1$ is —$CH_3$, $R_3$ is —$CH_3$, $R_4$ is —$CH_3$, $R_5$ is —H, and $R_6$ is -phenyl substituted at its para-position with a —$CF_3$.

In another embodiment, m is 1, $R_1$ is —$CF_3$, $R_3$ is —$CH_3$, $R_4$ is —$CH_3$, $R_5$ is —H, and $R_6$ is -phenyl substituted at its para-position with a —$CF_3$.

In another embodiment, m is 1, $R_1$ is —Cl, $R_3$ is —$CH_3$, $R_4$ is —$CH_3$, $R_5$ is —H, and $R_6$ is -phenyl substituted at its para-position with a —$CF_3$.

4.6 The Hydroxyiminepiperazine Compounds of Formula (VI)

The present invention also encompasses compounds of formula (VI):

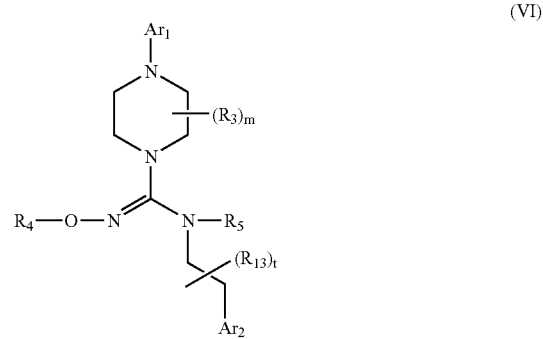

(VI)

and pharmaceutically acceptable salts thereof, where $Ar_1$, $Ar_2$, $R_3$-$R_5$, $R_{13}$, m and t are defined above for the Hydroxyiminepiperazine Compounds of formula (VI).

In one embodiment $Ar_1$ is a pyridyl group.

In another embodiment, $Ar_1$ is a pyrimidinyl group.

In another embodiment, $Ar_1$ is a pyridazinyl group.

In another embodiment, $Ar_1$ is a pyrazinyl group.

In another embodiment, $Ar_1$ is a thiadiazolyl group.

In another embodiment, $Ar_2$ is a benzothiazolyl group.

In another embodiment, $Ar_2$ is a benzoimidazolyl group.

In another embodiment, $Ar_2$ is a benzooxazolyl group.

In another embodiment, $Ar_2$ is

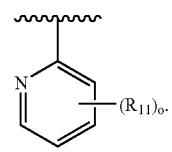

In another embodiment, $Ar_2$ is

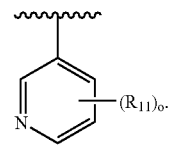

In another embodiment, $Ar_2$ is

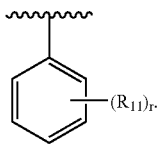

In another embodiment, $Ar_2$ is

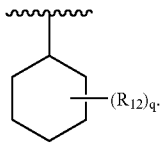

In another embodiment, $Ar_2$ is

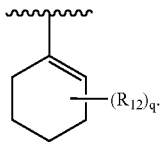

In another embodiment, $Ar_2$ is

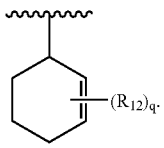

In another embodiment, $Ar_2$ is

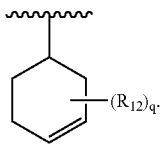

In another embodiment, $R_1$ is —H.
In another embodiment, $R_1$ is -halo.
In another embodiment, $R_1$ is —Cl.
In another embodiment, $R_1$ is —Br.
In another embodiment, $R_1$ is —I.
In another embodiment, $R_1$ is —F.
In another embodiment, $R_1$ is —CH$_3$.
In another embodiment, $R_1$ is —NO$_2$.
In another embodiment, $R_1$ is —CN.
In another embodiment, $R_1$ is —OH.
In another embodiment, $R_1$ is —OCH$_3$.
In another embodiment, $R_1$ is —NH$_2$.
In another embodiment, $R_1$ is —C(halo)$_3$.
In another embodiment, $R_1$ is —CH(halo)$_2$.
In another embodiment, $R_1$ is —CH$_2$(halo).
In another embodiment, m is 0.
In another embodiment, m is 1.
In another embodiment, m is 2.

In another embodiment, n is 0.
In another embodiment, n is 1.
In another embodiment, n is 2.
In another embodiment, n is 3.
In another embodiment, p is 0.
In another embodiment, p is 1.
In another embodiment, p is 2.
In another embodiment, t is 0.
In another embodiment, t is 1.
In another embodiment, t is 2.
In another embodiment, s is 0.
In another embodiment, s is 1.
In another embodiment, s is 2.
In another embodiment, s is 3.
In another embodiment, s is 4.
In another embodiment, o is 0.
In another embodiment, o is 1.
In another embodiment, o is 2.
In another embodiment, o is 3.
In another embodiment, o is 4.
In another embodiment, q is 0.
In another embodiment, q is 1.
In another embodiment, q is 2.
In another embodiment, q is 3.
In another embodiment, q is 4.
In another embodiment, q is 5.
In another embodiment, q is 6.
In another embodiment, r is 0.
In another embodiment, r is 1.
In another embodiment, r is 2.
In another embodiment, r is 3.
In another embodiment, r is 4.
In another embodiment, r is 5.

In another embodiment, n or p is 1 and $R_2$ is -halo, —CN, —OH, —NO$_2$, or —NH$_2$.

In another embodiment, n or p is 1 and $R_2$ is —($C_1$-$C_{10}$)alkyl, —($C_2$-$C_{10}$)alkenyl, —($C_2$-$C_{10}$)alkynyl, —($C_3$-$C_{10}$)cycloalkyl, —($C_8$-$C_{14}$)bicycloalkyl, —($C_8$-$C_{14}$)tricycloalkyl, —($C_5$-$C_{10}$)cycloalkenyl, —($C_8$-$C_{14}$)bicycloalkenyl, —($C_8$-$C_{14}$)tricycloalkenyl, -(3- to 7-membered)heterocycle, or -(7- to 10-membered)bicycloheterocycle, each of which is unsubstituted or substituted with one or more $R_7$ groups.

In another embodiment, n or p is 1 and $R_2$ is -phenyl, -naphthyl, —($C_{14}$)aryl or -(5- to 10-membered) heteroaryl, each of which is unsubstituted or substituted with one or more $R_8$ groups.

In another embodiment, m is 1 and $R_3$ is -halo, —CN, —OH, —NO$_2$, or —NH$_2$.

In another embodiment, m is 1 and $R_3$ is —($C_1$-$C_{10}$)alkyl, —($C_2$-$C_{10}$)alkenyl, ($C_2$-$C_{10}$)alkynyl, —($C_3$-$C_{10}$)cycloalkyl, —($C_8$-$C_{14}$)bicycloalkyl, —($C_8$-$C_{14}$)tricycloalkyl, —($C_5$-$C_{10}$)cycloalkenyl, —($C_8$-$C_{14}$)bicycloalkenyl, —($C_8$-$C_{14}$)tricycloalkenyl, -(3- to 7-membered)heterocycle, or -(7- to 10-membered)bicycloheterocycle, each of which is unsubstituted or substituted with one or more $R_7$ groups.

In another embodiment, m is 1 and $R_3$ is -phenyl, -naphthyl, —($C_{14}$)aryl or -(5- to 10-membered) heteroaryl, each of which is unsubstituted or substituted with one or more $R_8$ groups.

In another embodiment, m is 1 and $R_3$ is a —($C_1$-$C_{10}$)alkyl.

In another embodiment, m is 1, $R_3$ is a —($C_1$-$C_{10}$)alkyl, and the carbon to which the $R_3$ group is attached is in the (R)-configuration.

In another embodiment, m is 1, $R_3$ is a —($C_1$-$C_{10}$)alkyl, and the carbon to which the $R_3$ group is attached is in the (S)-configuration.

In another embodiment, m is 1 and $R_3$ is —CH$_3$.

In another embodiment, m is 1, $R_3$ is —$CH_3$, and the carbon atom to which the $R_3$ is attached is in the (R)-configuration.

In another embodiment, m is 1, $R_3$ is —$CH_3$, and the carbon atom to which the $R_3$ is attached is in the (S)-configuration.

4.7 The Hydroxyiminopiperazine Compounds of Formula (VII)

The present invention also encompasses compounds of formula (VII):

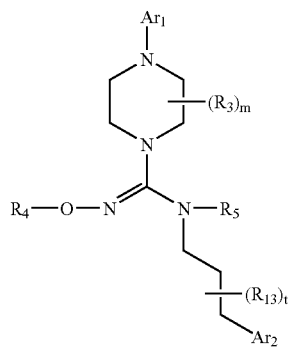

(VII)

and pharmaceutically acceptable salts thereof, where $Ar_1$, $Ar_2$, $R_3$-$R_5$, $R_{13}$, m and t are defined above for the Hydroxyiminopiperazine Compounds of formula (VII).

In one embodiment $Ar_1$ is a pyridyl group.
In another embodiment, $Ar_1$ is a pyrimidinyl group.
In another embodiment, $Ar_1$ is a pyridazinyl group.
In another embodiment, $Ar_1$ is a pyrazinyl group.
In another embodiment, $Ar_1$ is a thiadiazolyl group.
In another embodiment, $Ar_2$ is a benzothiazolyl group.
In another embodiment, $Ar_2$ is a benzoimidazolyl group.
In another embodiment, $Ar_2$ is a benzooxazolyl group.
In another embodiment, $Ar_2$ is

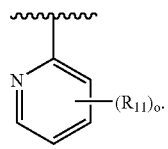

In another embodiment, $Ar_2$ is

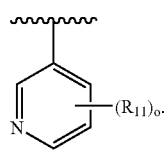

In another embodiment, $Ar_2$ is

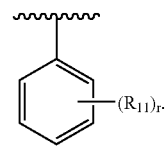

In another embodiment, $Ar_2$ is

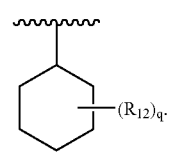

In another embodiment, $Ar_2$ is

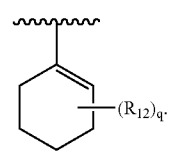

In another embodiment, $Ar_2$ is

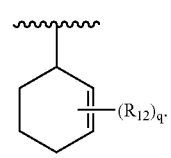

In another embodiment, $Ar_2$ is

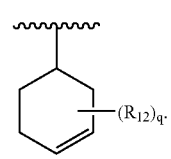

In another embodiment, $R_1$ is —H.
In another embodiment, $R_1$ is -halo.
In another embodiment, $R_1$ is —Cl.
In another embodiment, $R_1$ is —Br.
In another embodiment, $R_1$ is —I.
In another embodiment, $R_1$ is —F.
In another embodiment, $R_1$ is —$CH_3$.
In another embodiment, $R_1$ is —$NO_2$.
In another embodiment, $R_1$ is —CN.
In another embodiment, $R_1$ is —OH.
In another embodiment, $R_1$ is —$OCH_3$.
In another embodiment, $R_1$ is —$NH_2$.
In another embodiment, $R_1$ is —C(halo)$_3$.
In another embodiment, $R_1$ is —CH(halo)$_2$.
In another embodiment, $R_1$ is —$CH_2$(halo).
In another embodiment, m is 0.
In another embodiment, m is 1.
In another embodiment, m is 2.
In another embodiment, n is 0.

In another embodiment, n is 1.
In another embodiment, n is 2.
In another embodiment, n is 3.
In another embodiment, p is 0.
In another embodiment, p is 1.
In another embodiment, p is 2.
In another embodiment, t is 0.
In another embodiment, t is 1.
In another embodiment, t is 2.
In another embodiment, s is 0.
In another embodiment, s is 2.
In another embodiment, s is 3.
In another embodiment, s is 4.
In another embodiment, o is 4.
In another embodiment, o is 0.
In another embodiment, o is 2.
In another embodiment, o is 3.
In another embodiment, o is 4.
In another embodiment, o is 4.
In another embodiment, q is 0.
In another embodiment, q is 2.
In another embodiment, q is 3.
In another embodiment, q is 4.
In another embodiment, q is 4.
In another embodiment, q is 6.
In another embodiment, q is 6.
In another embodiment, r is 0.
In another embodiment, r is 2.
In another embodiment, r is 3.
In another embodiment, r is 4.
In another embodiment, r is 4.
In another embodiment, r is 5.

In another embodiment, n or p is 1 and $R_2$ is -halo, —CN, —OH, —NO$_2$, or —NH$_2$.

In another embodiment, n or p is 1 and $R_2$ is —($C_1$-$C_{10}$)alkyl, —($C_2$-$C_{10}$)alkenyl, —($C_2$-$C_{10}$)alkynyl, —($C_3$-$C_{10}$)cycloalkyl, —($C_8$-$C_{14}$)bicycloalkyl, —($C_8$-$C_{14}$)tricycloalkyl, —($C_5$-$C_{10}$)cycloalkenyl, —($C_8$-$C_{14}$)bicycloalkenyl, —($C_8$-$C_{14}$)tricycloalkenyl, -(3- to 7-membered)heterocycle, or -(7- to 10-membered)bicycloheterocycle, each of which is unsubstituted or substituted with one or more $R_7$ groups.

In another embodiment, n or p is 1 and $R_2$ is -phenyl, -naphthyl, —($C_{14}$aryl or -(5- to 10-membered) heteroaryl, each of which is unsubstituted or substituted with one or more $R_8$ groups.

In another embodiment, m is 1 and $R_3$ is -halo, —CN, —OH, —NO$_2$, or —NH$_2$.

In another embodiment, m is 1 and $R_3$ is —($C_1$-$C_{10}$)alkyl, —($C_2$-$C_{10}$)alkenyl, ($C_2$-$C_{10}$)alkynyl, —($C_3$-$C_{10}$)cycloalkyl, —($C_8$-$C_{14}$)bicycloalkyl, —($C_8$-$C_{14}$)tricycloalkyl, —($C_5$-$C_{10}$)cycloalkenyl, —($C_8$-$C_{14}$)bicycloalkenyl, —($C_8$-$C_{14}$)tricycloalkenyl, -(3- to 7-membered)heterocycle, or -(7- to 10-membered)bicycloheterocycle, each of which is unsubstituted or substituted with one or more $R_7$ groups.

In another embodiment, m is 1 and $R_3$ is -phenyl, -naphthyl, —($C_{14}$)aryl or -(5- to 10-membered) heteroaryl, each of which is unsubstituted or substituted with one or more $R_8$ groups.

In another embodiment, m is 1 and $R_3$ is a —($C_1$-$C_{10}$)alkyl.

In another embodiment, m is 1, $R_3$ is a —($C_1$-$C_{10}$)alkyl, and the carbon to which the $R_3$ group is attached is in the (R)-configuration.

In another embodiment, m is 1, $R_3$ is a —($C_1$-$C_{10}$)alkyl, and the carbon to which the $R_3$ group is attached is in the (S)-configuration.

In another embodiment, m is 1 and $R_3$ is —CH$_3$.

In another embodiment, m is 1, $R_3$ is —CH$_3$, and the carbon atom to which the $R_3$ is attached is in the (R)-configuration.

In another embodiment, m is 1, $R_3$ is —CH$_3$, and the carbon atom to which the $R_3$ is attached is in the (S)-configuration.

4.8 The Hydroxyiminopiperazine Compounds of Formula (I-VII)

In the Hydroxyiminopiperazine Compounds each $R_3$ can be on any carbon of the piperazine ring. In one embodiment, the Hydroxyiminopiperazine Compounds have only one $R_3$ group, and that $R_3$ group is attached to a carbon atom adjacent to the nitrogen atom attached to the pyridyl, pyrimidinyl, pyrazinyl, pyridazinyl, or thiadiazolyl group. In another embodiment, the Hydroxyiminopiperazine Compound has only one $R_3$ group, and that $R_3$ group is attached to a carbon atom adjacent to the nitrogen atom attached to the —C(=N—OR$_4$)—N(R$_5$)(R$_6$), —C(=N—OR$_4$)—N(R$_5$)-phenethyl group, or —C(=N—OR$_4$)—N(R$_5$)-phenpropyl group.

In another embodiment, two $R_3$ groups are on the same carbon atom of the piperazine ring.

In another embodiment, a first $R_3$ group is attached to a carbon atom adjacent to the nitrogen atom attached to the pyridyl, pyrimidinyl, pyrazinyl, pyridazinyl, or thiadiazolyl group and a second $R_3$ group is attached to a carbon atom adjacent to the nitrogen atom attached to the —C(=N—OR$_4$)—N(R$_5$)(R$_6$), —C(=N—OR$_4$)—N(R$_5$)-phenethyl group, or —C(=N—OR$_4$)—N(R$_5$)-phenpropyl group.

In another embodiment, the Hydroxyiminopiperazine Compound has two $R_3$ groups, each being attached to a different carbon atom adjacent to the nitrogen atom attached to the pyridyl, pyrimidinyl, pyrazinyl, pyridazinyl, or thiadiazolyl group. In another embodiment, the Hydroxyiminopiperazine Compound has two $R_3$ groups, each being attached to a different carbon atom adjacent to the nitrogen atom attached to the —C(=N—OR$_4$)—N(R$_5$)(R$_6$), —C(=N—OR$_4$)—N(R$_5$)-phenethyl group, or —C(=N—OR$_4$)—N(R$_5$)-phenpropyl group.

In another embodiment, wherein the Hydroxyiminopiperazine Compound has one or two $R_3$ groups, the carbon atom to which an $R_3$ group is attached has the (R) configuration. In another embodiment, wherein the Hydroxyiminopiperazine Compound has one or two $R_3$ groups, the carbon atom to which the $R_3$ group is attached has the (S) configuration. In another embodiment, the Hydroxyiminopiperazine Compound has one or two $R_3$ groups, and at least one of the carbon atoms to which an $R_3$ group is attached has the (R) configuration. In another embodiment, the Hydroxyiminopiperazine Compound has one or two $R_3$ groups, and at least one of the carbon atoms to which an $R_3$ group is attached has the (S) configuration.

In another embodiment, the Hydroxyiminopiperazine Compound has one or two $R_3$ groups; an $R_3$ group is attached to a carbon atom adjacent to the nitrogen atom attached to the pyridyl, pyrimidinyl, pyrazinyl, pyridazinyl, or thiadiazolyl group; and the carbon to which the $R_3$ group is attached is in the (R) configuration. In another embodiment, the Hydroxyiminopiperazine Compound has one or two $R_3$ groups; an $R_3$ group is attached to a carbon atom adjacent to the nitrogen attached to the pyridyl, pyrimidinyl, pyrazinyl, pyridazinyl, or thiadiazolyl group; the carbon to which the $R_3$ group is attached is in the (R) configuration; and $R_3$ is —($C_1$-$C_4$)alkyl unsubstituted or substituted with one or more halo groups. In another embodiment, the Hydroxyiminopiperazine Compound has one or two $R_3$ groups; an $R_3$ group is attached to a carbon atom adjacent to the nitrogen attached to the pyridyl, pyrimidinyl, pyrazinyl, pyridazinyl, or thiadiazolyl group; the carbon to which the $R_3$ group is attached is in the (R) configuration; and $R_3$ is —$CH_3$. In another embodiment, the Hydroxyiminopiperazine Compound has one or two $R_3$ groups; an $R_3$ group is attached to a carbon atom adjacent to the nitrogen attached to the pyridyl, pyrimidinyl, pyrazinyl, pyridazinyl, or thiadiazolyl group; the carbon to which the $R_3$ group is attached is in the (R) configuration; and $R_3$ is —$CF_3$. In another embodiment, the Hydroxyiminopiperazine Compound has one or two $R_3$ groups; an $R_3$ group is attached to a carbon atom adjacent to the nitrogen attached to the pyridyl, pyrimidinyl, pyrazinyl, pyridazinyl, or thiadiazolyl group; the carbon to which the $R_3$ group is attached is in the (R) configuration; and $R_3$ is —$CH_2CH_3$.

In another embodiment, the Hydroxyiminopiperazine Compound has one or two $R_3$ groups; an $R_3$ group is attached to a carbon atom adjacent to the nitrogen atom attached to the —C(=N—$OR_4$)—N($R_5$)($R_6$), —C(=N—$OR_4$)—N($R_5$)-phenethyl group, or —C(=N—$OR_4$)—N($R_5$)-phenpropyl group; and the carbon to which the $R_3$ group is attached is in the (R) configuration. In another embodiment, the Hydroxyiminopiperazine Compound has one or two $R_3$ groups; an $R_3$ group is attached to a carbon adjacent to the nitrogen attached to the —C(=N—$OR_4$)—N($R_5$)($R_6$), —C(=N—$OR_4$)—N($R_5$)-phenethyl group, or —C(=N—$OR_4$)—N(R5)-phenpropyl group; the carbon to which the $R_3$ group is attached is in the (R) configuration; and $R_3$ is —($C_1$-$C_4$)alkyl unsubstituted or substituted with one or more halo groups. In another embodiment, the Hydroxyiminopiperazine Compound has one or two $R_3$ groups; an $R_3$ group is attached to a carbon atom adjacent to the nitrogen attached to the —C(=N—$OR_4$)—N($R_5$)($R_6$), —C(=N—$OR_4$)—N($R_5$)-phenethyl group, or —C(=N—$OR_4$)—N($R_5$)-phenpropyl group; the carbon to which the $R_3$ group is attached is in the (R) configuration; and $R_3$ is —$CH_3$. In another embodiment, the Hydroxyiminopiperazine Compound has one or two $R_3$ groups; an $R_3$ group is attached to a carbon atom adjacent to the nitrogen attached to the —C(=N—$OR_4$)—N($R_5$)($R_6$), —C(=N—$OR_4$)—N($R_5$)-phenethyl group; or —C(=N—$OR_4$)—N($R_5$)-phenpropyl group; the carbon to which the $R_3$ group is attached is in the (R) configuration, and $R_3$ is —$CF_3$. In another embodiment, the Hydroxyiminopiperazine Compound has one or two $R_3$ groups; an $R_3$ group is attached to a carbon atom adjacent to the nitrogen attached to the —C(=N—$OR_4$)—N($R_5$)($R_6$), —C(=N—$OR_4$)—N($R_5$)-phenethyl group, or —C(=N—$OR_4$)—N($R_5$)-phenpropyl group; the carbon to which the $R_3$ group is attached is in the (R) configuration; and $R_3$ is —$CH_2CH_3$.

In another embodiment, the Hydroxyiminopiperazine Compound has one or two $R_3$ groups; an $R_3$ group is attached to a carbon atom adjacent to the nitrogen atom attached to the pyridyl, pyrimidinyl, pyrazinyl, pyridazinyl, or thiadiazolyl group; and the carbon to which the $R_3$ group is attached is in the (S) configuration. In another embodiment, the Hydroxyiminopiperazine Compound has one or two $R_3$ groups; an $R_3$ group is attached to a carbon atom adjacent to the nitrogen attached to the pyridyl, pyrimidinyl, pyrazinyl, pyridazinyl, or thiadiazolyl group; the carbon to which the $R_3$ group is attached is in the (S) configuration; and $R_3$ is —($C_1$-$C_4$)alkyl unsubstituted or substituted with one or more halo groups. In another embodiment, the Hydroxyiminopiperazine Compound has one or two $R_3$ groups; an $R_3$ group is attached to a carbon atom adjacent to the nitrogen attached to the pyridyl, pyrimidinyl, pyrazinyl, pyridazinyl, or thiadiazolyl group; the carbon to which the $R_3$ group is attached is in the (S) configuration; and $R_3$ is —$CH_3$. In another embodiment, the Hydroxyiminopiperazine Compound has one or two $R_3$ groups; an $R_3$ group is attached to a carbon atom adjacent to the nitrogen attached to the pyridyl, pyrimidinyl, pyrazinyl, pyridazinyl, or thiadiazolyl group; the carbon to which the $R_3$ group is attached is in the (S) configuration; and $R_3$ is —$CF_3$. In another embodiment, the Hydroxyiminopiperazine Compound has one or two $R_3$ groups; an $R_3$ group is attached to a carbon atom adjacent to the nitrogen attached to the pyridyl, pyrimidinyl, pyrazinyl, pyridazinyl, or thiadiazolyl group; the carbon to which the $R_3$ group is attached is in the (S) configuration; and $R_3$ is —$CH_2CH_3$.

In another embodiment, the Hydroxyiminopiperazine Compound has one or two $R_3$ groups; an $R_3$ group is attached to a carbon atom adjacent to the nitrogen atom attached to the —C(=N—$OR_4$)—N($R_5$)($R_6$), —C(=N—$OR_4$)—N($R_5$)-phenethyl group, or —C(=N—$OR_4$)—N($R_5$)-phenpropyl group; and the carbon to which the $R_3$ group is attached is in the (S) configuration. In another embodiment, the Hydroxyiminopiperazine Compound has one or two $R_3$ groups; an $R_3$ group is attached to a carbon atom adjacent to the nitrogen attached to the —C(=N—$OR_4$)—N($R_5$)($R_6$), —C(=N—$OR_4$)—N($R_5$)-phenethyl group, or —C(=N—$OR_4$)—N($R_5$)-phenpropyl group; the carbon to which the $R_3$ group is attached is in the (S) configuration; and $R_3$ is —($C_1$-$C_4$)alkyl unsubstituted or substituted with one or more halo groups. In another embodiment, the Hydroxyiminopiperazine Compound has one or two $R_3$ groups; an $R_3$ group is attached to a carbon atom adjacent to the nitrogen attached to the —C(=N—$OR_4$)—N($R_5$)($R_6$), —C(=N—$OR_4$)—N($R_5$)-phenethyl group or —C(=N—$OR_4$)—N($R_5$)-phenpropyl group; the carbon to which the $R_3$ group is attached is in the (S) configuration; and $R_3$ is —$CH_3$. In another embodiment, the Hydroxyiminopiperazine Compound has one or two $R_3$ groups; an $R_3$ group is attached to a carbon atom adjacent to the nitrogen attached to the —C(=N—$OR_4$)—N$R_5$)($R_6$), —C(=N—$OR_4$)—N($R_5$)-phenethyl group, or —C(=N—$OR_4$)—N($R_5$)-phenpropyl group; the carbon to which the $R_3$ group is attached is in the (S) configuration; and $R_3$ is —$CF_3$. In another embodiment, the Hydroxyiminopiperazine Compound has one or two $R_3$ groups; an $R_3$ group is attached to a carbon atom adjacent to the nitrogen attached to the —C(=N—$OR_4$)—N($R_5$)($R_6$), —C(=N—$OR_4$)—N($R_5$)-phenethyl group, or —C(=N—$OR_4$)—N($R_5$)-phenpropyl group; the carbon to which the $R_3$ group is attached is in the (S) configuration; and $R_3$ is —$CH_2CH_3$.

In another embodiment, the Hydroxyiminopiperazine Compound has only one $R_3$ group; the $R_3$ group is attached to a carbon atom adjacent to the nitrogen atom attached to the pyridyl, pyrimidinyl, pyrazinyl, pyridazinyl, or thiadiazolyl group; and the carbon to which the $R_3$ group is attached is in the (R) configuration. In another embodiment, the Hydroxyiminopiperazine Compound has only one $R_3$ group; the $R_3$ group is attached to a carbon atom adjacent to the nitrogen attached to the pyridyl, pyrimidinyl, pyrazinyl, pyridazinyl, or thiadiazolyl group; the carbon to which the $R_3$ group is attached is in the (R) configuration; and $R_3$ is —($C_1$-$C_4$)alkyl unsubstituted or substituted with one or more halo groups. In another embodiment, the Hydroxyiminopiperazine Compound has only one $R_3$ group; the $R_3$ group is attached to a carbon atom adjacent to the nitrogen attached to the pyridyl, pyrimidinyl, pyrazinyl, pyridazinyl, or thiadiazolyl group; the carbon to which the $R_3$ group is attached is in the (R) configuration; and $R_3$ is —$CH_3$. In another embodiment, the Hydroxyiminopiperazine Compound has only one $R_3$ group; the $R_3$ group is attached to a carbon atom adjacent to the nitrogen attached to the pyridyl, pyrimidinyl, pyrazinyl, pyridazinyl, or thiadiazolyl group; the carbon to which the $R_3$ group is attached is in the (R) configuration; and $R_3$ is —$CF_3$. In another embodiment, the Hydroxyiminopiperazine Compound has only one $R_3$ group; the $R_3$ group is attached to a carbon atom adjacent to the nitrogen attached to the pyridyl, pyrimidinyl, pyrazinyl, pyridazinyl, or thiadiazolyl group; the carbon to which the $R_3$ group is attached is in the (R) configuration; and $R_3$ is —$CH_2CH_3$.

In another embodiment, the Hydroxyiminopiperazine Compound has only one $R_3$ group; the $R_3$ group is attached to a carbon atom adjacent to the nitrogen atom attached to the —C(=N—$OR_4$)—N($R_5$)($R_6$), —C(=N—$OR_4$)—N($R_5$)-phenethyl group, or —C(=N—$OR_4$)—N$R_5$-phenpropyl group; and the carbon to which the $R_3$ group is attached is in the (R) configuration. In another embodiment, the Hydroxyiminopiperazine Compound has only one $R_3$ group; the $R_3$ group is attached to a carbon atom adjacent to the nitrogen attached to the —C(=N—$OR_4$)—N($R_5$)($R_6$), —C(=N—$OR_4$)—N($R_5$)-phenethyl group, or —C(=N—$OR_4$)—N($R_5$)-phenpropyl group; the carbon to which the $R_3$ group is attached is in the (R) configuration; and $R_3$ is —($C_1$-$C_4$)alkyl unsubstituted or substituted with one or more halo groups. In another embodiment, the Hydroxyiminopiperazine Compound has only one $R_3$ group; the $R_3$ group is attached to a carbon atom adjacent to the nitrogen attached to the —C(=N—$OR_4$)—N($R_5$)($R_6$), —C(=N—$OR_4$)—N($R_5$)-phenethyl group, or —C(=N—$OR_4$)—N($R_5$)-phenpropyl group; the carbon to which the $R_3$ group is attached is in the (R) configuration; and $R_3$ is —$CH_3$. In another embodiment, the Hydroxyiminopiperazine Compound has only one $R_3$ group; the $R_3$ group is attached to a carbon atom adjacent to the nitrogen attached to the —C(=N—$OR_4$)—N($R_5$)($R_6$), —C(=N—$OR_4$)—N($R_5$)-phenethyl group, or —C(=N—$OR_4$)—N($R_5$)-phenpropyl group; the carbon to which the $R_3$ group is attached is in the (R) configuration; and $R_3$ is —$CF_3$. In another embodiment, the Hydroxyiminopiperazine Compound has only one $R_3$ group; the $R_3$ group is attached to a carbon atom adjacent to the nitrogen attached to the —C(=N—$OR_4$)—N($R_5$)($R_6$), —C(=N—$OR_4$)—N($R_5$)-phenethyl group, or —C(=N—$OR_4$)—N($R_5$)-phenpropyl group; the carbon to which the $R_3$ group is attached is in the (R) configuration; and $R_3$ is —$CH_2CH_3$.

In another embodiment, the Hydroxyiminopiperazine Compound has only one $R_3$ group; the $R_3$ group is attached to a carbon atom adjacent to the nitrogen atom attached to the pyridyl, pyrimidinyl, pyrazinyl, pyridazinyl, or thiadiazolyl group; and the carbon to which the $R_3$ group is attached is in the (S) configuration. In another embodiment, the Hydroxyiminopiperazine Compound has only one $R_3$ group; the $R_3$ group is attached to a carbon atom adjacent to the nitrogen attached to the pyridyl, pyrimidinyl, pyrazinyl, pyridazinyl, or thiadiazolyl group; the carbon to which the $R_3$ group is attached is in the (S) configuration; and $R_3$ is —($C_1$-$C_4$)alkyl unsubstituted or substituted with one or more halo groups. In another embodiment, the Hydroxyiminopiperazine Compound has only one $R_3$ group; the $R_3$ group is attached to a carbon atom adjacent to the nitrogen attached to the pyridyl, pyrimidinyl, pyrazinyl, pyridazinyl, or thiadiazolyl group; the carbon to which the $R_3$ group is attached is in the (S) configuration; and $R_3$ is —$CH_3$. In another embodiment, the Hydroxyiminopiperazine Compound has only one $R_3$ group; the $R_3$ group is attached to a carbon atom adjacent to the nitrogen attached to the pyridyl, pyrimidinyl, pyrazinyl, pyridazinyl, or thiadiazolyl group; the carbon to which the $R_3$ group is attached is in the (S) configuration; and $R_3$ is —$CF_3$. In another embodiment, the Hydroxyiminopiperazine Compound has only one $R_3$ group; the $R_3$ group is attached to a carbon atom adjacent to the nitrogen attached to the pyridyl, pyrimidinyl, pyrazinyl, pyridazinyl, or thiadiazolyl group; the carbon to which the $R_3$ group is attached is in the (S) configuration; and $R_3$ is —$CH_2CH_3$.

In another embodiment, the Hydroxyiminopiperazine Compound has only one $R_3$ group; the $R_3$ group is attached to a carbon atom adjacent to the nitrogen atom attached to the —C(=N—$OR_4$)—N($R_5$)($R_6$), —C(=N—$OR_4$)—N($R_5$)-phenethyl group, or —C(=N—$OR_4$)—N($R_5$)-phenpropyl group; and the carbon to which the $R_3$ group is attached is in the (S) configuration. In another embodiment, the Hydroxyiminopiperazine Compound has only one $R_3$ group; the $R_3$ group is attached to a carbon atom adjacent to the nitrogen attached to the —C(=N—$OR_4$)—N($R_5$)($R_6$), —C(=N—$OR_4$)—N($R_5$)-phenethyl group, or —C(=N—$OR_4$)—N($R_5$)-phenpropyl group; the carbon to which the $R_3$ group is attached is in the (S) configuration; and $R_3$ is —($C_1$-$C_4$)alkyl unsubstituted or substituted with one or more halo groups. In another embodiment, the Hydroxyiminopiperazine Compound has only one $R_3$ group; the $R_3$ group is attached to a carbon atom adjacent to the nitrogen attached to the —C(=N—$OR_4$)—N($R_5$)($R_6$), —C(=N—$OR_4$)—N($R_5$)-phenethyl group, or —C(=N—$OR_4$)—N($R_5$)-phenpropyl group; the carbon to which the $R_3$ group is attached is in the (S) configuration; and $R_3$ is —$CH_3$. In another embodiment, the Hydroxyiminopiperazine Compound has only one $R_3$ group; the $R_3$ group is attached to a carbon atom adjacent to the nitrogen attached to the —C(=N—$OR_4$)—N($R_5$)($R_6$), —C(=N—$OR_4$)—N($R_5$)-phenethyl group, or —C(=N—$OR_4$)—N($R_5$)-phenpropyl group; the carbon to which the $R_3$ group is attached is in the (S) configuration; and $R_3$ is —$CF_3$. In another embodiment, the Hydroxyiminopiperazine Compound has only one $R_3$ group; the $R_3$ group is attached to a carbon atom adjacent to the nitrogen attached to the —C(=N—$OR_4$)—N($R_5$)($R_6$), —C(=N—$OR_4$)—N($R_5$)-phenethyl group, or —C(=N—$OR_4$)—N($R_5$)-phenpropyl group; the carbon to which the $R_3$ group is attached is in the (R) configuration; and $R_3$ is —$CH_2CH_3$.

In another embodiment, the $R_3$ group is attached to a carbon atom adjacent to the nitrogen attached to the —C(=N—$OR_4$)—N($R_5$)($R_6$), —C(=N—$OR_4$)—N($R_5$)-phenethyl, or —C(=N—$OR_4$)—N$R_5$-phenpropyl group. In another embodiment, the $R_3$ group is attached to a carbon atom adjacent to the nitrogen attached to the —C(=N—$OR_4$)—N($R_5$) ($R_6$), —C(=N—$OR_4$)—N($R_5$)-phenethyl, or —C(=N—$OR_4$)—N$R_5$-phenpropyl group and the $R_3$ group is a —$CH_3$. In another embodiment, the $R_3$ group is attached to a carbon atom adjacent to the nitrogen attached to the —C(=N—$OR_4$)—N($R_5$)($R_6$), —C(=N—$OR_4$)—N($R_5$)-phenethyl group, or —C(=N—$OR_4$)—N($R_5$)-phenpropyl group and the $R_3$ group is a —$CF_3$. In another embodiment, the $R_3$ group is attached to a carbon atom adjacent to the nitrogen attached to the —C(=N—$OR_4$)—N($R_5$)($R_6$), —C(=N—$OR_4$)—N ($R_5$)-phenethyl group, or —C(=N—$OR_4$)—N($R_5$)-phenpropyl group and the $R_3$ group is a —$CH_2CH_3$. In another embodiment, the $R_3$ group is attached to a carbon atom adjacent to the nitrogen attached to the —C(=N—$OR_4$)—N($R_5$) ($R_6$), —C(=N—$OR_4$)—N($R_5$)-phenethyl group, or —C(=N—$OR_4$)—N($R_5$)-phenpropyl group and the carbon to which the $R_3$ group is attached is in the (R) configuration. In another embodiment, the $R_3$ group is attached to a carbon atom adjacent to the nitrogen attached to the —C(=N—$OR_4$)—N($R_5$)($R_6$), —C(=N—$OR_4$)—N($R_5$)-phenethyl group, or —C(=N—$OR_4$)—N($R_5$)-phenpropyl group; the carbon to which the $R_3$ group is attached is in the (R) configuration; and the $R_3$ group is a —$CH_3$. In another embodiment, the $R_3$ group is attached to a carbon atom adjacent to the nitrogen attached to the —C(=N—OR$_4$)—N(R$_5$)(R$_6$), —C(=N—OR$_4$)—N(R$_5$)-phenethyl group, or —C(=N—OR$_4$)—N(R$_5$)-phenpropyl group; the carbon to which the R$_3$ group is attached is in the (R) configuration; and the R$_3$ group is a —CF$_3$. In another embodiment, the R$_3$ group is attached to a carbon atom adjacent to the nitrogen attached to the —C(=N—OR$_4$)—N(R$_5$)(R$_6$), —C(=N—OR$_4$)—N(R$_5$)-phenethyl group, or —C(=N—OR$_4$)—N(R$_5$)-phenpropyl group; the carbon to which the R$_3$ group is attached is in the (R) configuration; and the R$_3$ group is a —CH$_2$CH$_3$.

Illustrative Hydroxyiminopiperazine Compounds are listed below in Tables I-VII:

TABLE I

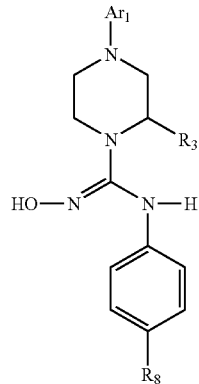

and pharmaceutically acceptable salts thereof, wherein:

| Compound | Ar$_1$ | R$_8$ |
|---|---|---|
| A1 (a, b, c, and d) | -2-(3-chloropyridyl) | -t-butyl |
| A2 (a, b, c, and d) | -2-(3-chloropyridyl) | -iso-butyl |
| A3 (a, b, c, and d) | -2-(3-chloropyridyl) | -sec-butyl |
| A4 (a, b, c, and d) | -2-(3-chloropyridyl) | -cyclohexyl |
| A5 (a, b, c, and d) | -2-(3-chloropyridyl) | -t-butoxy |
| A6 (a, b, c, and d) | -2-(3-chloropyridyl) | -isopropoxy |
| A7 (a, b, c, and d) | -2-(3-chloropyridyl) | —CF$_3$ |
| A8 (a, b, c, and d) | -2-(3-chloropyridyl) | —OCF$_3$ |
| A9 (a, b, c, and d) | -2-(3-chloropyridyl) | —Cl |
| A10 (a, b, c, and d) | -2-(3-chloropyridyl) | —Br |
| A11 (a, b, c, and d) | -2-(3-chloropyridyl) | —I |
| A12 (a, b, c, and d) | -2-(3-chloropyridyl) | -n-butyl |
| A13 (a, b, c, and d) | -2-(3-chloropyridyl) | -n-propyl |
| A14 (a, b, c, and d) | -2-(3-chloropyridyl) | -iso-propyl |
| A15 (a, b, c, and d) | -2-(3-fluoropyridyl) | -t-butyl |
| A16 (a, b, c, and d) | -2-(3-fluoropyridyl) | -iso-butyl |
| A17 (a, b, c, and d) | -2-(3-fluoropyridyl) | -sec-butyl |
| A18 (a, b, c, and d) | -2-(3-fluoropyridyl) | -cyclohexyl |
| A19 (a, b, c, and d) | -2-(3-fluoropyridyl) | -t-butoxy |
| A20 (a, b, c, and d) | -2-(3-fluoropyridyl) | -isopropoxy |
| A21 (a, b, c, and d) | -2-(3-fluoropyridyl) | —CF$_3$ |
| A22 (a, b, c, and d) | -2-(3-fluoropyridyl) | —OCF$_3$ |
| A23 (a, b, c, and d) | -2-(3-fluoropyridyl) | —Cl |
| A24 (a, b, c, and d) | -2-(3-fluoropyridyl) | —Br |
| A25 (a, b, c, and d) | -2-(3-fluoropyridyl) | —I |
| A26 (a, b, c, and d) | -2-(3-fluoropyridyl) | -n-butyl |
| A27 (a, b, c, and d) | -2-(3-fluoropyridyl) | -n-propyl |
| A28 (a, b, c, and d) | -2-(3-fluoropyridyl) | -iso-propyl |
| A29 (a, b, c, and d) | -2-(3-methylpyridyl) | -t-butyl |
| A30 (a, b, c, and d) | -2-(3-methylpyridyl) | -iso-butyl |
| A31 (a, b, c, and d) | -2-(3-methylpyridyl) | -sec-butyl |
| A32 (a, b, c, and d) | -2-(3-methylpyridyl) | -cyclohexyl |
| A33 (a, b, c, and d) | -2-(3-methylpyridyl) | -t-butoxy |
| A34 (a, b, c, and d) | -2-(3-methylpyridyl) | -isopropoxy |
| A35 (a, b, c, and d) | -2-(3-methylpyridyl) | —CF$_3$ |
| A36 (a, b, c, and d) | -2-(3-methylpyridyl) | —OCF$_3$ |
| A37 (a, b, c, and d) | -2-(3-methylpyridyl) | —Cl |
| A38 (a, b, c, and d) | -2-(3-methylpyridyl) | —Br |
| A39 (a, b, c, and d) | -2-(3-methylpyridyl) | —I |
| A40 (a, b, c, and d) | -2-(3-methylpyridyl) | -n-butyl |

TABLE I-continued

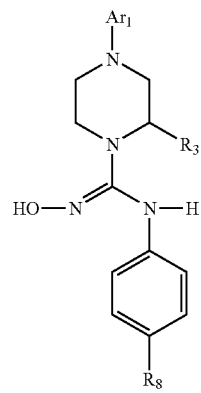

and pharmaceutically acceptable salts thereof, wherein:

| Compound | Ar$_1$ | R$_8$ |
|---|---|---|
| A41 (a, b, c, and d) | -2-(3-methylpyridyl) | -n-propyl |
| A42 (a, b, c, and d) | -2-(3-methylpyridyl) | -iso-propyl |
| A43 (a, b, c, and d) | -2-(3-CF$_3$-pyridyl) | -t-butyl |
| A44 (a, b, c, and d) | -2-(3-CF$_3$-pyridyl) | -iso-butyl |
| A45 (a, b, c, and d) | -2-(3-CF$_3$-pyridyl) | -sec-butyl |
| A46 (a, b, c, and d) | -2-(3-CF$_3$-pyridyl) | -cyclohexyl |
| A47 (a, b, c, and d) | -2-(3-CF$_3$-pyridyl) | -t-butoxy |
| A48 (a, b, c, and d) | -2-(3-CF$_3$-pyridyl) | -isopropoxy |
| A49 (a, b, c, and d) | -2-(3-CF$_3$-pyridyl) | —CF$_3$ |
| A50 (a, b, c, and d) | -2-(3-CF$_3$-pyridyl) | —OCF$_3$ |
| A51 (a, b, c, and d) | -2-(3-CF$_3$-pyridyl) | —Cl |
| A52 (a, b, c, and d) | -2-(3-CF$_3$-pyridyl) | —Br |
| A53 (a, b, c, and d) | -2-(3-CF$_3$-pyridyl) | —I |
| A54 (a, b, c, and d) | -2-(3-CF$_3$-pyridyl) | -n-butyl |
| A55 (a, b, c, and d) | -2-(3-CF$_3$-pyridyl) | -n-propyl |
| A56 (a, b, c, and d) | -2-(3-CF$_3$-pyridyl) | -iso-propyl |
| A57 (a, b, c, and d) | -2-(3-CHF$_2$-pyridyl) | -t-butyl |
| A58 (a, b, c, and d) | -2-(3-CHF$_2$-pyridyl) | -iso-butyl |
| A59 (a, b, c, and d) | -2-(3-CHF$_2$-pyridyl) | -sec-butyl |
| A60 (a, b, c, and d) | -2-(3-CHF$_2$-pyridyl) | -cyclohexyl |
| A61 (a, b, c, and d) | -2-(3-CHF$_2$-pyridyl) | -t-butoxy |
| A62 (a, b, c, and d) | -2-(3-CHF$_2$-pyridyl) | -isopropoxy |
| A63 (a, b, c, and d) | -2-(3-CHF$_2$-pyridyl) | —CF$_3$ |
| A64 (a, b, c, and d) | -2-(3-CHF$_2$-pyridyl) | —OCF$_3$ |
| A65 (a, b, c, and d) | -2-(3-CHF$_2$-pyridyl) | —Cl |
| A66 (a, b, c, and d) | -2-(3-CHF$_2$-pyridyl) | —Br |
| A67 (a, b, c, and d) | -2-(3-CHF$_2$-pyridyl) | —I |
| A68 (a, b, c, and d) | -2-(3-CHF$_2$-pyridyl) | -n-butyl |
| A69 (a, b, c, and d) | -2-(3-CHF$_2$-pyridyl) | -n-propyl |
| A70 (a, b, c, and d) | -2-(3-CHF$_2$-pyridyl) | -iso-propyl |
| A71 (a, b, c, and d) | -2-(3-hydroxypyridyl) | -t-butyl |
| A72 (a, b, c, and d) | -2-(3-hydroxypyridyl) | -iso-butyl |
| A73 (a, b, c, and d) | -2-(3-hydroxypyridyl) | -sec-butyl |
| A74 (a, b, c, and d) | -2-(3-hydroxypyridyl) | -cyclohexyl |
| A75 (a, b, c, and d) | -2-(3-hydroxypyridyl) | -t-butoxy |
| A76 (a, b, c, and d) | -2-(3-hydroxypyridyl) | -isopropoxy |
| A77 (a, b, c, and d) | -2-(3-hydroxypyridyl) | —CF$_3$ |
| A78 (a, b, c, and d) | -2-(3-hydroxypyridyl) | —OCF$_3$ |
| A79 (a, b, c, and d) | -2-(3-hydroxypyridyl) | —Cl |
| A80 (a, b, c, and d) | -2-(3-hydroxypyridyl) | —Br |
| A81 (a, b, c, and d) | -2-(3-hydroxypyridyl) | —I |
| A82 (a, b, c, and d) | -2-(3-hydroxypyridyl) | -n-butyl |
| A83 (a, b, c, and d) | -2-(3-hydroxypyridyl) | -n-propyl |
| A84 (a, b, c, and d) | -2-(3-hydroxypyridyl) | -iso-propyl |
| A85 (a, b, c, and d) | -2-(3-nitropyridyl) | -t-butyl |
| A86 (a, b, c, and d) | -2-(3-nitropyridyl) | -iso-butyl |
| A87 (a, b, c, and d) | -2-(3-nitropyridyl) | -sec-butyl |
| A88 (a, b, c, and d) | -2-(3-nitropyridyl) | -cyclohexyl |
| A89 (a, b, c, and d) | -2-(3-nitropyridyl) | -t-butoxy |
| A90 (a, b, c, and d) | -2-(3-nitropyridyl) | -isopropoxy |
| A91 (a, b, c, and d) | -2-(3-nitropyridyl) | —CF$_3$ |
| A92 (a, b, c, and d) | -2-(3-nitropyridyl) | —OCF$_3$ |
| A93 (a, b, c, and d) | -2-(3-nitropyridyl) | —Cl |
| A94 (a, b, c, and d) | -2-(3-nitropyridyl) | —Br |
| A95 (a, b, c, and d) | -2-(3-nitropyridyl) | —I |

TABLE I-continued

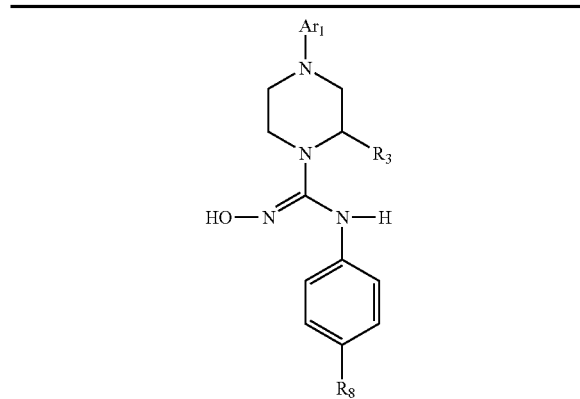

and pharmaceutically acceptable salts thereof, wherein:

| Compound | Ar$_1$ | R$_8$ |
|---|---|---|
| A96 (a, b, c, and d) | -2-(3-nitropyridyl) | -n-butyl |
| A97 (a, b, c, and d) | -2-(3-nitropyridyl) | -n-propyl |
| A98 (a, b, c, and d) | -2-(3-nitropyridyl) | -iso-propyl |
| A99 (a, b, c, and d) | -2-(3-cyanopyridyl) | -t-butyl |
| A100 (a, b, c, and d) | -2-(3-cyanopyridyl) | -iso-butyl |
| A101 (a, b, c, and d) | -2-(3-cyanopyridyl) | -sec-butyl |
| A102 (a, b, c, and d) | -2-(3-cyanopyridyl) | -cyclohexyl |
| A103 (a, b, c, and d) | -2-(3-cyanopyridyl) | -t-butoxy |
| A104 (a, b, c, and d) | -2-(3-cyanopyridyl) | -isopropoxy |
| A105 (a, b, c, and d) | -2-(3-cyanopyridyl) | —CF$_3$ |
| A106 (a, b, c, and d) | -2-(3-cyanopyridyl) | —OCF$_3$ |
| A107 (a, b, c, and d) | -2-(3-cyanopyridyl) | —Cl |
| A108 (a, b, c, and d) | -2-(3-cyanopyridyl) | —Br |
| A109 (a, b, c, and d) | -2-(3-cyanopyridyl) | —I |
| A110 (a, b, c, and d) | -2-(3-cyanopyridyl) | -n-butyl |
| A111 (a, b, c, and d) | -2-(3-cyanopyridyl) | -n-propyl |
| A112 (a, b, c, and d) | -2-(3-cyanopyridyl) | -isopropyl |
| A113 (a, b, c, and d) | -2-(3-bromopyridyl) | -t-butyl |
| A114 (a, b, c, and d) | -2-(3-bromopyridyl) | -iso-butyl |
| A115 (a, b, c, and d) | -2-(3-bromopyridyl) | -sec-butyl |
| A116 (a, b, c, and d) | -2-(3-bromopyridyl) | -cyclohexyl |
| A117 (a, b, c, and d) | -2-(3-bromopyridyl) | -t-butoxy |
| A118 (a, b, c, and d) | -2-(3-bromopyridyl) | -isopropoxy |
| A119 (a, b, c, and d) | -2-(3-bromopyridyl) | —CF$_3$ |
| A120 (a, b, c, and d) | -2-(3-bromopyridyl) | —OCF$_3$ |
| A121 (a, b, c, and d) | -2-(3-bromopyridyl) | —Cl |
| A122 (a, b, c, and d) | -2-(3-bromopyridyl) | —Br |
| A123 (a, b, c, and d) | -2-(3-bromopyridyl) | —I |
| A124 (a, b, c, and d) | -2-(3-bromopyridyl) | -n-butyl |
| A125 (a, b, c, and d) | -2-(3-bromopyridyl) | -n-propyl |
| A126 (a, b, c, and d) | -2-(3-bromopyridyl) | -iso-propyl |
| A127 (a, b, c, and d) | -2-(3-iodopyridyl) | -t-butyl |
| A128 (a, b, c, and d) | -2-(3-iodopyridyl) | -iso-butyl |
| A129 (a, b, c, and d) | -2-(3-iodopyridyl) | -sec-butyl |
| A130 (a, b, c, and d) | -2-(3-iodopyridyl) | -cyclohexyl |
| A131 (a, b, c, and d) | -2-(3-iodopyridyl) | -t-butoxy |
| A132 (a, b, c, and d) | -2-(3-iodopyridyl) | -isopropoxy |
| A133 (a, b, c, and d) | -2-(3-iodopyridyl) | —CF$_3$ |
| A134 (a, b, c, and d) | -2-(3-iodopyridyl) | —OCF$_3$ |
| A135 (a, b, c, and d) | -2-(3-iodopyridyl) | —Cl |
| A136 (a, b, c, and d) | -2-(3-iodopyridyl) | —Br |
| A137 (a, b, c, and d) | -2-(3-iodopyridyl) | —I |
| A138 (a, b, c, and d) | -2-(3-iodopyridyl) | -n-butyl |
| A139 (a, b, c, and d) | -2-(3-iodopyridyl) | -n-propyl |
| A140 (a, b, c, and d) | -2-(3-iodopyridyl) | -iso-propyl |
| A141 (a, b, c, and d) | -4-(5-chloropyrimidinyl) | -t-butyl |
| A142 (a, b, c, and d) | -4-(5-chloropyrimidinyl) | -iso-butyl |
| A143 (a, b, c, and d) | -4-(5-chloropyrimidinyl) | -sec-butyl |
| A144 (a, b, c, and d) | -4-(5-chloropyrimidinyl) | -cyclohexyl |
| A145 (a, b, c, and d) | -4-(5-chloropyrimidinyl) | -t-butoxy |
| A146 (a, b, c, and d) | -4-(5-chloropyrimidinyl) | -isopropoxy |
| A147 (a, b, c, and d) | -4-(5-chloropyrimidinyl) | —CF$_3$ |
| A148 (a, b, c, and d) | -4-(5-chloropyrimidinyl) | —OCF$_3$ |
| A149 (a, b, c, and d) | -4-(5-chloropyrimidinyl) | —Cl |
| A150 (a, b, c, and d) | -4-(5-chloropyrimidinyl) | —Br |

TABLE I-continued

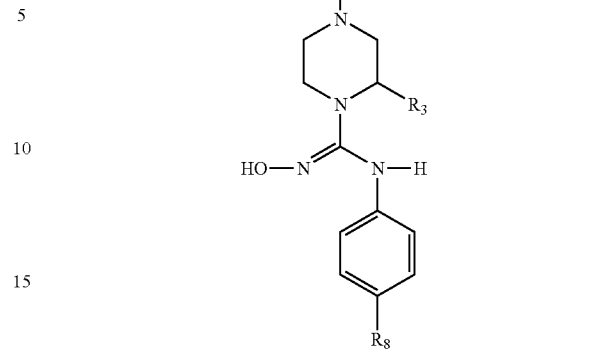

and pharmaceutically acceptable salts thereof, wherein:

| Compound | Ar$_1$ | R$_8$ |
|---|---|---|
| A151 (a, b, c, and d) | -4-(5-chloropyrimidinyl) | —I |
| A152 (a, b, c, and d) | -4-(5-chloropyrimidinyl) | -n-butyl |
| A153 (a, b, c, and d) | -4-(5-chloropyrimidinyl) | -n-propyl |
| A154 (a, b, c, and d) | -4-(5-chloropyrimidinyl) | -iso-propyl |
| A155 (a, b, c, and d) | -4-(5-methylpyrimidinyl) | -t-butyl |
| A156 (a, b, c, and d) | -4-(5-methylpyrimidinyl) | -iso-butyl |
| A157 (a, b, c, and d) | -4-(5-methylpyrimidinyl) | -sec-butyl |
| A158 (a, b, c, and d) | -4-(5-methylpyrimidinyl) | -cyclohexyl |
| A159 (a, b, c, and d) | -4-(5-methylpyrimidinyl) | -t-butoxy |
| A160 (a, b, c, and d) | -4-(5-methylpyrimidinyl) | -isopropoxy |
| A161 (a, b, c, and d) | -4-(5-methylpyrimidinyl) | —CF$_3$ |
| A162 (a, b, c, and d) | -4-(5-methylpyrimidinyl) | —OCF$_3$ |
| A163 (a, b, c, and d) | -4-(5-methylpyrimidinyl) | —Cl |
| A164 (a, b, c, and d) | -4-(5-methylpyrimidinyl) | —Br |
| A165 (a, b, c, and d) | -4-(5-methylpyrimidinyl) | —I |
| A166 (a, b, c, and d) | -4-(5-methylpyrimidinyl) | -n-butyl |
| A167 (a, b, c, and d) | -4-(5-methylpyrimidinyl) | -n-propyl |
| A168 (a, b, c, and d) | -4-(5-methylpyrimidinyl) | -iso-propyl |
| A169 (a, b, c, and d) | -4-(5-fluoropyrimidinyl) | -t-butyl |
| A170 (a, b, c, and d) | -4-(5-fluoropyrimidinyl) | -iso-butyl |
| A171 (a, b, c, and d) | -4-(5-fluoropyrimidinyl) | -sec-butyl |
| A172 (a, b, c, and d) | -4-(5-fluoropyrimidinyl) | -cyclohexyl |
| A173 (a, b, c, and d) | -4-(5-fluoropyrimidinyl) | -t-butoxy |
| A174 (a, b, c, and d) | -4-(5-fluoropyrimidinyl) | -isopropoxy |
| A175 (a, b, c, and d) | -4-(5-fluoropyrimidinyl) | —CF$_3$ |
| A176 (a, b, c, and d) | -4-(5-fluoropyrimidinyl) | —OCF$_3$ |
| A177 (a, b, c, and d) | -4-(5-fluoropyrimidinyl) | —Cl |
| A178 (a, b, c, and d) | -4-(5-fluoropyrimidinyl) | —Br |
| A179 (a, b, c, and d) | -4-(5-fluoropyrimidinyl) | —I |
| A180 (a, b, c, and d) | -4-(5-fluoropyrimidinyl) | -n-butyl |
| A181 (a, b, c, and d) | -4-(5-fluoropyrimidinyl) | -n-propyl |
| A182 (a, b, c, and d) | -4-(5-fluoropyrimidinyl) | -iso-propyl |
| A183 (a, b, c, and d) | -2-(3-chloropyrazinyl) | -t-butyl |
| A184 (a, b, c, and d) | -2-(3-chloropyrazinyl) | -iso-butyl |
| A185 (a, b, c, and d) | -2-(3-chloropyrazinyl) | -sec-butyl |
| A186 (a, b, c, and d) | -2-(3-chloropyrazinyl) | -cyclohexyl |
| A187 (a, b, c, and d) | -2-(3-chloropyrazinyl) | -t-butoxy |
| A188 (a, b, c, and d) | -2-(3-chloropyrazinyl) | -isopropoxy |
| A189 (a, b, c, and d) | -2-(3-chloropyrazinyl) | —CF$_3$ |
| A190 (a, b, c, and d) | -2-(3-chloropyrazinyl) | —OCF$_3$ |
| A191 (a, b, c, and d) | -2-(3-chloropyrazinyl) | —Cl |
| A192 (a, b, c, and d) | -2-(3-chloropyrazinyl) | —Br |
| A193 (a, b, c, and d) | -2-(3-chloropyrazinyl) | —I |
| A194 (a, b, c, and d) | -2-(3-chloropyrazinyl) | -n-butyl |
| A195 (a, b, c, and d) | -2-(3-chloropyrazinyl) | -n-propyl |
| A196 (a, b, c, and d) | -2-(3-chloropyrazinyl) | -iso-propyl |
| A197 (a, b, c, and d) | -2-(3-methylpyrazinyl) | -t-butyl |
| A198 (a, b, c, and d) | -2-(3-methylpyrazinyl) | -iso-butyl |
| A199 (a, b, c, and d) | -2-(3-methylpyrazinyl) | -sec-butyl |
| A200 (a, b, c, and d) | -2-(3-methylpyrazinyl) | -cyclohexyl |
| A201 (a, b, c, and d) | -2-(3-methylpyrazinyl) | -t-butoxy |
| A202 (a, b, c, and d) | -2-(3-methylpyrazinyl) | -isopropoxy |
| A203 (a, b, c, and d) | -2-(3-methylpyrazinyl) | —CF$_3$ |
| A204 (a, b, c, and d) | -2-(3-methylpyrazinyl) | —OCF$_3$ |
| A205 (a, b, c, and d) | -2-(3-methylpyrazinyl) | —Cl |

TABLE I-continued

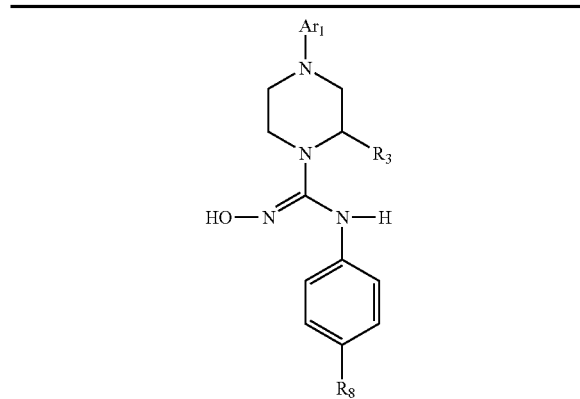

and pharmaceutically acceptable salts thereof, wherein:

| Compound | Ar$_1$ | R$_8$ |
|---|---|---|
| A206 (a, b, c, and d) | -2-(3-methylpyrazinyl) | —Br |
| A207 (a, b, c, and d) | -2-(3-methylpyrazinyl) | —I |
| A208 (a, b, c, and d) | -2-(3-methylpyrazinyl) | -n-butyl |
| A209 (a, b, c, and d) | -2-(3-methylpyrazinyl) | -n-propyl |
| A210 (a, b, c, and d) | -2-(3-methylpyrazinyl) | -iso-propyl |
| A211 (a, b, c, and d) | -2-(3-fluoropyrazinyl) | -t-butyl |
| A212 (a, b, c, and d) | -2-(3-fluoropyrazinyl) | -iso-butyl |
| A213 (a, b, c, and d) | -2-(3-fluoropyrazinyl) | -sec-butyl |
| A214 (a, b, c, and d) | -2-(3-fluoropyrazinyl) | -cyclohexyl |
| A215 (a, b, c, and d) | -2-(3-fluoropyrazinyl) | -t-butoxy |
| A216 (a, b, c, and d) | -2-(3-fluoropyrazinyl) | -isopropoxy |
| A217 (a, b, c, and d) | -2-(3-fluoropyrazinyl) | —CF$_3$ |
| A218 (a, b, c, and d) | -2-(3-fluoropyrazinyl) | —OCF$_3$ |
| A219 (a, b, c, and d) | -2-(3-fluoropyrazinyl) | —Cl |
| A220 (a, b, c, and d) | -2-(3-fluoropyrazinyl) | —Br |
| A221 (a, b, c, and d) | -2-(3-fluoropyrazinyl) | —I |
| A222 (a, b, c, and d) | -2-(3-fluoropyrazinyl) | -n-butyl |
| A223 (a, b, c, and d) | -2-(3-fluoropyrazinyl) | -n-propyl |
| A224 (a, b, c, and d) | -2-(3-fluoropyrazinyl) | -iso-propyl |
| A225 (a, b, c, and d) | -3-(4-chloropyridazinyl) | -t-butyl |
| A226 (a, b, c, and d) | -3-(4-chloropyridazinyl) | -iso-butyl |
| A227 (a, b, c, and d) | -3-(4-chloropyridazinyl) | -sec-butyl |
| A228 (a, b, c, and d) | -3-(4-chloropyridazinyl) | -cyclohexyl |
| A229 (a, b, c, and d) | -3-(4-chloropyridazinyl) | -t-butoxy |
| A230 (a, b, c, and d) | -3-(4-chloropyridazinyl) | -isopropoxy |
| A231 (a, b, c, and d) | -3-(4-chloropyridazinyl) | —CF$_3$ |
| A232 (a, b, c, and d) | -3-(4-chloropyridazinyl) | —OCF$_3$ |
| A233 (a, b, c, and d) | -3-(4-chloropyridazinyl) | —Cl |
| A234 (a, b, c, and d) | -3-(4-chloropyridazinyl) | —Br |
| A235 (a, b, c, and d) | -3-(4-chloropyridazinyl) | —I |
| A236 (a, b, c, and d) | -3-(4-chloropyridazinyl) | -n-butyl |
| A237 (a, b, c, and d) | -3-(4-chloropyridazinyl) | -n-propyl |
| A238 (a, b, c, and d) | -3-(4-chloropyridazinyl) | -iso-propyl |
| A239 (a, b, c, and d) | -3-(4-methylpyridazinyl) | -t-butyl |
| A240 (a, b, c, and d) | -3-(4-methylpyridazinyl) | -iso-butyl |
| A241 (a, b, c, and d) | -3-(4-methylpyridazinyl) | -sec-butyl |
| A242 (a, b, c, and d) | -3-(4-methylpyridazinyl) | -cyclohexyl |
| A243 (a, b, c, and d) | -3-(4-methylpyridazinyl) | -t-butoxy |
| A244 (a, b, c, and d) | -3-(4-methylpyridazinyl) | -isopropoxy |
| A245 (a, b, c, and d) | -3-(4-methylpyridazinyl) | —CF$_3$ |
| A246 (a, b, c, and d) | -3-(4-methylpyridazinyl) | —OCF$_3$ |
| A247 (a, b, c, and d) | -3-(4-methylpyridazinyl) | —Cl |
| A248 (a, b, c, and d) | -3-(4-methylpyridazinyl) | —Br |
| A249 (a, b, c, and d) | -3-(4-methylpyridazinyl) | —I |
| A250 (a, b, c, and d) | -3-(4-methylpyridazinyl) | -n-butyl |
| A251 (a, b, c, and d) | -3-(4-methylpyridazinyl) | -n-propyl |
| A252 (a, b, c, and d) | -3-(4-methylpyridazinyl) | -iso-propyl |
| A253 (a, b, c, and d) | -3-(4-fluoropyridazinyl) | -t-butyl |
| A254 (a, b, c, and d) | -3-(4-fluoropyridazinyl) | -iso-butyl |
| A255 (a, b, c, and d) | -3-(4-fluoropyridazinyl) | -sec-butyl |
| A256 (a, b, c, and d) | -3-(4-fluoropyridazinyl) | -cyclohexyl |
| A257 (a, b, c, and d) | -3-(4-fluoropyridazinyl) | -t-butoxy |
| A258 (a, b, c, and d) | -3-(4-fluoropyridazinyl) | -isopropoxy |
| A259 (a, b, c, and d) | -3-(4-fluoropyridazinyl) | —CF$_3$ |
| A260 (a, b, c, and d) | -3-(4-fluoropyridazinyl) | —OCF$_3$ |

TABLE I-continued

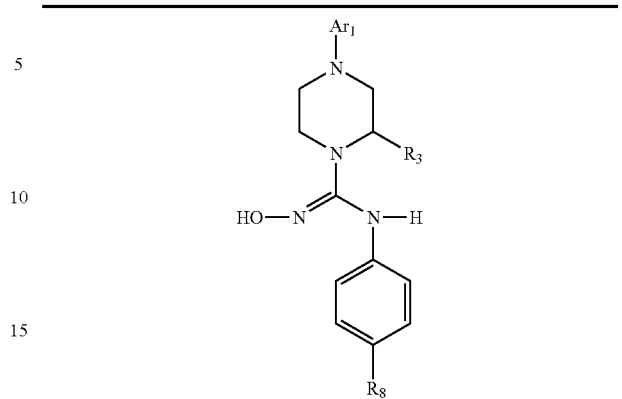

and pharmaceutically acceptable salts thereof, wherein:

| Compound | Ar$_1$ | R$_8$ |
|---|---|---|
| A261 (a, b, c, and d) | -3-(4-fluoropyridazinyl) | —Cl |
| A262 (a, b, c, and d) | -3-(4-fluoropyridazinyl) | —Br |
| A263 (a, b, c, and d) | -3-(4-fluoropyridazinyl) | —I |
| A264 (a, b, c, and d) | -3-(4-fluoropyridazinyl) | -n-butyl |
| A265 (a, b, c, and d) | -3-(4-fluoropyridazinyl) | -n-propyl |
| A266 (a, b, c, and d) | -3-(4-fluoropyridazinyl) | -iso-propyl |
| A267 (a, b, c, and d) | -5-(4-chlorothiadiazolyl) | -t-butyl |
| A268 (a, b, c, and d) | -5-(4-chlorothiadiazolyl) | -iso-butyl |
| A269 (a, b, c, and d) | -5-(4-chlorothiadiazolyl) | -sec-butyl |
| A270 (a, b, c, and d) | -5-(4-chlorothiadiazolyl) | -cyclohexyl |
| A271 (a, b, c, and d) | -5-(4-chlorothiadiazolyl) | -t-butoxy |
| A272 (a, b, c, and d) | -5-(4-chlorothiadiazolyl) | -isopropoxy |
| A273 (a, b, c, and d) | -5-(4-chlorothiadiazolyl) | —CF$_3$ |
| A274 (a, b, c, and d) | -5-(4-chlorothiadiazolyl) | —OCF$_3$ |
| A275 (a, b, c, and d) | -5-(4-chlorothiadiazolyl) | —Cl |
| A276 (a, b, c, and d) | -5-(4-chlorothiadiazolyl) | —Br |
| A277 (a, b, c, and d) | -5-(4-chlorothiadiazolyl) | —I |
| A278 (a, b, c, and d) | -5-(4-chlorothiadiazolyl) | -n-butyl |
| A279 (a, b, c, and d) | -5-(4-chlorothiadiazolyl) | -n-propyl |
| A280 (a, b, c, and d) | -5-(4-chlorothiadiazolyl) | -iso-propyl |
| A281 (a, b, c, and d) | -5-(4-methylthiadiazolyl) | -t-butyl |
| A282 (a, b, c, and d) | -5-(4-methylthiadiazolyl) | -iso-butyl |
| A283 (a, b, c, and d) | -5-(4-methylthiadiazolyl) | -sec-butyl |
| A284 (a, b, c, and d) | -5-(4-methylthiadiazolyl) | -cyclohexyl |
| A285 (a, b, c, and d) | -5-(4-methylthiadiazolyl) | -t-butoxy |
| A286 (a, b, c, and d) | -5-(4-methylthiadiazolyl) | -isopropoxy |
| A287 (a, b, c, and d) | -5-(4-methylthiadiazolyl) | —CF$_3$ |
| A288 (a, b, c, and d) | -5-(4-methylthiadiazolyl) | —OCF$_3$ |
| A289 (a, b, c, and d) | -5-(4-methylthiadiazolyl) | —Cl |
| A290 (a, b, c, and d) | -5-(4-methylthiadiazolyl) | —Br |
| A291 (a, b, c, and d) | -5-(4-methylthiadiazolyl) | —I |
| A292 (a, b, c, and d) | -5-(4-methylthiadiazolyl) | -n-butyl |
| A293 (a, b, c, and d) | -5-(4-methylthiadiazolyl) | -n-propyl |
| A294 (a, b, c, and d) | -5-(4-methylthiadiazolyl) | -iso-propyl |
| A295 (a, b, c, and d) | -5-(4-fluorothiadiazolyl) | -t-butyl |
| A296 (a, b, c, and d) | -5-(4-fluorothiadiazolyl) | -iso-butyl |
| A297 (a, b, c, and d) | -5-(4-fluorothiadiazolyl) | -sec-butyl |
| A298 (a, b, c, and d) | -5-(4-fluorothiadiazolyl) | -cyclohexyl |
| A299 (a, b, c, and d) | -5-(4-fluorothiadiazolyl) | -t-butoxy |
| A300 (a, b, c, and d) | -5-(4-fluorothiadiazolyl) | -isopropoxy |
| A301 (a, b, c, and d) | -5-(4-fluorothiadiazolyl) | —CF$_3$ |
| A302 (a, b, c, and d) | -5-(4-fluorothiadiazolyl) | —OCF$_3$ |
| A303 (a, b, c, and d) | -5-(4-fluorothiadiazolyl) | —Cl |
| A304 (a, b, c, and d) | -5-(4-fluorothiadiazolyl) | —Br |
| A305 (a, b, c, and d) | -5-(4-fluorothiadiazolyl) | —I |
| A306 (a, b, c, and d) | -5-(4-fluorothiadiazolyl) | -n-butyl |
| A307 (a, b, c, and d) | -5-(4-fluorothiadiazolyl) | -n-propyl |
| A308 (a, b, c, and d) | -5-(4-fluorothiadiazolyl) | -iso-propyl |

"a" means R$_3$ is —H.
"b" means R$_3$ is —CH$_3$ and the Hydroxyiminopiperazine Compound is racemic.
"c" means R$_3$ is —CH$_3$ and the carbon atom to which R$_3$ is attached is in the (R) configuration.
"d" means R$_3$ is —CH$_3$ and the carbon atom to which R$_3$ is attached is in the (S) configuration.

TABLE II

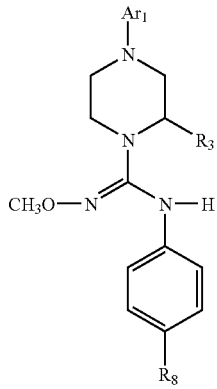

and pharmaceutically acceptable salts thereof, wherein:

| Compound | Ar₁ | R₈ |
|---|---|---|
| B1 (a, b, c, and d) | -2-(3-chloropyridyl) | -t-butyl |
| B2 (a, b, c, and d) | -2-(3-chloropyridyl) | -iso-butyl |
| B3 (a, b, c, and d) | -2-(3-chloropyridyl) | -sec-butyl |
| B4 (a, b, c, and d) | -2-(3-chloropyridyl) | -cyclohexyl |
| B5 (a, b, c, and d) | -2-(3-chloropyridyl) | -t-butoxy |
| B6 (a, b, c, and d) | -2-(3-chloropyridyl) | -isopropoxy |
| B7 (a, b, c, and d) | -2-(3-chloropyridyl) | —$CF_3$ |
| B8 (a, b, c, and d) | -2-(3-chloropyridyl) | —$OCF_3$ |
| B9 (a, b, c, and d) | -2-(3-chloropyridyl) | —Cl |
| B10 (a, b, c, and d) | -2-(3-chloropyridyl) | —Br |
| B11 (a, b, c, and d) | -2-(3-chloropyridyl) | —I |
| B12 (a, b, c, and d) | -2-(3-chloropyridyl) | -n-butyl |
| B13 (a, b, c, and d) | -2-(3-chloropyridyl) | -n-propyl |
| B14 (a, b, c, and d) | -2-(3-chloropyridyl) | -iso-propyl |
| B15 (a, b, c, and d) | -2-(3-fluoropyridyl) | -t-butyl |
| B16 (a, b, c, and d) | -2-(3-fluoropyridyl) | -iso-butyl |
| B17 (a, b, c, and d) | -2-(3-fluoropyridyl) | -sec-butyl |
| B18 (a, b, c, and d) | -2-(3-fluoropyridyl) | -cyclohexyl |
| B19 (a, b, c, and d) | -2-(3-fluoropyridyl) | -t-butoxy |
| B20 (a, b, c, and d) | -2-(3-fluoropyridyl) | -isopropoxy |
| B21 (a, b, c, and d) | -2-(3-fluoropyridyl) | —$CF_3$ |
| B22 (a, b, c, and d) | -2-(3-fluoropyridyl) | —$OCF_3$ |
| B23 (a, b, c, and d) | -2-(3-fluoropyridyl) | —Cl |
| B24 (a, b, c, and d) | -2-(3-fluoropyridyl) | —Br |
| B25 (a, b, c, and d) | -2-(3-fluoropyridyl) | —I |
| B26 (a, b, c, and d) | -2-(3-fluoropyridyl) | -n-butyl |
| B27 (a, b, c, and d) | -2-(3-fluoropyridyl) | -n-propyl |
| B28 (a, b, c, and d) | -2-(3-fluoropyridyl) | -iso-propyl |
| B29 (a, b, c, and d) | -2-(3-methylpyridyl) | -t-butyl |
| B30 (a, b, c, and d) | -2-(3-methylpyridyl) | -iso-butyl |
| B31 (a, b, c, and d) | -2-(3-methylpyridyl) | -sec-butyl |
| B32 (a, b, c, and d) | -2-(3-methylpyridyl) | -cyclohexyl |
| B33 (a, b, c, and d) | -2-(3-methylpyridyl) | -t-butoxy |
| B34 (a, b, c, and d) | -2-(3-methylpyridyl) | -isopropoxy |
| B35 (a, b, c, and d) | -2-(3-methylpyridyl) | —$CF_3$ |
| B36 (a, b, c, and d) | -2-(3-methylpyridyl) | —$OCF_3$ |
| B37 (a, b, c, and d) | -2-(3-methylpyridyl) | —Cl |
| B38 (a, b, c, and d) | -2-(3-methylpyridyl) | —Br |
| B39 (a, b, c, and d) | -2-(3-methylpyridyl) | —I |
| B40 (a, b, c, and d) | -2-(3-methylpyridyl) | -n-butyl |
| B41 (a, b, c, and d) | -2-(3-methylpyridyl) | -n-propyl |
| B42 (a, b, c, and d) | -2-(3-methylpyridyl) | -iso-propyl |
| B43 (a, b, c, and d) | -2-(3-$CF_3$-pyridyl) | -t-butyl |
| B44 (a, b, c, and d) | -2-(3-$CF_3$-pyridyl) | -iso-butyl |
| B45 (a, b, c, and d) | -2-(3-$CF_3$-pyridyl) | -sec-butyl |
| B46 (a, b, c, and d) | -2-(3-$CF_3$-pyridyl) | -cyclohexyl |
| B47 (a, b, c, and d) | -2-(3-$CF_3$-pyridyl) | -t-butoxy |
| B48 (a, b, c, and d) | -2-(3-$CF_3$-pyridyl) | -isopropoxy |
| B49 (a, b, c, and d) | -2-(3-$CF_3$-pyridyl) | —$CF_3$ |
| B50 (a, b, c, and d) | -2-(3-$CF_3$-pyridyl) | —$OCF_3$ |
| B51 (a, b, c, and d) | -2-(3-$CF_3$-pyridyl) | —Cl |
| B52 (a, b, c, and d) | -2-(3-$CF_3$-pyridyl) | —Br |
| B53 (a, b, c, and d) | -2-(3-$CF_3$-pyridyl) | —I |
| B54 (a, b, c, and d) | -2-(3-$CF_3$-pyridyl) | -n-butyl |
| B55 (a, b, c, and d) | -2-(3-$CF_3$-pyridyl) | -n-propyl |

TABLE II-continued

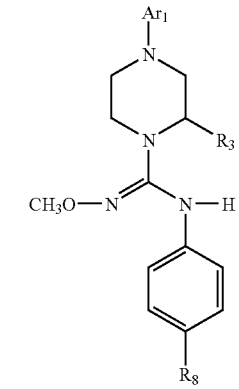

and pharmaceutically acceptable salts thereof, wherein:

| Compound | Ar₁ | R₈ |
|---|---|---|
| B56 (a, b, c, and d) | -2-(3-$CF_3$-pyridyl) | -iso-propyl |
| B57 (a, b, c, and d) | -2-(3-$CHF_2$-pyridyl) | -t-butyl |
| B58 (a, b, c, and d) | -2-(3-$CHF_2$-pyridyl) | -iso-butyl |
| B59 (a, b, c, and d) | -2-(3-$CHF_2$-pyridyl) | -sec-butyl |
| B60 (a, b, c, and d) | -2-(3-$CHF_2$-pyridyl) | -cyclohexyl |
| B61 (a, b, c, and d) | -2-(3-$CHF_2$-pyridyl) | -t-butoxy |
| B62 (a, b, c, and d) | -2-(3-$CHF_2$-pyridyl) | -isopropoxy |
| B63 (a, b, c, and d) | -2-(3-$CHF_2$-pyridyl) | —$CF_3$ |
| B64 (a, b, c, and d) | -2-(3-$CHF_2$-pyridyl) | —$OCF_3$ |
| B65 (a, b, c, and d) | -2-(3-$CHF_2$-pyridyl) | —Cl |
| B66 (a, b, c, and d) | -2-(3-$CHF_2$-pyridyl) | —Br |
| B67 (a, b, c, and d) | -2-(3-$CHF_2$-pyridyl) | —I |
| B68 (a, b, c, and d) | -2-(3-$CHF_2$-pyridyl) | -n-butyl |
| B69 (a, b, c, and d) | -2-(3-$CHF_2$-pyridyl) | -n-propyl |
| B70 (a, b, c, and d) | -2-(3-$CHF_2$-pyridyl) | -iso-propyl |
| B71 (a, b, c, and d) | -2-(3-hydroxypyridyl) | -t-butyl |
| B72 (a, b, c, and d) | -2-(3-hydroxypyridyl) | -iso-butyl |
| B73 (a, b, c, and d) | -2-(3-hydroxypyridyl) | -sec-butyl |
| B74 (a, b, c, and d) | -2-(3-hydroxypyridyl) | -cyclohexyl |
| B75 (a, b, c, and d) | -2-(3-hydroxypyridyl) | -t-butoxy |
| B76 (a, b, c, and d) | -2-(3-hydroxypyridyl) | -isopropoxy |
| B77 (a, b, c, and d) | -2-(3-hydroxypyridyl) | —$CF_3$ |
| B78 (a, b, c, and d) | -2-(3-hydroxypyridyl) | —$OCF_3$ |
| B79 (a, b, c, and d) | -2-(3-hydroxypyridyl) | —Cl |
| B80 (a, b, c, and d) | -2-(3-hydroxypyridyl) | —Br |
| B81 (a, b, c, and d) | -2-(3-hydroxypyridyl) | —I |
| B82 (a, b, c, and d) | -2-(3-hydroxypyridyl) | -n-butyl |
| B83 (a, b, c, and d) | -2-(3-hydroxypyridyl) | -n-propyl |
| B84 (a, b, c, and d) | -2-(3-hydroxypyridyl) | -iso-propyl |
| B85 (a, b, c, and d) | -2-(3-nitropyridyl) | -t-butyl |
| B86 (a, b, c, and d) | -2-(3-nitropyridyl) | -iso-butyl |
| B87 (a, b, c, and d) | -2-(3-nitropyridyl) | -sec-butyl |
| B88 (a, b, c, and d) | -2-(3-nitropyridyl) | -cyclohexyl |
| B89 (a, b, c, and d) | -2-(3-nitropyridyl) | -t-butoxy |
| B90 (a, b, c, and d) | -2-(3-nitropyridyl) | -isopropoxy |
| B91 (a, b, c, and d) | -2-(3-nitropyridyl) | —$CF_3$ |
| B92 (a, b, c, and d) | -2-(3-nitropyridyl) | —$OCF_3$ |
| B93 (a, b, c, and d) | -2-(3-nitropyridyl) | —Cl |
| B94 (a, b, c, and d) | -2-(3-nitropyridyl) | —Br |
| B95 (a, b, c, and d) | -2-(3-nitropyridyl) | —I |
| B96 (a, b, c, and d) | -2-(3-nitropyridyl) | -n-butyl |
| B97 (a, b, c, and d) | -2-(3-nitropyridyl) | -n-propyl |
| B98 (a, b, c, and d) | -2-(3-nitropyridyl) | -iso-propyl |
| B99 (a, b, c, and d) | -2-(3-cyanopyridyl) | -t-butyl |
| B100 (a, b, c, and d) | -2-(3-cyanopyridyl) | -iso-butyl |
| B101 (a, b, c, and d) | -2-(3-cyanopyridyl) | -sec-butyl |
| B102 (a, b, c, and d) | -2-(3-cyanopyridyl) | -cyclohexyl |
| B103 (a, b, c, and d) | -2-(3-cyanopyridyl) | -t-butoxy |
| B104 (a, b, c, and d) | -2-(3-cyanopyridyl) | -isopropoxy |
| B105 (a, b, c, and d) | -2-(3-cyanopyridyl) | —$CF_3$ |
| B106 (a, b, c, and d) | -2-(3-cyanopyridyl) | —$OCF_3$ |
| B107 (a, b, c, and d) | -2-(3-cyanopyridyl) | —Cl |
| B108 (a, b, c, and d) | -2-(3-cyanopyridyl) | —Br |
| B109 (a, b, c, and d) | -2-(3-cyanopyridyl) | —I |
| B110 (a, b, c, and d) | -2-(3-cyanopyridyl) | -n-butyl |

TABLE II-continued

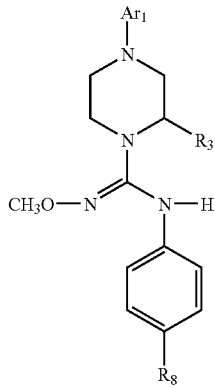

and pharmaceutically acceptable salts thereof, wherein:

| Compound | Ar₁ | R₈ |
|---|---|---|
| B111 (a, b, c, and d) | -2-(3-cyanopyridyl) | -n-propyl |
| B112 (a, b, c, and d) | -2-(3-cyanopyridyl) | -isopropyl |
| B113 (a, b, c, and d) | -2-(3-bromopyridyl) | -t-butyl |
| B114 (a, b, c, and d) | -2-(3-bromopyridyl) | -iso-butyl |
| B115 (a, b, c, and d) | -2-(3-bromopyridyl) | -sec-butyl |
| B116 (a, b, c, and d) | -2-(3-bromopyridyl) | -cyclohexyl |
| B117 (a, b, c, and d) | -2-(3-bromopyridyl) | -t-butoxy |
| B118 (a, b, c, and d) | -2-(3-bromopyridyl) | -isopropoxy |
| B119 (a, b, c, and d) | -2-(3-bromopyridyl) | —CF₃ |
| B120 (a, b, c, and d) | -2-(3-bromopyridyl) | —OCF₃ |
| B121 (a, b, c, and d) | -2-(3-bromopyridyl) | —Cl |
| B122 (a, b, c, and d) | -2-(3-bromopyridyl) | —Br |
| B123 (a, b, c, and d) | -2-(3-bromopyridyl) | —I |
| B124 (a, b, c, and d) | -2-(3-bromopyridyl) | -n-butyl |
| B125 (a, b, c, and d) | -2-(3-bromopyridyl) | -n-propyl |
| B126 (a, b, c, and d) | -2-(3-bromopyridyl) | -iso-propyl |
| B127 (a, b, c, and d) | -2-(3-iodopyridyl) | -t-butyl |
| B128 (a, b, c, and d) | -2-(3-iodopyridyl) | -iso-butyl |
| B129 (a, b, c, and d) | -2-(3-iodopyridyl) | -sec-butyl |
| B130 (a, b, c, and d) | -2-(3-iodopyridyl) | -cyclohexyl |
| B131 (a, b, c, and d) | -2-(3-iodopyridyl) | -t-butoxy |
| B132 (a, b, c, and d) | -2-(3-iodopyridyl) | -isopropoxy |
| B133 (a, b, c, and d) | -2-(3-iodopyridyl) | —CF₃ |
| B134 (a, b, c, and d) | -2-(3-iodopyridyl) | —OCF₃ |
| B135 (a, b, c, and d) | -2-(3-iodopyridyl) | —Cl |
| B136 (a, b, c, and d) | -2-(3-iodopyridyl) | —Br |
| B137 (a, b, c, and d) | -2-(3-iodopyridyl) | —I |
| B138 (a, b, c, and d) | -2-(3-iodopyridyl) | -n-butyl |
| B139 (a, b, c, and d) | -2-(3-iodopyridyl) | -n-propyl |
| B140 (a, b, c, and d) | -2-(3-iodopyridyl) | -iso-propyl |
| B141 (a, b, c, and d) | -4-(5-chloropyrimidinyl) | -t-butyl |
| B142 (a, b, c, and d) | -4-(5-chloropyrimidinyl) | -iso-butyl |
| B143 (a, b, c, and d) | -4-(5-chloropyrimidinyl) | -sec-butyl |
| B144 (a, b, c, and d) | -4-(5-chloropyrimidinyl) | -cyclohexyl |
| B145 (a, b, c, and d) | -4-(5-chloropyrimidinyl) | -t-butoxy |
| B146 (a, b, c, and d) | -4-(5-chloropyrimidinyl) | -isopropoxy |
| B147 (a, b, c, and d) | -4-(5-chloropyrimidinyl) | —CF₃ |
| B148 (a, b, c, and d) | -4-(5-chloropyrimidinyl) | —OCF₃ |
| B149 (a, b, c, and d) | -4-(5-chloropyrimidinyl) | —Cl |
| B150 (a, b, c, and d) | -4-(5-chloropyrimidinyl) | —Br |
| B151 (a, b, c, and d) | -4-(5-chloropyrimidinyl) | —I |
| B152 (a, b, c, and d) | -4-(5-chloropyrimidinyl) | -n-butyl |
| B153 (a, b, c, and d) | -4-(5-chloropyrimidinyl) | -n-propyl |
| B154 (a, b, c, and d) | -4-(5-chloropyrimidinyl) | -iso-propyl |
| B155 (a, b, c, and d) | -4-(5-methylpyrimidinyl) | -t-butyl |
| B156 (a, b, c, and d) | -4-(5-methylpyrimidinyl) | -iso-butyl |
| B157 (a, b, c, and d) | -4-(5-methylpyrimidinyl) | -sec-butyl |
| B158 (a, b, c, and d) | -4-(5-methylpyrimidinyl) | -cyclohexyl |
| B159 (a, b, c, and d) | -4-(5-methylpyrimidinyl) | -t-butoxy |
| B160 (a, b, c, and d) | -4-(5-methylpyrimidinyl) | -isopropoxy |
| B161 (a, b, c, and d) | -4-(5-methylpyrimidinyl) | —CF₃ |
| B162 (a, b, c, and d) | -4-(5-methylpyrimidinyl) | —OCF₃ |
| B163 (a, b, c, and d) | -4-(5-methylpyrimidinyl) | —Cl |
| B164 (a, b, c, and d) | -4-(5-methylpyrimidinyl) | —Br |
| B165 (a, b, c, and d) | -4-(5-methylpyrimidinyl) | —I |

TABLE II-continued

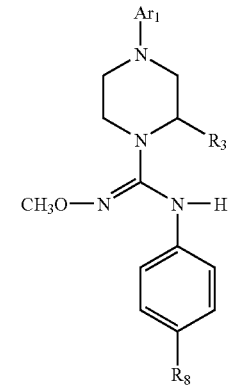

and pharmaceutically acceptable salts thereof, wherein:

| Compound | Ar₁ | R₈ |
|---|---|---|
| B166 (a, b, c, and d) | -4-(5-methylpyrimidinyl) | -n-butyl |
| B167 (a, b, c, and d) | -4-(5-methylpyrimidinyl) | -n-propyl |
| B168 (a, b, c, and d) | -4-(5-methylpyrimidinyl) | -iso-propyl |
| B169 (a, b, c, and d) | -4-(5-fluoropyrimidinyl) | -t-butyl |
| B170 (a, b, c, and d) | -4-(5-fluoropyrimidinyl) | -iso-butyl |
| B171 (a, b, c, and d) | -4-(5-fluoropyrimidinyl) | -sec-butyl |
| B172 (a, b, c, and d) | -4-(5-fluoropyrimidinyl) | -cyclohexyl |
| B173 (a, b, c, and d) | -4-(5-fluoropyrimidinyl) | -t-butoxy |
| B174 (a, b, c, and d) | -4-(5-fluoropyrimidinyl) | -isopropoxy |
| B175 (a, b, c, and d) | -4-(5-fluoropyrimidinyl) | —CF₃ |
| B176 (a, b, c, and d) | -4-(5-fluoropyrimidinyl) | —OCF₃ |
| B177 (a, b, c, and d) | -4-(5-fluoropyrimidinyl) | —Cl |
| B178 (a, b, c, and d) | -4-(5-fluoropyrimidinyl) | —Br |
| B179 (a, b, c, and d) | -4-(5-fluoropyrimidinyl) | —I |
| B180 (a, b, c, and d) | -4-(5-fluoropyrimidinyl) | -n-butyl |
| B181 (a, b, c, and d) | -4-(5-fluoropyrimidinyl) | -n-propyl |
| B182 (a, b, c, and d) | -4-(5-fluoropyrimidinyl) | -iso-propyl |
| B183 (a, b, c, and d) | -2-(3-chloropyrazinyl) | -t-butyl |
| B184 (a, b, c, and d) | -2-(3-chloropyrazinyl) | -iso-butyl |
| B185 (a, b, c, and d) | -2-(3-chloropyrazinyl) | -sec-butyl |
| B186 (a, b, c, and d) | -2-(3-chloropyrazinyl) | -cyclohexyl |
| B187 (a, b, c, and d) | -2-(3-chloropyrazinyl) | -t-butoxy |
| B188 (a, b, c, and d) | -2-(3-chloropyrazinyl) | -isopropoxy |
| B189 (a, b, c, and d) | -2-(3-chloropyrazinyl) | —CF₃ |
| B190 (a, b, c, and d) | -2-(3-chloropyrazinyl) | —OCF₃ |
| B191 (a, b, c, and d) | -2-(3-chloropyrazinyl) | —Cl |
| B192 (a, b, c, and d) | -2-(3-chloropyrazinyl) | —Br |
| B193 (a, b, c, and d) | -2-(3-chloropyrazinyl) | —I |
| B194 (a, b, C, and d) | -2-(3-chloropyrazinyl) | -n-butyl |
| B195 (a, b, c, and d) | -2-(3-chloropyrazinyl) | -n-propyl |
| B196 (a, b, c, and d) | -2-(3-chloropyrazinyl) | -iso-propyl |
| B197 (a, b, c, and d) | -2-(3-methylpyrazinyl) | -t-butyl |
| B198 (a, b, c, and d) | -2-(3-methylpyrazinyl) | -iso-butyl |
| B199 (a, b, c, and d) | -2-(3-methylpyrazinyl) | -sec-butyl |
| B200 (a, b, c, and d) | -2-(3-methylpyrazinyl) | -cyclohexyl |
| B201 (a, b, c, and d) | -2-(3-methylpyrazinyl) | -t-butoxy |
| B202 (a, b, c, and d) | -2-(3-methylpyrazinyl) | -isopropoxy |
| B203 (a, b, c, and d) | -2-(3-methylpyrazinyl) | —CF₃ |
| B204 (a, b, c, and d) | -2-(3-methylpyrazinyl) | —OCF₃ |
| B205 (a, b, c, and d) | -2-(3-methylpyrazinyl) | —Cl |
| B206 (a, b, c, and d) | -2-(3-methylpyrazinyl) | —Br |
| B207 (a, b, c, and d) | -2-(3-methylpyrazinyl) | —I |
| B208 (a, b, c, and d) | -2-(3-methylpyrazinyl) | -n-butyl |
| B209 (a, b, c, and d) | -2-(3-methylpyrazinyl) | -n-propyl |
| B210 (a, b, c, and d) | -2-(3-methylpyrazinyl) | -iso-propyl |
| B211 (a, b, c, and d) | -2-(3-fluoropyrazinyl) | -t-butyl |
| B212 (a, b, c, and d) | -2-(3-fluoropyrazinyl) | -iso-butyl |
| B213 (a, b, c, and d) | -2-(3-fluoropyrazinyl) | -sec-butyl |
| B214 (a, b, c, and d) | -2-(3-fluoropyrazinyl) | -cyclohexyl |
| B215 (a, b, c, and d) | -2-(3-fluoropyrazinyl) | -t-butoxy |
| B216 (a, b, c, and d) | -2-(3-fluoropyrazinyl) | -isopropoxy |
| B217 (a, b, c, and d) | -2-(3-fluoropyrazinyl) | —CF₃ |
| B218 (a, b, c, and d) | -2-(3-fluoropyrazinyl) | —OCF₃ |
| B219 (a, b, c, and d) | -2-(3-fluoropyrazinyl) | —Cl |
| B220 (a, b, c, and d) | -2-(3-fluoropyrazinyl) | —Br |

TABLE II-continued

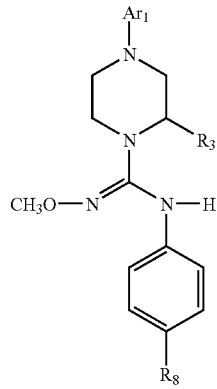

and pharmaceutically acceptable salts thereof, wherein:

| Compound | Ar$_1$ | R$_8$ |
|---|---|---|
| B221 (a, b, c, and d) | -2-(3-fluoropyrazinyl) | —I |
| B222 (a, b, c, and d) | -2-(3-fluoropyrazinyl) | -n-butyl |
| B223 (a, b, c, and d) | -2-(3-fluoropyrazinyl) | -n-propyl |
| B224 (a, b, c, and d) | -2-(3-fluoropyrazinyl) | -iso-propyl |
| B225 (a, b, c, and d) | -3-(4-chloropyridazinyl) | -t-butyl |
| B226 (a, b, c, and d) | -3-(4-chloropyridazinyl) | -iso-butyl |
| B227 (a, b, c, and d) | -3-(4-chloropyridazinyl) | -sec-butyl |
| B228 (a, b, c, and d) | -3-(4-chloropyridazinyl) | -cyclohexyl |
| B229 (a, b, c, and d) | -3-(4-chloropyridazinyl) | -t-butoxy |
| B230 (a, b, c, and d) | -3-(4-chloropyridazinyl) | -isopropoxy |
| B231 (a, b, c, and d) | -3-(4-chloropyridazinyl) | —CF$_3$ |
| B232 (a, b, c, and d) | -3-(4-chloropyridazinyl) | —OCF$_3$ |
| B233 (a, b, c, and d) | -3-(4-chloropyridazinyl) | —Cl |
| B234 (a, b, c, and d) | -3-(4-chloropyridazinyl) | —Br |
| B235 (a, b, c, and d) | -3-(4-chloropyridazinyl) | —I |
| B236 (a, b, c, and d) | -3-(4-chloropyridazinyl) | -n-butyl |
| B237 (a, b, c, and d) | -3-(4-chloropyridazinyl) | -n-propyl |
| B238 (a, b, c, and d) | -3-(4-chloropyridazinyl) | -iso-propyl |
| B239 (a, b, c, and d) | -3-(4-methylpyridazinyl) | -t-butyl |
| B240 (a, b, c, and d) | -3-(4-methylpyridazinyl) | -iso-butyl |
| B241 (a, b, c, and d) | -3-(4-methylpyridazinyl) | -sec-butyl |
| B242 (a, b, c, and d) | -3-(4-methylpyridazinyl) | -cyclohexyl |
| B243 (a, b, c, and d) | -3-(4-methylpyridazinyl) | -t-butoxy |
| B244 (a, b, c, and d) | -3-(4-methylpyridazinyl) | -isopropoxy |
| B245 (a, b, c, and d) | -3-(4-methylpyridazinyl) | —CF$_3$ |
| B246 (a, b, c, and d) | -3-(4-methylpyridazinyl) | —OCF$_3$ |
| B247 (a, b, c, and d) | -3-(4-methylpyridazinyl) | —Cl |
| B248 (a, b, c, and d) | -3-(4-methylpyridazinyl) | —Br |
| B249 (a, b, c, and d) | -3-(4-methylpyridazinyl) | —I |
| B250 (a, b, c, and d) | -3-(4-methylpyridazinyl) | -n-butyl |
| B251 (a, b, c, and d) | -3-(4-methylpyridazinyl) | -n-propyl |
| B252 (a, b, c, and d) | -3-(4-methylpyridazinyl) | -iso-propyl |
| B253 (a, b, c, and d) | -3-(4-fluoropyridazinyl) | -t-butyl |
| B254 (a, b, c, and d) | -3-(4-fluoropyridazinyl) | -iso-butyl |
| B255 (a, b, c, and d) | -3-(4-fluoropyridazinyl) | -sec-butyl |
| B256 (a, b, c, and d) | -3-(4-fluoropyridazinyl) | -cyclohexyl |
| B257 (a, b, c, and d) | -3-(4-fluoropyridazinyl) | -t-butoxy |
| B258 (a, b, c, and d) | -3-(4-fluoropyridazinyl) | -isopropoxy |
| B259 (a, b, c, and d) | -3-(4-fluoropyridazinyl) | —CF$_3$ |
| B260 (a, b, c, and d) | -3-(4-fluoropyridazinyl) | —OCF$_3$ |
| B261 (a, b, c, and d) | -3-(4-fluoropyridazinyl) | —Cl |
| B262 (a, b, c, and d) | -3-(4-fluoropyridazinyl) | —Br |
| B263 (a, b, c, and d) | -3-(4-fluoropyridazinyl) | —I |
| B264 (a, b, c, and d) | -3-(4-fluoropyridazinyl) | -n-butyl |
| B265 (a, b, c, and d) | -3-(4-fluoropyridazinyl) | -n-propyl |
| B266 (a, b, c, and d) | -3-(4-fluoropyridazinyl) | -iso-propyl |
| B267 (a, b, c, and d) | -5-(4-chlorothiadiazolyl) | -t-butyl |
| B268 (a, b, c, and d) | -5-(4-chlorothiadiazolyl) | -iso-butyl |
| B269 (a, b, c, and d) | -5-(4-chlorothiadiazolyl) | -sec-butyl |
| B270 (a, b, c, and d) | -5-(4-chlorothiadiazolyl) | -cyclohexyl |
| B271 (a, b, c, and d) | -5-(4-chlorothiadiazolyl) | -t-butoxy |
| B272 (a, b, c, and d) | -5-(4-chlorothiadiazolyl) | -isopropoxy |
| B273 (a, b, c, and d) | -5-(4-chlorothiadiazolyl) | —CF$_3$ |

TABLE II-continued

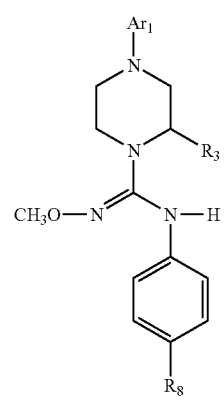

and pharmaceutically acceptable salts thereof, wherein:

| Compound | Ar$_1$ | R$_8$ |
|---|---|---|
| B274 (a, b, c, and d) | -5-(4-chlorothiadiazolyl) | —OCF$_3$ |
| B275 (a, b, c, and d) | -5-(4-chlorothiadiazolyl) | —Cl |
| B276 (a, b, c, and d) | -5-(4-chlorothiadiazolyl) | —Br |
| B277 (a, b, c, and d) | -5-(4-chlorothiadiazolyl) | —I |
| B278 (a, b, c, and d) | -5-(4-chlorothiadiazolyl) | -n-butyl |
| B279 (a, b, c, and d) | -5-(4-chlorothiadiazolyl) | -n-propyl |
| B280 (a, b, c, and d) | -5-(4-chlorothiadiazolyl) | -iso-propyl |
| B281 (a, b, c, and d) | -5-(4-methylthiadiazolyl) | -t-butyl |
| B282 (a, b, c, and d) | -5-(4-methylthiadiazolyl) | -iso-butyl |
| B283 (a, b, c, and d) | -5-(4-methylthiadiazolyl) | -sec-butyl |
| B284 (a, b, c, and d) | -5-(4-methylthiadiazolyl) | -cyclohexyl |
| B285 (a, b, c, and d) | -5-(4-methylthiadiazolyl) | -t-butoxy |
| B286 (a, b, c, and d) | -5-(4-methylthiadiazolyl) | -isopropoxy |
| B287 (a, b, c, and d) | -5-(4-methylthiadiazolyl) | —CF$_3$ |
| B288 (a, b, c, and d) | -5-(4-methylthiadiazolyl) | —OCF$_3$ |
| B289 (a, b, c, and d) | -5-(4-methylthiadiazolyl) | —Cl |
| B290 (a, b, c, and d) | -5-(4-methylthiadiazolyl) | —Br |
| B291 (a, b, c, and d) | -5-(4-methylthiadiazolyl) | —I |
| B292 (a, b, c, and d) | -5-(4-methylthiadiazolyl) | -n-butyl |
| B293 (a, b, c, and d) | -5-(4-methylthiadiazolyl) | -n-propyl |
| B294 (a, b, c, and d) | -5-(4-methylthiadiazolyl) | -iso-propyl |
| B295 (a, b, c, and d) | -5-(4-fluorothiadiazolyl) | -t-butyl |
| B296 (a, b, c, and d) | -5-(4-fluorothiadiazolyl) | -iso-butyl |
| B297 (a, b, c, and d) | -5-(4-fluorothiadiazolyl) | -sec-butyl |
| B298 (a, b, c, and d) | -5-(4-fluorothiadiazolyl) | -cyclohexyl |
| B299 (a, b, c, and d) | -5-(4-fluorothiadiazolyl) | -t-butoxy |
| B300 (a, b, c, and d) | -5-(4-fluorothiadiazolyl) | -isopropoxy |
| B301 (a, b, c, and d) | -5-(4-fluorothiadiazolyl) | —CF$_3$ |
| B302 (a, b, c, and d) | -5-(4-fluorothiadiazolyl) | —OCF$_3$ |
| B303 (a, b, c, and d) | -5-(4-fluorothiadiazolyl) | —Cl |
| B304 (a, b, c, and d) | -5-(4-fluorothiadiazolyl) | —Br |
| B305 (a, b, c, and d) | -5-(4-fluorothiadiazolyl) | —I |
| B306 (a, b, c, and d) | -5-(4-fluorothiadiazolyl) | -n-butyl |
| B307 (a, b, c, and d) | -5-(4-fluorothiadiazolyl) | -n-propyl |
| B308 (a, b, c, and d) | -5-(4-fluorothiadiazolyl) | -iso-propyl |

"a" means R$_3$ is —H.

"b" means R$_3$ is —CH$_3$ and the Hydroxyiminopiperazine Compound is racemic.

"c" means R$_3$ is —CH$_3$ and the carbon atom to which R$_3$ is attached is in the (R) configuration.

"d" means R$_3$ is —CH$_3$ and the carbon atom to which R$_3$ is attached is in the (S) configuration.

TABLE III

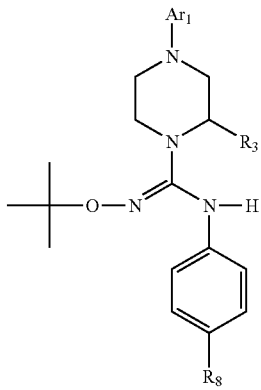

and pharmaceutically acceptable salts thereof, wherein:

| Compound | Ar$_1$ | R$_8$ |
|---|---|---|
| C1 (a, b, c, and d) | -2-(3-chloropyridyl) | -t-butyl |
| C2 (a, b, c, and d) | -2-(3-chloropyridyl) | -iso-butyl |
| C3 (a, b, c, and d) | -2-(3-chloropyridyl) | -sec-butyl |
| C4 (a, b, c, and d) | -2-(3-chloropyridyl) | -cyclohexyl |
| C5 (a, b, c, and d) | -2-(3-chloropyridyl) | -t-butoxy |
| C6 (a, b, c, and d) | -2-(3-chloropyridyl) | -isopropoxy |
| C7 (a, b, c, and d) | -2-(3-chloropyridyl) | —CF$_3$ |
| C8 (a, b, c, and d) | -2-(3-chloropyridyl) | —OCF$_3$ |
| C9 (a, b, c, and d) | -2-(3-chloropyridyl) | —Cl |
| C10 (a, b, c, and d) | -2-(3-chloropyridyl) | —Br |
| C11 (a, b, c, and d) | -2-(3-chloropyridyl) | —I |
| C12 (a, b, c, and d) | -2-(3-chloropyridyl) | -n-butyl |
| C13 (a, b, c, and d) | -2-(3-chloropyridyl) | -n-propyl |
| C14 (a, b, c, and d) | -2-(3-chloropyridyl) | -iso-propyl |
| C15 (a, b, c, and d) | -2-(3-fluoropyridyl) | -t-butyl |
| C16 (a, b, c, and d) | -2-(3-fluoropyridyl) | -iso-butyl |
| C17 (a, b, c, and d) | -2-(3-fluoropyridyl) | -sec-butyl |
| C18 (a, b, c, and d) | -2-(3-fluoropyridyl) | -cyclohexyl |
| C19 (a, b, c, and d) | -2-(3-fluoropyridyl) | -t-butoxy |
| C20 (a, b, c, and d) | -2-(3-fluoropyridyl) | -isopropoxy |
| C21 (a, b, c, and d) | -2-(3-fluoropyridyl) | —CF$_3$ |
| C22 (a, b, c, and d) | -2-(3-fluoropyridyl) | —OCF$_3$ |
| C23 (a, b, c, and d) | -2-(3-fluoropyridyl) | —Cl |
| C24 (a, b, c, and d) | -2-(3-fluoropyridyl) | —Br |
| C25 (a, b, c, and d) | -2-(3-fluoropyridyl) | —I |
| C26 (a, b, c, and d) | -2-(3-fluoropyridyl) | -n-butyl |
| C27 (a, b, c, and d) | -2-(3-fluoropyridyl) | -n-propyl |
| C28 (a, b, c, and d) | -2-(3-fluoropyridyl) | -iso-propyl |
| C29 (a, b, c, and d) | -2-(3-methylpyridyl) | -t-butyl |
| C30 (a, b, c, and d) | -2-(3-methylpyridyl) | -iso-butyl |
| C31 (a, b, c, and d) | -2-(3-methylpyridyl) | -sec-butyl |
| C32 (a, b, c, and d) | -2-(3-methylpyridyl) | -cyclohexyl |
| C33 (a, b, c, and d) | -2-(3-methylpyridyl) | -t-butoxy |
| C34 (a, b, c, and d) | -2-(3-methylpyridyl) | -isopropoxy |
| C35 (a, b, c, and d) | -2-(3-methylpyridyl) | —CF$_3$ |
| C36 (a, b, c, and d) | -2-(3-methylpyridyl) | —OCF$_3$ |
| C37 (a, b, c, and d) | -2-(3-methylpyridyl) | —Cl |
| C38 (a, b, c, and d) | -2-(3-methylpyridyl) | —Br |
| C39 (a, b, c, and d) | -2-(3-methylpyridyl) | —I |
| C40 (a, b, c, and d) | -2-(3-methylpyridyl) | -n-butyl |
| C41 (a, b, c, and d) | -2-(3-methylpyridyl) | -n-propyl |
| C42 (a, b, c, and d) | -2-(3-methylpyridyl) | -iso-propyl |
| C43 (a, b, c, and d) | -2-(3-CF$_3$-pyridyl) | -t-butyl |
| C44 (a, b, c, and d) | -2-(3-CF$_3$-pyridyl) | -iso-butyl |
| C45 (a, b, c, and d) | -2-(3-CF$_3$-pyridyl) | -sec-butyl |
| C46 (a, b, c, and d) | -2-(3-CF$_3$-pyridyl) | -cyclohexyl |
| C47 (a, b, c, and d) | -2-(3-CF$_3$-pyridyl) | -t-butoxy |
| C48 (a, b, c, and d) | -2-(3-CF$_3$-pyridyl) | -isopropoxy |
| C49 (a, b, c, and d) | -2-(3-CF$_3$-pyridyl) | —CF$_3$ |
| C50 (a, b, c, and d) | -2-(3-CF$_3$-pyridyl) | —OCF$_3$ |
| C51 (a, b, c, and d) | -2-(3-CF$_3$-pyridyl) | —Cl |
| C52 (a, b, c, and d) | -2-(3-CF$_3$-pyridyl) | —Br |
| C53 (a, b, c, and d) | -2-(3-CF$_3$-pyridyl) | —I |
| C54 (a, b, c, and d) | -2-(3-CF$_3$-pyridyl) | -n-butyl |
| C55 (a, b, c, and d) | -2-(3-CF$_3$-pyridyl) | -n-propyl |

TABLE III-continued

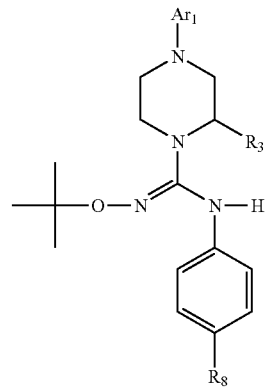

and pharmaceutically acceptable salts thereof, wherein:

| Compound | Ar$_1$ | R$_8$ |
|---|---|---|
| C56 (a, b, c, and d) | -2-(3-CF$_3$-pyridyl) | -iso-propyl |
| C57 (a, b, c, and d) | -2-(3-CHF$_2$-pyridyl) | -t-butyl |
| C58 (a, b, c, and d) | -2-(3-CHF$_2$-pyridyl) | -iso-butyl |
| C59 (a, b, c, and d) | -2-(3-CHF$_2$-pyridyl) | -sec-butyl |
| C60 (a, b, c, and d) | -2-(3-CHF$_2$-pyridyl) | -cyclohexyl |
| C61 (a, b, c, and d) | -2-(3-CHF$_2$-pyridyl) | -t-butoxy |
| C62 (a, b, c, and d) | -2-(3-CHF$_2$-pyridyl) | -isopropoxy |
| C63 (a, b, c, and d) | -2-(3-CHF$_2$-pyridyl) | —CF$_3$ |
| C64 (a, b, c, and d) | -2-(3-CHF$_2$-pyridyl) | —OCF$_3$ |
| C65 (a, b, c, and d) | -2-(3-CHF$_2$-pyridyl) | —Cl |
| C66 (a, b, c, and d) | -2-(3-CHF$_2$-pyridyl) | —Br |
| C67 (a, b, c, and d) | -2-(3-CHF$_2$-pyridyl) | —I |
| C68 (a, b, c, and d) | -2-(3-CHF$_2$-pyridyl) | -n-butyl |
| C69 (a, b, c, and d) | -2-(3-CHF$_2$-pyridyl) | -n-propyl |
| C70 (a, b, c, and d) | -2-(3-CHF$_2$-pyridyl) | -iso-propyl |
| C71 (a, b, c, and d) | -2-(3-hydroxypyridyl) | -t-butyl |
| C72 (a, b, c, and d) | -2-(3-hydroxypyridyl) | -iso-butyl |
| C73 (a, b, c, and d) | -2-(3-hydroxypyridyl) | -sec-butyl |
| C74 (a, b, c, and d) | -2-(3-hydroxypyridyl) | -cyclohexyl |
| C75 (a, b, c, and d) | -2-(3-hydroxypyridyl) | -t-butoxy |
| C76 (a, b, c, and d) | -2-(3-hydroxypyridyl) | -isopropoxy |
| C77 (a, b, c, and d) | -2-(3-hydroxypyridyl) | —CF$_3$ |
| C78 (a, b, c, and d) | -2-(3-hydroxypyridyl) | —OCF$_3$ |
| C79 (a, b, c, and d) | -2-(3-hydroxypyridyl) | —Cl |
| C80 (a, b, c, and d) | -2-(3-hydroxypyridyl) | —Br |
| C81 (a, b, c, and d) | -2-(3-hydroxypyridyl) | —I |
| C82 (a, b, c, and d) | -2-(3-hydroxypyridyl) | -n-butyl |
| C83 (a, b, c, and d) | -2-(3-hydroxypyridyl) | -n-propyl |
| C84 (a, b, c, and d) | -2-(3-hydroxypyridyl) | -iso-propyl |
| C85 (a, b, c, and d) | -2-(3-nitropyridyl) | -t-butyl |
| C86 (a, b, c, and d) | -2-(3-nitropyridyl) | -iso-butyl |
| C87 (a, b, c, and d) | -2-(3-nitropyridyl) | -sec-butyl |
| C88 (a, b, c, and d) | -2-(3-nitropyridyl) | -cyclohexyl |
| C89 (a, b, c, and d) | -2-(3-nitropyridyl) | -t-butoxy |
| C90 (a, b, c, and d) | -2-(3-nitropyridyl) | -isopropoxy |
| C91 (a, b, c, and d) | -2-(3-nitropyridyl) | —CF$_3$ |
| C92 (a, b, c, and d) | -2-(3-nitropyridyl) | —OCF$_3$ |
| C93 (a, b, c, and d) | -2-(3-nitropyridyl) | —Cl |
| C94 (a, b, c, and d) | -2-(3-nitropyridyl) | —Br |
| C95 (a, b, c, and d) | -2-(3-nitropyridyl) | —I |
| C96 (a, b, c, and d) | -2-(3-nitropyridyl) | -n-butyl |
| C97 (a, b, c, and d) | -2-(3-nitropyridyl) | -n-propyl |
| C98 (a, b, c, and d) | -2-(3-nitropyridyl) | -iso-propyl |
| C99 (a, b, c, and d) | -2-(3-cyanopyridyl) | -t-butyl |
| C100 (a, b, c, and d) | -2-(3-cyanopyridyl) | -iso-butyl |
| C101 (a, b, c, and d) | -2-(3-cyanopyridyl) | -sec-butyl |
| C102 (a, b, c, and d) | -2-(3-cyanopyridyl) | -cyclohexyl |
| C103 (a, b, c, and d) | -2-(3-cyanopyridyl) | -t-butoxy |
| C104 (a, b, c, and d) | -2-(3-cyanopyridyl) | -isopropoxy |
| C105 (a, b, c, and d) | -2-(3-cyanopyridyl) | —CF$_3$ |
| C106 (a, b, c, and d) | -2-(3-cyanopyridyl) | —OCF$_3$ |
| C107 (a, b, c, and d) | -2-(3-cyanopyridyl) | —Cl |
| C108 (a, b, c, and d) | -2-(3-cyanopyridyl) | —Br |
| C109 (a, b, c, and d) | -2-(3-cyanopyridyl) | —I |
| C110 (a, b, c, and d) | -2-(3-cyanopyridyl) | -n-butyl |

TABLE III-continued

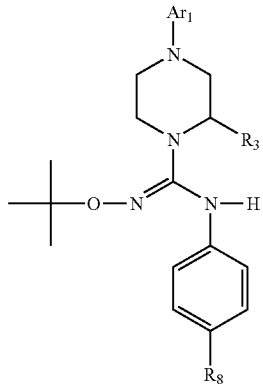

and pharmaceutically acceptable salts thereof, wherein:

| Compound | Ar₁ | R₈ |
|---|---|---|
| C111 (a, b, c, and d) | -2-(3-cyanopyridyl) | -n-propyl |
| C112 (a, b, c, and d) | -2-(3-cyanopyridyl) | -isopropyl |
| C113 (a, b, c, and d) | -2-(3-bromopyridyl) | -t-butyl |
| C114 (a, b, c, and d) | -2-(3-bromopyridyl) | -iso-butyl |
| C115 (a, b, c, and d) | -2-(3-bromopyridyl) | -sec-butyl |
| C116 (a, b, c, and d) | -2-(3-bromopyridyl) | -cyclohexyl |
| C117 (a, b, c, and d) | -2-(3-bromopyridyl) | -t-butoxy |
| C118 (a, b, c, and d) | -2-(3-bromopyridyl) | -isopropoxy |
| C119 (a, b, c, and d) | -2-(3-bromopyridyl) | —CF₃ |
| C120 (a, b, c, and d) | -2-(3-bromopyridyl) | —OCF₃ |
| C121 (a, b, c, and d) | -2-(3-bromopyridyl) | —Cl |
| C122 (a, b, c, and d) | -2-(3-bromopyridyl) | —Br |
| C123 (a, b, c, and d) | -2-(3-bromopyridyl) | —I |
| C124 (a, b, c, and d) | -2-(3-bromopyridyl) | -n-butyl |
| C125 (a, b, c, and d) | -2-(3-bromopyridyl) | -n-propyl |
| C126 (a, b, c, and d) | -2-(3-bromopyridyl) | -iso-propyl |
| C127 (a, b, c, and d) | -2-(3-iodopyridyl) | -t-butyl |
| C128 (a, b, c, and d) | -2-(3-iodopyridyl) | -iso-butyl |
| C129 (a, b, c, and d) | -2-(3-iodopyridyl) | -sec-butyl |
| C130 (a, b, c, and d) | -2-(3-iodopyridyl) | -cyclohexyl |
| C131 (a, b, c, and d) | -2-(3-iodopyridyl) | -t-butoxy |
| C132 (a, b, c, and d) | -2-(3-iodopyridyl) | -isopropoxy |
| C133 (a, b, c, and d) | -2-(3-iodopyridyl) | —CF₃ |
| C134 (a, b, c, and d) | -2-(3-iodopyridyl) | —OCF₃ |
| C135 (a, b, C, and d) | -2-(3-iodopyridyl) | —Cl |
| C136 (a, b, c, and d) | -2-(3-iodopyridyl) | —Br |
| C137 (a, b, c, and d) | -2-(3-iodopyridyl) | —I |
| C138 (a, b, c, and d) | -2-(3-iodopyridyl) | -n-butyl |
| C139 (a, b, c, and d) | -2-(3-iodopyridyl) | -n-propyl |
| C140 (a, b, c, and d) | -2-(3-iodopyridyl) | -iso-propyl |
| C141 (a, b, c, and d) | -4-(5-chloropyrimidinyl) | -t-butyl |
| C142 (a, b, c, and d) | -4-(5-chloropyrimidinyl) | -iso-butyl |
| C143 (a, b, c, and d) | -4-(5-chloropyrimidinyl) | -sec-butyl |
| C144 (a, b, c, and d) | -4-(5-chloropyrimidinyl) | -cyclohexyl |
| C145 (a, b, c, and d) | -4-(5-chloropyrimidinyl) | -t-butoxy |
| C146 (a, b, c, and d) | -4-(5-chloropyrimidinyl) | -isopropoxy |
| C147 (a, b, c, and d) | -4-(5-chloropyrimidinyl) | —CF₃ |
| C148 (a, b, c, and d) | -4-(5-chloropyrimidinyl) | —OCF₃ |
| C149 (a, b, c, and d) | -4-(5-chloropyrimidinyl) | —Cl |
| C150 (a, b, c, and d) | -4-(5-chloropyrimidinyl) | —Br |
| C151 (a, b, c, and d) | -4-(5-chloropyrimidinyl) | —I |
| C152 (a, b, c, and d) | -4-(5-chloropyrimidinyl) | -n-butyl |
| C153 (a, b, c, and d) | -4-(5-chloropyrimidinyl) | -n-propyl |
| C154 (a, b, c, and d) | -4-(5-chloropyrimidinyl) | -iso-propyl |
| C155 (a, b, c, and d) | -4-(5-methylpyrimidinyl) | -t-butyl |
| C156 (a, b, c, and d) | -4-(5-methylpyrimidinyl) | -iso-butyl |
| C157 (a, b, c, and d) | -4-(5-methylpyrimidinyl) | -sec-butyl |
| C158 (a, b, c, and d) | -4-(5-methylpyrimidinyl) | -cyclohexyl |
| C159 (a, b, c, and d) | -4-(5-methylpyrimidinyl) | -t-butoxy |
| C160 (a, b, c, and d) | -4-(5-methylpyrimidinyl) | -isopropoxy |
| C161 (a, b, c, and d) | -4-(5-methylpyrimidinyl) | —CF₃ |
| C162 (a, b, c, and d) | -4-(5-methylpyrimidinyl) | —OCF₃ |
| C163 (a, b, c, and d) | -4-(5-methylpyrimidinyl) | —Cl |
| C164 (a, b, c, and d) | -4-(5-methylpyrimidinyl) | —Br |
| C165 (a, b, c, and d) | -4-(5-methylpyrimidinyl) | —I |

TABLE III-continued

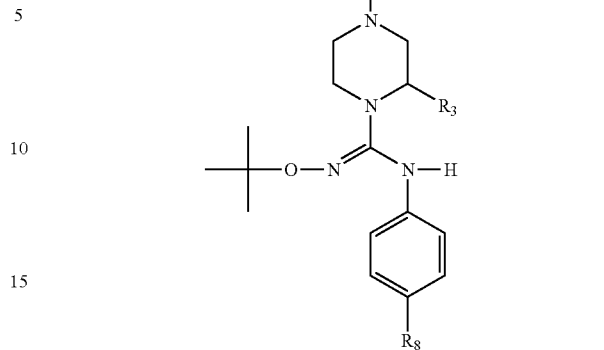

and pharmaceutically acceptable salts thereof, wherein:

| Compound | Ar₁ | R₈ |
|---|---|---|
| C166 (a, b, c, and d) | -4-(5-methylpyrimidinyl) | -n-butyl |
| C167 (a, b, c, and d) | -4-(5-methylpyrimidinyl) | -n-propyl |
| C168 (a, b, c, and d) | -4-(5-methylpyrimidinyl) | -iso-propyl |
| C169 (a, b, c, and d) | -4-(5-fluoropyrimidinyl) | -t-butyl |
| C170 (a, b, c, and d) | -4-(5-fluoropyrimidinyl) | -iso-butyl |
| C171 (a, b, c, and d) | -4-(5-fluoropyrimidinyl) | -sec-butyl |
| C172 (a, b, c, and d) | -4-(5-fluoropyrimidinyl) | -cyclohexyl |
| C173 (a, b, c, and d) | -4-(5-fluoropyrimidinyl) | -t-butoxy |
| C174 (a, b, c, and d) | -4-(5-fluoropyrimidinyl) | -isopropoxy |
| C175 (a, b, c, and d) | -4-(5-fluoropyrimidinyl) | —CF₃ |
| C176 (a, b, c, and d) | -4-(5-fluoropyrimidinyl) | —OCF₃ |
| C177 (a, b, c, and d) | -4-(5-fluoropyrimidinyl) | —Cl |
| C178 (a, b, c, and d) | -4-(5-fluoropyrimidinyl) | —Br |
| C179 (a, b, c, and d) | -4-(5-fluoropyrimidinyl) | —I |
| C180 (a, b, c, and d) | -4-(5-fluoropyrimidinyl) | -n-butyl |
| C181 (a, b, c, and d) | -4-(5-fluoropyrimidinyl) | -n-propyl |
| C182 (a, b, c, and d) | -4-(5-fluoropyrimidinyl) | -iso-propyl |
| C183 (a, b, c, and d) | -2-(3-chloropyrazinyl) | -t-butyl |
| C184 (a, b, c, and d) | -2-(3-chloropyrazinyl) | -iso-butyl |
| C185 (a, b, c, and d) | -2-(3-chloropyrazinyl) | -sec-butyl |
| C186 (a, b, C, and d) | -2-(3-chloropyrazinyl) | -cyclohexyl |
| C187 (a, b, c, and d) | -2-(3-chloropyrazinyl) | -t-butoxy |
| C188 (a, b, c, and d) | -2-(3-chloropyrazinyl) | -isopropoxy |
| C189 (a, b, c, and d) | -2-(3-chloropyrazinyl) | —CF₃ |
| C190 (a, b, c, and d) | -2-(3-chloropyrazinyl) | —OCF₃ |
| C191 (a, b, c, and d) | -2-(3-chloropyrazinyl) | —Cl |
| C192 (a, b, c, and d) | -2-(3-chloropyrazinyl) | —Br |
| C193 (a, b, c, and d) | -2-(3-chloropyrazinyl) | —I |
| C194 (a, b, c, and d) | -2-(3-chloropyrazinyl) | -n-butyl |
| C195 (a, b, c, and d) | -2-(3-chloropyrazinyl) | -n-propyl |
| C196 (a, b, c, and d) | -2-(3-chloropyrazinyl) | -iso-propyl |
| C197 (a, b, c, and d) | -2-(3-methylpyrazinyl) | -t-butyl |
| C198 (a, b, c, and d) | -2-(3-methylpyrazinyl) | -iso-butyl |
| C199 (a, b, c, and d) | -2-(3-methylpyrazinyl) | -sec-butyl |
| C200 (a, b, c, and d) | -2-(3-methylpyrazinyl) | -cyclohexyl |
| C201 (a, b, c, and d) | -2-(3-methylpyrazinyl) | -t-butoxy |
| C202 (a, b, c, and d) | -2-(3-methylpyrazinyl) | -isopropoxy |
| C203 (a, b, c, and d) | -2-(3-methylpyrazinyl) | —CF₃ |
| C204 (a, b, c, and d) | -2-(3-methylpyrazinyl) | —OCF₃ |
| C205 (a, b, c, and d) | -2-(3-methylpyrazinyl) | —Cl |
| C206 (a, b, c, and d) | -2-(3-methylpyrazinyl) | —Br |
| C207 (a, b, c, and d) | -2-(3-methylpyrazinyl) | —I |
| C208 (a, b, c, and d) | -2-(3-methylpyrazinyl) | -n-butyl |
| C209 (a, b, c, and d) | -2-(3-methylpyrazinyl) | -n-propyl |
| C210 (a, b, c, and d) | -2-(3-methylpyrazinyl) | -iso-propyl |
| C211 (a, b, c, and d) | -2-(3-fluoropyrazinyl) | -t-butyl |
| C212 (a, b, c, and d) | -2-(3-fluoropyrazinyl) | -iso-butyl |
| C213 (a, b, c, and d) | -2-(3-fluoropyrazinyl) | -sec-butyl |
| C214 (a, b, c, and d) | -2-(3-fluoropyrazinyl) | -cyclohexyl |
| C215 (a, b, c, and d) | -2-(3-fluoropyrazinyl) | -t-butoxy |
| C216 (a, b, c, and d) | -2-(3-fluoropyrazinyl) | -isopropoxy |
| C217 (a, b, c, and d) | -2-(3-fluoropyrazinyl) | —CF₃ |
| C218 (a, b, c, and d) | -2-(3-fluoropyrazinyl) | —OCF₃ |
| C219 (a, b, c, and d) | -2-(3-fluoropyrazinyl) | —Cl |
| C220 (a, b, c, and d) | -2-(3-fluoropyrazinyl) | —Br |

TABLE III-continued

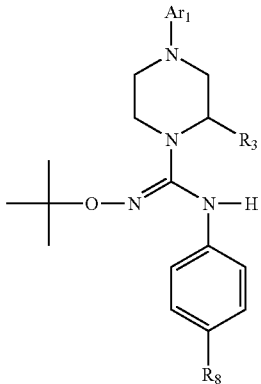

and pharmaceutically acceptable salts thereof, wherein:

| Compound | $Ar_1$ | $R_8$ |
|---|---|---|
| C221 (a, b, c, and d) | -2-(3-fluoropyrazinyl) | —I |
| C222 (a, b, c, and d) | -2-(3-fluoropyrazinyl) | -n-butyl |
| C223 (a, b, c, and d) | -2-(3-fluoropyrazinyl) | -n-propyl |
| C224 (a, b, c, and d) | -2-(3-fluoropyrazinyl) | -iso-propyl |
| C225 (a, b, c, and d) | -3-(4-chloropyridazinyl) | -t-butyl |
| C226 (a, b, c, and d) | -3-(4-chloropyridazinyl) | -iso-butyl |
| C227 (a, b, c, and d) | -3-(4-chloropyridazinyl) | -sec-butyl |
| C228 (a, b, c, and d) | -3-(4-chloropyridazinyl) | -cyclohexyl |
| C229 (a, b, c, and d) | -3-(4-chloropyridazinyl) | -t-butoxy |
| C230 (a, b, c, and d) | -3-(4-chloropyridazinyl) | -isopropoxy |
| C231 (a, b, c, and d) | -3-(4-chloropyridazinyl) | —$CF_3$ |
| C232 (a, b, c, and d) | -3-(4-chloropyridazinyl) | —$OCF_3$ |
| C233 (a, b, c, and d) | -3-(4-chloropyridazinyl) | —Cl |
| C234 (a, b, c, and d) | -3-(4-chloropyridazinyl) | —Br |
| C235 (a, b, c, and d) | -3-(4-chloropyridazinyl) | —I |
| C236 (a, b, c, and d) | -3-(4-chloropyridazinyl) | -n-butyl |
| C237 (a, b, c, and d) | -3-(4-chloropyridazinyl) | -n-propyl |
| C238 (a, b, c, and d) | -3-(4-chloropyridazinyl) | -iso-propyl |
| C239 (a, b, c, and d) | -3-(4-methylpyridazinyl) | -t-butyl |
| C240 (a, b, c, and d) | -3-(4-methylpyridazinyl) | -iso-butyl |
| C241 (a, b, c, and d) | -3-(4-methylpyridazinyl) | -sec-butyl |
| C242 (a, b, c, and d) | -3-(4-methylpyridazinyl) | -cyclohexyl |
| C243 (a, b, c, and d) | -3-(4-methylpyridazinyl) | -t-butoxy |
| C244 (a, b, c, and d) | -3-(4-methylpyridazinyl) | -isopropoxy |
| C245 (a, b, c, and d) | -3-(4-methylpyridazinyl) | —$CF_3$ |
| C246 (a, b, c, and d) | -3-(4-methylpyridazinyl) | —$OCF_3$ |
| C247 (a, b, c, and d) | -3-(4-methylpyridazinyl) | —Cl |
| C248 (a, b, c, and d) | -3-(4-methylpyridazinyl) | —Br |
| C249 (a, b, c, and d) | -3-(4-methylpyridazinyl) | —I |
| C250 (a, b, c, and d) | -3-(4-methylpyridazinyl) | -n-butyl |
| C251 (a, b, c, and d) | -3-(4-methylpyridazinyl) | -n-propyl |
| C252 (a, b, c, and d) | -3-(4-methylpyridazinyl) | -iso-propyl |
| C253 (a, b, c, and d) | -3-(4-fluoropyridazinyl) | -t-butyl |
| C254 (a, b, c, and d) | -3-(4-fluoropyridazinyl) | -iso-butyl |
| C255 (a, b, c, and d) | -3-(4-fluoropyridazinyl) | -sec-butyl |
| C256 (a, b, c, and d) | -3-(4-fluoropyridazinyl) | -cyclohexyl |
| C257 (a, b, c, and d) | -3-(4-fluoropyridazinyl) | -t-butoxy |
| C258 (a, b, c, and d) | -3-(4-fluoropyridazinyl) | -isopropoxy |
| C259 (a, b, c, and d) | -3-(4-fluoropyridazinyl) | —$CF_3$ |
| C260 (a, b, c, and d) | -3-(4-fluoropyridazinyl) | —$OCF_3$ |
| C261 (a, b, c, and d) | -3-(4-fluoropyridazinyl) | —Cl |
| C262 (a, b, c, and d) | -3-(4-fluoropyridazinyl) | —Br |
| C263 (a, b, c, and d) | -3-(4-fluoropyridazinyl) | —I |
| C264 (a, b, c, and d) | -3-(4-fluoropyridazinyl) | -n-butyl |
| C265 (a, b, c, and d) | -3-(4-fluoropyridazinyl) | -n-propyl |
| C266 (a, b, c, and d) | -3-(4-fluoropyridazinyl) | -iso-propyl |
| C267 (a, b, c, and d) | -5-(4-chlorothiadiazolyl) | -t-butyl |
| C268 (a, b, c, and d) | -5-(4-chlorothiadiazolyl) | -iso-butyl |
| C269 (a, b, c, and d) | -5-(4-chlorothiadiazolyl) | -sec-butyl |
| C270 (a, b, c, and d) | -5-(4-chlorothiadiazolyl) | -cyclohexyl |
| C271 (a, b, c, and d) | -5-(4-chlorothiadiazolyl) | -t-butoxy |
| C272 (a, b, c, and d) | -5-(4-chlorothiadiazolyl) | -isopropoxy |
| C273 (a, b, c, and d) | -5-(4-chlorothiadiazolyl) | —$CF_3$ |
| C274 (a, b, c, and d) | -5-(4-chlorothiadiazolyl) | —$OCF_3$ |
| C275 (a, b, c, and d) | -5-(4-chlorothiadiazolyl) | —Cl |

TABLE III-continued

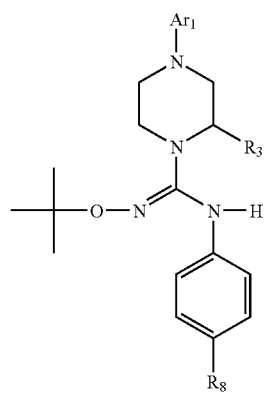

and pharmaceutically acceptable salts thereof, wherein:

| Compound | $Ar_1$ | $R_8$ |
|---|---|---|
| C276 (a, b, c, and d) | -5-(4-chlorothiadiazolyl) | —Br |
| C277 (a, b, c, and d) | -5-(4-chlorothiadiazolyl) | —I |
| C278 (a, b, c, and d) | -5-(4-chlorothiadiazolyl) | -n-butyl |
| C279 (a, b, c, and d) | -5-(4-chlorothiadiazolyl) | -n-propyl |
| C280 (a, b, c, and d) | -5-(4-chlorothiadiazolyl) | -iso-propyl |
| C281 (a, b, c, and d) | -5-(4-methylthiadiazolyl) | -t-butyl |
| C282 (a, b, c, and d) | -5-(4-methylthiadiazolyl) | -iso-butyl |
| C283 (a, b, c, and d) | -5-(4-methylthiadiazolyl) | -sec-butyl |
| C284 (a, b, c, and d) | -5-(4-methylthiadiazolyl) | -cyclohexyl |
| C285 (a, b, c, and d) | -5-(4-methylthiadiazolyl) | -t-butoxy |
| C286 (a, b, c, and d) | -5-(4-methylthiadiazolyl) | -isopropoxy |
| C287 (a, b, c, and d) | -5-(4-methylthiadiazolyl) | —$CF_3$ |
| C288 (a, b, c, and d) | -5-(4-methylthiadiazolyl) | —$OCF_3$ |
| C289 (a, b, c, and d) | -5-(4-methylthiadiazolyl) | —Cl |
| C290 (a, b, c, and d) | -5-(4-methylthiadiazolyl) | —Br |
| C291 (a, b, c, and d) | -5-(4-methylthiadiazolyl) | —I |
| C292 (a, b, c, and d) | -5-(4-methylthiadiazolyl) | -n-butyl |
| C293 (a, b, c, and d) | -5-(4-methylthiadiazolyl) | -n-propyl |
| C294 (a, b, c, and d) | -5-(4-methylthiadiazolyl) | -iso-propyl |
| C295 (a, b, c, and d) | -5-(4-fluorothiadiazolyl) | -t-butyl |
| C296 (a, b, c, and d) | -5-(4-fluorothiadiazolyl) | -iso-butyl |
| C297 (a, b, c, and d) | -5-(4-fluorothiadiazolyl) | -sec-butyl |
| C298 (a, b, c, and d) | -5-(4-fluorothiadiazolyl) | -cyclohexyl |
| C299 (a, b, c, and d) | -5-(4-fluorothiadiazolyl) | -t-butoxy |
| C300 (a, b, C, and d) | -5-(4-fluorothiadiazolyl) | -isopropoxy |
| C301 (a, b, c, and d) | -5-(4-fluorothiadiazolyl) | —$CF_3$ |
| C302 (a, b, c, and d) | -5-(4-fluorothiadiazolyl) | —$OCF_3$ |
| C303 (a, b, c, and d) | -5-(4-fluorothiadiazolyl) | —Cl |
| C304 (a, b, c, and d) | -5-(4-fluorothiadiazolyl) | —Br |
| C305 (a, b, c, and d) | -5-(4-fluorothiadiazolyl) | —I |
| C306 (a, b, c, and d) | -5-(4-fluorothiadiazolyl) | -n-butyl |
| C307 (a, b, c, and d) | -5-(4-fluorothiadiazolyl) | -n-propyl |
| C308 (a, b, c, and d) | -5-(4-fluorothiadiazolyl) | -iso-propyl |

"a" means $R_3$ is —H.

"b" means $R_3$ is —$CH_3$ and the Hydroxyiminopiperazine Compound is racemic.

"c" means $R_3$ is —$CH_3$ and the carbon atom to which $R_3$ is attached is in the (R) configuration.

"d" means $R_3$ is —$CH_3$ and the carbon atom to which $R_3$ is attached is in the (S) configuration.

TABLE IV

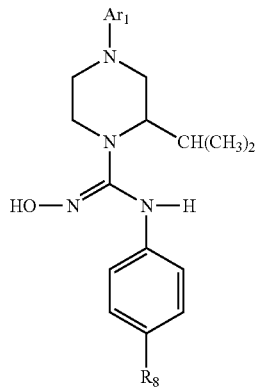

and pharmaceutically acceptable salts thereof, wherein:

| Compound | Ar₁ | R₈ |
|---|---|---|
| D1 (a, b, and c) | -2-(3-chloropyridyl) | -t-butyl |
| D2 (a, b, and c) | -2-(3-chloropyridyl) | -iso-butyl |
| D3 (a, b, and c) | -2-(3-chloropyridyl) | -sec-butyl |
| D4 (a, b, and c) | -2-(3-chloropyridyl) | -cyclohexyl |
| D5 (a, b, and c) | -2-(3-chloropyridyl) | -t-butoxy |
| D6 (a, b, and c) | -2-(3-chloropyridyl) | -isopropoxy |
| D7 (a, b, and c) | -2-(3-chloropyridyl) | —CF₃ |
| D8 (a, b, and c) | -2-(3-chloropyridyl) | —OCF₃ |
| D9 (a, b, and c) | -2-(3-chloropyridyl) | —Cl |
| D10 (a, b, and c) | -2-(3-chloropyridyl) | —Br |
| D11 (a, b, and c) | -2-(3-chloropyridyl) | —I |
| D12 (a, b, and c) | -2-(3-chloropyridyl) | -n-butyl |
| D13 (a, b, and c) | -2-(3-chloropyridyl) | -n-propyl |
| D14 (a, b, and c) | -2-(3-chloropyridyl) | -iso-propyl |
| D15 (a, b, and c) | -2-(3-fluoropyridyl) | -t-butyl |
| D16 (a, b, and c) | -2-(3-fluoropyridyl) | -iso-butyl |
| D17 (a, b, and c) | -2-(3-fluoropyridyl) | -sec-butyl |
| D18 (a, b, and c) | -2-(3-fluoropyridyl) | -cyclohexyl |
| D19 (a, b, and c) | -2-(3-fluoropyridyl) | -t-butoxy |
| D20 (a, b, and c) | -2-(3-fluoropyridyl) | -isopropoxy |
| D21 (a, b, and c) | -2-(3-fluoropyridyl) | —CF₃ |
| D22 (a, b, and c) | -2-(3-fluoropyridyl) | —OCF₃ |
| D23 (a, b, and c) | -2-(3-fluoropyridyl) | —Cl |
| D24 (a, b, and c) | -2-(3-fluoropyridyl) | —Br |
| D25 (a, b, and c) | -2-(3-fluoropyridyl) | —I |
| D26 (a, b, and c) | -2-(3-fluoropyridyl) | -n-butyl |
| D27 (a, b, and c) | -2-(3-fluoropyridyl) | -n-propyl |
| D28 (a, b, and c) | -2-(3-fluoropyridyl) | -iso-propyl |
| D29 (a, b, and c) | -2-(3-methylpyridyl) | -t-butyl |
| D30 (a, b, and c) | -2-(3-methylpyridyl) | -iso-butyl |
| D31 (a, b, and c) | -2-(3-methylpyridyl) | -sec-butyl |
| D32 (a, b, and c) | -2-(3-methylpyridyl) | -cyclohexyl |
| D33 (a, b, and c) | -2-(3-methylpyridyl) | -t-butoxy |
| D34 (a, b, and c) | -2-(3-methylpyridyl) | -isopropoxy |
| D35 (a, b, and c) | -2-(3-methylpyridyl) | —CF₃ |
| D36 (a, b, and c) | -2-(3-methylpyridyl) | —OCF₃ |
| D37 (a, b, and c) | -2-(3-methylpyridyl) | —Cl |
| D38 (a, b, and c) | -2-(3-methylpyridyl) | —Br |
| D39 (a, b, and c) | -2-(3-methylpyridyl) | —I |
| D40 (a, b, and c) | -2-(3-methylpyridyl) | -n-butyl |
| D41 (a, b, and c) | -2-(3-methylpyridyl) | -n-propyl |
| D42 (a, b, and c) | -2-(3-methylpyridyl) | -iso-propyl |
| D43 (a, b, and c) | -2-(3-CF₃-pyridyl) | -t-butyl |
| D44 (a, b, and c) | -2-(3-CF₃-pyridyl) | -iso-butyl |
| D45 (a, b, and c) | -2-(3-CF₃-pyridyl) | -sec-butyl |
| D46 (a, b, and c) | -2-(3-CF₃-pyridyl) | -cyclohexyl |
| D47 (a, b, and c) | -2-(3-CF₃-pyridyl) | -t-butoxy |
| D48 (a, b, and c) | -2-(3-CF₃-pyridyl) | -isopropoxy |
| D49 (a, b, and c) | -2-(3-CF₃-pyridyl) | —CF₃ |
| D50 (a, b, and c) | -2-(3-CF₃-pyridyl) | —OCF₃ |
| D51 (a, b, and c) | -2-(3-CF₃-pyridyl) | —Cl |
| D52 (a, b, and c) | -2-(3-CF₃-pyridyl) | —Br |
| D53 (a, b, and c) | -2-(3-CF₃-pyridyl) | —I |
| D54 (a, b, and c) | -2-(3-CF₃-pyridyl) | -n-butyl |
| D55 (a, b, and c) | -2-(3-CF₃-pyridyl) | -n-propyl |

TABLE IV-continued

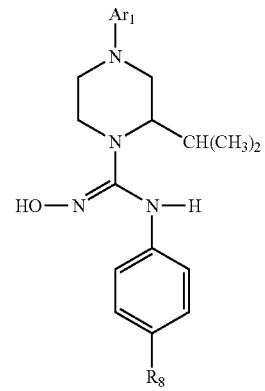

and pharmaceutically acceptable salts thereof, wherein:

| Compound | Ar₁ | R₈ |
|---|---|---|
| D56 (a, b, and c) | -2-(3-CF₃-pyridyl) | -iso-propyl |
| D57 (a, b, and c) | -2-(3-CHF₂-pyridyl) | -t-butyl |
| D58 (a, b, and c) | -2-(3-CHF₂-pyridyl) | -iso-butyl |
| D59 (a, b, and c) | -2-(3-CHF₂-pyridyl) | -sec-butyl |
| D60 (a, b, and c) | -2-(3-CHF₂-pyridyl) | -cyclohexyl |
| D61 (a, b, and c) | -2-(3-CHF₂-pyridyl) | -t-butoxy |
| D62 (a, b, and c) | -2-(3-CHF₂-pyridyl) | -isopropoxy |
| D63 (a, b, and c) | -2-(3-CHF₂-pyridyl) | —CF₃ |
| D64 (a, b, and c) | -2-(3-CHF₂-pyridyl) | —OCF₃ |
| D65 (a, b, and c) | -2-(3-CHF₂-pyridyl) | —Cl |
| D66 (a, b, and c) | -2-(3-CHF₂-pyridyl) | —Br |
| D67 (a, b, and c) | -2-(3-CHF₂-pyridyl) | —I |
| D68 (a, b, and c) | -2-(3-CHF₂-pyridyl) | -n-butyl |
| D69 (a, b, and c) | -2-(3-CHF₂-pyridyl) | -n-propyl |
| D70 (a, b, and c) | -2-(3-CHF₂-pyridyl) | -iso-propyl |
| D71 (a, b, and c) | -2-(3-hydroxypyridyl) | -t-butyl |
| D72 (a, b, and c) | -2-(3-hydroxypyridyl) | -iso-butyl |
| D73 (a, b, and c) | -2-(3-hydroxypyridyl) | -sec-butyl |
| D74 (a, b, and c) | -2-(3-hydroxypyridyl) | -cyclohexyl |
| D75 (a, b, and c) | -2-(3-hydroxypyridyl) | -t-butoxy |
| D76 (a, b, and c) | -2-(3-hydroxypyridyl) | -isopropoxy |
| D77 (a, b, and c) | -2-(3-hydroxypyridyl) | —CF₃ |
| D78 (a, b, and c) | -2-(3-hydroxypyridyl) | —OCF₃ |
| D79 (a, b, and c) | -2-(3-hydroxypyridyl) | —Cl |
| D80 (a, b, and c) | -2-(3-hydroxypyridyl) | —Br |
| D81 (a, b, and c) | -2-(3-hydroxypyridyl) | —I |
| D82 (a, b, and c) | -2-(3-hydroxypyridyl) | -n-butyl |
| D83 (a, b, and c) | -2-(3-hydroxypyridyl) | -n-propyl |
| D84 (a, b, and c) | -2-(3-hydroxypyridyl) | -iso-propyl |
| D85 (a, b, and c) | -2-(3-nitropyridyl) | -t-butyl |
| D86 (a, b, and c) | -2-(3-nitropyridyl) | -iso-butyl |
| D87 (a, b, and c) | -2-(3-nitropyridyl) | -sec-butyl |
| D88 (a, b, and c) | -2-(3-nitropyridyl) | -cyclohexyl |
| D89 (a, b, and c) | -2-(3-nitropyridyl) | -t-butoxy |
| D90 (a, b, and c) | -2-(3-nitropyridyl) | -isopropoxy |
| D91 (a, b, and c) | -2-(3-nitropyridyl) | —CF₃ |
| D92 (a, b, and c) | -2-(3-nitropyridyl) | —OCF₃ |
| D93 (a, b, and c) | -2-(3-nitropyridyl) | —Cl |
| D94 (a, b, and c) | -2-(3-nitropyridyl) | —Br |
| D95 (a, b, and c) | -2-(3-nitropyridyl) | —I |
| D96 (a, b, and c) | -2-(3-nitropyridyl) | -n-butyl |
| D97 (a, b, and c) | -2-(3-nitropyridyl) | -n-propyl |
| D98 (a, b, and c) | -2-(3-nitropyridyl) | -iso-propyl |
| D99 (a, b, and c) | -2-(3-cyanopyridyl) | -t-butyl |
| D100 (a, b, and c) | -2-(3-cyanopyridyl) | -iso-butyl |
| D101 (a, b, and c) | -2-(3-cyanopyridyl) | -sec-butyl |
| D102 (a, b, and c) | -2-(3-cyanopyridyl) | -cyclohexyl |
| D103 (a, b, and c) | -2-(3-cyanopyridyl) | -t-butoxy |
| D104 (a, b, and c) | -2-(3-cyanopyridyl) | -isopropoxy |
| D105 (a, b, and c) | -2-(3-cyanopyridyl) | —CF₃ |
| D106 (a, b, and c) | -2-(3-cyanopyridyl) | —OCF₃ |
| D107 (a, b, and c) | -2-(3-cyanopyridyl) | —Cl |
| D108 (a, b, and c) | -2-(3-cyanopyridyl) | —Br |
| D109 (a, b, and c) | -2-(3-cyanopyridyl) | —I |
| D110 (a, b, and c) | -2-(3-cyanopyridyl) | -n-butyl |

TABLE IV-continued

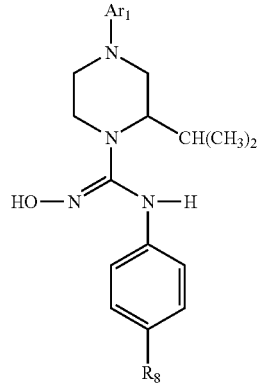

and pharmaceutically acceptable salts thereof, wherein:

| Compound | Ar₁ | R₈ |
|---|---|---|
| D111 (a, b, and c) | -2-(3-cyanopyridyl) | -n-propyl |
| D112 (a, b, and c) | -2-(3-cyanopyridyl) | -isopropyl |
| D113 (a, b, and c) | -2-(3-bromopyridyl) | -t-butyl |
| D114 (a, b, and c) | -2-(3-bromopyridyl) | -iso-butyl |
| D115 (a, b, and c) | -2-(3-bromopyridyl) | -sec-butyl |
| D116 (a, b, and c) | -2-(3-bromopyridyl) | -cyclohexyl |
| D117 (a, b, and c) | -2-(3-bromopyridyl) | -t-butoxy |
| D118 (a, b, and c) | -2-(3-bromopyridyl) | -isopropoxy |
| D119 (a, b, and c) | -2-(3-bromopyridyl) | —CF₃ |
| D120 (a, b, and c) | -2-(3-bromopyridyl) | —OCF₃ |
| D121 (a, b, and c) | -2-(3-bromopyridyl) | —Cl |
| D122 (a, b, and c) | -2-(3-bromopyridyl) | —Br |
| D123 (a, b, and c) | -2-(3-bromopyridyl) | —I |
| D124 (a, b, and c) | -2-(3-bromopyridyl) | -n-butyl |
| D125 (a, b, and c) | -2-(3-bromopyridyl) | -n-propyl |
| D126 (a, b, and c) | -2-(3-bromopyridyl) | -iso-propyl |
| D127 (a, b, and c) | -2-(3-iodopyridyl) | -t-butyl |
| D128 (a, b, and c) | -2-(3-iodopyridyl) | -iso-butyl |
| D129 (a, b, and c) | -2-(3-iodopyridyl) | -sec-butyl |
| D130 (a, b, and c) | -2-(3-iodopyridyl) | -cyclohexyl |
| D131 (a, b, and c) | -2-(3-iodopyridyl) | -t-butoxy |
| D132 (a, b, and c) | -2-(3-iodopyridyl) | -isopropoxy |
| D133 (a, b, and c) | -2-(3-iodopyridyl) | —CF₃ |
| D134 (a, b, and c) | -2-(3-iodopyridyl) | —OCF₃ |
| D135 (a, b, and c) | -2-(3-iodopyridyl) | —Cl |
| D136 (a, b, and c) | -2-(3-iodopyridyl) | —Br |
| D137 (a, b, and c) | -2-(3-iodopyridyl) | —I |
| D138 (a, b, and c) | -2-(3-iodopyridyl) | -n-butyl |
| D139 (a, b, and c) | -2-(3-iodopyridyl) | -n-propyl |
| D140 (a, b, and c) | -2-(3-iodopyridyl) | -iso-propyl |
| D141 (a, b, and c) | -4-(5-chloropyrimidinyl) | -t-butyl |
| D142 (a, b, and c) | -4-(5-chloropyrimidinyl) | -iso-butyl |
| D143 (a, b, and c) | -4-(5-chloropyrimidinyl) | -sec-butyl |
| D144 (a, b, and c) | -4-(5-chloropyrimidinyl) | -cyclohexyl |
| D145 (a, b, and c) | -4-(5-chloropyrimidinyl) | -t-butoxy |
| D146 (a, b, and c) | -4-(5-chloropyrimidinyl) | -isopropoxy |
| D147 (a, b, and c) | -4-(5-chloropyrimidinyl) | —CF₃ |
| D148 (a, b, and c) | -4-(5-chloropyrimidinyl) | —OCF₃ |
| D149 (a, b, and c) | -4-(5-chloropyrimidinyl) | —Cl |
| D150 (a, b, and c) | -4-(5-chloropyrimidinyl) | —Br |
| D151 (a, b, and c) | -4-(5-chloropyrimidinyl) | —I |
| D152 (a, b, and c) | -4-(5-chloropyrimidinyl) | -n-butyl |
| D153 (a, b, and c) | -4-(5-chloropyrimidinyl) | -n-propyl |
| D154 (a, b, and c) | -4-(5-chloropyrimidinyl) | -iso-propyl |
| D155 (a, b, and c) | -4-(5-methylpyrimidinyl) | -t-butyl |
| D156 (a, b, and c) | -4-(5-methylpyrimidinyl) | -iso-butyl |
| D157 (a, b, and c) | -4-(5-methylpyrimidinyl) | -sec-butyl |
| D158 (a, b, and c) | -4-(5-methylpyrimidinyl) | -cyclohexyl |
| D159 (a, b, and c) | -4-(5-methylpyrimidinyl) | -t-butoxy |
| D160 (a, b, and c) | -4-(5-methylpyrimidinyl) | -isopropoxy |
| D161 (a, b, and c) | -4-(5-methylpyrimidinyl) | —CF₃ |
| D162 (a, b, and c) | -4-(5-methylpyrimidinyl) | —OCF₃ |
| D163 (a, b, and c) | -4-(5-methylpyrimidinyl) | —Cl |
| D164 (a, b, and c) | -4-(5-methylpyrimidinyl) | —Br |
| D165 (a, b, and c) | -4-(5-methylpyrimidinyl) | —I |

TABLE IV-continued

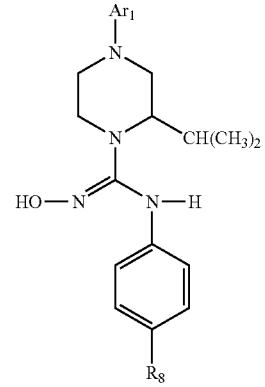

and pharmaceutically acceptable salts thereof, wherein:

| Compound | Ar₁ | R₈ |
|---|---|---|
| D166 (a, b, and c) | -4-(5-methylpyrimidinyl) | -n-butyl |
| D167 (a, b, and c) | -4-(5-methylpyrimidinyl) | -n-propyl |
| D168 (a, b, and c) | -4-(5-methylpyrimidinyl) | -iso-propyl |
| D169 (a, b, and c) | -4-(5-fluoropyrimidinyl) | -t-butyl |
| D170 (a, b, and c) | -4-(5-fluoropyrimidinyl) | -iso-butyl |
| D171 (a, b, and c) | -4-(5-fluoropyrimidinyl) | -sec-butyl |
| D172 (a, b, and c) | -4-(5-fluoropyrimidinyl) | -cyclohexyl |
| D173 (a, b, and c) | -4-(5-fluoropyrimidinyl) | -t-butoxy |
| D174 (a, b, and c) | -4-(5-fluoropyrimidinyl) | -isopropoxy |
| D175 (a, b, and c) | -4-(5-fluoropyrimidinyl) | —CF₃ |
| D176 (a, b, and c) | -4-(5-fluoropyrimidinyl) | —OCF₃ |
| D177 (a, b, and c) | -4-(5-fluoropyrimidinyl) | —Cl |
| D178 (a, b, and c) | -4-(5-fluoropyrimidinyl) | —Br |
| D179 (a, b, and c) | -4-(5-fluoropyrimidinyl) | —I |
| D180 (a, b, and c) | -4-(5-fluoropyrimidinyl) | -n-butyl |
| D181 (a, b, and c) | -4-(5-fluoropyrimidinyl) | -n-propyl |
| D182 (a, b, and c) | -4-(5-fluoropyrimidinyl) | -iso-propyl |
| D183 (a, b, and c) | -2-(3-chloropyrazinyl) | -t-butyl |
| D184 (a, b, and c) | -2-(3-chloropyrazinyl) | -iso-butyl |
| D185 (a, b, and c) | -2-(3-chloropyrazinyl) | -sec-butyl |
| D186 (a, b, and c) | -2-(3-chloropyrazinyl) | -cyclohexyl |
| D187 (a, b, and c) | -2-(3-chloropyrazinyl) | -t-butoxy |
| D188 (a, b, and c) | -2-(3-chloropyrazinyl) | -isopropoxy |
| D189 (a, b, and c) | -2-(3-chloropyrazinyl) | —CF₃ |
| D190 (a, b, and c) | -2-(3-chloropyrazinyl) | —OCF₃ |
| D191 (a, b, and c) | -2-(3-chloropyrazinyl) | —Cl |
| D192 (a, b, and c) | -2-(3-chloropyrazinyl) | —Br |
| D193 (a, b, and c) | -2-(3-chloropyrazinyl) | —I |
| D194 (a, b, and c) | -2-(3-chloropyrazinyl) | -n-butyl |
| D195 (a, b, and c) | -2-(3-chloropyrazinyl) | -n-propyl |
| D196 (a, b, and c) | -2-(3-chloropyrazinyl) | -iso-propyl |
| D197 (a, b, and c) | -2-(3-methylpyrazinyl) | -t-butyl |
| D198 (a, b, and c) | -2-(3-methylpyrazinyl) | -iso-butyl |
| D199 (a, b, and c) | -2-(3-methylpyrazinyl) | -sec-butyl |
| D200 (a, b, and c) | -2-(3-methylpyrazinyl) | -cyclohexyl |
| D201 (a, b, and c) | -2-(3-methylpyrazinyl) | -t-butoxy |
| D202 (a, b, and c) | -2-(3-methylpyrazinyl) | -isopropoxy |
| D203 (a, b, and c) | -2-(3-methylpyrazinyl) | —CF₃ |
| D204 (a, b, and c) | -2-(3-methylpyrazinyl) | —OCF₃ |
| D205 (a, b, and c) | -2-(3-methylpyrazinyl) | —Cl |
| D206 (a, b, and c) | -2-(3-methylpyrazinyl) | —Br |
| D207 (a, b, and c) | -2-(3-methylpyrazinyl) | —I |
| D208 (a, b, and c) | -2-(3-methylpyrazinyl) | -n-butyl |
| D209 (a, b, and c) | -2-(3-methylpyrazinyl) | -n-propyl |
| D210 (a, b, and c) | -2-(3-methylpyrazinyl) | -iso-propyl |
| D211 (a, b, and c) | -2-(3-fluoropyrazinyl) | -t-butyl |
| D212 (a, b, and c) | -2-(3-fluoropyrazinyl) | -iso-butyl |
| D213 (a, b, and c) | -2-(3-fluoropyrazinyl) | -sec-butyl |
| D214 (a, b, and c) | -2-(3-fluoropyrazinyl) | -cyclohexyl |
| D215 (a, b, and c) | -2-(3-fluoropyrazinyl) | -t-butoxy |
| D216 (a, b, and c) | -2-(3-fluoropyrazinyl) | -isopropoxy |
| D217 (a, b, and c) | -2-(3-fluoropyrazinyl) | —CF₃ |
| D218 (a, b, and c) | -2-(3-fluoropyrazinyl) | —OCF₃ |
| D219 (a, b, and c) | -2-(3-fluoropyrazinyl) | —Cl |
| D220 (a, b, and c) | -2-(3-fluoropyrazinyl) | —Br |

TABLE IV-continued

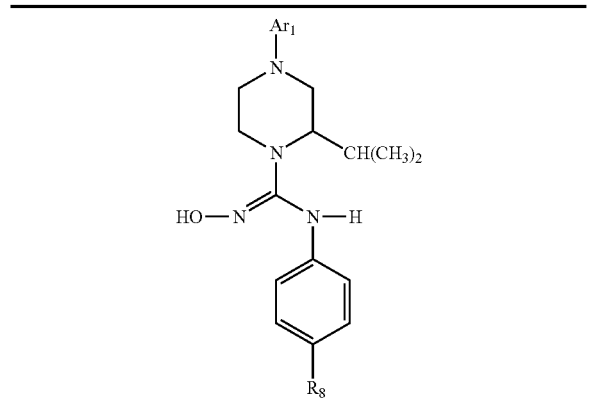

and pharmaceutically acceptable salts thereof, wherein:

| Compound | Ar₁ | R₈ |
| --- | --- | --- |
| D221 (a, b, and c) | -2-(3-fluoropyrazinyl) | —I |
| D222 (a, b, and c) | -2-(3-fluoropyrazinyl) | -n-butyl |
| D223 (a, b, and c) | -2-(3-fluoropyrazinyl) | -n-propyl |
| D224 (a, b, and c) | -2-(3-fluoropyrazinyl) | -iso-propyl |
| D225 (a, b, and c) | -3-(4-chloropyridazinyl) | -t-butyl |
| D226 (a, b, and c) | -3-(4-chloropyridazinyl) | -iso-butyl |
| D227 (a, b, and c) | -3-(4-chloropyridazinyl) | -sec-butyl |
| D228 (a, b, and c) | -3-(4-chloropyridazinyl) | -cyclohexyl |
| D229 (a, b, and c) | -3-(4-chloropyridazinyl) | -t-butoxy |
| D230 (a, b, and c) | -3-(4-chloropyridazinyl) | -isopropoxy |
| D231 (a, b, and c) | -3-(4-chloropyridazinyl) | —CF₃ |
| D232 (a, b, and c) | -3-(4-chloropyridazinyl) | —OCF₃ |
| D233 (a, b, and c) | -3-(4-chloropyridazinyl) | —Cl |
| D234 (a, b, and c) | -3-(4-chloropyridazinyl) | —Br |
| D235 (a, b, and c) | -3-(4-chloropyridazinyl) | —I |
| D236 (a, b, and c) | -3-(4-chloropyridazinyl) | -n-butyl |
| D237 (a, b, and c) | -3-(4-chloropyridazinyl) | -n-propyl |
| D238 (a, b, and c) | -3-(4-chloropyridazinyl) | -iso-propyl |
| D239 (a, b, and c) | -3-(4-methylpyridazinyl) | -t-butyl |
| D240 (a, b, and c) | -3-(4-methylpyridazinyl) | -iso-butyl |
| D241 (a, b, and c) | -3-(4-methylpyridazinyl) | -sec-butyl |
| D242 (a, b, and c) | -3-(4-methylpyridazinyl) | -cyclohexyl |
| D243 (a, b, and c) | -3-(4-methylpyridazinyl) | -t-butoxy |
| D244 (a, b, and c) | -3-(4-methylpyridazinyl) | -isopropoxy |
| D245 (a, b, and c) | -3-(4-methylpyridazinyl) | —CF₃ |
| D246 (a, b, and c) | -3-(4-methylpyridazinyl) | —OCF₃ |
| D247 (a, b, and c) | -3-(4-methylpyridazinyl) | —Cl |
| D248 (a, b, and c) | -3-(4-methylpyridazinyl) | —Br |
| D249 (a, b, and c) | -3-(4-methylpyridazinyl) | —I |
| D250 (a, b, and c) | -3-(4-methylpyridazinyl) | -n-butyl |
| D251 (a, b, and c) | -3-(4-methylpyridazinyl) | -n-propyl |
| D252 (a, b, and c) | -3-(4-methylpyridazinyl) | -iso-propyl |
| D253 (a, b, and c) | -3-(4-fluoropyridazinyl) | -t-butyl |
| D254 (a, b, and c) | -3-(4-fluoropyridazinyl) | -iso-butyl |
| D255 (a, b, and c) | -3-(4-fluoropyridazinyl) | -sec-butyl |
| D256 (a, b, and c) | -3-(4-fluoropyridazinyl) | -cyclohexyl |
| D257 (a, b, and c) | -3-(4-fluoropyridazinyl) | -t-butoxy |
| D258 (a, b, and c) | -3-(4-fluoropyridazinyl) | -isopropoxy |
| D259 (a, b, and c) | -3-(4-fluoropyridazinyl) | —CF₃ |
| D260 (a, b, and c) | -3-(4-fluoropyridazinyl) | —OCF₃ |
| D261 (a, b, and c) | -3-(4-fluoropyridazinyl) | —Cl |
| D262 (a, b, and c) | -3-(4-fluoropyridazinyl) | —Br |
| D263 (a, b, and c) | -3-(4-fluoropyridazinyl) | —I |
| D264 (a, b, and c) | -3-(4-fluoropyridazinyl) | -n-butyl |
| D265 (a, b, and c) | -3-(4-fluoropyridazinyl) | -n-propyl |
| D266 (a, b, and c) | -3-(4-fluoropyridazinyl) | -iso-propyl |
| D267 (a, b, and c) | -5-(4-chlorothiadiazolyl) | -t-butyl |
| D268 (a, b, and c) | -5-(4-chlorothiadiazolyl) | -iso-butyl |
| D269 (a, b, and c) | -5-(4-chlorothiadiazolyl) | -sec-butyl |
| D270 (a, b, and c) | -5-(4-chlorothiadiazolyl) | -cyclohexyl |
| D271 (a, b, and c) | -5-(4-chlorothiadiazolyl) | -t-butoxy |
| D272 (a, b, and c) | -5-(4-chlorothiadiazolyl) | -isopropoxy |
| D273 (a, b, and c) | -5-(4-chlorothiadiazolyl) | —CF₃ |

TABLE IV-continued

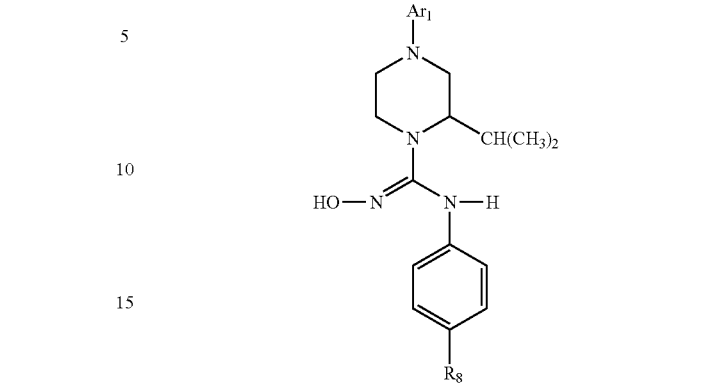

and pharmaceutically acceptable salts thereof, wherein:

| Compound | Ar₁ | R₈ |
| --- | --- | --- |
| D274 (a, b, and c) | -5-(4-chlorothiadiazolyl) | —OCF₃ |
| D275 (a, b, and c) | -5-(4-chlorothiadiazolyl) | —Cl |
| D276 (a, b, and c) | -5-(4-chlorothiadiazolyl) | —Br |
| D277 (a, b, and c) | -5-(4-chlorothiadiazolyl) | —I |
| D278 (a, b, and c) | -5-(4-chlorothiadiazolyl) | -n-butyl |
| D279 (a, b, and c) | -5-(4-chlorothiadiazolyl) | -n-propyl |
| D280 (a, b, and c) | -5-(4-chlorothiadiazolyl) | -iso-propyl |
| D281 (a, b, and c) | -5-(4-methylthiadiazolyl) | -t-butyl |
| D282 (a, b, and c) | -5-(4-methylthiadiazolyl) | -iso-butyl |
| D283 (a, b, and c) | -5-(4-methylthiadiazolyl) | -sec-butyl |
| D284 (a, b, and c) | -5-(4-methylthiadiazolyl) | -cyclohexyl |
| D285 (a, b, and c) | -5-(4-methylthiadiazolyl) | -t-butoxy |
| D286 (a, b, and c) | -5-(4-methylthiadiazolyl) | -isopropoxy |
| D287 (a, b, and c) | -5-(4-methylthiadiazolyl) | —CF₃ |
| D288 (a, b, and c) | -5-(4-methylthiadiazolyl) | —OCF₃ |
| D289 (a, b, and c) | -5-(4-methylthiadiazolyl) | —Cl |
| D290 (a, b, and c) | -5-(4-methylthiadiazolyl) | —Br |
| D291 (a, b, and c) | -5-(4-methylthiadiazolyl) | —I |
| D292 (a, b, and c) | -5-(4-methylthiadiazolyl) | -n-butyl |
| D293 (a, b, and c) | -5-(4-methylthiadiazolyl) | -n-propyl |
| D294 (a, b, and c) | -5-(4-methylthiadiazolyl) | -iso-propyl |
| D295 (a, b, and c) | -5-(4-fluorothiadiazolyl) | -t-butyl |
| D296 (a, b, and c) | -5-(4-fluorothiadiazolyl) | -iso-butyl |
| D297 (a, b, and c) | -5-(4-fluorothiadiazolyl) | -sec-butyl |
| D298 (a, b, and c) | -5-(4-fluorothiadiazolyl) | -cyclohexyl |
| D299 (a, b, and c) | -5-(4-fluorothiadiazolyl) | -t-butoxy |
| D300 (a, b, and c) | -5-(4-fluorothiadiazolyl) | -isopropoxy |
| D301 (a, b, and c) | -5-(4-fluorothiadiazolyl) | —CF₃ |
| D302 (a, b, and c) | -5-(4-fluorothiadiazolyl) | —OCF₃ |
| D303 (a, b, and c) | -5-(4-fluorothiadiazolyl) | —Cl |
| D304 (a, b, and c) | -5-(4-fluorothiadiazolyl) | —Br |
| D305 (a, b, and c) | -5-(4-fluorothiadiazolyl) | —I |
| D306 (a, b, and c) | -5-(4-fluorothiadiazolyl) | -n-butyl |
| D307 (a, b, and c) | -5-(4-fluorothiadiazolyl) | -n-propyl |
| D308 (a, b, and c) | -5-(4-fluorothiadiazolyl) | -iso-propyl |

"a" means that the Hydroxyiminopiperazine Compound is racemic.

"b" means that the carbon atom to which —CH(CH₃)₂ is attached is in the (R) configuration.

"c" means that the carbon atom to which —CH(CH₃)₂ is attached is in the (S) configuration.

TABLE V

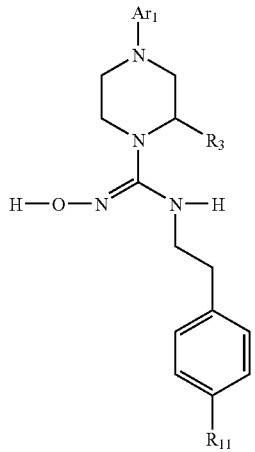

and pharmaceutically acceptable salts thereof, wherein:

| Compound | Ar$_1$ | R$_{11}$ |
|---|---|---|
| E1 (a, b, c, and d) | -2-(3-chloropyridyl) | -t-butyl |
| E2 (a, b, c, and d) | -2-(3-chloropyridyl) | -iso-butyl |
| E3 (a, b, c, and d) | -2-(3-chloropyridyl) | -sec-butyl |
| E3 (a, b, c, and d) | -2-(3-chloropyridyl) | -cyclohexyl |
| E5 (a, b, c, and d) | -2-(3-chloropyridyl) | -t-butoxy |
| E6 (a, b, c, and d) | -2-(3-chloropyridyl) | -isopropoxy |
| E7 (a, b, c, and d) | -2-(3-chloropyridyl) | —CF$_3$ |
| E8 (a, b, c, and d) | -2-(3-chloropyridyl) | —OCF$_3$ |
| E9 (a, b, c, and d) | -2-(3-chloropyridyl) | —Cl |
| E10 (a, b, c, and d) | -2-(3-chloropyridyl) | —Br |
| E11 (a, b, c, and d) | -2-(3-chloropyridyl) | —I |
| E12 (a, b, c, and d) | -2-(3-chloropyridyl) | -n-butyl |
| E13 (a, b, c, and d) | -2-(3-chloropyridyl) | -n-propyl |
| E14 (a, b, c, and d) | -2-(3-chloropyridyl) | -iso-propyl |
| E15 (a, b, c, and d) | -2-(3-fluoropyridyl) | -t-butyl |
| E16 (a, b, c, and d) | -2-(3-fluoropyridyl) | -iso-butyl |
| E17 (a, b, c, and d) | -2-(3-fluoropyridyl) | -sec-butyl |
| E18 (a, b, c, and d) | -2-(3-fluoropyridyl) | -cyclohexyl |
| E19 (a, b, c, and d) | -2-(3-fluoropyridyl) | -t-butoxy |
| E20 (a, b, c, and d) | -2-(3-fluoropyridyl) | -isopropyl |
| E21 (a, b, c, and d) | -2-(3-fluoropyridyl) | —CF$_3$ |
| E22 (a, b, c, and d) | -2-(3-fluoropyridyl) | —OCF$_3$ |
| E23 (a, b, c, and d) | -2-(3-fluoropyridyl) | —Cl |
| E24 (a, b, c, and d) | -2-(3-fluoropyridyl) | —Br |
| E25 (a, b, c, and d) | -2-(3-fluoropyridyl) | —I |
| E26 (a, b, c, and d) | -2-(3-fluoropyridyl) | -n-butyl |
| E27 (a, b, c, and d) | -2-(3-fluoropyridyl) | -n-propyl |
| E28 (a, b, c, and d) | -2-(3-fluoropyridyl) | -iso-propyl |
| E29 (a, b, c, and d) | -2-(3-methylpyridyl) | -t-butyl |
| E30 (a, b, c, and d) | -2-(3-fluoropyridyl) | -iso-butyl |
| E31 (a, b, c, and d) | -2-(3-fluoropyridyl) | -sec-butyl |
| E32 (a, b, c, and d) | -2-(3-fluoropyridyl) | -cyclohexyl |
| E33 (a, b, c, and d) | -2-(3-fluoropyridyl) | -t-butoxy |
| E34 (a, b, c, and d) | -2-(3-fluoropyridyl) | -isopropoxy |
| E35 (a, b, c, and d) | -2-(3-fluoropyridyl) | —CF$_3$ |
| E36 (a, b, c, and d) | -2-(3-fluoropyridyl) | —OCF$_3$ |
| E37 (a, b, c, and d) | -2-(3-fluoropyridyl) | —Cl |
| E38 (a, b, c, and d) | -2-(3-fluoropyridyl) | —Br |
| E39 (a, b, c, and d) | -2-(3-fluoropyridyl) | —I |
| E40 (a, b, c, and d) | -2-(3-fluoropyridyl) | -n-butyl |
| E41 (a, b, c, and d) | -2-(3-fluoropyridyl) | -n-propyl |
| E42 (a, b, c, and d) | -2-(3-fluoropyridyl) | -iso-propyl |
| E43 (a, b, c, and d) | -2-(3-CF$_3$-pyridyl) | -t-butyl |
| E44 (a, b, c, and d) | -2-(3-CF$_3$-pyridyl) | -iso-butyl |
| E45 (a, b, c, and d) | -2-(3-CF$_3$-pyridyl) | -sec-butyl |
| E46 (a, b, c, and d) | -2-(3-CF$_3$-pyridyl) | -cyclohexyl |
| E47 (a, b, c, and d) | -2-(3-CF$_3$-pyridyl) | -t-butoxy |
| E48 (a, b, c, and d) | -2-(3-CF$_3$-pyridyl) | -isopropoxy |
| E49 (a, b, c, and d) | -2-(3-CF$_3$-pyridyl) | —CF$_3$ |
| E50 (a, b, c, and d) | -2-(3-CF$_3$-pyridyl) | —OCF$_3$ |
| E51 (a, b, c, and d) | -2-(3-CF$_3$-pyridyl) | —Cl |
| E52 (a, b, c, and d) | -2-(3-CF$_3$-pyridyl) | —Br |

TABLE V-continued

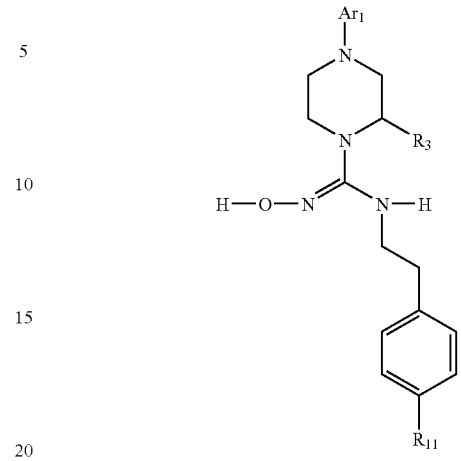

and pharmaceutically acceptable salts thereof, wherein:

| Compound | Ar$_1$ | R$_{11}$ |
|---|---|---|
| E53 (a, b, c, and d) | -2-(3-CF$_3$-pyridyl) | —I |
| E54 (a, b, c, and d) | -2-(3-CF$_3$-pyridyl) | -n-butyl |
| E55 (a, b, c, and d) | -2-(3-CF$_3$-pyridyl) | -n-propyl |
| E56 (a, b, c, and d) | -2-(3-CF$_3$-pyridyl) | -iso-propyl |
| E57 (a, b, c, and d) | -2-(3-CHF$_2$-pyridyl) | -t-butyl |
| E58 (a, b, c, and d) | -2-(3-CHF$_2$-pyridyl) | -iso-butyl |
| E59 (a, b, c, and d) | -2-(3-CHF$_2$-pyridyl) | -sec-butyl |
| E60 (a, b, c, and d) | -2-(3-CHF$_2$-pyridyl) | -cyclohexyl |
| E61 (a, b, c, and d) | -2-(3-CHF$_2$-pyridyl) | -t-butoxy |
| E62 (a, b, c, and d) | -2-(3-CHF$_2$-pyridyl) | -isopropoxy |
| E63 (a, b, c, and d) | -2-(3-CHF$_2$-pyridyl) | —CF$_3$ |
| E64 (a, b, c, and d) | -2-(3-CHF$_2$-pyridyl) | —OCF$_3$ |
| E65 (a, b, c, and d) | -2-(3-CHF$_2$-pyridyl) | —Cl |
| E66 (a, b, c, and d) | -2-(3-CHF$_2$-pyridyl) | —Br |
| E67 (a, b, c, and d) | -2-(3-CHF$_2$-pyridyl) | —I |
| E68 (a, b, c, and d) | -2-(3-CHF$_2$-pyridyl) | -n-butyl |
| E69 (a, b, c, and d) | -2-(3-CHF$_2$-pyridyl) | -n-propyl |
| E70 (a, b, c, and d) | -2-(3-CHF$_2$-pyridyl) | -iso-propyl |
| E71 (a, b, c, and d) | -2-(3-hydroxypyridyl) | -t-butyl |
| E72 (a, b, c, and d) | -2-(3-hydroxypyridyl) | -iso-butyl |
| E73 (a, b, c, and d) | -2-(3-hydroxypyridyl) | -sec-butyl |
| E74 (a, b, c, and d) | -2-(3-hydroxypyridyl) | -cyclohexyl |
| E75 (a, b, c, and d) | -2-(3-hydroxypyridyl) | -t-butoxy |
| E76 (a, b, c, and d) | -2-(3-hydroxypyridyl) | -isopropoxy |
| E77 (a, b, c, and d) | -2-(3-hydroxypyridyl) | —CF$_3$ |
| E78 (a, b, c, and d) | -2-(3-hydroxypyridyl) | —OCF$_3$ |
| E79 (a, b, c, and d) | -2-(3-hydroxypyridyl) | —Cl |
| E80 (a, b, c, and d) | -2-(3-hydroxypyridyl) | —Br |
| E81 (a, b, c, and d) | -2-(3-hydroxypyridyl) | —I |
| E82 (a, b, c, and d) | -2-(3-hydroxypyridyl) | -n-butyl |
| E83 (a, b, c, and d) | -2-(3-hydroxypyridyl) | -n-propyl |
| E84 (a, b, c, and d) | -2-(3-hydroxypyridyl) | -iso-propyl |
| E85 (a, b, c, and d) | -2-(3-nitropyridyl) | -t-butyl |
| E86 (a, b, c, and d) | -2-(3-nitropyridyl) | -iso-butyl |
| E87 (a, b, c, and d) | -2-(3-nitropyridyl) | -sec-butyl |
| E88 (a, b, c, and d) | -2-(3-nitropyridyl) | -cyclohexyl |
| E89 (a, b, c, and d) | -2-(3-nitropyridyl) | -t-butoxy |
| E90 (a, b, c, and d) | -2-(3-nitropyridyl) | -isopropoxy |
| E91 (a, b, c, and d) | -2-(3-nitropyridyl) | —CF$_3$ |
| E92 (a, b, c, and d) | -2-(3-nitropyridyl) | —OCF$_3$ |
| E93 (a, b, c, and d) | -2-(3-nitropyridyl) | —Cl |
| E94 (a, b, c, and d) | -2-(3-nitropyridyl) | —Br |
| E95 (a, b, c, and d) | -2-(3-nitropyridyl) | —I |
| E96 (a, b, c, and d) | -2-(3-nitropyridyl) | -n-butyl |
| E97 (a, b, c, and d) | -2-(3-nitropyridyl) | -n-propyl |
| E98 (a, b, c, and d) | -2-(3-nitropyridyl) | -iso-propyl |
| E99 (a, b, c, and d) | -2-(3-cyanopyridyl) | -t-butyl |
| E100 (a, b, c, and d) | -2-(3-cyanopyridyl) | -iso-butyl |
| E101 (a, b, c, and d) | -2-(3-cyanopyridyl) | -sec-butyl |
| E102 (a, b, c, and d) | -2-(3-cyanopyridyl) | -cyclohexyl |
| E103 (a, b, c, and d) | -2-(3-cyanopyridyl) | -t-butoxy |
| E104 (a, b, c, and d) | -2-(3-cyanopyridyl) | -isopropoxy |

TABLE V-continued

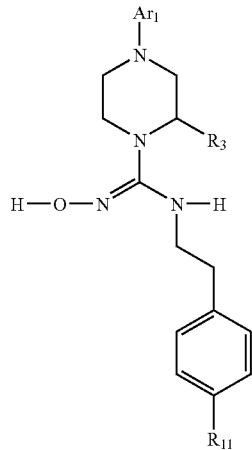

and pharmaceutically acceptable salts thereof, wherein:

| Compound | Ar₁ | R₁₁ |
|---|---|---|
| E105 (a, b, c, and d) | -2-(3-cyanopyridyl) | —CF₃ |
| E106 (a, b, c, and d) | -2-(3-cyanopyridyl) | —OCF₃ |
| E107 (a, b, c, and d) | -2-(3-cyanopyridyl) | —Cl |
| E108 (a, b, c, and d) | -2-(3-cyanopyridyl) | —Br |
| E109 (a, b, c, and d) | -2-(3-cyanopyridyl) | —I |
| E110 (a, b, c, and d) | -2-(3-cyanopyridyl) | -n-butyl |
| E111 (a, b, c, and d) | -2-(3-cyanopyridyl) | -n-propyl |
| E112 (a, b, c, and d) | -2-(3-cyanopyridyl) | -isopropyl |
| E113 (a, b, c, and d) | -2-(3-bromopyridyl) | -t-butyl |
| E114 (a, b, c, and d) | -2-(3-bromopyridyl) | -iso-butyl |
| E115 (a, b, c, and d) | -2-(3-bromopyridyl) | -sec-butyl |
| E115 (a, b, c, and d) | -2-(3-bromopyridyl) | -cyclohexyl |
| E117 (a, b, c, and d) | -2-(3-bromopyridyl) | -t-butoxy |
| E118 (a, b, c, and d) | -2-(3-bromopyridyl) | -isopropoxy |
| E119 (a, b, c, and d) | -2-(3-bromopyridyl) | —CF₃ |
| E120 (a, b, c, and d) | -2-(3-bromopyridyl) | —OCF₃ |
| E121 (a, b, c, and d) | -2-(3-bromopyridyl) | —Cl |
| E122 (a, b, c, and d) | -2-(3-bromopyridyl) | —Br |
| E123 (a, b, c, and d) | -2-(3-bromopyridyl) | —I |
| E124 (a, b, c, and d) | -2-(3-bromopyridyl) | -n-butyl |
| E125 (a, b, c, and d) | -2-(3-bromopyridyl) | -n-propyl |
| E126 (a, b, c, and d) | -2-(3-bromopyridyl) | -iso-propyl |
| E127 (a, b, c, and d) | -2-(3-iodopyridyl) | -t-butyl |
| E128 (a, b, c, and d) | -2-(3-iodopyridyl) | -iso-butyl |
| E129 (a, b, c, and d) | -2-(3-iodopyridyl) | -sec-butyl |
| E130 (a, b, c, and d) | -2-(3-iodopyridyl) | -cyclohexyl |
| E131 (a, b, c, and d) | -2-(3-iodopyridyl) | -t-butoxy |
| E132 (a, b, c, and d) | -2-(3-iodopyridyl) | -isopropoxy |
| E133 (a, b, c, and d) | -2-(3-iodopyridyl) | —CF₃ |
| E134 (a, b, c, and d) | -2-(3-iodopyridyl) | —OCF₃ |
| E135 (a, b, c, and d) | -2-(3-iodopyridyl) | —Cl |
| E136 (a, b, c, and d) | -2-(3-iodopyridyl) | —Br |
| E137 (a, b, c, and d) | -2-(3-iodopyridyl) | —I |
| E138 (a, b, c, and d) | -2-(3-iodopyridyl) | -n-butyl |
| E139 (a, b, c, and d) | -2-(3-iodopyridyl) | -n-propyl |
| E140 (a, b, c, and d) | -2-(3-iodopyridyl) | -iso-propyl |
| E141 (a, b, c, and d) | -4-(5-chloropyrimidinyl) | -t-butyl |
| E142 (a, b, c, and d) | -4-(5-chloropyrimidinyl) | -iso-butyl |
| E143 (a, b, c, and d) | -4-(5-chloropyrimidinyl) | -sec-butyl |
| E144 (a, b, c, and d) | -4-(5-chloropyrimidinyl) | -cyclohexyl |
| E145 (a, b, c, and d) | -4-(5-chloropyrimidinyl) | -t-butoxy |
| E146 (a, b, c, and d) | -4-(5-chloropyrimidinyl) | -isopropoxy |
| E147 (a, b, c, and d) | -4-(5-chloropyrimidinyl) | —CF₃ |
| E148 (a, b, c, and d) | -4-(5-chloropyrimidinyl) | —OCF₃ |
| E149 (a, b, c, and d) | -4-(5-chloropyrimidinyl) | —Cl |
| E150 (a, b, c, and d) | -4-(5-chloropyrimidinyl) | —Br |
| E151 (a, b, c, and d) | -4-(5-chloropyrimidinyl) | —I |
| E152 (a, b, c, and d) | -4-(5-chloropyrimidinyl) | -n-butyl |
| E153 (a, b, c, and d) | -4-(5-chloropyrimidinyl) | -n-propyl |
| E154 (a, b, c, and d) | -4-(5-chloropyrimidinyl) | -iso-propyl |
| E155 (a, b, c, and d) | -4-(5-methylpyrimidinyl) | -t-butyl |
| E156 (a, b, c, and d) | -4-(5-methylpyrimidinyl) | -iso-butyl |

TABLE V-continued

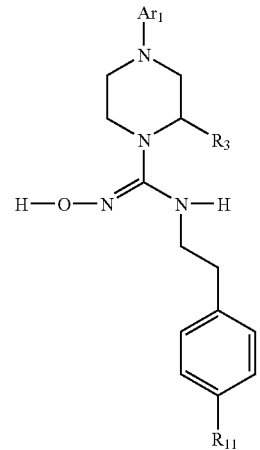

and pharmaceutically acceptable salts thereof, wherein:

| Compound | Ar₁ | R₁₁ |
|---|---|---|
| E157 (a, b, c, and d) | -4-(5-methylpyrimidinyl) | -sec-butyl |
| E158 (a, b, c, and d) | -4-(5-methylpyrimidinyl) | -cyclohexyl |
| E159 (a, b, c, and d) | -4-(5-methylpyrimidinyl) | -t-butoxy |
| E160 (a, b, c, and d) | -4-(5-methylpyrimidinyl) | -isopropoxy |
| E161 (a, b, c, and d) | -4-(5-methylpyrimidinyl) | —CF₃ |
| E162 (a, b, c, and d) | -4-(5-methylpyrimidinyl) | —OCF₃ |
| E163 (a, b, c, and d) | -4-(5-methylpyrimidinyl) | —Cl |
| E164 (a, b, c, and d) | -4-(5-methylpyrimidinyl) | —Br |
| E165 (a, b, c, and d) | -4-(5-methylpyrimidinyl) | —I |
| E166 (a, b, c, and d) | -4-(5-methylpyrimidinyl) | -n-butyl |
| E167 (a, b, c, and d) | -4-(5-methylpyrimidinyl) | -n-propyl |
| E168 (a, b, c, and d) | -4-(5-methylpyrimidinyl) | -iso-propyl |
| E169 (a, b, c, and d) | -4-(5-fluoropyrimidinyl) | -t-butyl |
| E170 (a, b, c, and d) | -4-(5-fluoropyrimidinyl) | -iso-butyl |
| E171 (a, b, c, and d) | -4-(5-fluoropyrimidinyl) | -sec-butyl |
| E172 (a, b, c, and d) | -4-(5-fluoropyrimidinyl) | -cyclohexyl |
| E173 (a, b, c, and d) | -4-(5-fluoropyrimidinyl) | -t-butoxy |
| E174 (a, b, c, and d) | -4-(5-fluoropyrimidinyl) | -isopropoxy |
| E175 (a, b, c, and d) | -4-(5-fluoropyrimidinyl) | —CF₃ |
| E176 (a, b, c, and d) | -4-(5-fluoropyrimidinyl) | —OCF₃ |
| E177 (a, b, c, and d) | -4-(5-fluoropyrimidinyl) | —Cl |
| E178 (a, b, c, and d) | -4-(5-fluoropyrimidinyl) | —Br |
| E179 (a, b, c, and d) | -4-(5-fluoropyrimidinyl) | —I |
| E180 (a, b, c, and d) | -4-(5-fluoropyrimidinyl) | -n-butyl |
| E181 (a, b, c, and d) | -4-(5-fluoropyrimidinyl) | -n-propyl |
| E182 (a, b, c, and d) | -4-(5-fluoropyrimidinyl) | -iso-propyl |
| E183 (a, b, c, and d) | -2-(3-chloropyrazinyl) | -t-butyl |
| E184 (a, b, c, and d) | -2-(3-chloropyrazinyl) | -iso-butyl |
| E185 (a, b, c, and d) | -2-(3-chloropyrazinyl) | -sec-butyl |
| E186 (a, b, c, and d) | -2-(3-chloropyrazinyl) | -cyclohexyl |
| E187 (a, b, c, and d) | -2-(3-chloropyrazinyl) | -t-butoxy |
| E188 (a, b, c, and d) | -2-(3-chloropyrazinyl) | -isopropoxy |
| E189 (a, b, c, and d) | -2-(3-chloropyrazinyl) | —CF₃ |
| E190 (a, b, c, and d) | -2-(3-chloropyrazinyl) | —OCF₃ |
| E191 (a, b, c, and d) | -2-(3-chloropyrazinyl) | —Cl |
| E192 (a, b, c, and d) | -2-(3-chloropyrazinyl) | —Br |
| E193 (a, b, c, and d) | -2-(3-chloropyrazinyl) | —I |
| E194 (a, b, c, and d) | -2-(3-chloropyrazinyl) | -n-butyl |
| E195 (a, b, c, and d) | -2-(3-chloropyrazinyl) | -n-propyl |
| E196 (a, b, c, and d) | -2-(3-chloropyrazinyl) | -iso-propyl |
| E197 (a, b, c, and d) | -2-(3-methylpyrazinyl) | -t-butyl |
| E198 (a, b, c, and d) | -2-(3-methylpyrazinyl) | -iso-butyl |
| E199 (a, b, c, and d) | -2-(3-methylpyrazinyl) | -sec-butyl |
| E200 (a, b, c, and d) | -2-(3-methylpyrazinyl) | -cyclohexyl |
| E201 (a, b, c, and d) | -2-(3-methylpyrazinyl) | -t-butoxy |
| E202 (a, b, c, and d) | -2-(3-methylpyrazinyl) | -isopropoxy |
| E203 (a, b, c, and d) | -2-(3-methylpyrazinyl) | —CF₃ |
| E204 (a, b, c, and d) | -2-(3-methylpyrazinyl) | —OCF₃ |
| E205 (a, b, c, and d) | -2-(3-methylpyrazinyl) | —Cl |
| E206 (a, b, c, and d) | -2-(3-methylpyrazinyl) | —Br |
| E207 (a, b, c, and d) | -2-(3-methylpyrazinyl) | —I |
| E208 (a, b, c, and d) | -2-(3-methylpyrazinyl) | -n-butyl |

TABLE V-continued

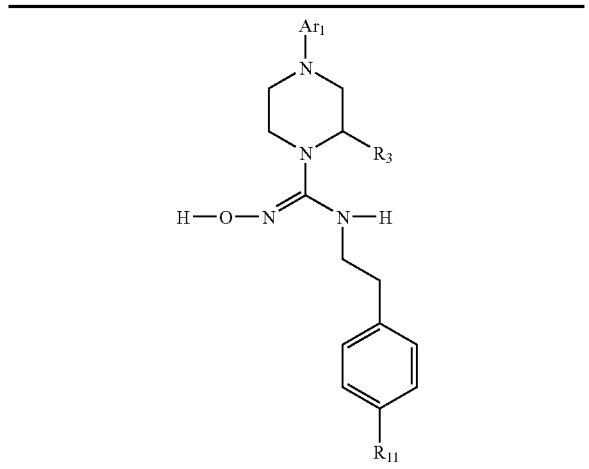

and pharmaceutically acceptable salts thereof, wherein:

| Compound | Ar$_1$ | R$_{11}$ |
|---|---|---|
| E209 (a, b, c, and d) | -2-(3-methylpyrazinyl) | -n-propyl |
| E210 (a, b, c, and d) | -2-(3-methylpyrazinyl) | -iso-propyl |
| E211 (a, b, c, and d) | -2-(3-fluoropyrazinyl) | -t-butyl |
| E212 (a, b, c, and d) | -2-(3-fluoropyrazinyl) | -iso-butyl |
| E213 (a, b, c, and d) | -2-(3-fluoropyrazinyl) | -sec-butyl |
| E214 (a, b, c, and d) | -2-(3-fluoropyrazinyl) | -cyclohexyl |
| E215 (a, b, c, and d) | -2-(3-fluoropyrazinyl) | -t-butoxy |
| E216 (a, b, c, and d) | -2-(3-fluoropyrazinyl) | -isopropoxy |
| E217 (a, b, c, and d) | -2-(3-fluoropyrazinyl) | —CF$_3$ |
| E218 (a, b, c, and d) | -2-(3-fluoropyrazinyl) | —OCF$_3$ |
| E219 (a, b, c, and d) | -2-(3-fluoropyrazinyl) | —Cl |
| E220 (a, b, c, and d) | -2-(3-fluoropyrazinyl) | —Br |
| E221 (a, b, c, and d) | -2-(3-fluoropyrazinyl) | —I |
| E222 (a, b, c, and d) | -2-(3-fluoropyrazinyl) | -n-butyl |
| E223 (a, b, c, and d) | -2-(3-fluoropyrazinyl) | -n-propyl |
| E224 (a, b, c, and d) | -2-(3-fluoropyrazinyl) | -iso-propyl |
| E225 (a, b, c, and d) | -3-(4-chloropyridazinyl) | -t-butyl |
| E226 (a, b, c, and d) | -3-(4-chloropyridazinyl) | -iso-butyl |
| E227 (a, b, c, and d) | -3-(4-chloropyridazinyl) | -sec-butyl |
| E228 (a, b, c, and d) | -3-(4-chloropyridazinyl) | -cyclohexyl |
| E229 (a, b, c, and d) | -3-(4-chloropyridazinyl) | -t-butoxy |
| E230 (a, b, c, and d) | -3-(4-chloropyridazinyl) | -isopropoxy |
| E231 (a, b, c, and d) | -3-(4-chloropyridazinyl) | —CF$_3$ |
| E232 (a, b, c, and d) | -3-(4-chloropyridazinyl) | —OCF$_3$ |
| E223 (a, b, c, and d) | -3-(4-chloropyridazinyl) | —Cl |
| E234 (a, b, c, and d) | -3-(4-chloropyridazinyl) | —Br |
| E235 (a, b, c, and d) | -3-(4-chloropyridazinyl) | —I |
| E236 (a, b, c, and d) | -3-(4-chloropyridazinyl) | -n-butyl |
| E237 (a, b, c, and d) | -3-(4-chloropyridazinyl) | -n-propyl |
| E238 (a, b, c, and d) | -3-(4-chloropyridazinyl) | -iso-propyl |
| E239 (a, b, c, and d) | -3-(4-methylpyridazinyl) | -t-butyl |
| E240 (a, b, c, and d) | -3-(4-methylpyridazinyl) | -iso-butyl |
| E241 (a, b, c, and d) | -3-(4-methylpyridazinyl) | -sec-butyl |
| E242 (a, b, c, and d) | -3-(4-methylpyridazinyl) | -cyclohexyl |
| E243 (a, b, c, and d) | -3-(4-methylpyridazinyl) | -t-butoxy |
| E244 (a, b, c, and d) | -3-(4-methylpyridazinyl) | -isopropoxy |
| E245 (a, b, c, and d) | -3-(4-methylpyridazinyl) | —CF$_3$ |
| E246 (a, b, c, and d) | -3-(4-methylpyridazinyl) | —OCF$_3$ |
| E247 (a, b, c, and d) | -3-(4-methylpyridazinyl) | —Cl |
| E248 (a, b, c, and d) | -3-(4-methylpyridazinyl) | —Br |
| E249 (a, b, c, and d) | -3-(4-methylpyridazinyl) | —I |
| E250 (a, b, c, and d) | -3-(4-methylpyridazinyl) | -n-butyl |
| E251 (a, b, c, and d) | -3-(4-methylpyridazinyl) | -n-propyl |
| E252 (a, b, c, and d) | -3-(4-methylpyridazinyl) | -iso-propyl |
| E253 (a, b, c, and d) | -3-(4-fluoropyridazinyl) | -t-butyl |
| E254 (a, b, c, and d) | -3-(4-fluoropyridazinyl) | -iso-butyl |
| E255 (a, b, c, and d) | -3-(4-fluoropyridazinyl) | -sec-butyl |
| E256 (a, b, c, and d) | -3-(4-fluoropyridazinyl) | -cyclohexyl |
| E257 (a, b, c, and d) | -3-(4-fluoropyridazinyl) | -t-butoxy |
| E258 (a, b, c, and d) | -3-(4-fluoropyridazinyl) | -isopropoxy |
| E259 (a, b, c, and d) | -3-(4-fluoropyridazinyl) | —CF$_3$ |
| E260 (a, b, c, and d) | -3-(4-fluoropyridazinyl) | —OCF$_3$ |
| E261 (a, b, c, and d) | -3-(4-fluoropyridazinyl) | —Cl |
| E262 (a, b, c, and d) | -3-(4-fluoropyridazinyl) | —Br |
| E263 (a, b, c, and d) | -3-(4-fluoropyridazinyl) | —I |
| E264 (a, b, c, and d) | -3-(4-fluoropyridazinyl) | -n-butyl |
| E265 (a, b, c, and d) | -3-(4-fluoropyridazinyl) | -n-propyl |
| E266 (a, b, c, and d) | -3-(4-fluoropyridazinyl) | -iso-propyl |
| E267 (a, b, c, and d) | -5-(4-chlorothiadiazolyl) | -t-butyl |
| E268 (a, b, c, and d) | -5-(4-chlorothiadiazolyl) | -iso-butyl |
| E269 (a, b, c, and d) | -5-(4-chlorothiadiazolyl) | -sec-butyl |
| E270 (a, b, c, and d) | -5-(4-chlorothiadiazolyl) | -cyclohexyl |
| E271 (a, b, c, and d) | -5-(4-chlorothiadiazolyl) | -t-butoxy |
| E272 (a, b, c, and d) | -5-(4-chlorothiadiazolyl) | -isopropoxy |
| E273 (a, b, c, and d) | -5-(4-chlorothiadiazolyl) | —CF$_3$ |
| E274 (a, b, c, and d) | -5-(4-chlorothiadiazolyl) | —OCF$_3$ |
| E275 (a, b, c, and d) | -5-(4-chlorothiadiazolyl) | —Cl |
| E276 (a, b, c, and d) | -5-(4-chlorothiadiazolyl) | —Br |
| E277 (a, b, c, and d) | -5-(4-chlorothiadiazolyl) | —I |
| E278 (a, b, c, and d) | -5-(4-chlorothiadiazolyl) | -n-butyl |
| E279 (a, b, c, and d) | -5-(4-chlorothiadiazolyl) | -n-propyl |
| E280 (a, b, c, and d) | -5-(4-chlorothiadiazolyl) | -iso-propyl |
| E281 (a, b, c, and d) | -5-(4-methylthiadiazolyl) | -t-butyl |
| E282 (a, b, c, and d) | -5-(4-methylthiadiazolyl) | -iso-butyl |
| E283 (a, b, c, and d) | -5-(4-methylthiadiazolyl) | -sec-butyl |
| E284 (a, b, c, and d) | -5-(4-methylthiadiazolyl) | -cyclohexyl |
| E285 (a, b, c, and d) | -5-(4-methylthiadiazolyl) | -t-butoxy |
| E286 (a, b, c, and d) | -5-(4-methylthiadiazolyl) | -isopropoxy |
| E287 (a, b, c, and d) | -5-(4-methylthiadiazolyl) | —CF$_3$ |
| E288 (a, b, c, and d) | -5-(4-methylthiadiazolyl) | —OCF$_3$ |
| E289 (a, b, c, and d) | -5-(4-methylthiadiazolyl) | —Cl |
| E290 (a, b, c, and d) | -5-(4-methylthiadiazolyl) | —Br |
| E291 (a, b, c, and d) | -5-(4-methylthiadiazolyl) | —I |
| E292 (a, b, c, and d) | -5-(4-methylthiadiazolyl) | -n-butyl |
| E293 (a, b, c, and d) | -5-(4-methylthiadiazolyl) | -n-propyl |
| E294 (a, b, c, and d) | -5-(4-methylthiadiazolyl) | -iso-propyl |
| E295 (a, b, c, and d) | -5-(4-fluorothiadiazolyl) | -t-butyl |
| E296 (a, b, c, and d) | -5-(4-fluorothiadiazolyl) | -iso-butyl |
| E297 (a, b, c, and d) | -5-(4-fluorothiadiazolyl) | -sec-butyl |
| E298 (a, b, c, and d) | -5-(4-fluorothiadiazolyl) | -cyclohexyl |
| E299 (a, b, c, and d) | -5-(4-fluorothiadiazolyl) | -t-butoxy |
| E300 (a, b, c, and d) | -5-(4-fluorothiadiazolyl) | -isopropoxy |
| E301 (a, b, c, and d) | -5-(4-fluorothiadiazolyl) | —CF$_3$ |
| E302 (a, b, c, and d) | -5-(4-fluorothiadiazolyl) | —OCF$_3$ |
| E303 (a, b, c, and d) | -5-(4-fluorothiadiazolyl) | —Cl |
| E304 (a, b, c, and d) | -5-(4-fluorothiadiazolyl) | —Br |
| E305 (a, b, c, and d) | -5-(4-fluorothiadiazolyl) | —I |
| E306 (a, b, c, and d) | -5-(4-fluorothiadiazolyl) | -n-butyl |

TABLE V-continued

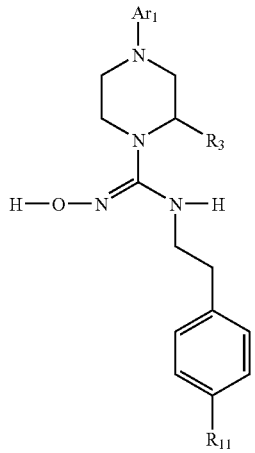

and pharmaceutically acceptable salts thereof, wherein:

| Compound | $Ar_1$ | $R_{11}$ |
|---|---|---|
| E307 (a, b, c, and d) | -5-(4-fluorothiadiazolyl) | -n-propyl |
| E308 (a, b, c, and d) | -5-(4-fluorothiadiazolyl) | -iso-propyl |

"a" means $R_3$ is —H.
"b" means $R_3$ is —$CH_3$ and the Hydroxyiminopiperazine Compound is racemic.
"c" means $R_3$ is —$CH_3$ and the carbon atom to which $R_3$ is attached is in the (R) configuration.
"d" means $R_3$ is —$CH_3$ and the carbon atom to which $R_3$ is attached is in the (S) configuration.

TABLE VI

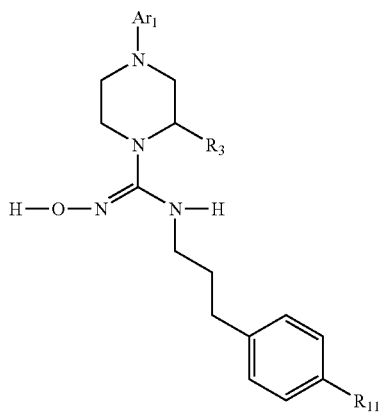

and pharmaceutically acceptable salts thereof, wherein:

| Compound | $Ar_1$ | $R_{11}$ |
|---|---|---|
| F1 (a, b, c, and d) | -2-(3-chloropyridyl) | -t-butyl |
| F2 (a, b, c, and d) | -2-(3-chloropyridyl) | -iso-butyl |
| F3 (a, b, c, and d) | -2-(3-chloropyridyl) | -sec-butyl |
| F4 (a, b, c, and d) | -2-(3-chloropyridyl) | -cyclohexyl |
| F5 (a, b, c, and d) | -2-(3-chloropyridyl) | -t-butoxy |
| F6 (a, b, c, and d) | -2-(3-chloropyridyl) | -isopropoxy |
| F7 (a, b, c, and d) | -2-(3-chloropyridyl) | —$CF_3$ |
| F8 (a, b, c, and d) | -2-(3-chloropyridyl) | —$OCF_3$ |
| F9 (a, b, c, and d) | -2-(3-chloropyridyl) | —Cl |
| F10 (a, b, c, and d) | -2-(3-chloropyridyl) | —Br |
| F11 (a, b, c, and d) | -2-(3-chloropyridyl) | —I |
| F12 (a, b, c, and d) | -2-(3-chloropyridyl) | -n-butyl |
| F13 (a, b, c, and d) | -2-(3-chloropyridyl) | -n-propyl |
| F14 (a, b, c, and d) | -2-(3-chloropyridyl) | -iso-propyl |

TABLE VI-continued

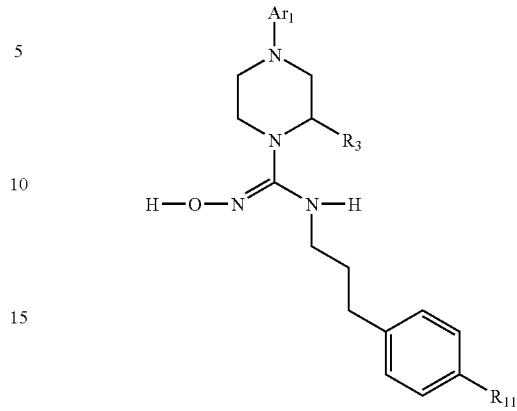

and pharmaceutically acceptable salts thereof, wherein:

| Compound | $Ar_1$ | $R_{11}$ |
|---|---|---|
| F15 (a, b, c, and d) | -2-(3-fluoropyridyl) | -t-butyl |
| F16 (a, b, c, and d) | -2-(3-fluoropyridyl) | -iso-butyl |
| F17 (a, b, c, and d) | -2-(3-fluoropyridyl) | -sec-butyl |
| F18 (a, b, c, and d) | -2-(3-fluoropyridyl) | -cyclohexyl |
| F19 (a, b, c, and d) | -2-(3-fluoropyridyl) | -t-butoxy |
| F20 (a, b, c, and d) | -2-(3-fluoropyridyl) | -isopropoxy |
| F21 (a, b, c, and d) | -2-(3-fluoropyridyl) | —$CF_3$ |
| F22 (a, b, c, and d) | -2-(3-fluoropyridyl) | —$OCF_3$ |
| F23 (a, b, c, and d) | -2-(3-fluoropyridyl) | —Cl |
| F24 (a, b, c, and d) | -2-(3-fluoropyridyl) | —Br |
| F25 (a, b, c, and d) | -2-(3-fluoropyridyl) | —I |
| F26 (a, b, c, and d) | -2-(3-fluoropyridyl) | -n-butyl |
| F27 (a, b, c, and d) | -2-(3-fluoropyridyl) | -n-propyl |
| F28 (a, b, c, and d) | -2-(3-fluoropyridyl) | -iso-propyl |
| F29 (a, b, c, and d) | -2-(3-methylpyridyl) | -t-butyl |
| F30 (a, b, c, and d) | -2-(3-methylpyridyl) | -isobutyl |
| F31 (a, b, c, and d) | -2-(3-methylpyridyl) | -sec-butyl |
| F32 (a, b, c, and d) | -2-(3-methylpyridyl) | -cyclohexyl |
| F33 (a, b, c, and d) | -2-(3-methylpyridyl) | -t-butoxy |
| F34 (a, b, c, and d) | -2-(3-methylpyridyl) | -isopropoxy |
| F35 (a, b, c, and d) | -2-(3-methylpyridyl) | —$CF_3$ |
| F36 (a, b, c, and d) | -2-(3-methylpyridyl) | —$OCF_3$ |
| F37 (a, b, c, and d) | -2-(3-methylpyridyl) | —Cl |
| F38 (a, b, c, and d) | -2-(3-methylpyridyl) | —Br |
| F39 (a, b, c, and d) | -2-(3-methylpyridyl) | —I |
| F40 (a, b, c, and d) | -2-(3-methylpyridyl) | -n-butyl |
| F41 (a, b, c, and d) | -2-(3-methylpyridyl) | -n-propyl |
| F42 (a, b, c, and d) | -2-(3-methylpyridyl) | -iso-propyl |
| F43 (a, b, c, and d) | -2-(3-$CF_3$-pyridyl) | -t-butyl |
| F44 (a, b, c, and d) | -2-(3-$CF_3$-pyridyl) | -iso-butyl |
| F45 (a, b, c, and d) | -2-(3-$CF_3$-pyridyl) | -sec-butyl |
| F46 (a, b, c, and d) | -2-(3-$CF_3$-pyridyl) | -cyclohexyl |
| F47 (a, b, c, and d) | -2-(3-$CF_3$-pyridyl) | -t-butoxy |
| F48 (a, b, c, and d) | -2-(3-$CF_3$-pyridyl) | -isopropoxy |
| F49 (a, b, c, and d) | -2-(3-$CF_3$-pyridyl) | —$CF_3$ |
| F50 (a, b, c, and d) | -2-(3-$CF_3$-pyridyl) | —$OCF_3$ |
| F51 (a, b, c, and d) | -2-(3-$CF_3$-pyridyl) | —Cl |
| F52 (a, b, c, and d) | -2-(3-$CF_3$-pyridyl) | —Br |
| F53 (a, b, c, and d) | -2-(3-$CF_3$-pyridyl) | —I |
| F54 (a, b, c, and d) | -2-(3-$CF_3$-pyridyl) | -n-butyl |
| F55 (a, b, c, and d) | -2-(3-$CF_3$-pyridyl) | -n-propyl |
| F56 (a, b, c, and d) | -2-(3-$CF_3$-pyridyl) | -iso-propyl |
| F57 (a, b, c, and d) | -2-(3-$CHF_2$-pyridyl) | -t-butyl |
| F58 (a, b, c, and d) | -2-(3-$CHF_2$-pyridyl) | -iso-butyl |
| F59 (a, b, c, and d) | -2-(3-$CHF_2$-pyridyl) | -sec-butyl |
| F60 (a, b, c, and d) | -2-(3-$CHF_2$-pyridyl) | -cyclohexyl |
| F61 (a, b, c, and d) | -2-(3-$CHF_2$-pyridyl) | -t-butoxy |
| F62 (a, b, c, and d) | -2-(3-$CHF_2$-pyridyl) | -isopropoxy |
| F63 (a, b, c, and d) | -2-(3-$CHF_2$-pyridyl) | —$CF_3$ |
| F64 (a, b, c, and d) | -2-(3-$CHF_2$-pyridyl) | —$OCF_3$ |
| F65 (a, b, c, and d) | -2-(3-$CHF_2$-pyridyl) | —Cl |
| F66 (a, b, c, and d) | -2-(3-$CHF_2$-pyridyl) | —Br |
| F67 (a, b, c, and d) | -2-(3-$CHF_2$-pyridyl) | —I |
| F68 (a, b, c, and d) | -2-(3-$CHF_2$-pyridyl) | -n-butyl |

TABLE VI-continued

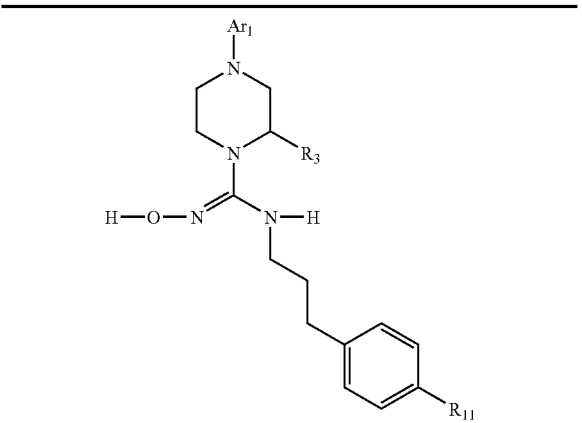

and pharmaceutically acceptable salts thereof, wherein:

| Compound | Ar$_1$ | R$_{11}$ |
|---|---|---|
| F69 (a, b, c, and d) | -2-(3-CHF$_2$-pyridyl) | -n-propyl |
| F70 (a, b, c, and d) | -2-(3-CHF$_2$-pyridyl) | -iso-propyl |
| F71 (a, b, c, and d) | -2-(3-hydroxypyridyl) | -t-butyl |
| F72 (a, b, c, and d) | -2-(3-hydroxypyridyl) | -iso-butyl |
| F73 (a, b, c, and d) | -2-(3-hydroxypyridyl) | -sec-butyl |
| F74 (a, b, c, and d) | -2-(3-hydroxypyridyl) | -cyclohexyl |
| F75 (a, b, c, and d) | -2-(3-hydroxypyridyl) | -t-butoxy |
| F76 (a, b, c, and d) | -2-(3-hydroxypyridyl) | -isopropoxy |
| F77 (a, b, c, and d) | -2-(3-hydroxypyridyl) | —CF$_3$ |
| F78 (a, b, c, and d) | -2-(3-hydroxypyridyl) | —OCF$_3$ |
| F79 (a, b, c, and d) | -2-(3-hydroxypyridyl) | —Cl |
| F80 (a, b, c, and d) | -2-(3-hydroxypyridyl) | —Br |
| F81 (a, b, c, and d) | -2-(3-hydroxypyridyl) | —I |
| F82 (a, b, c, and d) | -2-(3-hydroxypyridyl) | -n-butyl |
| F83 (a, b, c, and d) | -2-(3-hydroxypyridyl) | -n-propyl |
| F84 (a, b, c, and d) | -2-(3-hydroxypyridyl) | -iso-propyl |
| F85 (a, b, c, and d) | -2-(3-nitropyridyl) | -t-butyl |
| F86 (a, b, c, and d) | -2-(3-nitropyridyl) | -iso-butyl |
| F87 (a, b, c, and d) | -2-(3-nitropyridyl) | -sec-butyl |
| F88 (a, b, c, and d) | -2-(3-nitropyridyl) | -cyclohexyl |
| F89 (a, b, c, and d) | -2-(3-nitropyridyl) | -t-butoxy |
| F90 (a, b, c, and d) | -2-(3-nitropyridyl) | -isopropoxy |
| F91 (a, b, c, and d) | -2-(3-nitropyridyl) | —CF$_3$ |
| F92 (a, b, c, and d) | -2-(3-nitropyridyl) | —OCF$_3$ |
| F93 (a, b, c, and d) | -2-(3-nitropyridyl) | —Cl |
| F94 (a, b, c, and d) | -2-(3-nitropyridyl) | —Br |
| F95 (a, b, c, and d) | -2-(3-nitropyridyl) | —I |
| F96 (a, b, c, and d) | -2-(3-nitropyridyl) | -n-butyl |
| F97 (a, b, c, and d) | -2-(3-nitropyridyl) | -n-propyl |
| F98 (a, b, c, and d) | -2-(3-nitropyridyl) | -iso-propyl |
| F99 (a, b, c, and d) | -2-(3-cyanopyridyl) | -t-butyl |
| F100 (a, b, c, and d) | -2-(3-cyanopyridyl) | -iso-butyl |
| F101 (a, b, c, and d) | -2-(3-cyanopyridyl) | -sec-butyl |
| F102 (a, b, c, and d) | -2-(3-cyanopyridyl) | -cyclohexyl |
| F103 (a, b, c, and d) | -2-(3-cyanopyridyl) | -t-butoxy |
| F104 (a, b, c, and d) | -2-(3-cyanopyridyl) | -isopropoxy |
| F105 (a, b, c, and d) | -2-(3-cyanopyridyl) | —CF$_3$ |
| F106 (a, b, c, and d) | -2-(3-cyanopyridyl) | —OCF$_3$ |
| F107 (a, b, c, and d) | -2-(3-cyanopyridyl) | —Cl |
| F108 (a, b, c, and d) | -2-(3-cyanopyridyl) | —Br |
| F109 (a, b, c, and d) | -2-(3-cyanopyridyl) | —I |
| F110 (a, b, c, and d) | -2-(3-cyanopyridyl) | -n-butyl |
| F111 (a, b, c, and d) | -2-(3-cyanopyridyl) | -n-propyl |
| F112 (a, b, c, and d) | -2-(3-cyanopyridyl) | -isopropyl |
| F113 (a, b, c, and d) | -2-(3-bromopyridyl) | -t-butyl |
| F114 (a, b, c, and d) | -2-(3-bromopyridyl) | -iso-btuyl |
| F115 (a, b, c, and d) | -2-(3-bromopyridyl) | -sec-butyl |
| F116 (a, b, c, and d) | -2-(3-bromopyridyl) | -cyclohexyl |
| F117 (a, b, c, and d) | -2-(3-bromopyridyl) | -t-butoxy |
| F118 (a, b, c, and d) | -2-(3-bromopyridyl) | -isopropoxy |
| F119 (a, b, c, and d) | -2-(3-bromopyridyl) | —CF$_3$ |
| F120 (a, b, c, and d) | -2-(3-bromopyridyl) | —OCF$_3$ |
| F121 (a, b, c, and d) | -2-(3-bromopyridyl) | —Cl |
| F122 (a, b, c, and d) | -2-(3-bromopyridyl) | —Br |
| F123 (a, b, c, and d) | -2-(3-bromopyridyl) | —I |
| F124 (a, b, c, and d) | -2-(3-bromopyridyl) | -n-butyl |
| F125 (a, b, c, and d) | -2-(3-bromopyridyl) | -n-propyl |
| F126 (a, b, c, and d) | -2-(3-bromopyridyl) | -iso-propyl |
| F127 (a, b, c, and d) | -2-(3-iodopyridyl) | -t-butyl |
| F128 (a, b, c, and d) | -2-(3-iodopyridyl) | -iso-butyl |
| F129 (a, b, c, and d) | -2-(3-iodopyridyl) | -sec-butyl |
| F130 (a, b, c, and d) | -2-(3-iodopyridyl) | -cyclohexyl |
| F131 (a, b, c, and d) | -2-(3-iodopyridyl) | -t-butoxy |
| F132 (a, b, c, and d) | -2-(3-iodopyridyl) | -isopropoxy |
| F133 (a, b, c, and d) | -2-(3-iodopyridyl) | —CF$_3$ |
| F134 (a, b, c, and d) | -2-(3-iodopyridyl) | —OCF$_3$ |
| F135 (a, b, c, and d) | -2-(3-iodopyridyl) | —Cl |
| F136 (a, b, c, and d) | -2-(3-iodopyridyl) | —Br |
| F137 (a, b, c, and d) | -2-(3-iodopyridyl) | —I |
| F138 (a, b, c, and d) | -2-(3-iodopyridyl) | -n-butyl |
| F139 (a, b, c, and d) | -2-(3-iodopyridyl) | -n-propyl |
| F140 (a, b, c, and d) | -2-(3-iodopyridyl) | -isopropyl |
| F141 (a, b, c, and d) | -4-(5-chloropyrimidinyl) | -t-butyl |
| F142 (a, b, c, and d) | -4-(5-chloropyrimidinyl) | -iso-butyl |
| F143 (a, b, c, and d) | -4-(5-chloropyrimidinyl) | -sec-butyl |
| F144 (a, b, c, and d) | -4-(5-chloropyrimidinyl) | -cyclohexyl |
| F145 (a, b, c, and d) | -4-(5-chloropyrimidinyl) | -t-butoxy |
| F146 (a, b, c, and d) | -4-(5-chloropyrimidinyl) | -isopropoxy |
| F147 (a, b, c, and d) | -4-(5-chloropyrimidinyl) | —CF$_3$ |
| F148 (a, b, c, and d) | -4-(5-chloropyrimidinyl) | —OCF$_3$ |
| F149 (a, b, c, and d) | -4-(5-chloropyrimidinyl) | —Cl |
| F150 (a, b, c, and d) | -4-(5-chloropyrimidinyl) | —Br |
| F151 (a, b, c, and d) | -4-(5-chloropyrimidinyl) | —I |
| F152 (a, b, c, and d) | -4-(5-chloropyrimidinyl) | -n-butyl |
| F153 (a, b, c, and d) | -4-(5-chloropyrimidinyl) | -n-propyl |
| F154 (a, b, c, and d) | -4-(5-chloropyrimidinyl) | -iso-propyl |
| F155 (a, b, c, and d) | -4-(5-methylpyrimidinyl) | -t-butyl |
| F156 (a, b, c, and d) | -4-(5-methylpyrimidinyl) | -iso-butyl |
| F157 (a, b, c, and d) | -4-(5-methylpyrimidinyl) | -sec-butyl |
| F158 (a, b, c, and d) | -4-(5-methylpyrimidinyl) | -cyclohexyl |
| F159 (a, b, c, and d) | -4-(5-methylpyrimidinyl) | -t-butoxy |
| F160 (a, b, c, and d) | -4-(5-methylpyrimidinyl) | -isopropoxy |
| F161 (a, b, c, and d) | -4-(5-methylpyrimidinyl) | —CF$_3$ |
| F162 (a, b, c, and d) | -4-(5-methylpyrimidinyl) | —OCF$_3$ |
| F163 (a, b, c, and d) | -4-(5-methylpyrimidinyl) | —Cl |
| F164 (a, b, c, and d) | -4-(5-methylpyrimidinyl) | —Br |
| F165 (a, b, c, and d) | -4-(5-methylpyrimidinyl) | —I |
| F166 (a, b, c, and d) | -4-(5-methylpyrimidinyl) | -n-butyl |
| F167 (a, b, c, and d) | -4-(5-methylpyrimidinyl) | -n-propyl |
| F168 (a, b, c, and d) | -4-(5-methylpyrimidinyl) | -iso-propyl |
| F169 (a, b, c, and d) | -4-(5-fluoropyrimidinyl) | -t-butyl |
| F170 (a, b, c, and d) | -4-(5-fluoropyrimidinyl) | -iso-butyl |
| F171 (a, b, c, and d) | -4-(5-fluoropyrimidinyl) | -sec-butyl |
| F172 (a, b, c, and d) | -4-(5-fluoropyrimidinyl) | -cyclohexyl |
| F173 (a, b, c, and d) | -4-(5-fluoropyrimidinyl) | -t-butoxy |
| F174 (a, b, c, and d) | -4-(5-fluoropyrimidinyl) | -isopropoxy |
| F175 (a, b, c, and d) | -4-(5-fluoropyrimidinyl) | —CF$_3$ |
| F176 (a, b, c, and d) | -4-(5-fluoropyrimidinyl) | —OCF$_3$ |

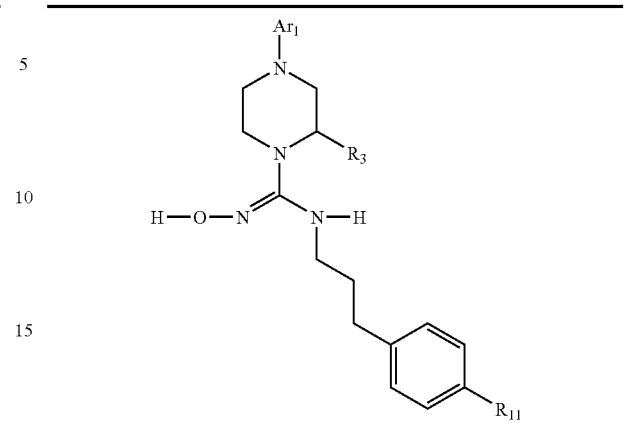

TABLE VI-continued

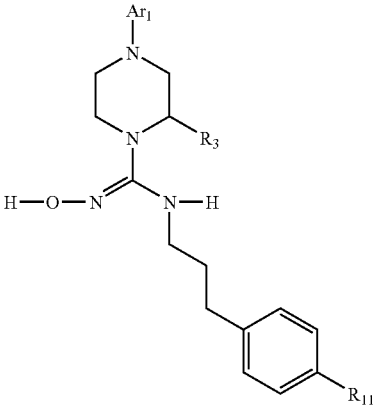

and pharmaceutically acceptable salts thereof, wherein:

| Compound | Ar₁ | R₁₁ |
|---|---|---|
| F177 (a, b, c, and d) | -4-(5-fluoropyrimidinyl) | —Cl |
| F178 (a, b, c, and d) | -4-(5-fluoropyrimidinyl) | —Br |
| F179 (a, b, c, and d) | -4-(5-fluoropyrimidinyl) | —I |
| F180 (a, b, c, and d) | -4-(5-fluoropyrimidinyl) | -n-butyl |
| F181 (a, b, c, and d) | -4-(5-fluoropyrimidinyl) | -n-propyl |
| F182 (a, b, c, and d) | -4-(5-fluoropyrimidinyl) | -iso-propyl |
| F183 (a, b, c, and d) | -2-(3-chloropyrazinyl) | -t-butyl |
| F184 (a, b, c, and d) | -2-(3-chloropyrazinyl) | -iso-butyl |
| F185 (a, b, c, and d) | -2-(3-chloropyrazinyl) | -sec-butyl |
| F186 (a, b, c, and d) | -2-(3-chloropyrazinyl) | -cyclohexyl |
| F187 (a, b, c, and d) | -2-(3-chloropyrazinyl) | -t-butoxy |
| F188 (a, b, c, and d) | -2-(3-chloropyrazinyl) | -isopropoxy |
| F189 (a, b, c, and d) | -2-(3-chloropyrazinyl) | —CF₃ |
| F190 (a, b, c, and d) | -2-(3-chloropyrazinyl) | —OCF₃ |
| F191 (a, b, c, and d) | -2-(3-chloropyrazinyl) | —Cl |
| F192 (a, b, c, and d) | -2-(3-chloropyrazinyl) | —Br |
| F193 (a, b, c, and d) | -2-(3-chloropyrazinyl) | —I |
| F194 (a, b, c, and d) | -2-(3-chloropyrazinyl) | -n-butyl |
| F195 (a, b, c, and d) | -2-(3-chloropyrazinyl) | -n-propyl |
| F196 (a, b, c, and d) | -2-(3-chloropyrazinyl) | -iso-propyl |
| F197 (a, b, c, and d) | -2-(3-methylpyrazinyl) | -t-butyl |
| F198 (a, b, c, and d) | -2-(3-methylpyrazinyl) | -iso-butyl |
| F199 (a, b, c, and d) | -2-(3-methylpyrazinyl) | -sec-butyl |
| F200 (a, b, c, and d) | -2-(3-methylpyrazinyl) | -cyclohexyl |
| F201 (a, b, c, and d) | -2-(3-methylpyrazinyl) | -isopropoxy |
| F203 (a, b, c, and d) | -2-(3-methylpyrazinyl) | —CF₃ |
| F204 (a, b, c, and d) | -2-(3-methylpyrazinyl) | —OCF₃ |
| F205 (a, b, c, and d) | -2-(3-methylpyrazinyl) | —Cl |
| F206 (a, b, c, and d) | -2-(3-methylpyrazinyl) | —Br |
| F207 (a, b, c, and d) | -2-(3-methylpyrazinyl) | —I |
| F208 (a, b, c, and d) | -2-(3-methylpyrazinyl) | -n-butyl |
| F209 (a, b, c, and d) | -2-(3-methylpyrazinyl) | -n-propyl |
| F210 (a, b, c, and d) | -2-(3-methylpyrazinyl) | -iso-propyl |
| F211 (a, b, c, and d) | -2-(3-fluoropyrazinyl) | -t-butyl |
| F212 (a, b, c, and d) | -2-(3-fluoropyrazinyl) | -iso-butyl |
| F213 (a, b, c, and d) | -2-(3-fluoropyrazinyl) | -sec-butyl |
| F214 (a, b, c, and d) | -2-(3-fluoropyrazinyl) | -cyclohexyl |
| F215 (a, b, c, and d) | -2-(3-fluoropyrazinyl) | -t-butoxy |
| F216 (a, b, c, and d) | -2-(3-fluoropyrazinyl) | -isopropoxy |
| F217 (a, b, c, and d) | -2-(3-fluoropyrazinyl) | —CF₃ |
| F218 (a, b, c, and d) | -2-(3-fluoropyrazinyl) | —OCF₃ |
| F219 (a, b, c, and d) | -2-(3-fluoropyrazinyl) | —Cl |
| F220 (a, b, c, and d) | -2-(3-fluoropyrazinyl) | —Br |
| F221 (a, b, c, and d) | -2-(3-fluoropyrazinyl) | —I |
| F222 (a, b, c, and d) | -2-(3-fluoropyrazinyl) | -n-butyl |
| F223 (a, b, c, and d) | -2-(3-fluoropyrazinyl) | -n-propyl |
| F224 (a, b, c, and d) | -2-(3-fluoropyrazinyl) | -iso-propyl |
| F225 (a, b, c, and d) | -3-(4-chloropyridazinyl) | -t-butyl |
| F226 (a, b, c, and d) | -3-(4-chloropyridazinyl) | -iso-butyl |
| F227 (a, b, c, and d) | -3-(4-chloropyridazinyl) | -sec-butyl |
| F228 (a, b, c, and d) | -3-(4-chloropyridazinyl) | -cyclohexyl |
| F229 (a, b, c, and d) | -3-(4-chloropyridazinyl) | -t-butoxy |
| F230 (a, b, c, and d) | -3-(4-chloropyridazinyl) | -isopropoxy |
| F231 (a, b, c, and d) | -3-(4-chloropyridazinyl) | —CF₃ |
| F232 (a, b, c, and d) | -3-(4-chloropyridazinyl) | —OCF₃ |
| F233 (a, b, c, and d) | -3-(4-chloropyridazinyl) | —Cl |
| F234 (a, b, c, and d) | -3-(4-chloropyridazinyl) | —Br |
| F235 (a, b, c, and d) | -3-(4-chloropyridazinyl) | —I |
| F236 (a, b, c, and d) | -3-(4-chloropyridazinyl) | -n-butyl |
| F237 (a, b, c, and d) | -3-(4-chloropyridazinyl) | -n-propyl |
| F238 (a, b, c, and d) | -3-(4-chloropyridazinyl) | -iso-propyl |
| F239 (a, b, c, and d) | -3-(4-methylpyridazinyl) | -t-butyl |
| F240 (a, b, c, and d) | -3-(4-methylpyridazinyl) | -iso-butyl |
| F241 (a, b, c, and d) | -3-(4-methylpyridazinyl) | -sec-butyl |
| F242 (a, b, c, and d) | -3-(4-methylpyridazinyl) | -cyclohexyl |
| F243 (a, b, c, and d) | -3-(4-methylpyridazinyl) | -t-butoxy |
| F244 (a, b, c, and d) | -3-(4-methylpyridazinyl) | -isopropoxy |
| F245 (a, b, c, and d) | -3-(4-methylpyridazinyl) | —CF₃ |
| F246 (a, b, c, and d) | -3-(4-methylpyridazinyl) | —OCF₃ |
| F247 (a, b, c, and d) | -3-(4-methylpyridazinyl) | —Cl |
| F248 (a, b, c, and d) | -3-(4-methylpyridazinyl) | —Br |
| F249 (a, b, c, and d) | -3-(4-methylpyridazinyl) | —I |
| F250 (a, b, c, and d) | -3-(4-methylpyridazinyl) | -n-butyl |
| F251 (a, b, c, and d) | -3-(4-methylpyridazinyl) | -n-propyl |
| F252 (a, b, c, and d) | -3-(4-methylpyridazinyl) | -iso-propyl |
| F253 (a, b, c, and d) | -3-(4-fluoropyridazinyl) | -t-butyl |
| F254 (a, b, c, and d) | -3-(4-fluoropyridazinyl) | -iso-butyl |
| F255 (a, b, c, and d) | -3-(4-fluoropyridazinyl) | -sec-butyl |
| F256 (a, b, c, and d) | -3-(4-fluoropyridazinyl) | -cyclohexyl |
| F257 (a, b, c, and d) | -3-(4-fluoropyridazinyl) | -t-butoxy |
| F258 (a, b, c, and d) | -3-(4-fluoropyridazinyl) | -isopropoxy |
| F259 (a, b, c, and d) | -3-(4-fluoropyridazinyl) | —CF₃ |
| F260 (a, b, c, and d) | -3-(4-fluoropyridazinyl) | —OCF₃ |
| F261 (a, b, c, and d) | -3-(4-fluoropyridazinyl) | —Cl |
| F262 (a, b, c, and d) | -3-(4-fluoropyridazinyl) | —Br |
| F263 (a, b, c, and d) | -3-(4-fluoropyridazinyl) | —I |
| F264 (a, b, c, and d) | -3-(4-fluoropyridazinyl) | -n-butyl |
| F265 (a, b, c, and d) | -3-(4-fluoropyridazinyl) | -n-propyl |
| F266 (a, b, c, and d) | -3-(4-fluoropyridazinyl) | -iso-propyl |
| F267 (a, b, c, and d) | -5-(4-chlorothiadiazolyl) | -t-butyl |
| F268 (a, b, c, and d) | -5-(4-chlorothiadiazolyl) | -iso-butyl |
| F269 (a, b, c, and d) | -5-(4-chlorothiadiazolyl) | -sec-butyl |
| F270 (a, b, c, and d) | -5-(4-chlorothiadiazolyl) | -cyclohexyl |
| F271 (a, b, c, and d) | -5-(4-chlorothiadiazolyl) | -t-butoxy |
| F272 (a, b, c, and d) | -5-(4-chlorothiadiazolyl) | -isopropoxy |
| F273 (a, b, c, and d) | -5-(4-chlorothiadiazolyl) | —CF₃ |
| F274 (a, b, c, and d) | -5-(4-chlorothiadiazolyl) | —OCF₃ |
| F275 (a, b, c, and d) | -5-(4-chlorothiadiazolyl) | —Cl |
| F276 (a, b, c, and d) | -5-(4-chlorothiadiazolyl) | —Br |
| F277 (a, b, c, and d) | -5-(4-chlorothiadiazolyl) | —I |
| F278 (a, b, c, and d) | -5-(4-chlorothiadiazolyl) | -n-butyl |
| F279 (a, b, c, and d) | -5-(4-chlorothiadiazolyl) | -n-propyl |
| F280 (a, b, c, and d) | -5-(4-chlorothiadiazolyl) | -iso-propyl |
| F281 (a, b, c, and d) | -5-(4-methylthiadiazolyl) | -t-butyl |
| F282 (a, b, c, and d) | -5-(4-methylthiadiazolyl) | -iso-butyl |
| F283 (a, b, c, and d) | -5-(4-methylthiadiazolyl) | -sec-butyl |
| F284 (a, b, c, and d) | -5-(4-methylthiadiazolyl) | -cyclohexyl |
| F285 (a, b, c, and d) | -5-(4-methylthiadiazolyl) | -t-butoxy |

TABLE VI-continued

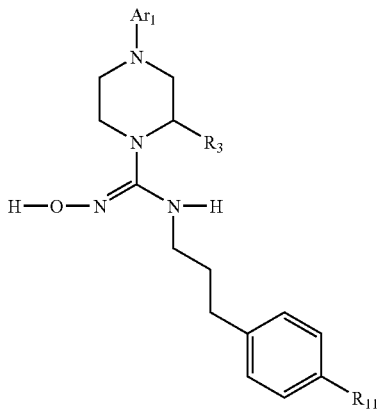

and pharmaceutically acceptable salts thereof, wherein:

| Compound | Ar₁ | R₁₁ |
|---|---|---|
| F286 (a, b, c, and d) | -5-(4-methylthiadiazolyl) | -isopropoxy |
| F287 (a, b, c, and d) | -5-(4-methylthiadiazolyl) | —CF₃ |
| F288 (a, b, c, and d) | -5-(4-methylthiadiazolyl) | —OCF₃ |
| F289 (a, b, c, and d) | -5-(4-methylthiadiazolyl) | —Cl |
| F290 (a, b, c, and d) | -5-(4-methylthiadiazolyl) | —Br |
| F291 (a, b, c, and d) | -5-(4-methylthiadiazolyl) | —I |
| F292 (a, b, c, and d) | -5-(4-methylthiadiazolyl) | -n-butyl |
| F293 (a, b, c, and d) | -5-(4-methylthiadiazolyl) | -n-propyl |
| F294 (a, b, c, and d) | -5-(4-methylthiadiazolyl) | -iso-propyl |
| F295 (a, b, c, and d) | -5-(4-fluorothiadiazolyl) | -t-butyl |
| F296 (a, b, c, and d) | -5-(4-fluorothiadiazolyl) | -iso-butyl |
| S297 (a, b, c, and d) | -5-(4-fluorothiadiazolyl) | -sec-butyl |
| F298 (a, b, c, and d) | -5-(4-fluorothiadiazolyl) | -cyclohexyl |
| F299 (a, b, c, and d) | -5-(4-fluorothiadiazolyl) | -t-butoxy |
| F300 (a, b, c, and d) | -5-(4-fluorothiadiazolyl) | -isopropoxy |
| F301 (a, b, c, and d) | -5-(4-fluorothiadiazolyl) | —CF₃ |
| F302 (a, b, c, and d) | -5-(4-fluorothiadiazolyl) | —OCF₃ |
| F303 (a, b, c, and d) | -5-(4-fluorothiadiazolyl) | —Cl |
| F304 (a, b, c, and d) | -5-(4-fluorothiadiazolyl) | —Br |
| F305 (a, b, c, and d) | -5-(4-fluorothiadiazolyl) | —I |
| F306 (a, b, c, and d) | -5-(4-fluorothiadiazolyl) | -n-butyl |
| F307 (a, b, c, and d) | -5-(4-fluorothiadiazolyl) | -n-propyl |
| F308 (a, b, c, and d) | -5-(4-fluorothiadiazolyl) | -iso-propyl |

"a" means R₃ is —H.
"b" means R₃ is —CH₃ and the Hydroxyiminopiperazine Compound is racemic.
"c" means R₃ is —CH₃ and the carbon atom to which R₃ is attached is in the (R) configuration.
"d" means R₃ is —CH₃ and the carbon atom to which R₃ is attached is in the (S) configuration.

4.9 Definitions

As used herein, the terms used above having following meaning:

"—(C₁-C₁₀)alkyl" means a straight chain or branched non-cyclic hydrocarbon having from 1 to 10 carbon atoms. Representative straight chain —(C₁-C₁₀)alkyls include -methyl, -ethyl, -n-propyl, -n-butyl, -n-pentyl, -n-hexyl, -n-heptyl, -n-octyl, -n-nonyl, and -n-decyl. Representative branched —(C₁-C₁₀)alkyls include -isopropyl, -sec-butyl, -isobutyl, -tert-butyl, -isopentyl, -neopentyl, 1-methylbutyl, 2-methylbutyl, 3-methylbutyl, 1,1-dimethylpropyl, 1,2-dimethylpropyl, 1-methylpentyl, 2-methylpentyl, 3-methylpentyl, 4-methylpentyl, 1-ethylbutyl, 2-ethylbutyl, 3-ethylbutyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-methylhexyl, 2-methylhexyl, 3-methylhexyl, 4-methylhexyl, 5-methylhexyl, 1,2-dimethylpentyl, 1,3-dimethylpentyl, 1,2-dimethylhexyl, 1,3-dimethylhexyl, 3,3-dimethylhexyl, 1,2-dimethylheptyl, 1,3-dimethylheptyl, and 3,3-dimethylheptyl.

"—(C₁-C₆)alkyl" means a straight chain or branched non-cyclic hydrocarbon having from 1 to 6 carbon atoms. Representative straight chain —(C₁-C₆)alkyls include -methyl, -ethyl, -n-propyl, -n-butyl, -n-pentyl, and -n-hexyl. Representative branched —(C₁-C₆)alkyls include -isopropyl, -sec-butyl, -isobutyl, -tert-butyl, -isopentyl, -neopentyl, 1-methylbutyl, 2-methylbutyl, 3-methylbutyl, 1,1-dimethylpropyl, 1,2-dimethylpropyl, 1-methylpentyl, 2-methylpentyl, 3-methylpentyl, 4-methylpentyl, 1-ethylbutyl, 2-ethylbutyl, 3-ethylbutyl, 1,1-dimethtylbutyl, 1,2-dimethylbutyl, 1,3-dimethylbutyl, 2,2-dimethylbutyl, 2,3-dimethylbutyl, and 3,3-dimethylbutyl.

"—(C₂-C₁₀)alkenyl" means a straight chain or branched non-cyclic hydrocarbon having from 2 to 10 carbon atoms and including at least one carbon-carbon double bond. Representative straight chain and branched (C₂-C₁₀)alkenyls include -vinyl, -allyl, -1-butenyl, -2-butenyl, -isobutylenyl, -1-pentenyl, -2-pentenyl, -3-methyl-1-butenyl, -2-methyl-2-butenyl, -2,3-dimethyl-2-butenyl, -1-hexenyl, -2-hexenyl, -3-hexenyl, -1-heptenyl, -2-heptenyl, -3-heptenyl, -1-octenyl, -2-octenyl, -3-octenyl, -1-nonenyl, -2-nonenyl, -3-nonenyl, -1-decenyl, -2-decenyl, -3-decenyl and the like.

"—(C₂-C₆)alkenyl" means a straight chain or branched non-cyclic hydrocarbon having from 2 to 6 carbon atoms and including at least one carbon-carbon double bond. Representative straight chain and branched (C₂-C₆)alkenyls include -vinyl, -allyl, -1-butenyl, -2-butenyl, -isobutylenyl, -1-pentenyl, -2-pentenyl, -3-methyl-1-butenyl, -2-methyl-2-butenyl, -2,3-dimethyl-2-butenyl, -1-hexenyl, 2-hexenyl, 3-hexenyl and the like.

"—(C₂-C₁₀)alkynyl" means a straight chain or branched non-cyclic hydrocarbon having from 2 to 10 carbon atoms and including at lease one carbon-carbon triple bond. Representative straight chain and branched —(C₂-C₁₀)alkynyls include -acetylenyl, -propynyl, -1-butynyl, -2-butynyl, -1-pentynyl, -2-pentynyl, -3-methyl-1-butynyl, -4-pentynyl, -1-hexynyl, -2-hexynyl, -5-hexynyl, -1-heptynyl, -2-heptynyl, -6-heptynyl, -1-octynyl, -2-octynyl, -7-octynyl, -1-nonynyl, -2-nonynyl, -8-nonynyl, -1-decynyl, -2-decynyl, -9-decynyl and the like.

"—(C₂-C₆)alkynyl" means a straight chain or branched non-cyclic hydrocarbon having from 2 to 6 carbon atoms and including at lease one carbon-carbon triple bond. Representative straight chain and branched (C₂-C₆)allynyls include -acetylenyl, -propynyl, -1-butynyl, -2-butynyl, -1-pentynyl, -2-pentynyl, -3-methyl-1-butynyl, -4-pentynyl, -1-hexynyl, -2-hexynyl, -5-hexynyl and the like.

"—(C₃-C₁₀)cycloalkyl" means a saturated cyclic hydrocarbon having from 3 to 10 carbon atoms. Representative (C₃-C₁₀)cycloalkyls are -cyclopropyl, -cyclobutyl, -cyclopentyl, -cyclohexyl, -cycloheptyl, -cyclooctyl, -cyclononyl, and -cyclodecyl.

"—(C₃-C₈)cycloalkyl" means a saturated cyclic hydrocarbon having from 3 to 8 carbon atoms. Representative (C₃-C₈) cycloalkyls include -cyclopropyl, -cyclobutyl, -cyclopentyl, -cyclohexyl, -cycloheptyl, and -cyclooctyl.

"—($C_8$-$C_{14}$)bicycloalkyl" means a bi-cyclic hydrocarbon ring system having from 8 to 14 carbon atoms and at least one saturated cyclic alkyl ring. Representative —($C_8$-$C_{14}$)bicycloalkyls include -indanyl, -1,2,3,4-tetrahydronaphthyl, -5,6,7,8-tetrahydronaphthyl, -perhydronaphthyl and the like.

"—($C_8$-$C_{14}$)tricycloalkyl" means a tri-cyclic hydrocarbon ring system having from 8 to 14 carbon atoms and at least one saturated cyclic ring. Representative —($C_8$-$C_{14}$)tricycloalkyls include -pyrenyl, -1,2,3,4-tetrahydroanthracenyl, -perhydroanthracenyl -aceanthrenyl, -1,2,3,4-tetrahydropenanthrenyl, -5,6,7,8-tetrahydrophenanthrenyl, -perhydrophenanthrenyl and the like.

"—($C_5$-$C_{10}$)cycloalkenyl" means a cyclic non-aromatic hydrocarbon having at least one carbon-carbon double bond in the cyclic system and from 5 to 10 carbon atoms. Representative ($C_5$-$C_{10}$)cycloalkenyls include -cyclopentenyl, -cyclopentadienyl, -cyclohexenyl, -cyclohexadienyl, -cycloheptenyl, -cycloheptadienyl, -cycloheptatrienyl, -cyclooctenyl, -cyclooctadienyl, -cyclooctatrienyl, -cyclooctatetraenyl, -cyclononenyl -cyclononadienyl, -cyclodecenyl, -cyclodecadienyl and the like.

"—($C_5$-$C_8$)cycloalkenyl" means a cyclic non-aromatic hydrocarbon having at least one carbon-carbon double bond in the cyclic system and from 5 to 8 carbon atoms. Representative ($C_5$-$C_8$)cycloalkenyls include -cyclopentenyl, -cyclopentadienyl, -cyclohexenyl, -cyclohexadienyl, -cycloheptenyl, -cycloheptadienyl, -cycloheptatrienyl, -cyclooctenyl, -cyclooctadienyl, -cyclooctatrienyl, -cyclooctatetraenyl and the like.

"—($C_8$-$C_{14}$)bicycloalkenyl" means a bi-cyclic hydrocarbon ring system having at least one carbon-carbon double bond in each ring and from 8 to 14 carbon atoms. Representative —($C_8$-$C_{14}$)bicycloalkenyls include -indenyl, -pentalenyl, -naphthalenyl, -azulenyl, -heptalenyl, -1,2,7,8-tetrahydronaphthalenyl and the like.

"—($C_8$-$C_{14}$)tricycloalkenyl" means a tri-cyclic hydrocarbon ring system having at least one carbon-carbon double bond in each ring and from 8 to 14 carbon atoms. Representative —($C_8$-$C_{14}$)tricycloalkenyls include -anthracenyl, -phenanthrenyl -phenalenyl, -acenaphthalenyl, as-indacenyl, s-indacenyl and the like.

"-(3- to 7-membered)heterocycle" or "-(3- to 7-membered) heterocyclo" means a 3- to 7-membered monocyclic heterocyclic ring which is either saturated, unsaturated non-aromatic, or aromatic. A 3-membered -(3- to 7-membered) heterocycle can contain up to 3 heteroatoms, and a 4- to 7-membered -(3- to 7-membered)heterocycle can contain up to 4 heteroatoms. Each heteroatom is independently selected from nitrogen, which can be quaternized; oxygen; and sulfur, including sulfoxide and sulfone. The -(3- to 7-membered) heterocycle can be attached via a nitrogen, sulfur, or carbon atom. Representative -(3- to 7-membered)heterocycles include pyridyl, furyl, thiophenyl, pyrrolyl, oxazolyl, imidazolyl, thiazolyl, thiadiazolyl, isoxazolyl, pyrazolyl, isothiazolyl, pyridazinyl, pyrimidinyl, pyrazinyl, triazinyl, morpholinyl, pyrrolidinonyl, pyrrolidinyl, piperidinyl, piperazinyl, hydantoinyl, valerolactamyl, oxiranyl, oxetanyl, tetrahydrofuranyl, tetrahydropyranyl, tetrahydropyrindinyl, tetrahydropyrimidinyl, tetrahydrothiophenyl, tetrahydrothiopyranyl and the like.

"-(3- to 5-membered)heterocycle" or "-(3- to 5-membered) heterocyclo" means a 3- to 5-membered monocyclic heterocyclic ring which is either saturated, unsaturated non-aromatic, or aromatic. A 3-membered -(3- to 5-membered) heterocycle can contain up to 3 heteroatoms, and a 4- to 5-membered -(3- to 5-membered)heterocycle can contain up to 4 heteroatoms. Each heteroatom is independently selected from nitrogen, which can be quaternized; oxygen; and sulfur, including sulfoxide and sulfone. The -(3- to 5-membered) heterocycle can be attached via a nitrogen, sulfur, or carbon atom. Representative -(3- to 5-membered)heterocycles include furyl, thiophenyl, pyrrolyl, oxazolyl, imidazolyl, thiazolyl, isoxazolyl, pyrazolyl, isothiazolyl, triazinyl, pyrrolidinonyl, pyrrolidinyl, hydantoinyl, oxiranyl, oxetanyl, tetrahydrofuranyl, tetrahydrothiophenyl and the like.

"-(7- to 10-membered)bicycloheterocycle" or "-(7- to 10-membered)bicycloheterocyclo" means a 7- to 10-membered bicyclic, heterocyclic ring which is either saturated, unsaturated non-aromatic, or aromatic. A -(7- to 10-membered)bicycloheterocycle contains from 1 to 4 heteroatoms independently selected from nitrogen, which can be quaternized; oxygen; and sulfur, including sulfoxide and sulfone. The -(7- to 10-membered)bicycloheterocycle can be attached via a nitrogen, sulfur, or carbon atom. Representative -(7- to 10-membered)bicycloheterocycles include -quinolinyl, -isoquinolinyl, -chromonyl, -coumarinyl, -indolyl, -indolizinyl, -benzo[b]furanyl, -benzo[b]thiophenyl, -indazolyl, -purinyl, -4H-quinolizinyl, -isoquinolyl, -quinolyl, -phthalazinyl, -naphthyridinyl, -carbazolyl, β-carbolinyl and the like.

"—($C_{14}$)aryl" means a 14-membered aromatic carbocyclic moiety such as -anthryl or -phenanthryl.

"-(5- to 10-membered)heteroaryl" means an aromatic heterocycle ring of 5 to 10 members, including both mono- and bicyclic ring systems, wherein at least one carbon atom of one or both of the rings is replaced with a heteroatom independently selected from nitrogen, oxygen, and sulfur. One or both of the -(5- to 10-membered)heteroaryl's rings contain at least one carbon atom. Representative -(5- to 10-membered) heteroaryls include pyridyl, furyl, benzofuranyl, thiophenyl, benzothiophenyl, quinolinyl, pyrrolyl, indolyl, oxazolyl, benzoxazolyl, imidazolyl, benzimidazolyl, thiazolyl, benzothiazolyl, isoxazolyl, pyrazolyl, isothiazolyl, pyridazinyl, pyrimidinyl, pyrazinyl, thiadiazolyl, triazinyl, cinnolinyl, phthalazinyl, and quinazolinyl.

"—$CH_2$(halo)" means a methyl group wherein one of the hydrogens of the methyl group has been replaced with a halogen. Representative —$CH_2$(halo) groups include —$CH_2F$, —$CH_2Cl$, —$CH_2Br$, and —$CH_2I$.

"—CH(halo)$_2$" means a methyl group wherein two of the hydrogens of the methyl group have been replaced with a halogen. Representative —CH(halo)$_2$ groups include —$CHF_2$, —$CHCl_2$, —$CHBr_2$, CHBrCl, CHClI, and —$CHI_2$.

"—C(halo)$_3$" means a methyl group wherein each of the hydrogens of the methyl group has been replaced with a halogen. Representative —C(halo)$_3$ groups include —$CF_3$, —$CCl_3$, —$CBr_3$, and —$CI_3$.

"-Halogen" or "-Halo" means —F, —Cl, —Br, or —I.

The phrase "pyridyl group" means

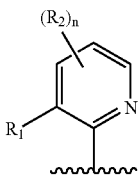

wherein R₁, R₂, and n are defined above for the Hydroxyiminopiperazine Compounds of formula (I).

The phrase "pyrazinyl group" means,

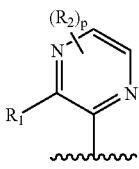

wherein R₁, R₂, and p are defined above for the Hydroxyiminopiperazine Compounds of formula (II).

The phrase "pyrimidinyl group" means

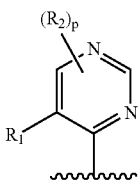

wherein R₁, R₂, and p are defined above for the Hydroxyiminopiperazine Compounds of formula (III).

The phrase "pyridazinyl group" means

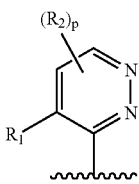

wherein R₁, R₂, and p are defined above for the Hydroxyiminopiperazine Compounds of formula (IV).

The phrase "thiadiazolyl group" means

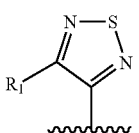

wherein R₁ is defined above for the Hydroxyiminopiperazine Compounds of formula (I)-(VI).

The phrase "2-(3-chloropyridyl)" means

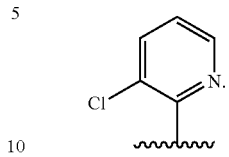

The phrase "2-(3-fluoropyridyl)" means

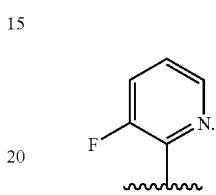

The phrase "2-(3-methylpyridyl)" means

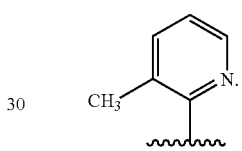

The phrase "2-(3—CF₃-methylpyridyl)" means

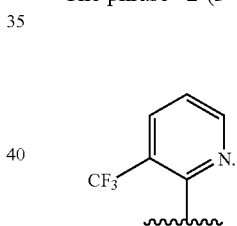

The phrase "2-(3—CHF₂-pyridyl)" means

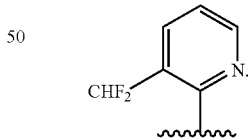

The phrase "2-(3-hydroxypyridyl)" means

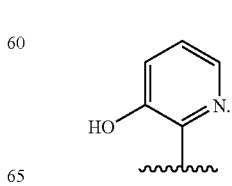

The phrase "2-(3-nitropyridyl)" means

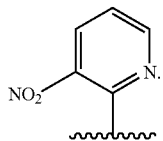

The phrase "2-(3-cyanopyridyl)" means

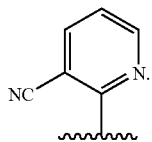

The phrase "2-(3-bromopyridyl)" means

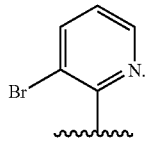

The phrase "2-(3-iodopyridyl)" means

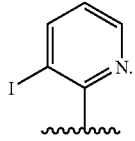

The phrase "4-(5-chloropyrimidinyl)" means

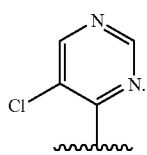

The phrase "4-(5-methylpyrimidinyl)" means

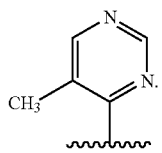

The phrase "4-(5-fluoropyrimidinyl)" means

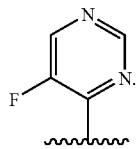

The phrase "2-(3-chloropyrazinyl)" means

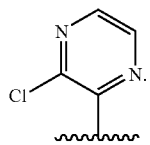

The phrase "2-(3-methylpyrazinyl)" means

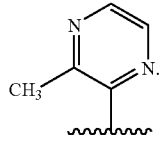

The phrase "2-(3-fluoropyrazinyl)" means

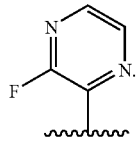

The phrase "3-(4-chloropyridazinyl)" means

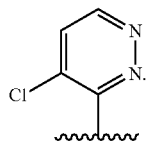

The phrase "3-(4-methylpyridazinyl)" means

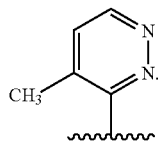

The phrase "3-(4-fluoropyridazinyl)" means

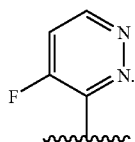

The phrase "5-(4-chlorothiadiazolyl)" means

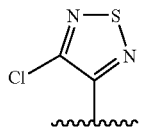

The phrase "5-(4-methyltiadiazolyl)" means

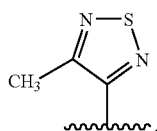

The phrase "5-(4-fluorothiadiazolyl)" means

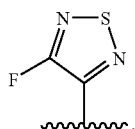

The phrase "benzoimidiazolyl group" means

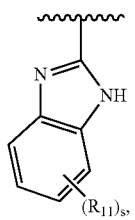

wherein $R_{11}$ and s are defined above for the Hydroxyiminopiperazine Compounds of formula (VI) or (VII).

The phrase "benzothiazolyl group" means

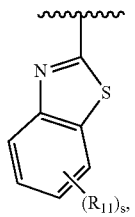

wherein $R_{11}$ and s are defined above for the Hydroxyiminopiperazine Compounds of formula (VI) or (VII).

The phrase "benzooxazolyl group" means

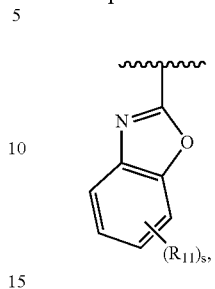

wherein $R_{11}$ and s are defined above for the Hydroxyiminopiperazine Compounds of formula (VI) or (VII).

The phrase "piperazine ring" means

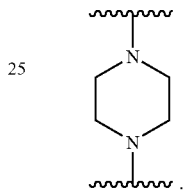

The phrase "phenethyl group" means an ethylene group attached to a terminal $Ar_2$ group, wherein one or each of two hydrogens of the ethylene group can be optionally substituted with an $R_{13}$ group. A phenethyl group is depicted below:

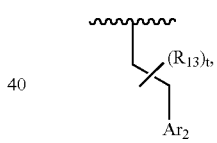

wherein $R_{13}$, $Ar_2$, and t are defined above for the Hydroxyiminopiperazine Compounds of formula (VI).

The phrase "phenpropyl group" means an n-propylene group attached to a terminal $Ar_2$ group, wherein one or each of two hydrogens of the n-propylene group can be optionally substituted with an $R_{13}$ group. A phenpropyl group is depicted below:

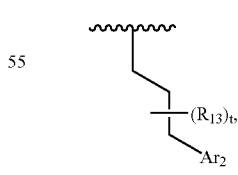

wherein $R_{13}$, $Ar_2$, and t are defined above for the Hydroxyiminopiperazine Compounds of formula (VI).

The term "animal," includes, but is not limited to, a cow, monkey, chimpanzee, baboon, horse, sheep, pig, chicken, turkey, quail, cat, dog, mouse, rat, rabbit, guinea pig, and human.

The phrase "pharmaceutically acceptable salt," as used herein, is a salt formed from an acid and a basic functional group, such as a nitrogen group, of one of the Hydroxyiminopiperazine Compounds. Illustrative salts include, but are not limited, to sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate, and pamoate (i.e., 1,1'-methylene-bis-(2-hydroxy-3-naphthoate)) salts. The term "pharmaceutically acceptable salt" also refers to a salt formed from a Hydroxyiminopiperazine Compound having an acidic functional group, such as a carboxylic acid fuinctional group, and an inorganic or organic base. Suitable bases include, but are not limited to, hydroxides of alkali metals such as sodium, potassium, and lithium; hydroxides of alkaline earth metal such as calcium and magnesium; hydroxides of other metals, such as aluminum and zinc; ammonia and organic amines, such as unsubstituted or hydroxy-substituted mono-, di-, or trialkylamines; dicyclohexylamine; tributyl amine; pyridine; N-methyl,N-ethylamine; diethylamine; triethylamine; mono-, bis-, or tris-(2-hydroxy-lower alkyl amines), such as mono-, bis-, or tris-(2-hydroxyethyl)amine, 2-hydroxy-tert-butylamine, or tris-(hydroxymethyl)methylamine, N,N,-di-lower alkyl-N-(hydroxy lower alkyl)-amines, such as N,N,-dimethyl-N-(2-hydroxyethyl)amine, or tri-(2-hydroxyethyl)amine; N-methyl-D-glucamine; and amino acids such as arginine, lysine and the like.

The phrase "effective amount," when used in connection with a Hydroxyiminopiperazine Compound means an amount effective for treating or preventing a Condition.

The phrase "effective amount," when used in connection with another therapeutic agent means an amount for providing the therapeutic effect of the therapeutic agent.

When a first group is "substituted with one or more" second groups, each of one or more of the first group's hydrogen atoms is replaced with a second group. In one embodiment, each carbon atom of a first group is independently substituted with one or two second groups. In another embodiment, each carbon atom of a first group is independently substituted with only one second group.

The term "UI" means urinary incontinence.

The term "IBD" means inflammatory-bowel disease.

The term "IBS" means irritable-bowel syndrome.

The term "ALS" means amyotrophic lateral sclerosis.

The phrases "treatment of," "treating," and the like include the amelioration or cessation of a Condition, or a symptom thereof.

The phrases "prevention of," "preventing," and the like include the avoidance of the onset of a Condition, or a symptom thereof.

4.10 Methods for Making the Hydroxyiminopiperazine Compounds

The Hydroxyiminopiperazine Compounds can be made using conventional organic synthesis including the following illustrative methods shown in the schemes below. The Hydroxyiminopiperazine Compounds wherein $R_4$ is —H can be obtained by the following illustrative method shown below in Scheme A:

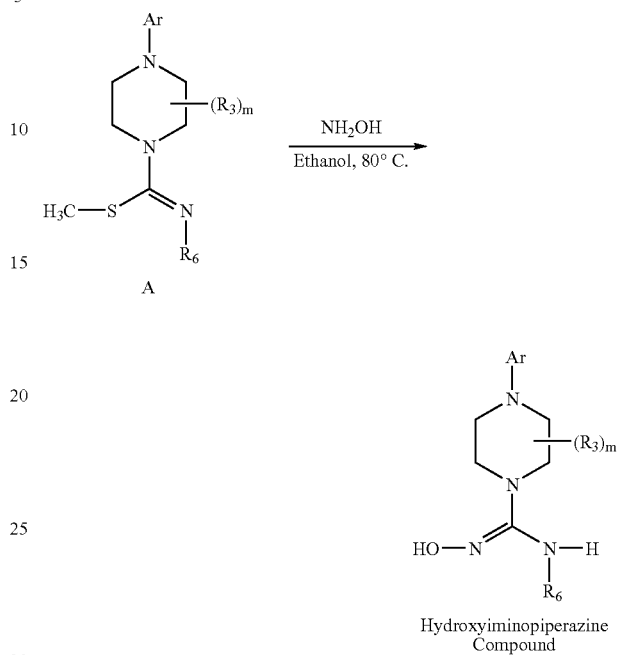

wherein $R_3$, $R_6$, and m are defined above for the Hydroxyiminopiperazine Compounds and Ar is

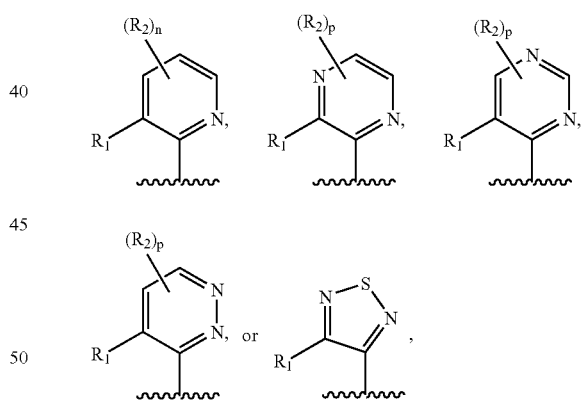

wherein $R_1$, $R_2$, n, and p are defined above for the Hydroxyiminopiperazine Compounds of formulas (I)-(VII).

A compound of formula A (about 0.3 mmol) is reacted with hydroxylamine (50 weight percent in water, about 5.8 mmol) in about 1.5 mL of ethanol with stirring at a temperature of about 80° C. for about 2 h. The mixture is then concentrated under reduced pressure to provide the Hydroximinopiperazine Compound, which can then be purified. In one embodiment, the Hydroximinopiperazine Compound is purified using column chromatography or recrystallization.

The compound of formula A can be obtained as shown below in Scheme B:

Scheme B

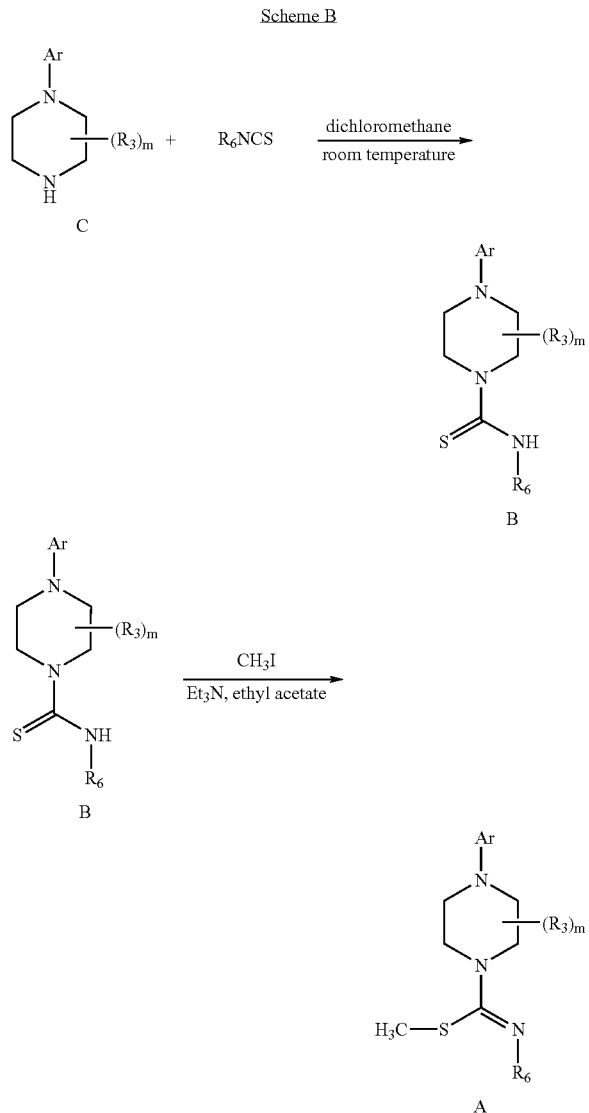

A solution of a compound of formula C (about 1 mmol) and isothiocyanate, R₆NCS, (about 1 mmol) in 1.5 mL of dichloromethane is stirred at room temperature for about 5 h. The resulting mixture is then concentrated under reduced pressure to provide the compound of formula B, which can then be purified. In one embodiment, the compound of formula B is purified using column chromatography or recrystallization. The compound of formula B (about 0.6 mmol) is then reacted with iodomethane (about 0.9 mmol) in about 3 mL of tetrahydrofuran with stirring at room temperature for about 12 h. Excess iodomethane is removed from the mixture using reduced pressure. A solution of triethylamine (about 1.74 mmol) in about 2.5 mL of ethyl acetate is then added to the mixture and the mixture is allowed to stir for about 2 h. The mixture is then concentrated under reduced pressure to provide the compound of formula A, which can then be purified. In one embodiment, the compound of formula A is purified using column chromatography or recrystallization.

If the Ar group of the compound of formula C is substituted with a hydroxyl or amino group or —R₃ is a hydroxyl or amino group, the hydroxyl or amino group is protected using a suitable protecting group, using methods well known to those skilled in the art, before the compound of formula C is reacted with R₆NCS. Suitable protecting groups for hydroxyl group include, but are not limited to, methyl ether, methoxymethyl ether, methoxythiomethyl ether, 2-methoxyethoxymethyl ether, bis(2-chloroethoxy)ethyl ether, tetrahydropyranyl ether, tetrahydrothiopyranyl ether, 4-methoxytetrahydropyranyl ether, methoxytetrahydrothiopyranyl ether, tetrahydrofuranyl ether, tetrahydrothiofuranyl ether, 1-ethoxyethyl ether, 1-methyl-1-methoxyethyl ether, 2-(phenylselenyl ether), t-butyl ether, allyl ether, benzyl ether, o-nitrobenzyl ether, triphenylmethyl ether, o-napthyldiphenylmethyl ether, p-methoxydiphenylmethyl ether, 9-(9-phenyl-10-oxo)anthryl ether (tritylone), trimethylsilyl ether, isopropyldimethylsilyl ether, t-butyldimethylsilyl ether, t-butyldiphenylsilyl ether, tribenzylsilyl ether, triisopropylsilyl ether, formate ester, acetate ester, trichloroacetate ester, phenoxyacetate ester, isobutyrate ester, pivaloate ester, adamnantoate ester, benzoate ester, 2,4,6-trimethyl (mesitoate) ester, methyl carbonate, 2,2,2-trichlorocarbonate, allyl carbonate, p-nitrophenyl carbonate, benzyl carbonate, p-nitrobenzyl carbonate, S-benzylthiocarbonate, N-phenylcarbamate, nitrate ester, and 2,4-dinitrophenylsulfenate ester (See, e.g., T. W. Greene, *Protective Groups in Organic Synthesis*, John Wiley-Interscience Publication, New York, (1981)). Suitable protecting groups for an amino group include, but are not limited to, 1,1-dimethyl-2,2,2-trichloroethyl carbamate, 1-methyl-1-(4-biphenylyl)ethyl carbamate, 2-trimethylsilylethyl carbamate, 9-fluorenylmethyl carbamate, and tert-butyl carbamate (T. W. Greene et al., *Protective Groups in Organic Synthesis*, 309-405 (2d ed. 1991)).

The compound of formula C can be obtained as shown below in Scheme C:

Scheme C

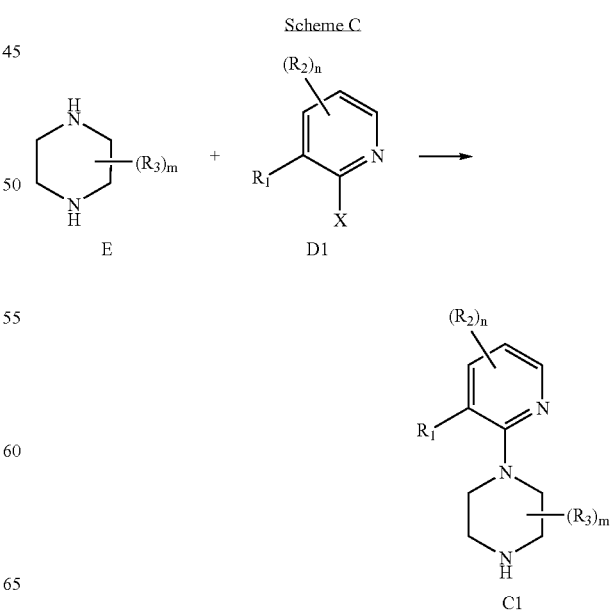

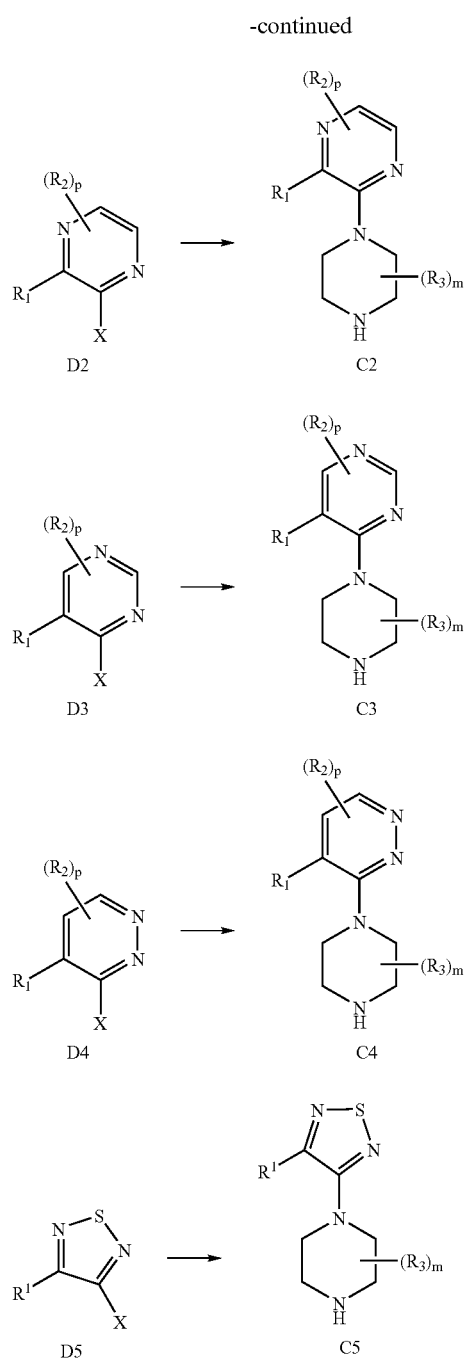

wherein $R_1$, $R_2$, $R_3$, m, n, and p are defined above for the Hydroxyiminopiperazine Compounds of formula (I)-(VII) and X is a halogen. In one embodiment, X is bromide, chloride, or iodide.

A compound of formula D1-D5 (about 20 mmol) is reacted with a compound of formula E (about 27.5 mmol) in about 15 mL of dimethyl sulfoxide in the presence of triethylamine (about 30 mmol), optionally with heating, for about 24 h to provide a compound of formula C. The compound of formula C can be isolated from the reaction mixture and purified. In one embodiment, the compound of formula C is purified using column chromatography or recrystallization. If the compound of formula E is substituted with a hydroxyl or amino group, the hydroxyl or amino group can be protected using a suitable protecting group, using methods well known to those skilled in the art, before being reacted with a compound of formula D1-D5. Suitable protecting groups include, but are not limited to, those described above.

Compounds of formula D and E are commercially available or can be prepared by methods well known to those skilled in the art. The compound of formula E wherein m is 0 is commercially available from Sigrna-Aldrich, St. Louis, Mo. (www.sigma-aldrich.com).

The isothiocyanantes, $R_6NCS$, are commercially available or can be prepared by methods well known to those skilled in the art (See, e.g. J. March, *Advanced Organic Chemistry Reactions, Mechanisms, and Structure* 417, 429, 670, 904, and 930 ($4^{th}$ ed. 1992)).

The Hydroxyiminopiperazine Compounds wherein $R_4$ is —$(C_1$-$C_{10})$alkyl can be obtained by reacting a Hydroxyiminopiperazine Compound wherein $R_4$ is —H (about 0.2 mmol), that can be prepared as described above, dissolved in dimethylformamide (about 1.5 mL) with NaH (60 weight percent, about 0.21 mmol) with stiring for about 0.5 h. A —$(C_1$-$C_{10})$alkyl halide (about 0.2 mmol), for example, methyl iodide, is then added to the resulting mixture and the mixture allowed to stir for about 4 h. The resulting mixture is then quenched with water, extracted with ethyl ether, the organic layer dried, and the solvent removed under reduced pressure to provide the Hydroxyiminopiperazine Compounds wherein $R_4$ is —$(C_1$-$C_{10})$alkyl. The Hydroxyiminopiperazine Compounds wherein $R_4$ is —$(C_1$-$C_{10})$alkyl can then be purified. In one embodiment, the Hydroxyiminopiperazine Compounds wherein $R_4$ is —$(C_1$-$C_{10})$alkyl is purified using column chromatography or recrystallization. If the Hydroxyiminopiperazine Compound wherein $R_4$ is —H is substituted with a hydroxyl or amino group, the hydroxyl or amino group is protected using a suitable protecting group, using methods well known to those skilled in the art, before being reacted with the —$(C_1$-$C_{10})$alkyl halide. Suitable protecting groups include, but are not limited to, those described above.

The Hydroxyiminopiperazine Compounds wherein $R_4$ is —$C(O)R_9$ can be obtained by reacting a Hydroxyiminopiperaxine Compound wherein $R_4$ is —H with an acid halide of formula X—$C(O)R_9$, wherein X and $R_9$ are defined above, to provide the Hydroxyiminopiperaxine Compound wherein $R_4$ is —$C(O)R_9$ as shown below in Scheme D.

Scheme D

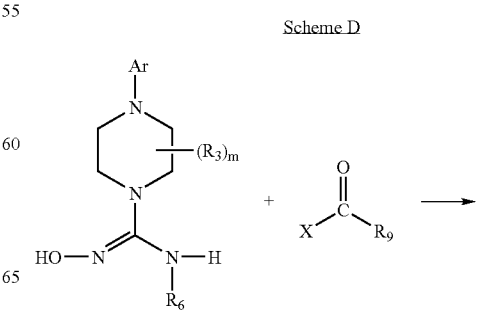

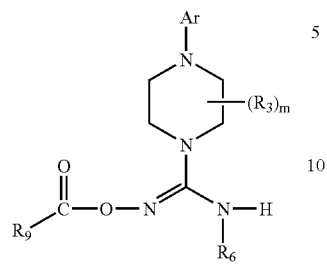

wherein X is —Cl, —Br, —I, or —F and Ar, $R_3$, $R_6$, $R_9$, and m are defined above. If the Ar group of the Hydroxyiminopiperazine Compound wherein $R_4$ is —H is substituted with a hydroxyl or amino group or —$R_3$ is a hydroxyl or amino group, the hydroxyl or amino group is protected using a suitable protecting group, using methods well known to those skilled in the art, before being reacted with the acid halide of formula X—(O)$R_9$. Suitable protecting groups include, but are not limited to, those described above.

A representative procedure for coupling an acid chloride with an amine is provided in T. R. Herrin et al., *J. Med. Chem.* 1216-1223 (1975). Methods for preparing acid halides are well known to those skilled in the art and are described in J. March, *Advanced Organic Chemistry, Reaction Mechanisms and Structure* 437-8 (4th ed. 1992). For example, acid halides can be prepared by reacting the carboxylic acid with thionyl chloride, bromide, or iodide. An acid chloride can also be prepared by reacting a carboxylic acid with phosphorous trichloride or tribromide. An acid chloride can also be prepared by reacting the carboxylic acid with $Ph_3P$ in carbon tetrachloride. An acid fluoride can be obtained by reacting a carboxylic acid with cyanuric fluoride.

The Hydroxyiminopiperazine Compounds wherein $R_4$ is —C(O)NH$R_9$ can be obtained by reacting a Hydroxyiminopiperaxine Compound wherein $R_4$ is —H with an isocyanate, $R^9$—N=C=O, in a suitable solvent, fore example toluene, at a suitable temperature, for example at reflux temperature, to provide the Hydroxyiminopiperaxine Compound wherein $R_4$ is —C(O)NH$R_9$ as shown below in Scheme E:

Scheme E

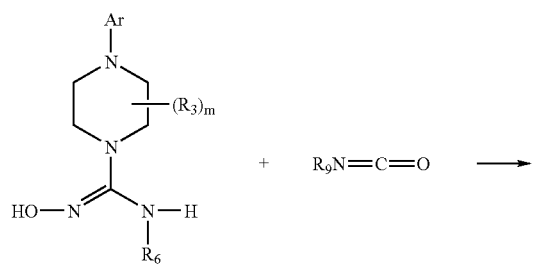

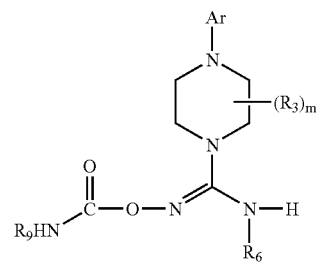

wherein Ar, $R_3$, $R_6$, $R_9$, and m are defined above. If the Ar group of the Hydroxyiminopiperazine Compound wherein $R_4$ is —H is substituted with a hydroxyl or amino group or —$R_3$ is a hydroxyl or amino group, the hydroxyl or amino group is protected using a suitable protecting group, using methods well known to those skilled in the art, before being reacted with the isocyanate of formula $R_9$—N=C=O. Suitable protecting groups include, but are not limited to, those described above.

Isocyanates $R_9$—N=C=O are commercially available or preparable by reacting $R_9NH_2$ with phosgene according to well-known methods (See, e.g., H. Eckert et al., *Angew. Chem. Int. Ed. Engl.* 26:894 (1987); H. Eckert, Ger. Offen. DE 3 440 141; *Chem Abstr.* 106:4294d (1987); and L. Contarca et al., *Synthesis* 553-576 (1996)). For example an amine, $R_9$—$NH_2$, can be reacted with triphosgene in dichloromethane as depicted below in Scheme F.

Scheme F

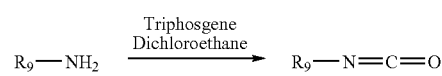

Typically, a solution of triphosgene (0.3 equivalents) in 1,2-dichloroethane (0.3 M) is slowly added to a stirred solution of $R_9NH_2$ (1.0 equivalents) in 1,2-dichloroethane (0.3 M) at room temperature. The reaction mixture is then stirred at room temperature for about 10 min. and the temperature then raised to about 70° C. After stirring at about 70° C. for about 3 h, the reaction mixture is cooled to room temperature, filtered, and the filtrate concentrated to give the desired isocyanate.

The Hydroxyiminopiperazine Compounds wherein $R_5$ is —($C_1$-$C_{10}$)alkyl can be obtained as shown below in Scheme G:

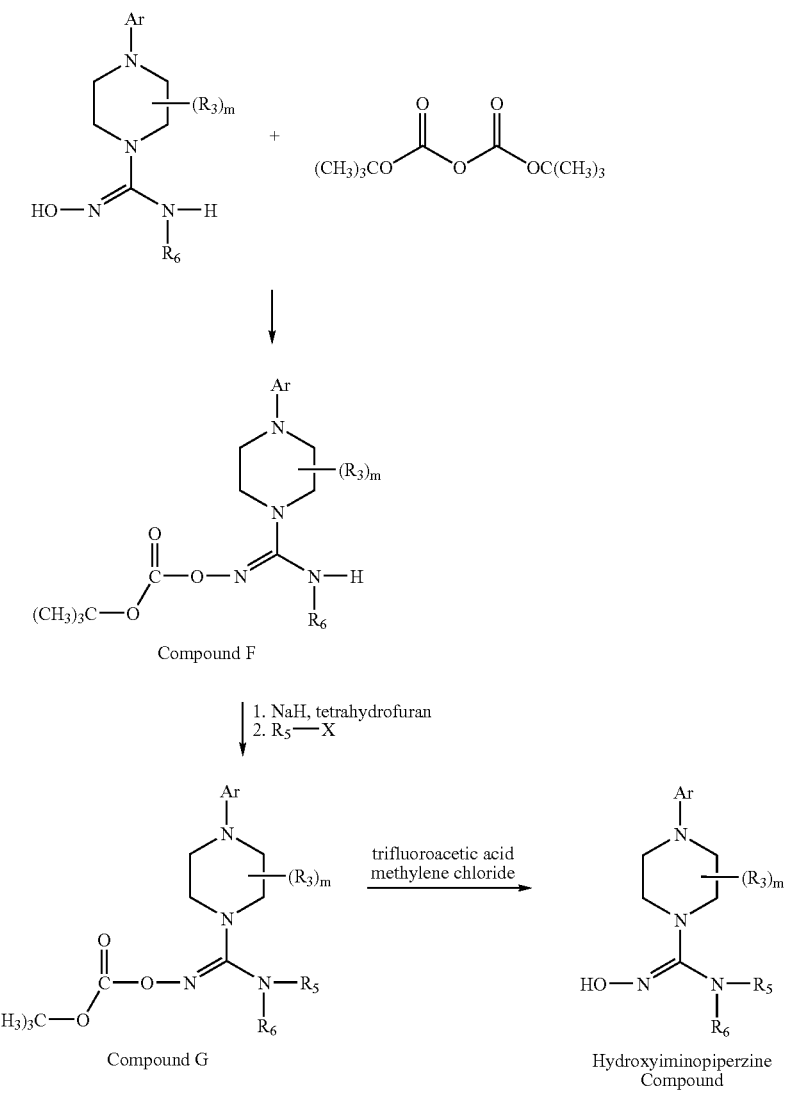

Scheme G wherein Ar, $R_3$, $R_6$, and m are defined above; X is —Cl, —Br, —I, or —F; and $R_5$—($C_1$-$C_{10}$)alkyl.

A Hydroxyiminopiperazine Compound wherein $R_4$ is —H and $R_5$ is —H is reacted with di-tert-butyldicarbonate in the presence of dimethylaminopyridine in methylene chloride according to well known techniques to provide a compound of formula F. The compound of formula F is then reacted with sodium hydride in tetrahydrofuran followed by an alkyl halide, $R_5$—X, wherein $R_5$ is —($C_1$-$C_{10}$)alkyl and X is —Cl, —Br, —I, or —F, to provide a compound of formula G. The compound of formula G is then reacted with trifluoroacetic acid in methylene chloride according to well known techniques to provide the Hydroxyiminopiperazine Compound wherein $R_5$ is —($C_1$-$C_{10}$)alkyl.

The Hydroxyiminopiperazine Compounds of formula VI and VII can be obtained by methods analogous to those described above in Scheme A-G wherein $R_6$ of the isothiocyanate, $R_6$NCS, in Scheme B is a phenethyl group or a phenpropyl group.

Certain Hydroxyiminopiperazine Compounds can have one or more asymmetric centers and therefore exist in different enantiomeric and diastereomeric forms. A Hydroxyiminopiperazine Compound can be in the form of an optical isomer or a diastereomer. Accordingly, the invention encompasses Hydroxyiminopiperazine Compounds and their uses as described herein in the form of their optical isomers, diasteriomers, and mixtures thereof, including a racemic mixture.

In addition, one or more hydrogen, carbon or other atoms of a Hydroxyiminopiperazine Compound can be replaced by an isotope of the hydrogen, carbon or other atoms. Such compounds, which are encompassed by the present invention, are useful as research and diagnostic tools in metabolism pharmacokinetic studies and in binding assays.

4.11 Therapeutic Uses of the Hydroxyiminopiperazine Compounds

In accordance with the invention, the Hydroxyiminopiperazine Compounds are administered to an animal in need of treatment or prevention of a Condition.

In one embodiment, an effective amount of a Hydroxyiminopiperazine Compound can be used to treat or prevent any condition treatable or preventable by inhibiting VR1. Examples of conditions that are treatable or preventable by inhibiting VR1 include, but are not limited to, pain, UI, an ulcer, IBD, and IBS.

In another embodiment, an effective amount of a Hydroxyiminopiperazine Compound can be used to treat or prevent any condition treatable or preventable by inhibiting mGluR5. Examples of conditions that are treatable or preventable by inhibiting mGluR5 include, but are not limited to, pain, an addictive disorder, Parkinson's disease, parkinsonism, anxiety, a pruritic condition, and psychosis.

In another embodiment, an effective amount of a Hydroxyiminopiperazine Compound can be used to treat or prevent any condition treatable or preventable by inhibiting mGluR1. Examples of conditions that are treatable or preventable by inhibiting mGluR1 include, but are not limited to, pain, UI, an addictive disorder, Parkinson's disease, parkinsonism, anxiety, epilepsy, stroke, a seizure, a pruritic condition, psychosis, a cognitive disorder, a memory deficit, restricted brain function, Huntington's chorea, ALS, dementia, retinopathy, a muscle spasm, a migraine, vomiting, dyskinesia, and depression.

The Hydroxyiminopiperazine Compounds can be used to treat or prevent acute or chronic pain. Examples of pain treatable or preventable using the Hydroxyiminopiperazine Compounds include, but are not limited to, cancer pain, central pain, labor pain, myocardial infarction pain, pancreatic pain, colic pain, post-operative pain, headache pain, muscle pain, arthritic pain, and pain associated with a periodontal disease, including gingivitis and periodontitis.

The pain to be treated or prevented may be associated with inflammation associated with an inflammatory disease, which can arise where there is an inflammation of the body tissue, and which can be a local inflammatory response and/or a systemic inflammation. For example, the Phenylene Compounds can be used to treat, or prevent pain associated with inflammatory disease including, but not limited to: organ transplant rejection; reoxygenation injury resulting from organ transplantation (see Grupp et al., *J. Mol, Cell Cardiol.* 31:297-303 (1999)) including, but not limited to, transplantation of the heart, lung, liver, or kidney; chronic inflammatory diseases of the joints, including arthritis, rheumatoid arthritis, osteoarthritis and bone diseases associated with increased bone resorption; inflammatory bowel diseases, such as ileitis, ulcerative colitis, Barrett's syndrome, and Crohn's disease; inflammatory lung diseases, such as asthma, adult respiratory distress syndrome, and chronic obstructive airway disease; inflammatory diseases of the eye, including corneal dystrophy, trachoma, onchocerciasis, uveitis, sympathetic ophthalmitis and endophthalmitis; chronic inflammatory disease of the gum, including gingivitis and periodontitis; tuberculosis; leprosy; inflammatory diseases of the kidney, including uremic complications, glomerulonephritis and nephrosis; inflammatory disease of the skin, including sclerodermatitis, psoriasis and eczema; inflammatory diseases of the central nervous system, including chronic demyelinating diseases of the nervous system, multiple sclerosis, AIDS-related neurodegeneration and Alzheimer's disease, infectious meningitis, encephalomyelitis, Parkinson's disease, Huntington's disease, amyotrophic lateral sclerosis and viral or autoimmune encephalitis; autoimmune diseases, including Type I and Type II diabetes mellitus; diabetic complications, including, but not limited to, diabetic cataract, glaucoma, retinopathy, nephropathy (such as microaluminuria and progressive diabetic nephropathy), polyneuropathy, mononeuropathies, autonomic neuropathy, gangrene of the feet, atherosclerotic coronary arterial disease, peripheral arterial disease, nonketotic hyperglycemic-hyperosmolar coma, foot ulcers, joint problems, and a skin or mucous membrane complication (such as an infection, a shin spot, a candidal infection or necrobiosis lipoidica diabeticorum); immune-complex vasculitis, and systemic lupus erythematosus (SLE); inflammatory disease of the heart, such as cardiomyopathy, ischemic heart disease hypercholesterolemia, and artherosclerosis; as well as various other diseases that can have significant inflammatory components, including preeclampsia, chronic liver failure, brain and spinal cord trauma, and cancer. The Phenylene Compounds can also be used for inhibiting, treating, or preventing pain associated with inflammatory disease that can, for example, be a systemic inflammation of the body, exemplified by gram-positive or gram negative shock, hemorrhagic or anaphylactic shock, or shock induced by cancer chemotherapy in response to pro-inflammatory cytokines, e.g., shock associated with pro-inflammatory cytokines. Such shock can be induced, e.g., by a chemotherapeutic agent that is administered as a treatment for cancer.

The Hydroxyiminopiperazine Compounds can be used to treat or prevent UI. Examples of UI treatable or preventable using the Hydroxyiminopiperazine Compounds include, but are not limited to, urge incontinence, stress incontinence, overflow incontinence, neurogenic incontinence, and total incontinence.

The Hydroxyiminopiperazine Compounds can be used to treat or prevent an ulcer. Examples of ulcers treatable or preventable using the Hydroxyiminopiperazine Compounds include, but are not limited to, a duodenal ulcer, a gastric ulcer, a marginal ulcer, an esophageal ulcer, and a stress ulcer.

The Hydroxyiminopiperazine Compounds can be used to treat or prevent IBD, including Crohn's disease and ulcerative colitis.

The Hydroxyiminopiperazine Compounds can be used to treat or prevent IBS. Examples of IBS treatable or preventable using the Hydroxyiminopiperazine Compounds include, but are not limited to, spastic-colon-type IBS and constipation-predominant IBS.

The Hydroxyiminopiperazine Compounds can be used to treat or prevent an addictive disorder, including but not limited to, an eating disorder, an impulse-control disorder, an alcohol-related disorder, a nicotine-related disorder, an amphetamine-related disorder, a cannabis-related disorder, a cocaine-related disorder, an hallucinogen-related disorder, an inhalant-related disorders, and an opioid-related disorder, all of which are further sub-classified as listed below.

Eating disorders include, but are not limited to, Bulimia Nervosa, Nonpurging Type; Bulimia Nervosa, Purging Type; Anorexia; and Eating Disorder not otherwise specified (NOS).

Impulse control disorders include, but are not limited to, Intermittent Explosive Disorder, Kleptomania, Pyromania, Pathological Gambling, Trichotillomania, and Impulse Control Disorder not otherwise specified (NOS).

Alcohol-related disorders include, but are not limited to, Alcohol-Induced Psychotic Disorder with delusions, Alcohol Abuse, Alcohol Intoxication, Alcohol Withdrawal, Alcohol Intoxication Delirium, Alcohol Withdrawal Delirium, Alcohol-Induced Persisting Dementia, Alcohol-Induced Persisting Amnestic Disorder, Alcohol Dependence, Alcohol-Induced Psychotic Disorder with hallucinations, Alcohol-Induced Mood Disorder, Alcohol-Induced Anxiety Disorder, Alcohol-Induced Sexual Dysfunction, Alcohol-Induced Sleep Disorder, Alcohol-Related Disorder not otherwise specified (NOS), Alcohol Intoxication, and Alcohol Withdrawal.

Nicotine-related disorders include, but are not limited to, Nicotine Dependence, Nicotine Withdrawal, and Nicotine-Related Disorder not otherwise specified (NOS).

Amphetamine-related disorders include, but are not limited to, Amphetamine Dependence, Amphetamine Abuse, Amphetamine Intoxication, Amphetamine Withdrawal, Amphetamine Intoxication Delirium, Amphetamine-Induced Psychotic Disorder with delusions, Amphetamine-Induced Psychotic Disorders with hallucinations, Amphetamine-Induced Mood Disorder, Amphetamine-Induced Anxiety Disorder, Amphetamine-Induced Sexual Dysfunction, Amphetamine-Induced Sleep Disorder, Amphetamine Related Disorder not otherwise specified (NOS), Amphetamine Intoxication, and Amphetamine Withdrawal.

Cannabis-related disorders include, but are not limited to, Cannabis Dependence, Cannabis Abuse, Cannabis Intoxication, Cannabis Intoxication Delirium, Cannabis-Induced Psychotic Disorder with delusions, Cannabis-Induced Psychotic Disorder with hallucinations, Cannabis-Induced Anxiety Disorder, Cannabis Related Disorder not otherwise specified (NOS), and Cannabis Intoxication.

Cocaine-related disorders include, but are not limited to, Cocaine Dependence, Cocaine Abuse, Cocaine Intoxication, Cocaine Withdrawal, Cocaine Intoxication Delirium, Cocaine-Induced Psychotic Disorder with delusions, Cocaine-Induced Psychotic Disorders with hallucinations, Cocaine-Induced Mood Disorder, Cocaine-Induced Anxiety Disorder, Cocaine-Induced Sexual Dysfunction, Cocaine-Induced Sleep Disorder, Cocaine Related Disorder not otherwise specified (NOS), Cocaine Intoxication, and Cocaine Withdrawal.

Hallucinogen-related disorders include, but are not limited to, Hallucinogen Dependence, Hallucinogen Abuse, Hallucinogen Intoxication, Hallucinogen Withdrawal, Hallucinogen Intoxication Delirium, Hallucinogen-Induced Psychotic Disorder with delusions, Hallucinogen-Induced Psychotic Disorders with hallucinations, Hallucinogen-Induced Mood Disorder, Hallucinogen-Induced Anxiety Disorder, Hallucinogen-Induced Sexual Dysfunction, Hallucinogen-Induced Sleep Disorder, Hallucinogen Related Disorder not otherwise specified (NOS), Hallucinogen Intoxication, and Hallucinogen Persisting Perception Disorder (Flashbacks).

Inhalant-related disorders include, but are not limited to, Inhalant Dependence, Inhalant Abuse, Inhalant Intoxication, Inhalant Intoxication Delirium, Inhalant-Induced Psychotic Disorder with delusions, Inhalant-Induced Psychotic Disorder with hallucinations, Inhalant-Induced Anxiety Disorder, Inhalant Related Disorder not otherwise specified (NOS), and Inhalant Intoxication.

Opioid-related disorders include, but are not limited to, Opioid Dependence, Opioid Abuse, Opioid Intoxication, Opioid Intoxication Delirium, Opioid-Induced Psychotic Disorder with delusions, Opioid-Induced Psychotic Disorder with hallucinations, Opioid-Induced Anxiety Disorder, Opioid Related Disorder not otherwise specified (NOS), Opioid Intoxication, and Opioid Withdrawal.

The Hydroxyiminopiperazine Compounds can be used to treat or prevent Parkinson's disease and parkinsonism and the symptoms associated with Parkinson's disease and parkinsonism, including but not limited to, bradykinesia, muscular rigidity, resting tremor, and impairment of postural balance.

The Hydroxyiminopiperazine Compounds can be used to treat or prevent generalized anxiety or severe anxiety and the symptoms associated with anxiety, including but not limited to, restlessness; tension; tachycardia; dyspnea; depression, including chronic "neurotic" depression; panic disorder; agoraphobia and other specific phobias; eating disorders; and personality disorders.

The Hydroxyiminopiperazine Compounds can be used to treat or prevent epilepsy, including but not limited to, partial epilepsy, generalized epilepsy, and the symptoms associated with epilepsy, including but not limited to, simple partial seizures, jacksonian seizures, complex partial (psychomotor) seizures, convulsive seizures (grand mal or tonic-clonic seizures), petit mal (absence) seizures, and status epilepticus.

The Hydroxyiminopiperazine Compounds can be used to treat or prevent strokes, including but not limited to, ischemic strokes and hemorrhagic strokes.

The Hydroxyiminopiperazine Compounds can be used to treat or prevent a seizure, including but not limited to, infantile spasms, febrile seizures, and epileptic seizures.

The Hydroxyiminopiperazine Compounds can be used to treat or prevent a pruritic condition, including but not limited to, pruritus caused by dry skin, scabies, dermatitis, herpetiformis, atopic dermatitis, pruritus vulvae et ani, miliaria, insect bites, pediculosis, contact dermatitis, drug reactions, urticaria, urticarial eruptions of pregnancy, psoriasis, lichen planus, lichen simplex chronicus, exfoliative dermatitis, folliculitis, bullous pemphigoid, or fiberglass dermatitis.

The Hydroxyiminopiperazine Compounds can be used to treat or prevent psychosis, including but not limited to, schizophrenia, including paranoid schizophrenia, hebephrenic or disorganized schizophrenia, catatonic schizophrenia, undifferentiated schizophrenia, negative or deficit subtype schizophrenia, and non-deficit schizophrenia; a delusional disorder, including erotomanic subtype delusional disorder, grandiose subtype delusional disorder, jealous subtype delusional disorder, persecutory subtype delusional disorder, and somatic subtype delusional disorder; and brief psychosis.

The Hydroxyiminopiperazine Compounds can be used to treat or prevent a cognitive disorder, including but not limited to, delirium and dementia such as multi-infarct dementia, dementia pugilistica, dimentia caused by AIDS, and dementia caused by Alzheimer's disease.

The Hydroxyiminopiperazine Compounds can be used to treat or prevent a memory deficiency, including but not limited to, dissociative amnesia and dissociative fugue.

The Hydroxyiminopiperazine Compounds can be used to treat or prevent restricted brain function, including but not limited to, that caused by surgery or an organ transplant, restricted blood supply to the brain, a spinal cord injury, a head injury, hypoxia, cardiac arrest, or hypoglycemia.

The Hydroxyiminopiperazine Compounds can be used to treat or prevent Huntington's chorea.

The Hydroxyiminopiperazine Compounds can be used to treat or prevent ALS.

The Hydroxyiminopiperazine Compounds can be used to treat or prevent retinopathy, including but not limited to, arteriosclerotic retinopathy, diabetic arteriosclerotic retinopathy, hypertensive retinopathy, non-proliferative retinopathy, and proliferative retinopathy. The Hydroxyiminopiperazine Compounds can be used to treat or prevent a muscle spasm.

The Hydroxyiminopiperazine Compounds can be used to treat or prevent a migraine including, but not limited to, migraine without aura ("common migraine"), migraine with aura ("classic migraine"), migraine without headache, basilar migraine, familial hemiplegic migraine, migrainous infarction, and migraine with prolonged aura.

The Hydroxyiminopiperazine Compounds can be used to treat or vomiting, including but not limited to, nausea vomiting, dry vomiting (retching), and regurgitation.

The Hydroxyiminopiperazine Compounds can be used to treat or prevent dyskinesia, including but not limited to, tardive dyskinesia and biliary dyskinesia.

The Hydroxyiminopiperazine Compounds can be used to treat or prevent depression, including but not limited to, major depression and bipolar disorder.

Without wishing to be bound by theory, Applicants believe that the Hydroxyiminopiperazine Compounds are antagonists for VR1.

The invention also relates to methods for inhibiting VR1 function in a cell, comprising contacting a cell capable of expressing VR1 with an amount of a Hydroxyiminopiperazine Compound effective to inhibit VR1 function in the cell. This method can be used in vitro, for example, as an assay to select cells that express VR1 and, accordingly, are useful as part of an assay to select compounds useful for treating or preventing pain, UI, an ulcer, IBD, or IBS. The method is also useful for inhibiting VR1 function in a cell in vivo, in an animal (e.g., a human), by contacting a cell in an animal with an effective amount of a Hydroxyiminopiperazine Compound. In one embodiment, the method is useful for treating or preventing pain in an animal in need thereof. In another embodiment, the method is useful for treating or preventing UI in an animal in need thereof. In another embodiment, the method is useful for treating or preventing an ulcer in an animal in need thereof. In another embodiment, the method is useful for treating or preventing IBD in an animal in need thereof. In another embodiment, the method is useful for treating or preventing IBS in an animal in need thereof.

Examples of tissue comprising cells capable of expressing VR1 include, but are not limited to, neuronal, brain, kidney, urothelium, and bladder tissue. Methods for assaying cells that express VR1 are well known in the art.

Without wishing to be bound by theory, Applicants believe that the Hydroxyiminopiperazine Compounds are antagonists for mGluR5.

The invention further relates to methods for inhibiting mGluR5 function in a cell, comprising contacting a cell capable of expressing mGluR5 with an amount of a Hydroxyiminopiperazine Compound effective to inhibit mGluR5 function in the cell. This method can be used in vitro, for example, as an assay to select cells that express mGluR5 and, accordingly, are useful as part of an assay to select compounds useful for treating or preventing pain, an addictive disorder, Parkinson's disease, parkinsonism, anxiety, a pruritic condition, or psychosis. The method is also useful for inhibiting mGluR5 function in a cell in vivo, in an animal (e.g., a human), by contacting a cell in an animal with an amount of a Hydroxyiminopiperazine Compound effective to inhibit mGluR5 function in the cell. In one embodiment, the method is useful for treating or preventing pain in an animal in need thereof. In another embodiment, the method is useful for treating or preventing an addictive disorder in an animal in need thereof. In another embodiment, the method is useful for treating or preventing Parkinson's disease in an animal in need thereof. In another embodiment, the method is useful for treating or preventing parkinsonism in an animal in need thereof. In another embodiment, the method is useful for treating or preventing anxiety in an animal in need thereof. In another embodiment, the method is useful for treating or preventing a pruritic condition in an animal in need thereof. In another embodiment, the method is useful for treating or preventing psychosis in an animal in need thereof.

Examples of cells capable of expressing mGluR5 are neuronal and glial cells of the central nervous system, particularly the brain, especially in the nucleus accumbens. Methods for assaying cells that express mGluR5 are well known in the art.

Without wishing to be bound by theory, Applicants believe that the Hydroxyiminopiperazine Compounds are antagonists for mGluR1.

The invention further relates to methods for inhibiting mGluR1 function in a cell, comprising contacting a cell capable of expressing mGluR1 with an amount of a Hydroxyiminopiperazine Compound effective to inhibit mGluR1 function in the cell. This method can be used in vitro, for example, as an assay to select cells that express mGluR1 and, accordingly, are useful as part of an assay to select compounds useful for treating or preventing pain, UI, an addictive disorder, Parkinson's disease, parkinsonism, anxiety, epilepsy, stroke, a seizure, a pruritic condition, psychosis, a cognitive disorder, a memory deficit, restricted brain function, Huntington's chorea, ALS, dementia, retinopathy, a muscle spasm, a migraine, vomiting, dyskinesia, or depression. The method is also useful for inhibiting mGluR1 function in a cell in vivo, in an animal (e.g., a human), by contacting a cell in an animal with an amount of a Hydroxyiminopiperazine Compound effective to inhibit mGluR1 function in the cell. In one embodiment, the method is useful for treating or preventing pain in an animal in need thereof. In another embodiment, the method is useful for treating or preventing UI in an animal in need thereof. In another embodiment, the method is useful for treating or preventing an addictive disorder in an animal in need thereof. In another embodiment, the method is useful for treating or preventing Parkinson's disease in an animal in need thereof. In another embodiment, the method is useful for treating or preventing parkinsonism in an animal in need thereof. In another embodiment, the method is useful for treating or preventing anxiety in an animal in need thereof. In another embodiment, the method is useful for treating or preventing epilepsy in an animal in need thereof. In another embodiment, the method is useful for treating or preventing stroke in an animal in need thereof. In another embodiment, the method is useful for treating or preventing a seizure in an animal in need thereof. In another embodiment, the method is useful for treating or preventing a pruritic condition in an animal in need thereof. In another embodiment, the method is useful for treating or preventing psychosis in an animal in need thereof. In another embodiment, the method is useful for treating or preventing a cognitive disorder in an animal in need thereof. In another embodiment, the method is useful for treating or preventing a memory deficit in an animal in need thereof. In another embodiment, the method is useful for treating or preventing restricted brain function in an animal in need thereof In another embodiment, the method is useful for treating or preventing Huntington's chorea in an animal in need thereof. In another embodiment, the method is useful for treating or preventing ALS in an animal in need thereof. In another embodiment, the method is useful for treating or preventing dementia in an animal in need thereof. In another embodiment, the method is useful for treating or preventing retinopathy in an animal in need thereof. In another embodiment, the method is useful for treating or preventing a muscle spasm in an animal in need thereof In another embodiment, the method is useful for treating or preventing a migraine in an animal in need thereof. In another embodiment, the method is useful for treating, preventing, or inhibiting vomiting in an animal in need thereof In another embodiment, the method is useful for treating or preventing dyskinesia in an animal in need thereof. In another embodiment, the method is useful for treating or preventing depression in an animal in need thereof.

Examples of cells capable of expressing mGluR1 include, but are not limited to, cerebellar Purkinje neuron cells, Purkinje cell bodies (punctate), cells of spine(s) of the cerebellum; neurons and neurophil cells of olfactory-bulb glomeruli; cells of the superficial layer of the cerebral cortex; hippocampus cells; thalamus cells; superior colliculus cells; and spinal trigeminal nucleus cells. Methods for assaying cells that express MGluR1 are well known in the art.

4.11.1 Therapeutic/Prophylactic Administration and Compositions of the Invention Due to their activity, the Hydroxyiminopiperazine Compounds are advantageously useful in veterinary and human medicine. As described above, the Hydroxyiminopiperazine Compounds are useful for treating or preventing a Condition in an animal in need thereof.

When administered to an animal, the Hydroxyiminopiperazine Compounds are administered as a component of a composition that comprises a pharmaceutically acceptable carrier or excipient. The present compositions, which comprise a Hydroxyiminopiperazine Compound, can be administered orally. The Hydroxyiminopiperazine Compounds of the invention can also be administered by any other convenient route, for example, by infusion or bolus injection, by absorption through epithelial or mucocutaneous linings (e.g., oral, rectal, and intestinal mucosa, etc.) and can be administered together with another biologically active agent. Administration can be systemic or local. Various delivery systems are known, e.g., encapsulation in liposomes, microparticles, microcapsules, capsules, etc., and can be used to administer the Hydroxyiminopiperazine Compound.

Methods of administration include, but are not limited to, intradermal, intramuscular, intraperitoneal, intravenous, subcutaneous, intranasal, epidural, oral, sublingual, intracerebral, intravaginal, transdermal, rectal, by inhalation, or topical, particularly to the ears, nose, eyes, or skin. The mode of administration is left to the discretion of the practitioner. In most instances, administration will result in the release of the Hydroxyiminopiperazine Compounds into the bloodstream.

In specific embodiments, it can be desirable to administer the Hydroxyiminopiperazine Compounds locally. This can be achieved, for example, and not by way of limitation, by local infusion during surgery, topical application, e.g., in conjunction with a wound dressing after surgery, by injection, by means of a catheter, by means of a suppository or enema, or by means of an implant, said implant being of a porous, non-porous, or gelatinous material, including membranes, such as sialastic membranes, or fibers.

In certain embodiments, it can be desirable to introduce the Hydroxyiminopiperazine Compounds into the central nervous system or gastrointestinal tract by any suitable route, including intraventricular, intrathecal, and epidural injection, and enema. Intraventricular injection can be facilitated by an intraventricular catheter, for example, attached to a reservoir, such as an Ommaya reservoir.

Pulmonary administration can also be employed, e.g., by use of an inhaler or nebulizer, and formulation with an aerosolizing agent, or via perfusion in a fluorocarbon or synthetic pulmonary surfactant. In certain embodiments, the Hydroxyiminopiperazine Compounds can be formulated as a suppository, with traditional binders and excipients such as triglycerides.

In another embodiment, the Hydroxyiminopiperazine Compounds can be delivered in a vesicle, in particular a liposome (see Langer, Science 249:1527-1533 (1990) and Treat et al., Liposomes in the Therapy of infectious Disease and Cancer 317-327 and 353-365 (1989).

In yet another embodiment, the Hydroxyiminopiperazine Compounds can be delivered in a controlled-release system or sustained-release system (see, e.g., Goodson, in Medical Applications of Controlled Release, supra, vol. 2, pp. 115-138 (1984)). Other controlled- or sustained-release systems discussed in the review by Langer, Science 249:1527-1533 (1990) can be used. In one embodiment, a pump can be used (Langer, Science 249:1527-1533 (1990); Sefton, CRC Crit. Ref. Biomed. Eng. 14:201 (1987); Buchwald et al., Surgery 88:507 (1980); and Saudek et al., N. Engl. J. Med. 321:574 (1989)). In another embodiment, polymeric materials can be used (see Medical Applications of Controlled Release (Langer and Wise eds., 1974); Controlled Drug Bioavailability, Drug Product Design and Performance (Smolen and Ball eds., 1984); Ranger and Peppas, J. Macromol. Sci. Rev. Macromol. Chem. 23:61 (1983); Levy et al., Science 228:190 (1985); During et al., Ann. Neurol. 25:351 (1989); and Howard et al., J. Neurosurg. 71:105 (1989)). In yet another embodiment, a controlled- or sustained-release system can be placed in proximity of a target of the Hydroxyiminopiperazine Compounds, e.g., the spinal column, brain, or gastrointestinal tract, thus requiring only a fraction of the systemic dose.

The present compositions can optionally comprise a suitable amount of a pharmaceutically acceptable excipient so as to provide the form for proper administration to the animal. Such a pharmaceutical excipient can be a liquid, such as water or an oil, including those of petroleum, animal, vegetable, or synthetic origin, such as peanut oil, soybean oil, mineral oil, sesame oil and the like. The pharmaceutical excipient can be saline, gum acacia, gelatin, starch paste, talc, keratin, colloidal silica, urea and the like. In addition, auxiliary, stabilizing, thickening, lubricating, and coloring agents can be used. In one embodiment, the pharmaceutically acceptable excipient is sterile when administered to an animal. Water is a particularly useful excipient when the Hydroxyiminopiperazine Compound is administered intravenously. Saline solutions and aqueous dextrose and glycerol solutions can also be employed as liquid excipients, particularly for injectable solutions. Suitable pharmaceutical excipients also include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The present compositions, if desired, can also contain minor amounts of wetting or emulsifying agents, or pH buffering agents.

The present compositions can take the form of solutions, suspensions, emulsions, tablets, pills, pellets, capsules, capsules containing liquids, powders, sustained-release formulations, suppositories, emulsions, aerosols, sprays, suspensions, or any other form suitable for use. In one embodiment, the composition is in the form of a capsule (see e.g., U.S. Pat. No. 5,698,155). Other examples of suitable pharmaceutical excipients are described in Remington's Pharmaceutical Sciences 1447-1676 (Alfonso R. Gennaro ed., 19th ed. 1995), incorporated herein by reference.

In one embodiment, the Hydroxyiminopiperazine Compounds are formulated in accordance with routine procedures as a composition adapted for oral administration to human beings. Compositions for oral delivery can be in the form of tablets, lozenges, aqueous or oily suspensions, granules, powders, emulsions, capsules, syrups, or elixirs, for example. Orally administered compositions can contain one or more agents, for example, sweetening agents such as fructose, aspartame or saccharin; flavoring agents such as peppermint, oil of wintergreen, or cherry; coloring agents; and preserving agents, to provide a pharmaceutically palatable preparation. Moreover, where in tablet or pill form, the compositions can be coated to delay disintegration and absorption in the gastrointestinal tract thereby providing a sustained action over an extended period of time. Selectively permeable membranes surrounding an osmotically active driving compound are also suitable for orally administered compositions. In these latter platforms, fluid from the environment surrounding the capsule is imbibed by the driving compound, which swells to displace the agent or agent composition through an aperture. These delivery platforms can provide an essentially zero order delivery profile as opposed to the spiked profiles of immediate release formulations. A time-delay material such as glycerol monostearate or glycerol stearate can also be used. Oral compositions can include standard excipients such as mannitol, lactose, starch, magnesium stearate, sodium saccharin, cellulose, and magnesium carbonate. In one embodiment, the excipients are of pharmaceutical grade.

In another embodiment, the Hydroxyiminopiperazine Compounds can be formulated for intravenous administration. Typically, compositions for intravenous administration comprise sterile isotonic aqueous buffer. Where necessary, the compositions can also include a solubilizing agent. Compositions for intravenous administration can optionally include a local anesthetic such as lignocaine to lessen pain at the site of the injection. Generally, the ingredients are supplied either separately or mixed together in unit dosage form, for example, as a dry lyophilized powder or water free concentrate in a hermetically sealed container such as an ampule or sachette indicating the quantity of active agent. Where the Hydroxyiminopiperazine Compounds are to be administered by infusion, they can be dispensed, for example, with an infusion bottle containing sterile pharmaceutical grade water or saline. Where the Hydroxyiminopiperazine Compounds are administered by injection, an ampule of sterile water for injection or saline can be provided so that the ingredients can be mixed prior to administration.

The Hydroxyiminopiperazine Compounds can be administered by controlled-release or sustained-release means or by delivery devices that are well known to those of ordinary skill in the art. Examples include, but are not limited to, those described in U.S. Pat. Nos. 3,845,770; 3,916,899; 3,536,809; 3,598,123; 4,008,719; 5,674,533; 5,059,595; 5,591,767; 5,120,548; 5,073,543; 5,639,476; 5,354,556; and 5,733,566, each of which is incorporated herein by reference. Such dosage forms can be used to provide controlled- or sustained-release of one or more active ingredients using, for example, hydropropylmethyl cellulose, other polymer matrices, gels, permeable membranes, osmotic systems, multilayer coatings, microparticles, liposomes, microspheres, or a combination thereof to provide the desired release profile in varying proportions. Suitable controlled- or sustained-release formulations known to those of ordinary skill in the art, including those described herein, can be readily selected for use with the active ingredients of the invention. The invention thus encompasses single unit dosage forms suitable for oral administration such as, but not limited to, tablets, capsules, gelcaps, and caplets that are adapted for controlled- or sustained-release.

Controlled- or sustained-release pharmaceutical compositions can have a common goal of improving drug therapy over that achieved by their non-controlled or non-sustained-release counterparts. In one embodiment, a controlled- or sustained-release composition comprises a minimal amount of a Hydroxyiminopiperazine Compound to treat or prevent the Condition in a minimum amount of time. Advantages of controlled- or sustained-release compositions include extended activity of the drug, reduced dosage frequency, and increased patient compliance. In addition, controlled- or sustained-release compositions can favorably affect the time of onset of action or other characteristics, such as blood levels of the Hydroxyiminopiperazine Compound, and can thus reduce the occurrence of adverse side effects.

Controlled- or sustained-release compositions can initially release an amount of a Hydroxyiminopiperazine Compound that promptly produces the desired therapeutic or prophylactic effect, and gradually and continually release other amounts of the Hydroxyiminopiperazine Compound to maintain this level of therapeutic or prophylactic effect over an extended period of time. To maintain a constant level of the Hydroxyiminopiperazine Compound in the body, the Hydroxyiminopiperazine Compound can be released from the dosage form at a rate that will replace the amount of Hydroxyiminopiperazine Compound being metabolized and excreted from the body. Controlled- or sustained-release of an active ingredient can be stimulated by various conditions, including but not limited to, changes in pH, changes in temperature, concentration or availability of enzymes, concentration or availability of water, or other physiological conditions or compounds.

The amount of the Hydroxyiminopiperazine Compound that is effective for the treatment or prevention of a Condition can be determined by standard clinical techniques. In addition, in vitro or in vivo assays can optionally be employed to help identify optimal dosage ranges. The precise dose to be employed will also depend on the route of administration, and the seriousness of the Condition and can be decided according to the judgment of a practitioner and/or each animal's circumstances. Suitable effective dosage amounts, however, range from about 0.01 mg/kg of body weight to about 2500 mg/kg of body weight, although they are typically about 100 mg/kg of body weight or less. In one embodiment, the effective dosage amount ranges from about 0.01 mg/kg of body weight to about 100 mg/kg of body weight of a Hydroxyiminopiperazine Compound, in another embodiment, about 0.020 mg/kg of body weight to about 50 mg/kg of body weight, and in another embodiment, about 0.025 mg/kg of body weight to about 20 mg/kg of body weight. In one embodiment, an effective dosage amount is administered about every 24 h until the Condition is abated. In another embodiment, an effective dosage amount is administered about every 12 h until the Condition is abated. In another embodiment, an effective dosage amount is administered about every 8 h until the Condition is abated. In another embodiment, an effective dosage amount is administered about every 6 h until the Condition is abated. In another embodiment, an effective dosage amount is administered about every 4 h until the Condition is abated. The effective dosage amounts described herein refer to total amounts administered; that is, if more than one Hydroxyiminopiperazine Compound is administered, the effective dosage amounts correspond to the total amount administered.

Where a cell capable of expressing VR1, mGluR5, or mGluR1 is contacted with a Hydroxyininopiperazine Compound in vitro, the amount effective for inhibiting the VR1, mGluR5, or mGluR1 receptor function in a cell will typically range from about 0.01 µg/L to about 5 mg/L, in one embodiment, from about 0.01 µg/L to about 2.5 mg/L, in another embodiment, from about 0.01 µg/L to about 0.5 mg/L, and in another embodiment, from about 0.01 µg/L to about 0.25 mg/L of a solution or suspension of a pharmaceutically acceptable carrier or excipient. In one embodiment, the volume of solution or suspension comprising the Hydroxyiminopiperazine Compound is from about 0.01 μL to about 1 mL. In another embodiment, the volume of solution or suspension is about 200 μL.

Where a cell capable of expressing VR1, mGluR5, or mGluR1 is contacted with a Hydroxyiminopiperazine Compound in vivo, the amount effective for inhibiting the receptor function in a cell will typically range from about 0.01 mg/kg of body weight to about 2500 mg/kg of body weight, although it typically ranges from about 100 mg/kg of body weight or less. In one embodiment, the effective dosage amount ranges from about 0.01 mg/kg of body weight to about 100 mg/kg of body weight of a Hydroxyiminopiperazine Compound, in another embodiment, about 0.02 mg/kg of body weight to about 50 mg/kg of body weight, and in another embodiment, about 0.025 mg/kg of body weight to about 20 mg/kg of body weight. In one embodiment, an effective dosage amount is administered about every 24 h. In another embodiment, an effective dosage amount is administered about every 12. In another embodiment, an effective dosage amount is administered about every 8. In another embodiment, an effective dosage amount is administered about every 6 h. In another embodiment, an effective dosage amount is administered about every 4 h.

The Hydroxyiminopiperazine Compounds can be assayed in vitro or in vivo for the desired therapeutic or prophylactic activity prior to use in humans. Animal model systems can be used to demonstrate safety and efficacy.

The present methods for treating or preventing a Condition in an animal in need thereof can further comprise administering to the animal being administered a Hydroxyiminopiperazine Compound another therapeutic agent. In one embodiment, the other therapeutic agent is administered in an effective amount.

The present methods for inhibiting VR1 function in a cell capable of expressing VR1 can further comprise contacting the cell with an effective amount of another therapeutic agent.

The present methods for inhibiting mGluR5 function in a cell capable of expressing mGluR5 can further comprise contacting the cell with an effective amount of another therapeutic agent.

The present methods for inhibiting mGluR1 function in a cell capable of expressing mGluR1 can further comprise contacting the cell with an effective amount of another therapeutic agent.

The other therapeutic agent includes, but is not limited to, an opioid agonist, a non-opioid analgesic, a non-steroid anti-inflammatory agent, an antimigraine agent, a Cox-II inhibitor, an antiemetic, a β-adrenergic blocker, an anticonvulsant, an antidepressant, a Ca2+-channel blocker, an anticancer agent, an agent for treating or preventing UI, an agent for treating or preventing an ulcer, an agent for treating or preventing IBD, an agent for treating or preventing IBS, an agent for treating addictive disorder, an agent for treating Parkinson's disease and parkinsonism, an agent for treating anxiety, an agent for treating epilepsy, an agent for treating a stroke, an agent for treating a seizure, an agent for treating a pruritic condition, an agent for treating psychosis, an agent for treating Huntington's chorea, an agent for treating ALS, an agent for treating a cognitive disorder, an agent for treating a migraine, an agent for treating or inhibiting vomiting, an agent for treating dyskinesia, or an agent for treating depression, and mixtures thereof.

Effective amounts of the other therapeutic agents are well known to those skilled in the art. However, it is well within the skilled artisan's purview to determine the other therapeutic agent's optimal effective-amount range. In one embodiment of the invention, where another therapeutic agent is administered to an animal, the effective amount of the Hydroxyiminopiperazine Compound is less than its effective amount would be where the other therapeutic agent is not administered. In this case, without being bound by theory, it is believed that the Hydroxyiminopiperazine Compounds and the other therapeutic agent act synergistically to treat or prevent a Condition.

Examples of useful opioid agonists include, but are not limited to, alfentanil, allylprodine, alphaprodine, anileridine, benzylmorphine, bezitramide, buprenorphine, butorphanol, clonitazene, codeine, desomorphine, dextromoramide, dezocine, diampromide, diamorphone, dihydrocodeine, dihydromorphine, dimenoxadol, dimepheptanol, dimethylthiambutene, dioxaphetyl butyrate, dipipanone, eptazocine, ethoheptazine, ethylmethylthiambutene, ethylmorphine, etonitazene fentanyl, heroin, hydrocodone, hydromorphone, hydroxypethidine, isomethadone, ketobemidone, levorphanol, levophenacylmorphan, lofentanil, meperidine, meptazinol, metazocine, methadone, metopon, morphine, myrophine, nalbuphine, narceine, nicomorphine, norlevorphanol, normethadone, nalorphine, normorphine, norpipanone, opium, oxycodone, oxymorphone, papaveretum, pentazocine, phenadoxone, phenomorphan, phenazocine, phenoperidine, piminodine, piritramide, proheptazine, promedol, properidine, propiram, propoxyphene, sufentanil, tilidine, tramadol, pharmaceutically acceptable salts thereof, and mixtures thereof.

In certain embodiments, the opioid agonist is selected from codeine, hydromorphone, hydrocodone, oxycodone, dihydrocodeine, dihydromorphine, morphine, tramadol, oxymorphone, pharmaceutically acceptable salts thereof, and mixtures thereof.

Examples of useful non-opioid analgesics include nonsteroidal anti-inflammatory agents, such as aspirin, ibuprofen, diclofenac, naproxen, benoxaprofen, flurbiprofen, fenoprofen, flubufen, ketoprofen, indoprofen, piroprofen, carprofen, oxaprozin, pramoprofen, muroprofen, trioxaprofen, suprofen, aminoprofen, tiaprofenic acid, fluprofen, bucloxic acid, indomethacin, sulindac, tolmetin, zomepirac, tiopinac, zidometacin, acemetacin, fentiazac, clidanac, oxpinac, mefenamic acid, meclofenamic acid, flufenamic acid, niflumic acid, tolfenamic acid, diflurisal, flufenisal, piroxicam, sudoxicam, isoxicam, and pharmaceutically acceptable salts thereof, and mixtures thereof Other suitable non-opioid analgesics include the following, non-limiting, chemical classes of analgesic, antipyretic, nonsteroidal anti-inflammatory drugs: salicylic acid derivatives, including aspirin, sodium salicylate, choline magnesium trisalicylate, salsalate, diflunisal, salicylsalicylic acid, sulfasalazine, and olsalazin; para-aminophennol derivatives including acetaminophen and phenacetin; indole and indene acetic acids, including indomethacin, sulindac, and etodolac; heteroaryl acetic acids, including tolmetin, diclofenac, and ketorolac; anthranilic acids (fenamates), including mefenamic acid and meclofenamic acid; enolic acids, including oxicams (piroxicam, tenoxicam), and pyrazolidinediones (phenylbutazone, oxyphenthartazone); and alkanones, including nabumetone. For a more detailed description of the NSAIDs, see Paul A. Insel, *Analgesic-Antipyretic and Anti-inflammatory Agents and Drugs Employed in the Treatment of Gout*, in Goodman &Gilman's The Pharmacological Basis of Therapeutics 617-57 (Perry B. Molinhoff and Raymond W. Ruddon eds., 9$^{th}$ ed 1996) and Glen R. Hanson, *Analgesic, Antipyretic and Anti-Inflammatory Drugs in Remington: The Science and Practice of Pharmacy Vol. II* 1196-1221 (A. R. Gennaro ed. 19th ed. 1995) which are hereby incorporated by reference in their entireties.

Examples of useful Cox-II inhibitors and 5-lipoxygenase inhibitors, as well as combinations thereof, are described in U.S. Pat. No. 6,136,839, which is hereby incorporated by reference in its entirety. Examples of useful Cox-II inhibitors include, but are not limited to, rofecoxib and celecoxib.

Examples of useful antimigraine agents include, but are not limited to, alpiropride, dihydroergotamine, dolasetron, ergocornine, ergocorninine, ergocryptine, ergot, ergotamine, flumedroxone acetate, fonazine, lisuride, lomerizine, methysergide oxetorone, pizotyline, and mixtures thereof.

The other therapeutic agent can also be an antiemetic agent. Examples of useful antiemetic agents include, but are not limited to, metoclopromide, domperidone, prochlorperazine, promethazine, chlorpromazine, trimethobenzamide, ondansetron, granisetron, hydroxyzine, acetylleucine monoethanolamine, alizapride, azasetron, benzquinamide, bietanautine, bromopride, buclizine, clebopride, cyclizine, dimenhydrinate, diphenidol, dolasetron, meclizine, methallatal, metopimazine, nabilone, oxyperndyl, pipamazine, scopolamine, sulpiride, tetrahydrocannabinol, thiethylperazine, thioproperazine, tropisetron, and mixtures thereof.

Examples of useful β-adrenergic blockers include, but are not limited to, acebutolol, alprenolol, amosulabol, arotinolol, atenolol, befinolol, betaxolol, bevantolol, bisoprolol, bopindolol, bucumolol, bufetolol, bufuralol, bunitrolol, bupranolol, butidrine hydrochloride, butofilolol, carazolol, carteolol, carvedilol, celiprolol, cetamolol, cloranolol, dilevalol, epanolol, esmolol, indenolol, labetalol, levobunolol, mepindolol, metipranolol, metoprolol, moprolol, nadolol, nadoxolol, nebivalol, nifenalol, nipradilol, oxprenolol, penbutolol, pindolol, practolol, pronethalol, propranolol, sotalol, sulfinalol, talinolol, tertatolol, tilisolol, timolol, toliprolol, and xibenolol.

Examples of useful anticonvulsants include, but are not limited to, acetylpheneturide, albutoin, aloxidone, aminoglutethimide, 4-amino-3-hydroxybutyric acid, atrolactamide, beclamide, buramate, calcium bromide, carbamazepine, cinromide, clomethiazole, clonazepam, decimemide, diethadione, dimethadione, doxenitroin, eterobarb, ethadione, ethosuximide, ethotoin, felbamate, fluoresone, gabapentin, 5-hydroxytryptophan, lamotrigine, magnesium bromide, magnesium sulfate, mephenytoin, mephobarbital, metharbital, methetoin, methsuximide, 5-methyl-5-(3-phenanthryl)-hydantoin, 3-methyl-5-phenylhydantoin, narcobarbital, nimetazepam, nitrazepam, oxcarbazepine, paramethadione, phenacemide, phenetharbital, pheneturide, phenobarbital, phensuximide, phenylmethylbarbituric acid, phenytoin, phethenylate sodium, potassium bromide, pregabaline, primidone, progabide, sodium bromide, solanum, strontium bromide, suclofenide, sulthiame, tetrantoin, tiagabine, topiramate, trimethadione, valproic acid, valpromide, vigabatrin, and zonisamide.

Examples of useful antidepressants include, but are not limited to, binedaline, caroxazone, citalopram, (S)-citalopram, dimethazan, fencamine, indalpine, indeloxazine hydrocholoride, nefopam, nomifensine, oxitriptan, oxypertine, paroxetine, sertraline, thiazesim, trazodone, benmoxine, iproclozide, iproniazid, isocarboxazid, nialamide, octamoxin, phenelzine, cotinine, rolicyprine, rolipram, maprotiline, metralindole, mianserin, mirtazepine, adinazolam, amitriptyline, amitriptylinoxide, amoxapine, butriptyline, clomipramine, demexiptiline, desipramine, dibenzepin, dimetacrine, dothiepin, doxepin, fluacizine, imipramine, imipramine N-oxide, iprindole, lofepramine, melitracen, metaprarnine, nortriptyline, noxiptilin, opipramol, pizotyline, propizepine, protriptyline, quinuprarnine, tianeptine, trimipramine, adrafinil, benactyzine, bupropion, butacetin, dioxadrol, duloxetine, etoperidone, febarbamate, femoxetine, fenpentadiol, fluoxetine, fluvoxamine, hematoporphyrin, hypericin, levophacetoperane, medifoxamine, milnacipran, minaprine, moclobemide, nefazodone, oxaflozane, piberaline, prolintane, pyrisuccideanol, ritanserin, roxindole, rubidium chloride, sulpiride, tandospirone, thozalinone, tofenacin, toloxatone, tranylcypromine, L-tryptophan, venlafaxine, viloxazine, and zimeldine.

Examples of useful Ca2+-channel blockers include, but are not limited to, bepridil, clentiazem, diltiazem, fendiline, gallopamil, mibefradil, prenylamine, semotiadil, terodiline, verapamil, amlodipine, aranidipine, bamidipine, benidipine, cilnidipine, efonidipine, elgodipine, felodipine, isradipine, lacidipine, lercanidipine, manidipine, nicardipine, nifedipine, nilvadipine, nimodipine, nisoldipine, nitrendipine, cinnarizine, flunarizine, lidoflazine, lomerizine, bencyclane, etafenone, fantofarone, and perhexiline.

Examples of useful anticancer agents include, but are not limited to, acivicin, aclarubicin, acodazole hydrochloride, acronine, adozelesin, aldesleukin, altretamine, ambomycin, ametantrone acetate, aminoglutethimide, amsacrine, anastrozole, anthramycin, asparaginase, asperlin, azacitidine, azetepa, azotomycin, batimastat, benzodepa, bicalutamide, bisantrene hydrochloride, bisnafide dimesylate, bizelesin, bleomycin sulfate, brequinar sodium, bropirimine, busulfan, cactinomycin, calusterone, caracemide, carbetimer, carboplatin, carmustine, carubicin hydrochloride, carzelesin, cedefingol, chlorambucil, cirolemycin, cisplatin, cladribine, crisnatol mesylate, cyclophosphamide, cytarabine, dacarbazine, dactinomycin, daunorubicin hydrochloride, decitabine, dexormaplatin, dezaguanine, dezaguanine mesylate, diaziquone, docetaxel, doxorubicin, doxorubicin hydrochloride, droloxifene, droloxifene citrate, dromostanolone propionate, duazomycin, edatrexate, eflornithine hydrochloride, elsamitrucin, enloplatin, enpromate, epipropidine, epirubicin hydrochloride, erbulozole, esorubicin hydrochloride, estramustine, estramustine phosphate sodium, etanidazole, etoposide, etoposide phosphate, etoprine, fadrozole hydrochloride, fazarabine, fenretinide, floxuridine, fludarabine phosphate, fluorouracil, flurocitabine, fosquidone, fostriecin sodium, gemcitabine, gemcitabine hydrochloride, hydroxyurea, idarubicin hydrochloride, ifosfamide, ilmofosine, interleukin II (including recombinant interleukin II or rIL2), interferon alfa-2a, interferon alfa-2b, interferon alfa-n1, interferon alfa-n3, interferon beta-I a, interferon gamma-I b, iproplatin, irinotecan hydrochloride, lanreotide acetate, letrozole, leuprolide acetate, liarozole hydrochloride, lometrexol sodium, lomustine, losoxantrone hydrochloride, masoprocol, maytansine, mechlorethamine hydrochloride, megestrol acetate, melengestrol acetate, melphalan, menogaril, mercaptopurine, methotrexate, methotrexate sodium, metoprine, meturedepa, mitindomide, mitocarcin, mitocromin, mitogillin, mitomalcin, mitomycin, mitosper, mitotane, mitoxantrone hydrochloride, mycophenolic acid, nocodazole, nogalamycin, ormaplatin, oxisuran, paclitaxel, pegaspargase, peliomycin, pentamustine, peplomycin sulfate, perfosfamide, pipobroman, piposulfan, piroxantrone hydrochloride, plicamycin, plomestane, porfimer sodium, porfiromycin, prednimustine, procarbazine hydrochloride, puromycin, puromycin hydrochloride, pyrazofurin, riboprine, rogletimide, safingol, safingol hydrochloride, semustine, simtrazene, sparfosate sodium, sparsomycin, spirogermanium hydrochloride, spiromustine, spiroplatin, streptonigrin, streptozocin, sulofenur, talisomycin, tecogalan sodium, tegafur, teloxantrone hydrochloride, temoporfin, teniposide, teroxirone, testolactone, thiamiprine, thioguanine, thiotepa, tiazofurin, tirapazamine, toremifene citrate, trestolone acetate, triciribine phosphate, trimetrexate, trimetrexate glucuronate, triptorelin, tubulozole hydrochloride, uracil mustard, uredepa, vapreotide, verteporfin, vinblastine sulfate, vincristine sulfate, vindesine, vindesine sulfate, vinepidine sulfate, vinglycinate sulfate, vinleurosine sulfate, vinorelbine tartrate, vinrosidine sulfate, vinzolidine sulfate, vorozole, zeniplatin, zinostatin, zorubicin hydrochloride.

Examples of other anti-cancer drugs include, but are not limited to, 20-epi-1,25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimnustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactamn derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-aminotriazole; carboxyamidotriazole; CaRest M3; CARN 700; cartilage derived inhibitor; carzelesin; casein kinase inhibitors (ICOS); castanospermine; cecropin B; cetrorelix; chlorlns; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; dihydrotaxol, 9-; dioxamycin; diphenyl spiromustine; docetaxel; docosanol; dolasetron; doxifluridine; droloxifene; dronabinol; duocarmycin SA; ebselen; ecomustine; edelfosine; edrecolomab; eflornithine; elemene; emitefur; epirubicin; episteride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine, lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; O6-benzylguanine; octreotide; okicenone; oligonucleotides; onapristone; ondansetron; ondansetron; oracin; oral cytokine inducer; ormaplatin; osaterone; oxaliplatin; oxaunomycin; paclitaxel; paclitaxel analogues; paclitaxel derivatives; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylene conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rogletimide; rohitukine; romurtide; roquinimex; rubiginone B1; ruboxyl; safingol; saintopin; SarCNU; sarcophytol A; sargramostim; Sdi 1 rnimetics; semustine; senescence derived inhibitor 1; sense oligonucleotides; signal transduction inhibitors; signal transduction modulators; single chain antigen binding protein; sizofiran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; and zinostatin stimalamer.

Examples of useful therapeutic agents for treating or preventing UI include, but are not limited to, propantheline, imipramine, hyoscyamine, oxybutynin, and dicyclomine.

Examples of useful therapeutic agents for treating or preventing an ulcer include, antacids such as aluminum hydroxide, magnesium hydroxide, sodium bicarbonate, and calcium bicarbonate; sucraflate; bismuth compounds such as bismuth subsalicylate and bismuth subcitrate; $H_2$ antagonists such as cimetidine, ranitidine, famotidine, and nizatidine; $H^+$, $K^+$-ATPase inhibitors such as omeprazole, iansoprazole, and lansoprazole; carbenoxolone; misprostol; and antibiotics such as tetracycline, metronidazole, timidazole, clarithromycin, and amoxicillin.

Examples of useful therapeutic agents for treating or preventing IBD include, but are not limited to, anticholinergic drugs; diphenoxylate; loperamide; deodorized opium tincture; codeine; broad-spectrum antibiotics such as metronidazole; sulfasalazine; olsalazie; mesalamine; prednisone; azathioprine; mercaptopurine; and methotrexate.

Examples of useful therapeutic agents for treating or preventing IBS include, but are not limited to, propantheline; muscarine receptor antagonists such as pirenzapine, methoctramine, ipratropium, tiotropium, scopolamine, methscopolamine, homatropine, homatropine methylbromide, and methantheline; and antidiarrheal drugs such as diphenoxylate and loperamide.

Examples of useful therapeutic agents for treating or preventing an addictive disorder include, but are not limited to, methadone, desipramine, amantadine, fluoxetine, buprenorphine, an opiate agonist, 3-phenoxypyridine, levomethadyl acetate hydrochloride, and serotonin antagonists.

Examples of useful therapeutic agents for treating or preventing Parkinson's disease and parkinsonism include, but are not limited to, carbidopa/levodopa, pergolide, bromocriptine, ropinirole, pramipexole, entacapone, tolcapone, selegiline, amantadine, and trihexyphenidyl hydrochloride.

Examples of useful therapeutic agents for treating or preventing anxiety include, but are not limited to, benzodiazepines, such as alprazolam, brotizolam, chlordiazepoxide, clobazam, clonazepam, clorazepate, demoxepam, diazepam, estazolam, flumazenil, flurazepam, halazepam, lorazepam, midazolam, nitrazepam, nordazepam, oxazepam, prazepam, quazepam, temazepam, and triazolam; non-benzodiazepine agents, such as buspirone, gepirone, ipsaprione, tiospirone, zolpicone, zolpidem, and zaleplon; tranquilizers, such as barbituates, e.g., amobarbital, aprobarbital, butabarbital, butalbital, mephobarbital, methohexital, pentobarbital, phenobarbital, secobarbital, and thiopental; and propanediol carbamates, such as meprobamate and tybamate.

Examples of useful therapeutic agents for treating or preventing epilepsy include, but are not limited to, carbamazepine, ethosuximide, gabapentin, lamotrignine, phenobarbital, phenytoin, primidone, valproic acid, trimethadione, bemzodiaepines, gabapentin, lamotrigine, γ-vinyl GABA, acetazolamide, and felbamate.

Examples of useful therapeutic agents for treating or preventing stroke include, but are not limited to, anticoagulants such as heparin, agents that break up clots such as streptokinase or tissue plasminogen activator, agents that reduce swelling such as mannitol or corticosteroids, and acetylsalicylic acid.

Examples of useful therapeutic agents for treating or preventing a seizure include, but are not limited to, carbamazepine, ethosuximide, gabapentin, lamotrignine, phenobarbital, phenytoin, primidone, valproic acid, trimethadione, bemzodiaepines, gabapentin, lamotrigine, γ-vinyl GABA, acetazolamide, and felbamate.

Examples of useful therapeutic agents for treating or preventing a pruritic condition include, but are not limited to, naltrexone; nalnefene; danazol; tricyclics such as amitriptyline, imipramine, and doxepin; antidepressants such as those given below, menthol; camphor; phenol; pramoxine; capsaicin; tar; steroids; and antihistamines.

Examples of useful therapeutic agents for treating or preventing psychosis include, but are not limited to, phenothiazines such as chlorpromazine hydrochloride, mesoridazine besylate, and thoridazine hydrochloride; thioxanthenes such as chloroprothixene and thiothixene hydrochloride; clozapine; risperidone; olanzapine; quetiapine; quetiapine flumarate; haloperidol; haloperidol decanoate; loxapine succinate; molindone hydrochloride; pimozide; and ziprasidone.

Examples of useful therapeutic agents for treating or preventing Huntington's chorea include, but are not limited to, haloperidol and pimozide.

Examples of useful therapeutic agents for treating or preventing ALS include, but are not limited to, baclofen, neurotrophic factors, riluzole, tizanidine, benzodiazepines such as clonazepan and dantrolene.

Examples of useful therapeutic agents for treating or preventing cognitive disorders include, but are not limited to, agents for treating or preventing dementia such as tacrine; donepezil; ibuprofen; antipsychotic drugs such as thioridazine and haloperidol; and antidepressant drugs such as those given below.

Examples of useful therapeutic agents for treating or preventing a migraine include, but are not limited to, sumatriptan; methysergide; ergotamine; caffeine; and beta-blockers such as propranolol, verapamil, and divalproex.

Examples of useful therapeutic agents for treating, preventing, or inhibiting vomiting include, but are not limited to, 5-$HT_3$ receptor antagonists such as ondansetron, dolasetron, granisetron, and tropisetron; dopamine receptor antagonists such as prochlorperazine, thiethylperazine, chlorpromazin, metoclopramide, and domperidone; glucocorticoids such as dexamethasone; and benzodiazepines such as lorazepam and alprazolam.

Examples of useful therapeutic agents for treating or preventing dyskinesia include, but are not limited to, reserpine and tetrabenazine.

Examples of useful therapeutic agents for treating or preventing depression include, but are not limited to, tricyclic antidepressants such as amitryptyline, amoxapine, bupropion, citalopram, (S)-citalopram, clomipramine, desipramine, doxepin, imipramine, maprotilinr, nefazadone, nortriptyline, protriptyline, trazodone, trimipramine, and venlaflaxine; selective serotonin reuptake inhibitors such as fluoxetine, fluvoxamine, paroxetine, and setraline; monoamine oxidase inhibitors such as isocarboxazid, pargyline, phenelzine, and tranylcypromine; and psychostimulants such as dextroamphetamine and methylphenidate.

A Hydroxyiminopiperazine Compound and the other therapeutic agent can act additively or, in one embodiment, synergistically. In one embodiment, a Hydroxyiminopiperazine Compound is administered concurrently with another therapeutic agent. In one embodiment, a composition comprising an effective amount of a Hydroxyiminopiperazine Compound and an effective amount of another therapeutic agent can be administered. Alternatively, a composition comprising an effective amount of a Hydroxyiminopiperazine Compound and a different composition comprising an effective amount of another therapeutic agent can be concurrently administered. In another embodiment, an effective amount of a Hydroxyiminopiperazine Compound is administered prior or subsequent to administration of an effective amount of another therapeutic agent. In this embodiment, the Hydroxyiminopiperazine Compound is administered while the other therapeutic agent exerts its therapeutic effect, or the other therapeutic agent is administered while the Hydroxyiminopiperazine Compound exerts its preventative or therapeutic effect for treating or preventing a Condition in an animal.

A composition of the invention is prepared by a method comprising admixing a Hydroxyiminopiperazine Compound and a pharmaceutically acceptable carrier or excipient. Admixing can be accomplished using methods well known for admixing a compound (or salt) and a pharmaceutically acceptable carrier or excipient. In one embodiment, the Hydroxyiminopiperazine Compound is present in the composition in an effective amount.

4.11.1 Kits

The invention encompasses kits that can simplify the administration of a Hydroxyiminopiperazine Compound to an animal.

A typical kit of the invention comprises a unit dosage form of a Hydroxyiminopiperazine Compound. In one embodiment, the unit dosage form is a container, which can be sterile, containing an effective amount of a Hydroxyiminopiperazine Compound and a pharmaceutically acceptable carrier or excipient. The kit can further comprise a label or printed instructions instructing the use of the Hydroxyiminopiperazine Compound to treat a Condition. The kit can also further comprise a unit dosage form of another therapeutic agent, for example, a container containing an effective amount of the other therapeutic agent. In one embodiment, the kit comprises a container containing an effective amount of a Hydroxyiminopiperazine Compound and an effective amount of another therapeutic agent. Examples of other therapeutic agents include, but are not limited to, those listed above.

Kits of the invention can further comprise a device that is useful for administering the unit dosage forms. Examples of such a device includes, but are not limited to, a syringe, a drip bag, a patch, an inhaler, and an enema bag.

The following examples are set forth to assist in understanding the invention and should not, of course, be construed as specifically limiting the invention described and claimed herein. Such variations of the invention, including the substitution of all equivalents now known or later developed, which would be within the purview of those skilled in the art, and changes in formulation or changes in experimental design, are to be considered to fall within the scope of the invention incorporated herein.

5. EXAMPLES

Examples 1-10 relate to the synthesis of illustrative Hydroxyiminopiperazine Compounds.

5.1 Example 1

Synthesis of Compound A1(c)

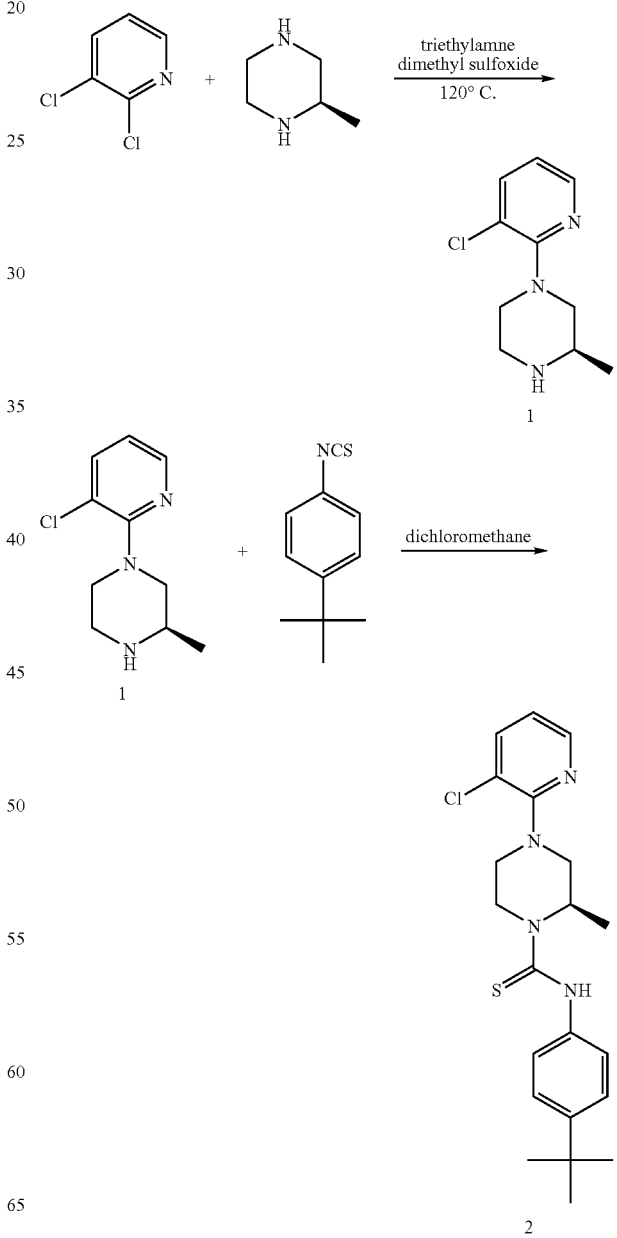

-continued

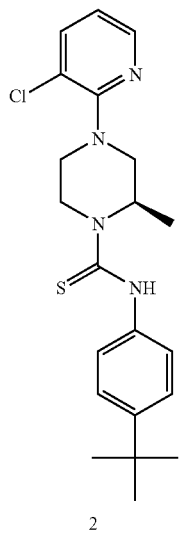

2

1. CH₃I, tetrahydrofuran
2. triethylamine, ethyl acetate
→

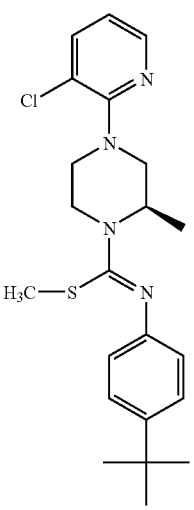

3

NH₂OH
―――――
ethanol, 80° C.

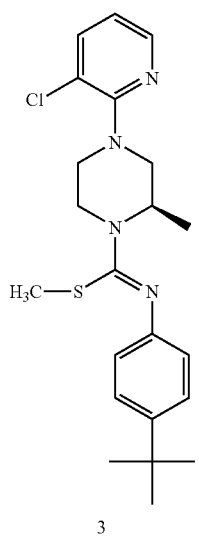

3

-continued

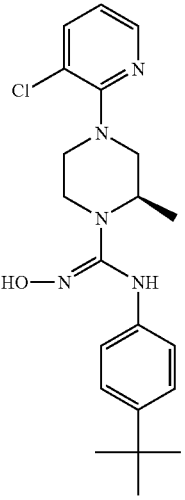

Compound A1(e)

2,3-Dichloropyridine (2.94 g, 20.0 mmol), (R)-2-methylpiperazine (2.75 g, 27.5 mmol) (Commercially available from Sigma-Aldrich, St. Louis, Mo. (www.sigma-aldrich.com)), and triethylamine (3.04 g, 30 mmol) were dissolved in 15 mL of dimethylsulfoxide and the resulting mixture was heated at about 100° C. for about 24 h. The reaction mixture was then cooled to room temperature and extracted with a saturated aqueous sodium bicarbonate solution. The organic layer was dried, concentrated, and purified using a silica gel column eluted with a gradient elution (ethyl acetate to 2:1 ethyl acetate:methanol) to provide Compound 1(N-(3-chloropyridin-2-yl)-piperazine) as a yellow liquid (90% yield).

A solution of Compound 1 (1.0 mmol) and 4-(tert-butyl)-phenylisothiocyanate (commercially available from Ryan Scientific Inc. of Isle of Palms, S.C. (www.ryansci.com)) (1.0 mmol) in 1.5 mL of dichloromethane was stirred at room temperature (about 25° C.) for about 5 h. The mixture was then concentrated under reduced pressure and directly purified using a silica gel column eluted with a gradient elution (10:1 hexane:ethyl acetate to 3:1 hexane:ethyl acetate) to provide Compound 2 (63% yield). The identity of Compound 2 was confirmed using ¹H NMR.

Compound 2: ¹H NMR (CDCl₃) δ 8.21 (dd, J=1.6, 4.8 Hz, 1H), 7.63 (dd, J=1.6, 7.8 Hz, 1H), 7.39 (d, J=8.6 Hz, 2H), 7.15 (d, J=8.6 Hz, 2H), 6.91 (dd, J=4.8, 7.8 Hz, 1H), 5.14 (br, 1H), 4.41 (dd, J=13.1 Hz, 1H), 3.76 (m, 2H), 3.58 (dt, J=3.4, 12.5 Hz, 1H), 3.17 (dd, J=3.4, 12.5 Hz, 1H), 3.02 (dt, J=3.4, 12.5 Hz, 1H), 1.51 (d, J=6.75 Hz, 3H), 1.33 (s, 9H) ppm.

A solution of Compound 2 (234.0 mg, 0.58 mmol), prepared as described above, and iodomethane (124 mg, 0.87 mmol) in 3.0 mL of dimethylformamide was stirred at room temperature (about 25° C.) for about 12 h. The reaction mixture was then concentrated under reduced pressure to remove excess iodomethane. Triethylamine (1.74 mmol) in ethyl acetate (2.5 mL) was added to the mixture and the mixture was allowed to stir for about 2 h. The mixture was then concentrated under reduced pressure and purified using column chromatography (silica gel eluted with 2:1 hexane:ethyl acetate) to provide Compound 3 (65% yield). The identity of Compound 3 was confirmed using ¹H NMR.

Compound 3: ¹H NMR (CDCl₃) δ 8.22 (dd, J=1.6, 4.8 Hz, 1H), 7.63 (dd, J=1.6, 7.8 Hz, 1H), 7.30 (d, J=8.6 Hz, 2H), 6.90 (dd, J=4.8, 7.8 Hz, 1H), 6.88 (d, J=8.6 Hz, 2H), 5.14 (br, 1H), 4.64 (m, 1H), 4.07 (dd, J=13.1 Hz, 1H), 3.75 (m, 1H), 3.50 (dt, J=3.4, 13.1 Hz, 1H), 3.15 (dd, J=3.4, 12.5 Hz, 1H), 3.02 (dt, J=3.4, 12.5 Hz, 1H), 2.09 (s, 3H), 1.47 (d, J=6.75 Hz, 3H), 1.33 (s, 9H) ppm.

A solution of Compound 3 (120 mg, 0.29 mmol), prepared as described above, and hydroxylamine (50 wt % in water, 383.0 mg, 5.8 mmol) in ethanol (1.5. mL) was stirred at about 80° C. for about 2 h. The mixture was then cooled to room temperature (about 25° C.), concentrated, and purified using column chromatography (silica gel eluted with gradient elution from 10:1 hexane:ethyl acetate to 2:1 hexane:ethyl acetate) to provide Compound A1(c), i.e., N-(4-tert-Butyl-phenyl)-4-(3-chloro-pyridin-2-yl)-N-hydroxy-(R)-2-methyl-piperazine-1-carboxamidine (71% yield). The identity of Compound A1(c) was confirmed using $^1$H NMR.

Compound A1(c): $^1$H NMR (CDCl$_3$) δ 8.21 (dd, J=1.6, 4.8 Hz, 1H), 7.61 (dd, J=1.6, 7.8 Hz, 1H), 7.29 (d, J=8.7 Hz, 2H), 7.18 (d, J=8.6 Hz, 2H), 6.88 (dd, J=4.8, 7.8 Hz, 1H), 6.68 (br, 1H), 3.67 (m, 1H), 3.50 (m, 1H), 3.35 (m, 2H), 3.10 (m, 2H), 1.63 (br, 1H), 1.32 (d, J=6.75 Hz, 3H), 1.31 (s, 9H) ppm.

5.2 Example 2

Synthesis of Compound A1(d)

Compound A1(d) was prepared by a procedure that is analogous to that used to prepare Compound A1(c) except that (S)-2-methylpiperazine (Commercially available from Sigma-Aldrich, St. Louis, Mo. (www.sigma-aldrich.com)) was used in place of (R)-2-methylpiperazine. The identity of Compound A1(d), i.e., N-(4-tert-Butyl-phenyl)-4-(3-chloro-pyridin-2-yl)—N-hydroxy-(S)-2-methyl-piperazine-1-carboxamidine), was confirmed using $^1$H NMR.

Compound A1(d): $^1$H NMR (CDCl$_3$) δ 8.21 (dd, J=1.6, 4.8 Hz, 1H), 7.61 (dd, J=1.6, 7.8 Hz, 1H), 7.29 (d, J=8.7 Hz, 2H), 7.18 (d, J=8.6 Hz, 2H), 6.88 (dd, J=4.8, 7.8 Hz, 1H), 6.68 (br, 1H), 3.67 (m, 1H), 3.50 (m, 1H), 3.35 (m, 2H), 3.10 (m, 2H), 1.63 (br, 1H), 1.32 (d, J=6.75 Hz, 3H), 1.31 (s, 9H) ppm.

5.3 Example 3

Synthesis of Compound A1(a)

Compound A1(a) was prepared by a procedure that is analagous to that used to prepare Compound A1(c) except that piperazine was used in place of (R)-2-methylpiperazine. The identity of Compound A1(a) was confirmed using $^1$H NMR.

Compound A1(a): $^1$H NMR (CDCl$_3$) δ 8.21 (dd, J=1.6, 4.8 Hz, 1H), 7.61 (dd, J=1.6, 7.8 Hz, 1H), 7.29 (d, J=8.6 Hz, 2H), 7.18 (d, J=8.7 Hz, 2H), 6.88 (dd, J=4.8, 7.8 Hz, 1H), 6.68 (br, 1H), 3.35 (m, 4H), 3.25 (m, 4H), 1.63 (br, 1H), 1.28 (s, 9H) ppm.

5.4 Example 4

Synthesis of Compound A29(a)

Compound A29(a) was prepared by a procedure that is analogous to that used to prepare Compound A1(a) except that 2-chloro-3-methylpyridine was used in place of 2,3-dichloropyridine. The identity of Compound A29(a) was confirmed using $^1$H NMR.

Compound A29(a): $^1$H NMR (CDCl$_3$) δ 8.18 (dd, J=1.3, 4.8 Hz, 1H), 7.43 (dd, J=1.3, 7.3 Hz, 1H), 7.30 (d, J=8.7 Hz, 2H), 7.20 (d, J=8.7 Hz, 2H), 6.89 (dd, J=4.8, 7.3 Hz, 1H), 6.73 (br, 1H), 3.23 (m, 4H), 3.16 (m, 4H), 2.28 (s, 3H), 1.63 (br, 1H), 1.31 (s, 9H) ppm.

5.5 Example 5

Synthesis of Compound A35(a)

Compound A35(a) was prepared by a procedure that is analogous to that used to prepare Compound A29(a) except that 4-(trifluoromethyl)-phenylisothiocyanate was used in place of 4-(tert-butyl)-phenylisothiocyanate. The identity of Compound A35(a) was confirmed using $^1$H NMR.

Compound A35(a): $^1$H NMR (CDCl$_3$) δ 8.19 (dd, J=1.2, 4.8 Hz, 1H), 7.54 (d, J=8.6 Hz, 2H), 7.43 (dd, J=1.2, 7.3 Hz, 1H), 7.34 (d, J=8.6 Hz, 2H), 7.06 (br, 1H), 6.90 (dd, J=4.9, 7.3 Hz, 1H), 6.72 (br, 1H), 3.25 (m, 4H), 3.18 (m, 4H), 2.19 (s, 3H) ppm.

5.6 Example 6

Synthesis of Compound A43(c)

Compound A43(c) was prepared by a procedure that is analogous to that used to prepare Compound A1(c) except that 2-chloro-3-trifluoromethylpyridine was used in place of 2,3-dichloropyridine. The identity of Compound A43(c) was confirmed using $^1$H NMR.

Compound A43(c): $^1$H NMR (CDCl$_3$) δ 8.48 (dd, J=1.5, 4.7 Hz, 1H), 7.91 (dd, J=1.5, 7.8 Hz, 1H), 7.30 (d, J=8.7 Hz, 2H), 7.19 (d, J=8.7 Hz, 2H), 7.07 (dd, J=4.7, 7.8 Hz, 1H), 6.32 (br, 1H), 3.65 (m, 1H), 3.43 (m, 1H), 3.32 (m, 2H), 3.25 (m, 2H), 3.14 (m, 1H), 1.63 (br, 1H), 1.32 (s, 9H), 1.25 (d, J=7.6 Hz, 3H) ppm.

5.7 Example 7

Synthesis of Compound A183(a)

Compound A183(a) was prepared by a procedure that is analogous to that used to prepare Compound A1(a) except that 2,3-dichloropyrazine was used in place of 2,3-dichloropyridine. The identity of Compound A183(a) was confirmed using $^1$H NMR.

Compound A183(a): $^1$H NMR (CDCl$_3$) δ 8.21 (s, 1H), 7.89 (s, 1H), 729 (m, 2H), 7.18 (m, 2H), 6.68 (bs, 1H), 3.35 (bs, 4H), 3.25 (bs, 4H), 1.28 (s, 9H) ppm.

5.8 Example 8

Synthesis of Compound A267(a)

Compound A267(a) was prepared by a procedure that is analogous to that used to prepare Compound A1(a) except that 4,5-dichloro-2-thia-1,3-diazole was used in place of 2,3-dichloropyridine. The identity of Compound A267(a) was confirmed using $^1$H NMR.

Compound A267(a): $^1$H NMR (CDCl$_3$) δ 7.39 (m, 2H), 7.19 (m, 2H), 6.78 (bs, 1H), 3.55 (bs, 4H), 3.25 (bs, 4H), 1.28 (s, 9H) ppm).

5.9 Example 9

Synthesis of Compound A43(a)

Compound A43(a) was prepared by a procedure that is analogous to that used to prepare Compound A1(a) except that 2-chloro-3-trifluoromethylpyridine was used in place of 2,3-dichloropyridine. The identity of Compound A43(a) was confirmed using $^1$H NMR.

Compound A43(a): $^1$H NMR (CDCl$_3$) δ 8.47-8.44 (m, 1H), 7.90-7.87 (m, 1H), 7.31-7.29 (m, 2H), 7.18-716 (m, 2H), 7.06-7.01 (m, 1H), 6.7- (s, 1H), 3.30-3.27 (m, 4H), 3.24-3.21 (m, 4H), 1.31 (s, 9H) ppm.

5.10 Example 10

Synthesis of Compound B1(a)

A solution of Compound A1(a) (77.4 mg, 0.20 mmol), prepared as described above in Example 5.3, in 1.5 mL of anhydrous dimethylformamide was added NaH (60 wt %, 8.4 mg, 0.21 mmol) and the resulting mixture was allowed to stir at room temperature (about 25° C.) for about 0.5 h. Iodomethane (28.4 mg, 0.20 mmol) was then added to the reaction mixture and the mixture was allowed to stir at room temperature (about 25° C.) for about 4 h. The reaction mixture was then quenched with water and extracted with diethyl ether. The organic layers were combined, dried (MgSO$_4$), and concentrated under reduced pressure. The resulting residue was then purified using column chromatography (silica gel eluted with gradient elution (10:1 hexane:ethyl acetate to 2:1 hexane:ethyl acetate) to provide Compound B1(a) (64% yield). The identity of Compound B1(a) was confirmed using $^1$H NMR.

Compound B1(a): $^1$H NMR (CDCl$_3$) δ 8.21 (dd, J=1.6, 4.8 Hz, 1H), 7.61 (dd, J=1.6, 7.8 Hz, 1H), 7.29 (d, J=7.8 Hz, 2H), 7.16 (d, J=8.7 Hz, 2H), 6.88 (dd, J=4.8, 7.8 Hz, 1H), 6.60 (br, 1H), 3.79 (s, 3H), 3.36 (m, 4H), 3.25 (m, 4H), 1.31 (s, 9H) ppm.

5.11 Example 11

Binding of Hydroxyiminopiperazine Compounds to mGluR5

The following assay can be used to demonstrate that Hydroxyiminopiperazine Compounds bind to mGluR5.

Cell cultures: Primary glial cultures are prepared from cortices of Sprague-Dawley 18 days old embryos. The cortices are dissected and then dissociated by trituration. The resulting cell homogenate is plated onto poly-D-lysine pre-coated T175 flasks (BIOCOAT, commercially available from Becton Dickinson and Company Inc. of Franklin Lakes, N.J.) in Dulbelcco's Modified Eagle's Medium ("DMEM," pH 7.4), buffered with 25 mM HEPES, and supplemented with 15% fetal calf serum ("FCS," commercially available from Hyclone Laboratories Inc. of Omaha, Nebr.), and incubated at 37° C. and 5% CO$_2$. After 24 h, FCS supplementation is reduced to 10%. On day six, oligodendrocytes and microglia are removed by strongly tapping the sides of the flasks. One day following this purification step, secondary astrocytes cultures are established by subplating onto 96 poly-D-lysine precoated T175 flasks (BIOCOAT) at a density of 65,000 cells/well in DMEM and 10% FCS. After 24 h, the astrocytes are washed with serum free medium and then cultured in DMEM, without glutamate, supplemented with 0.5% FCS, 20 mM HEPES, 10 ng/mL epidermal growth factor ("EGF"), 1 mM sodium pyruvate, and 1× penicillin/streptomycin at pH 7.5 for 3 to 5 days at 37° C. and 5% CO$_2$. The procedure allows the expression of the mGluR5 receptor by astrocytes, as demonstrated by S. Miller et al., *J. Neuroscience* 15(9): 6103-6109 (1995).

Assay Protocol: After 3-5 days incubation with EGF, the astrocytes are washed with 127 mM NaCl, 5 mM KCl, 2 mM MgCl$_2$, 700 mM NaH$_2$PO$_4$, 2 mM CaCl$_2$, 5 mM NaHCO$_3$, 8 mM HEPES, 10 mM Glucose at pH 7.4 ("Assay Buffer") and loaded with the dye Fluo-4 (commercially available from Molecular Probes Inc. of Eugene, Oreg.) using 0.1 mL of Assay Buffer containing Fluo-4 (3 mM final). After 90 minutes of dye loading, the cells are then washed twice with 0.2 mL Assay Buffer and resuspended in 0.1 mL of Assay Buffer. The plates containing the astrocytes are then transferred to a Fluorometric Imaging Plate reader (commercially available from Molecular Devices Corporation of Sunnyvale, Calif.) for the assessment of calcium mobilization flux in the presence of glutamate and in the presence or absence of antagonist. After monitoring fluorescence for 15 seconds to establish a base line, DMSO solutions containing various concentrations of the Hydroxyiminopiperazine Compounds diluted in Assay Buffer (0.05 mL of 4× dilutions for competition curves) are added to the cell plate and fluorescence is monitored for 2 minutes. 0.05 mL of a 4× glutamate solution (agonist) is then added to each well to provide a final glutamate concentration in each well of 10 mM. Plate fluorescence is then monitored for an additional 60 seconds after agonist addition. The final DMSO concentration in the assay is 1.0%. In each experiment, fluorescence is monitored as a function of time and the data analyzed using Microsoft Excel and GraphPad Prism. Dose-response curves are fit using a non-linear regression to determine IC$_{50}$ value. In each experiment, each data point is determined two times.

5.12 Example 12

In Vivo Assays for Prevention or Treatment of Pain

Test Animals: Each experiment uses rats weighing between 200-260 g at the start of the experiment. The rats are group-housed and have free access to food and water at all times, except prior to oral administration of a Hydroxyiminopiperazine Compound when food is removed for 16 h before dosing. A control group acts as a comparison to rats treated with a Hydroxyiminopiperazine Compound. The control group is administered the carrier for the Hydroxyiminopiperazine Compound. The volume of carrier administered to the control group is the same as the volume of carrier and Hydroxyiminopiperazine Compound administered to the test group.

Acute Pain: To assess the actions of the Hydroxyiminopiperazine Compounds for the treatment or prevention of acute pain the rat tail flick test can be used. Rats are placed inside a cotton pouch and the tail exposed to a focused beam of radiant heat at a point 3 cm from the tip using a tail flick unit (Model 7360, commercially available from Ugo Basile of Italy). Tail flick latencies are defined as the interval between the onset of the thermal stimulus and the flick of the tail. Animals not responding within 15 seconds are removed from the tail flick unit and assigned a withdrawal latency of 15 seconds. Tail flick latencies are measured immediately before (pre-treatment) and 1, 3, and 6 h following administration of a Hydroxyiminopiperazine Compound. Data are expressed as tail flick latency(s) and the percentage of the maximal possible effect (% MPE), i.e., 15 seconds, is calculated as follows:

$$\% \ MPE = \frac{\left[\begin{array}{c}(\text{post administration latency}) - \\ (\text{pre-administration latency})\end{array}\right]}{(15 \ s \ \text{pre-administration latency})} \times 100$$

The rat tail flick test is described in F. E. D'Amour et al, "A Method for Determining Loss of Pain Sensation," *J. Pharmacol. Exp. Ther.* 72:74-79 (1941).

Acute pain can also be assessed by measuring the animal's response to noxious mechanical stimuli by determining the paw withdrawal threshold (PWT), as described below.

Inflammatory Pain: To assess the actions of the Hydroxyiminopiperazine Compounds for the treatment or prevention of inflammatory pain the Freund's complete adjuvant (FCA) model of inflammatory pain is used. FCA-induced inflammation of the rat hind paw is associated with the development of persistent inflammatory mechanical hyperalgesia and provides reliable prediction of the anti-hyperalgesic action of clinically useful analgesic drugs (L. Bartho et al., "Involvement of Capsaicin-sensitive Neurones in Hyperalgesia and Enhanced Opioid Antinociception in Inflammation," *Naunyn-Schmiedeberg's Archives of Pharmacology* 342:666-670 (1990)). The left hind paw of each animal is administered a 50 µL intraplantar injection of 100% FCA. 24 h post injection, the animal is assessed for response to noxious mechanical stimuli by determining the PWT, as described below. Rats are then administered a single injection of 1, 3, 10, or 30 mg/Kg of either a Hydroxyiminopiperazine Compound, 30 mg/Kg indomethacin or carrier. Responses to noxious mechanical stimuli are then determined 2, 4, 6, and 24 h post administration. Percentage reversal of hyperalgesia for each animal is defined as:

$$\% \text{ Reversal} = \frac{\left[\begin{array}{c}(\text{post administration } PWT) - \\ (\text{pre-administration } PWT)\end{array}\right]}{(\text{Baseline pre-administration } PWT)} \times 100$$

Neuropathic Pain: To assess the actions of the Hydroxyiminopiperazine Compounds for the treatment or prevention of neuropathic pain either the Seltzer model or the Chung model can be used.

In the Seltzer model, the partial sciatic nerve ligation model of neuropathic pain is used to produce neuropathic hyperalgesia in rats (Z. Seltzer et al., "A Novel Behavioral Model of Neuropathic Pain Disorders Produced in Rats by Partial Sciatic Nerve Injury," *Pain* 43:205-218 (1990)). Partial ligation of the left sciatic nerve is performed under enflurane/$O_2$ inhalation anaesthesia. Following induction of anesthesia, the left thigh of the rat is shaved and the sciatic nerve exposed at high thigh level through a small incision and is carefully cleared of surrounding connective tissues at a site near the trocanther just distal to the point at which the posterior biceps semitendinosus nerve branches off of the common sciatic nerve. A 7-0 silk suture is inserted into the nerve with a 3/8 curved, reversed-cutting mini-needle and tightly ligated so that the dorsal 1/3 to 1/2 of the nerve thickness is held within the ligature. The wound is closed with a single muscle suture (7-0 silk) and a Michelle clip. Following surgery, the wound area is dusted with antibiotic powder. Sham-treated rats undergo an identical surgical procedure except that the sciatic nerve is not manipulated. Following surgery, animals are weighed and placed on a warm pad until they recover from anesthesia. Animals are then returned to their home cages until behavioral testing begins. The animal is assessed for response to noxious mechanical stimuli by determining PWT, as described below, immediately prior to and 1, 3, and 6 h after drug administration for both the left rear paw and right rear paw of the animal. Percentage reversal of neuropathic hyperalgesia is defined as:

% reversal=100−[(right pre-administration PWT−left post-administration PWT)/(right pre-administration PWT−left pre-administration PWT)]×100.

In the Chung model, the spinal nerve ligation model of neuropathic pain is used to produce mechanical hyperalgesia, themal hyperalgesia and tactile allodynia in rats. Surgery is performed under isoflurane/$O_2$ inhalation anaesthesia. Following induction of anaesthesia a 3 cm incision is made and the left paraspinal muscles are separated from the spinous process at the $L_4$-$S_2$ levels. The $L_6$ transverse process is carefully removed with a pair of small rongeurs to identify visually the $L_4$-$L_6$ spinal nerves. The left $L_5$ (or $L_5$ and $L_6$) spinal nerve(s) is isolated and tightly ligated with silk thread. A complete hemostasis is confirmed and the wound is sutured using non-absorbable sutures, such as nylon sutures or stainless steel staples. Sham-treated rats undergo an identical surgical procedure except that the spinal nerve(s) is not manipulated. Following surgery animals are weighed, administered a subcutaneous (s.c.) injection of saline or ringers lactate, the wound area is dusted with antibiotic powder and they are kept on a warm pad until they recover from the anesthesia. Animals are then be returned to their home cages until behavioral testing begins. The animals are assessed for response to noxious mechanical stimuli by determining PWT, as described below, immediately prior to and 1, 3, and 5 h after being administered a Hydroxyiminopiperazine Compound for both the left rear paw and right rear paw of the animal. The animal can also be assessed for response to noxious thermal stimuli or for tactile allodynia, as described below. The Chung model for neuropathic pain is described in S. H. Kim, "An Experimental Model for Peripheral Neuropathy Produced by Segmental Spinal Nerve Ligation in the Rat," *Pain* 50(3):355-363 (1992).

Response to Mechanical Stimuli as an Assessment of Mechanical Hyperalgesia: The paw pressure assay can be used to assess mechanical hyperalgesia. For this assay, hind paw withdrawal thresholds (PWT) to a noxious mechanical stimulus are determined using an analgesymeter (Model 7200, commercially available from Ugo Basile of Italy) as described in C. Stein, "Unilateral Inflammation of the Hindpaw in Rats as a Model of Prolonged Noxious Stimulation: Alterations in Behavior and Nociceptive Thresholds," *Pharmacology Biochemistry and Behavior* 31:451-455 (1988). The maximum weight that can be applied to the hind paw is set at 250 g and the end point is taken as complete withdrawal of the paw. PWT is determined once for each rat at each time point and only the affected (ipsilateral) paw is tested.

Response to Thermal Stimuli as an Assessment of Thermal Hyperalgesia: The plantar test can be used to assess thermal hyperalgesia. For this test, hind paw withdrawal latencies to a noxious thermal stimulus are determined using a plantar test apparatus (commercially available from Ugo Basile of Italy) following the technique described by K. Hargreaves et al., "A New and Sensitive Method for Measuring Thermal Nociception in Cutaneous Hyperalgesia," *Pain* 32(1):77-88 (1988). The maximum exposure time is set at 32 seconds to avoid tissue damage and any directed paw withdrawal from the heat source is taken as the end point. Three latencies are determined at each time point and averaged. Only the affected (ipsilateral) paw is tested.

Assessment of Tactile Allodynia: To assess tactile allodynia, rats are placed in clear, plexiglass compartments with a wire mesh floor and allowed to habituate for a period of at least 15 minutes. After habituation, a series of von Frey monofilaments are presented to the plantar surface of the left (operated) foot of each rat. The series of von Frey monofilaments consists of six monofilaments of increasing diameter, with the smallest diameter fiber presented first. Five trials are conducted with each filament with each trial separated by approximately 2 minutes. Each presentation lasts for a period of 4-8 seconds or until a nociceptive withdrawal behavior is observed. Flinching, paw withdrawal or licking of the paw are considered nociceptive behavioral responses.

5.13 Example 13

In Vivo Assays for Prevention or Treatment of Anxiety

The elevated plus maze test or the shock-probe burying test can be used to assess the anxiolytic activity of Hydroxyiminopiperazine Compounds in rats or mice.

The Elevated Plus Maze Test: The elevated plus maze consists of a platform with 4 arms, two open and two closed (50×10×50 cm enclosed with an open roof). Rats (or mice) are placed in the center of the platform, at the crossroad of the 4 arms, facing one of the closed arms. Time spent in the open arms vs the closed arms and number of open arm entries during the testing period are recorded. This test is conducted prior to drug administration and again after drug administration. Test results are expressed as the mean time spent in open arms and the mean number of entries into open arms. Known anxiolytic drugs increase both the time spent in open arms and number of open arm entries. The elevated plus maze test is described in D. Treit, "Animal Models for the Study of Anti-anxiety Agents: A Review," *Neuroscience & Biobehavioral Reviews* 2(2):203-222 (1985).

The Shock-Probe Burying Test: For the shock-probe burying test the testing apparatus consists of a plexiglass box measuring 40×30×40 cm, evenly covered with approximately 5 cm of bedding material (odor absorbent kitty litter) with a small hole in one end through which a shock probe (6.5 cm long and 0.5 cm in diameter) is inserted. The plexiglass shock probe is helically wrapped with two copper wires through which an electric current is administered. The current is set at 2 mA. Rats are habituated to the testing apparatus for 30 min on 4 consecutive days without the shock probe in the box. On test day, rats are placed in one corner of the test chamber following drug administration. The probe is not electrified until the rat touches it with its snout or fore paws, at which point the rat receives a brief 2 mA shock. The 15 min testing period begins once the rat receives its first shock and the probe remains electrified for the remainder of the testing period. The shock elicits burying behavior by the rat. Following the first shock, the duration of time the rat spends spraying bedding material toward or over the probe with its snout or fore paws (burying behavior) is measured as well as the number of contact-induced shocks the rat receives from the probe. Known anxiolytic drugs reduce the amount of burying behavior. In addition, an index of the rat's reactivity to each shock is scored on a 4 point scale. The total time spent immobile during the 15 min testing period is used as an index of general activity. The shock-probe burying test is described in D. Treit, 1985, supra.

5.14 Example 14

In Vivo Assays for Prevention or Treatment of an Addictive Disorder

The condition place preference test or drug self-administration test can be used to assess the ability of Hydroxyiminopiperazine Compounds to attenuate the rewarding properties of known drugs of abuse.

The Condition Place Preference Test: The apparatus for the conditioned place preference test consists of two large compartments (45×45×30 cm) made of wood with a plexiglass front wall. These two large compartments are distinctly different. Doors at the back of each large compartment lead to a smaller box (36×18×20 cm) box made of wood, painted grey, with a ceiling of wire mesh. The two large compartments differ in terms of shading (white vs black), level of illumination (the plexiglass door of the white compartment is covered with aluminum foil except for a window of 7×7 cm), texture (the white compartment has a 3 cm thick floor board (40×40 cm) with nine equally spaced 5 cm diameter holes and the black has a wire mesh floor), and olfactory cues (saline in the white compartment and 1 mL of 10% acetic acid in the black compartment). On habituation and testing days, the doors to the small box remain open, giving the rat free access to both large compartments.

The first session that a rat is placed in the apparatus is a habituation session and entrances to the smaller grey compartment remain open giving the rat free access to both large compartments. During habituation, rats generally show no preference for either compartment. Following habituation, rats are given 6 conditioning sessions. Rats are divided into 4 groups: carrier pre-treatment+carrier (control group), Hydroxyiminopiperazine Compound pre-treatment+carrier, carrier pre-treatment+morphine, Hydroxyiminopiperazine Compound pre-treatment+morphine. During each conditioning session the rat is injected with one of the drug combinations and confined to one compartment for 30 min. On the following day, the rat receives a carrier+carrier treatment and is confined to the other large compartment. Each rat receives three conditioning sessions consisting of 3 drug combination-compartment and 3 carrier-compartment pairings. The order of injections and the drug/compartment pairings are counter-balanced within groups. On the test day, rats are injected prior to testing (30 min to 1 h) with either morphine or carrier and the rat is placed in the apparatus, the doors to the grey compartment remain open and the rat is allowed to explore the entire apparatus for 20 min. The time spent in each compartment is recorded. Known drugs of abuse increase the time spent in the drug-paired compartment during the testing session. If the Hydroxyiminopiperazine Compound blocks the acquisition of morphine conditioned place preference (reward), there will be no difference in time spent in each side in rats pre-treated with a Hydroxyiminopiperazine Compound and the group will not be different from the group of rats that was given carrier+carrier in both compartments. Data will be analyzed as time spent in each compartment (drug combination-paired vs carrier-paired). Generally, the experiment is repeated with a minimum of 3 doses of a Hydroxyiminopiperazine Compound.

The Drug Self-Administration Test: The apparatus for the drug self-administration test is a standard commercially available operant conditioning chamber. Before drug trials begin rats are trained to press a lever for a food reward. After stable lever pressing behavior is acquired, rats are tested for acquisition of lever pressing for drug reward. Rats are implanted with chronically indwelling jugular catheters for i.v. administration of compounds and are allowed to recover for 7 days before training begins. Experimental sessions are conducted daily for 5 days in 3 h sessions. Rats are trained to self-administer a known drug of abuse, such as morphine. Rats are then presented with two levers, an "active" lever and an "inactive" lever. Pressing of the active lever results in drug infusion on a fixed ratio 1 (FR1) schedule (i.e., one lever press gives an infusion) followed by a 20 second time out period (signaled by illumination of a light above the levers). Pressing of the inactive lever results in infusion of excipient. Training continues until the total number of morphine infusions stabilizes to within ±10% per session. Trained rats are then used to evaluate the effect of Hydroxyiminopiperazine Compounds pre-treatment on drug self-administration. On test day, rats are pre-treated with a Hydroxyiminopiperazine Compound or excipient and then are allowed to self-administer drug as usual. If the Hydroxyiminopiperazine Compound blocks the rewarding effects of morphine, rats pre-treated with the Hydroxyiminopiperazine Compound will show a lower rate of responding compared to their previous rate of responding and compared to excipient pre-treated rats. Data is analyzed as the change in number of drug infusions per testing session (number of infusions during test session—number of infusions during training session).

5.15 Example 15

Functional Assay for Characterizing mGluR 1 Antagonistic Properties

Functional assays for the characterization of mGluR 1 antagonistic properties are well known in the art. For example, the following procedure can be used.

A CHO-rat mGluR1 cell line is generated using cDNA encoding rat mGluR1 receptor (M. Masu and S. Nakanishi, *Nature* 349: 760-765 (1991)). The cDNA encoding rat mGluR1 receptor can be obtained from, e.g., Prof. S. Nakanishi (Kyoto, Japan).

40,000 CHO-rat mGluR1 cells/well are plated into a Costar 3409, black, clear bottom, 96 well, tissue culture treated plate (commercially available from Fisher Scientific of Chicago, Ill.) and are incubated in Dulbecco's Modified Eagle's Medium (DMEM, pH 7.4) supplemented with glutamine, 10% FBS, 1% Pen/Strep, and 500 µg/mL Geneticin for about 12 h. The CHO-rat mGluR1 cells are then washed and treated with Optimem medium (commercially available from Invitrogen, Carlsbad, Calif.) and incubated for a time period ranging from 1 to 4 hours prior to loading the cells with the dye Fluo-4 (commercially available from Molecular Probes Inc., Eugene Oreg.). After incubation, the cell plates are washed with loading buffer (127 mM NaCl, 5 mM KCl, 2 mM $MgCl_2$, 700 µM, $NaH_2PO_4$, 2 mM $CaCl_2$, 5 mM $NaHCO_3$, 8 mM HEPES, and 10 mM glucose, pH 7.4) and incubated with 3 µM Fluo-4 in 0.1 mL loading buffer for 90 min. The cells are then washed twice with 0.2 mL loading buffer, resuspended in 0.1 mL of loading buffer, and transferred to a Fluorometric Imaging Plate Reader (FLIPR) (commercially available from Molecular Devices Corp., Sunnyvale, Calif.) for measurement of calcium mobilization flux in the presence of glutamate and in the presence or absence of a Hydroxyiminopiperazine Compound.

To measure calcium mobilization flux, fluoresence is monitored for about 15 s to establish a baseline and DMSO solutions containing various concentrations of a Hydroxyiminopiperazine Compound ranging from about 50 µM to about 0.8 nM diluted in loading buffer (0.05 mL of a 4× dilution) are added to the cell plate and fluoresence is monitored for about 2 min. 0.05 mL of a 4× Glutamate solution (agonist) is then added to each well to provide a final glutamate concentration in each well of 10 µM and fluoresence is monitored for about 1 additional min. The final DMSO concentration in the assay is 1%. In each experiment fluoresence is monitored as a function of time and the data is analyzed using a non-linear regression to determine the $IC_{50}$ value. In each expereiment each data point is determined twice.

5.16 Example 16

Binding of Hydroxyiminopiperazine Compounds to VR1

Methods for assaying compounds capable of inhibiting VR1 are well known to those skilled in the art, for example, those methods disclosed in U.S. Pat. No. 6,239,267 to Duckworth et al.; U.S. Pat. No. 6,406,908 to McIntyre et al.; or U.S. Pat. No. 6,335,180 to Julius et al.

Binding of Compound A1 (a) to VR1: Assay Protocol

Human VR1 cloning. Human spinal cord RNA (commercially available from Clontech, Palo Alto, Calif.) was used. Reverse transcription was conducted on 1.0 µg total RNA using Thermoscript Reverse Transcriptase (commercially available from Invitrogen, Carlsbad, Calif.) and oligo dT primers as detailed in its product description. Reverse transcription reactions were incubated at 55° C. for 1 h, heat-inactivated at 85° C. for 5 min, and RNase H-treated at 37° C. for 20 min.

Human VR1 cDNA sequence was obtained by comparison of the human genomic sequence, prior to annotation, to the published rat sequence. Intron sequences were removed and flanking exonic sequences were joined to generate the hypothetical human cDNA. Primers flanking the coding region of human VR1 were designed as follows: forward primer, AAGATCTTCGCTGGTTGCACACTGGGCCACA; and reverse primer, GAAGATCTTCGGGGACAGTGACGGT-TGGATGT.

PCR of VR1 was performed on one tenth of the Reverse transcription reaction mixture using Expand Long Template Polymerase and Expand Buffer 2 in a final volume of 50 µL according to the manufacturer's instructions (Roche Applied Sciences, Indianapolis, Ind.). After denaturation at 94° C. for 2 min PCR amplification was performed for 25 cycles at 94° C. for 15 sec, 58° C. for 30 sec, and 68° C. for 3 min followed by a final incubation at 72° C. for 7 min to complete the amplification. A PCR product of 2.8 kb was gel-isolated using a 1.0% agarose, Tris-Acetate gel containing 1.6 µg/mL of crystal violet and purified with a S.N.A.P. UV-Free Gel Purification Kit (commercially available from Invitrogen). The VR1 PCR product was cloned into the pIND/V5-His-TOPO vector (commercially available from Invitrogen) according to the manufacturer's instructions. DNA preparations, restriction enzyme digestions, and preliminary DNA sequencing were performed according to standard protocols. Full-length sequencing confirmed the identity of the human VR1.

Generation of inducible cell lines. Unless noted otherwise, cell culture reagents were purchased from Life Technologies of Rockville, Md. HEK293-EcR cells expressing the ecdysone receptor (commercially available from Invitrogen) were cultured in Growth Medium (Dulbecco's Modified Eagles Medium containing 10% fetal bovine serum (commercially available from HYCLONE, Logan, Utah), 1× penicillin/streptomycin, 1× glutamine, 1 mM sodium pyruvate and 400 µg/mL Zeocin (commercially available from Invitrogen)). The VR1-pIND constructs were transfected into the HEK293-EcR cell line using Fugene transfection reagent (commercially available from Roche Applied Sciences, Basel, Switzerland). After 48 h, cells were transferred to Selection Medium (Growth Medium containing 300 µg/mL G418 (commercially available from Invitrogen)). Approximately 3 weeks later individual Zeocin/G418 resistant colonies were isolated and expanded. To identify functional clones, multiple colonies were plated into 96-well plates and expression was induced for 48 h using Selection Medium supplemented with 5 μM ponasterone A ("PonA") (commercially available from Invitrogen). On the day of assay, cells were loaded with Fluo-4 (a calcium-sensitive dye that is commercially available from Molecular Probes, Eugene, Oreg.) and CAP-mediated calcium influx was measured using a Fluorometric Imaging Plate Reader ("FLIPR") (commercially available from Molecular Devices Corp., Sunnyvale, Calif.) as described below. Functional clones were re-assayed, expanded, and cryopreserved.

pH-Based Assay. Two days prior to performing this assay, cells were seeded on poly-D-lysine-coated 96-well clear-bottom black plates (commercially available from Becton-Dickinson) at 75,000 cells/well in growth media containing 5 μM PonA (commercially available from Invitrogen) to induce expression. On the day of the assay, the plates were washed with 0.2 mL 1× Hank's Balanced Salt Solution (commercially available from Life Technologies) containing 1.6 mM $CaCl_2$ and 20 mM HEPES, pH 7.4 ("wash buffer"), and loaded using 0.1 mL of wash buffer containing Fluo-4 (3 μM final concentration, commercially available from Molecular Probes). After 1 h, the cells were washed twice with 0.2 mL wash buffer and resuspended in 0.05 mL 1× Hank's Balanced Salt Solution (commercially available from Life Technologies) containing 3.5 mM $CaCl_2$ and 10 mM Citrate, pH 7.4 ("assay buffer"). Plates were then transferred to a FLIPR (commercially available from Molecular Devices) for assay. Compound A1(a) was diluted in assay buffer, and 50 mL of the resultant solution were added to the cell plates and the solution monitored for two minutes. The final concentration of Compound A1(a) ranged from about 50 pM to about 3 μM. Agonist buffer (wash buffer titrated with 1N HCl to provide a solution having a pH of 5.5 when mixed 1:1 with assay buffer) (0.1 mL) was then added to each well, and the plates were incubated for 1 additional min. Data were collected over the entire time course and analyzed using Excel and Graph Pad Prism. Compound A1(a) when assayed according to this protocol had an $IC_{50}$ of 40.9±16.7 nM (n=4).

Capsaicin-based Assay. Two days prior to performing this assay, cells were seeded in poly-D-lysine-coated 96-well clear-bottom black plates (50,000 cells/well) in growth media containing 5 μM PonA (commercially available from Invitrogen) to induce expression. On the day of the assay, the plates were washed with 0.2 mL 1× Hank's Balanced Salt Solution (commercially available from Life Technologies) containing 1 mM $CaCl_2$ and 20 mM HEPES, pH 7.4, and cells were loaded using 0.1 mL of wash buffer containing Fluo-4 (3 μM final). After one h, the cells were washed twice with 0.2 mL of wash buffer and resuspended in 0.1 mL of wash buffer. The plates were transferred to a FLIPR (commercially available from Molecular Devices) for assay. 50 μL of Compound A1(a) diluted with assay buffer were added to the cell plates and incubated for 2 min. The final concentration of Compound A1(a) ranged from about 50 pM to about 3 μM. Human VR1 was activated by the addition of 50 μL of capsaicin (400 nM), and the plates were incubated for an additional 3 min. Data were collected over the entire time course and analyzed using Excel and GraphPad Prism. Compound A1(a) when assayed according to this protocol had an $IC_{50}$ of 58.3±10.1 nM (n=4).

The results of the pH-based assay and the capsaicin-based assay demonstrate that Compound A1(a), an illustrative Hydroxyiminopiperazine Compound, binds to and modulates the activity of human VR1 and, accordingly, is useful for treating ot preventing pain, UI, an ulcer, IBD, or IBS.

The present invention is not to be limited in scope by the specific embodiments disclosed in the examples which are intended as illustrations of a few aspects of the invention and any embodiments that are functionally equivalent are within the scope of this invention. Indeed, various modifications of the invention in addition to those shown and described herein will become apparent to those skilled in the art and are intended to fall within the scope of the appended claims.

A number of references have been cited, the entire disclosures of which are incorporated herein by reference.

What is claimed is:

1. A method for treating pain modulated by VR1, comprising administering to an animal in need thereof an effective amount of a compound or a pharmaceutically acceptable salt of the compound of formula I:

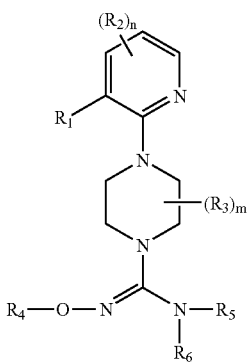

wherein:
- $R_1$ is -halo, —$CH_3$, —$NO_2$, —CN, —OH, —$OCH_3$, —$NH_2$, —C(halo)$_3$, —CH(halo)$_2$, or —$CH_2$(halo);
- each $R_2$ is independently:
  - (a) -halo, —CN, —OH, —$NO_2$, —O($C_1$-$C_6$)alkyl, or —$NH_2$;
  - (b) —($C_1$-$C_{10}$)alkyl, —($C_2$-$C_{10}$)alkenyl, —($C_2$-$C_{10}$) alkynyl, —($C_3$-$C_{10}$)cycloalkyl, —($C_8$-$C_{14}$)bicycloalkyl, —($C_8$-$C_{14}$)tricycloalkyl, —($C_5$-$C_{10}$)cycloalkenyl, —($C_8$-$C_{14}$)bicycloalkenyl, —($C_8$-$C_{14}$) tricycloalkenyl, -(3- to 7-membered)heterocycle, or -(7- to 10-membered)bicycloheterocycle, each of which is unsubstituted or substituted with one or more $R_7$ groups; or
  - (c) -phenyl, -naphthyl, —($C_{14}$)aryl or -(5- to 10-membered)heteroaryl, each of which is unsubstituted or substituted with one or more $R_8$ groups;
- each $R_3$ is independently:
  - (a) -halo, —CN, —OH, —$NO_2$, —O($C_1$-$C_6$)alkyl, or —$NH_2$;
  - (b) —($C_1$-$C_{10}$)alkyl, —($C_2$-$C_{10}$)alkenyl, —($C_2$-$C_{10}$) alkynyl, —($C_3$-$C_{10}$)cycloalkyl, —($C_8$-$C_{14}$)bicycloalkyl, —($C_8$-$C_{14}$)tricycloalkyl, —($C_5$-$C_{10}$)cycloalkenyl, —($C_8$-$C_{14}$)bicycloalkenyl, —($C_8$-$C_{14}$) tricycloalkenyl, -(3- to 7-membered)heterocycle, or -(7- to 10-membered)bicycloheterocycle, each of which is unsubstituted or substituted with one or more $R_7$ groups; or
  - (c) -phenyl, -naphthyl, —($C_{14}$)aryl or -(5- to 10-membered)heteroaryl, each of which is unsubstituted or substituted with one or more $R_8$ groups;
- $R_4$ is —H, —($C_1$-$C_{10}$)alkyl, —C(O)$R_9$, or —C(O)NHR$_9$;
- $R_5$ is —H or —($C_1$-$C_{10}$)alkyl;
- $R_6$ is:
  - (a) —($C_1$-$C_{10}$)alkyl, —($C_2$-$C_{10}$)alkenyl, —($C_2$-$C_{10}$) alkynyl, —($C_3$-$C_{10}$)cycloalkyl, —($C_8$-$C_{14}$)bicycloalkyl, —($C_8$-$C_{14}$)tricycloalkyl, —($C_5$-$C_{10}$)cycloalkenyl, —($C_8$-$C_{14}$)bicycloalkenyl, —($C_8$-$C_{14}$) tricycloalkenyl, -(3- to 7-membered)heterocycle, or -(7- to 10-membered)bicycloheterocycle, each of which is unsubstituted or substituted with one or more $R_7$ groups; or
  - (b) -phenyl, -naphthyl, —($C_{14}$)aryl, or -(5- to 10-membered)heteroaryl, each of which is unsubstituted or substituted with one or more $R_8$ groups;
- each $R_7$ and $R_8$ is independently —($C_1$-$C_6$)alkyl, —($C_2$-$C_6$)alkenyl, —($C_2$-$C_6$)alkynyl, —($C_3$-$C_8$)cycloalkyl, —($C_5$-$C_8$)cycloalkenyl, -phenyl, -(3- to 5-membered) heterocycle, —C(halo)$_3$, —CH(halo)$_2$, —$CH_2$(halo), —CN, —OH, -halo, —$N_3$, —$NO_2$, —N($R_{10}$)$_2$, —CH=$NR_{10}$, —$NR_{10}$OH, —$OR_{10}$, —$COR_{10}$, —C(O) $OR_{10}$, —OC(O)$R_{10}$, —OC(O)$OR_{10}$, —$SR_{10}$, —S(O) $R_{10}$, or —S(O)$_2R_{10}$;
- each $R_9$ is independently —H, —($C_1$-$C_6$)alkyl, —($C_2$-$C_6$) alkenyl, —($C_2$-$C_6$)alkynyl, —($C_3$-$C_8$)cycloalkyl, —($C_5$-$C_8$)cycloalkenyl, -phenyl, -(3- to 5-membered) heterocycle, —C(halo)$_3$, —CH(halo)$_2$, —$CH_2$(halo), —OH, —N($R_{10}$)$_2$, —CH=$NR_{10}$, —$NR_{10}$OH, —$OR_{10}$, or —$SR_{10}$;
- each $R_{10}$ is independently —H, —($C_1$-$C_6$)alkyl, —($C_2$-$C_6$) alkenyl, —($C_2$-$C_6$)alkynyl, —($C_3$-$C_8$)cycloalkyl, —($C_5$-$C_8$)cycloalkenyl, -phenyl, -(3- to 5-membered) heterocycle, —C(halo)$_3$, —CH(halo)$_2$, or —$CH_2$(halo);
- each halo is independently —F, —Cl, —Br, or —I;
- n is an integer ranging from 0 to 2; and
- m is an integer ranging from 0 to 2.

2. The method of claim 1, wherein:
- $R_1$ is -halo, —$CH_3$ or —C(halo)$_3$;
- n is 0;
- m is 0; and
- $R_6$ is phenyl.

3. The method of claim 1, wherein:
- $R_1$ is -halo, —$CH_3$ or —C(halo)$_3$;
- n is 0;
- m is 1;
- $R_3$ is methyl; and
- $R_6$ is phenyl.

4. A method for treating pain modulated by VR1, comprising administering to an animal in need thereof an effective amount of a compound or a pharmaceutically acceptable salt of the compound of formula VIIIa:

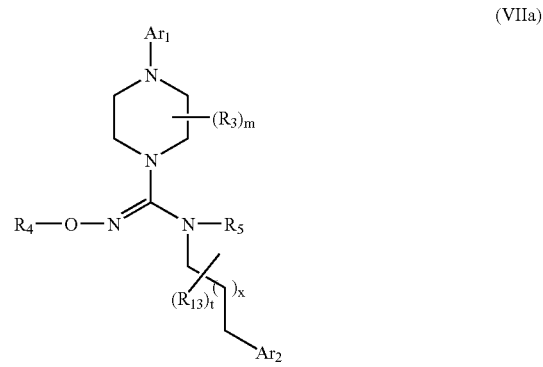

wherein:

Ar₁ is

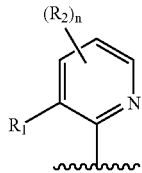

Ar₂ is

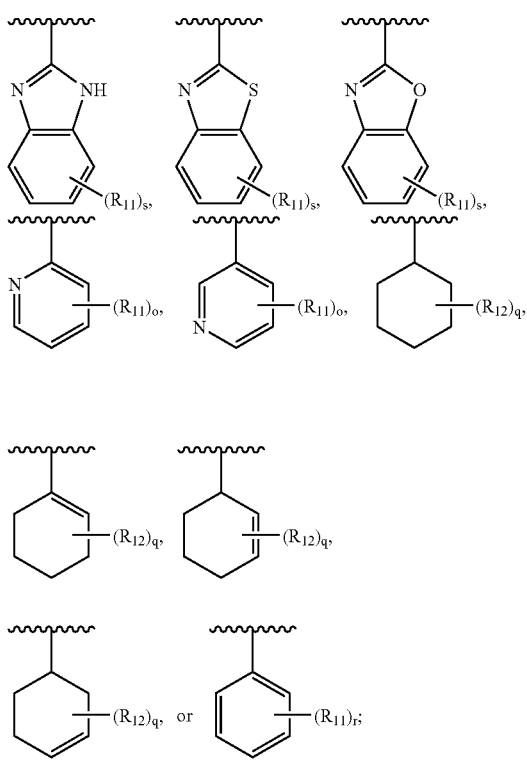

$R_1$ is —H, -halo, —$CH_3$, —$NO_2$, —CN, —OH, —$OCH_3$, —$NH_2$, —C(halo)$_3$, —CH(halo)$_2$, or —CH$_2$(halo);

each $R_2$ is independently:
  (a) -halo, —CN, —OH, —$NO_2$, —O($C_1$-$C_6$)alkyl, or —$NH_2$;
  (b) —($C_1$-$C_{10}$)alkyl, —($C_2$-$C_{10}$)alkenyl, —($C_2$-$C_{10}$)alkynyl, —($C_3$-$C_{10}$)cycloalkyl, —($C_8$-$C_{14}$)bicycloalkyl, —($C_8$-$C_{14}$)tricycloalkyl, —($C_5$-$C_{10}$)cycloalkenyl, —($C_8$-$C_{14}$)bicycloalkenyl, —($C_8$-$C_{14}$)tricycloalkenyl, -(3- to 7-membered)heterocycle, or -(7- to 10-membered)bicycloheterocycle, each of which is unsubstituted or substituted with one or more $R_7$ groups; or
  (c) -phenyl, -naphthyl, —($C_{14}$)aryl, or -(5- to 10-membered)heteroaryl, each of which is unsubstituted or substituted with one or more $R_8$ groups;

each $R_3$ is independently:
  (a) -halo, —CN, —OH, —$NO_2$, —O($C_1$-$C_6$)alkyl, or —$NH_2$;
  (b) —($C_1$-$C_{10}$)alkyl, —($C_2$-$C_{10}$)alkenyl, —($C_2$-$C_{10}$)alkynyl, —($C_3$-$C_{10}$)cycloalkyl, —($C_8$-$C_{14}$)bicycloalkyl, —($C_8$-$C_{14}$)tricycloalkyl, —($C_5$-$C_{10}$)cycloalkenyl, —($C_8$-$C_{14}$)bicycloalkenyl, —($C_8$-$C_{14}$)tricycloalkenyl, -(3- to 7-membered)heterocycle, or -(7- to 10-membered)bicycloheterocycle, each of which is unsubstituted or substituted with one or more $R_7$ groups; or
  (c) -phenyl, -naphthyl, —($C_{14}$)aryl, or -(5- to 10-membered)heteroaryl, each of which is unsubstituted or substituted with one or more $R_8$ groups;

$R_4$ is —H, —($C_1$-$C_{10}$)alkyl, —C(O)$R_9$, or —C(O)NHR$_9$;

$R_5$ is —H or —($C_1$-$C_{10}$)alkyl;

each $R_7$ and $R_8$ is independently —($C_1$-$C_6$)alkyl, —($C_2$-$C_6$)alkenyl, —($C_2$-$C_6$)alkynyl, —($C_3$-$C_8$)cycloalkyl, —($C_5$-$C_8$)cycloalkenyl, -phenyl, -(3- to 5-membered)heterocycle, —C(halo)$_3$, —CH(halo)$_2$, —CH$_2$(halo), —CN, —OH, -halo, —$N_3$, —$NO_2$, —N($R_{10}$)$_2$, —CH=NR$_{10}$, —NR$_{10}$OH, —OR$_{10}$, —COR$_{10}$, —C(O)OR$_{10}$, —OC(O)R$_{10}$, —OC(O)OR$_{10}$, —SR$_{10}$, —S(O)R$_{10}$, or —S(O)$_2$R$_{10}$;

each $R_9$ is independently —H, —($C_1$-$C_6$)alkyl, —($C_2$-$C_6$)alkenyl, —($C_2$-$C_6$)alkynyl, —($C_3$-$C_8$)cycloalkyl, —($C_5$-$C_8$)cycloalkenyl, -phenyl, -(3- to 5-membered)heterocycle, —C(halo)$_3$, —CH(halo)$_2$, —CH$_2$(halo), —OH, —N($R_{10}$)$_2$, —CH=NR$_{10}$, —NR$_{10}$OH, —OR$_{10}$, or —SR$_{10}$;

each $R_{10}$ is independently —H, —($C_1$-$C_6$)alkyl, —($C_2$-$C_6$)alkenyl, —($C_2$-$C_6$)alkynyl, —($C_3$-$C_8$)cycloalkyl, —($C_5$-$C_8$)cycloalkenyl, -phenyl, -(3- to 5-membered)heterocycle, —C(halo)$_3$, —CH(halo)$_2$, or —CH$_2$(halo);

each $R_{11}$ and $R_{12}$ is independently —($C_1$-$C_6$)alkyl, —($C_2$-$C_6$)alkenyl, —($C_2$-$C_6$)alkynyl, —($C_3$-$C_8$)cycloalkyl, —($C_5$-$C_8$)cycloalkenyl, -phenyl, —C(halo)$_3$, —CH(halo)$_2$, —CH$_2$(halo), —CN, —OH, -halo, —$N_3$, —$NO_2$, —N($R_7$)$_2$, —CH=NR$_7$, —NR$_{10}$H, —OR$_7$, —COR$_7$, —C(O)OR—, —OC(O)R$_7$, —OC(O)OR$_7$, —SR$_7$, —S(O)R$_7$, or —S(O)$_2$R$_7$;

each $R_{13}$ is independently —($C_1$-$C_6$)alkyl, —($C_2$-$C_6$)alkenyl, —($C_2$-$C_6$)alkynyl, —($C_3$-$C_8$)cycloalkyl, —($C_5$-$C_8$)cycloalkenyl, -phenyl, -(3- to 5-membered)heterocycle, —C(halo)$_3$, —CH(halo)$_2$, —CH$_2$(halo), or -halo;

each halo is independently —F, —Cl, —Br, or —I;

s is an integer ranging from 0 to 4;
o is an integer ranging from 0 to 4;
q is an integer ranging from 0 to 6;
r is an integer ranging from 0 to 5;
t is an integer ranging from 0 to 2;
n is an integer ranging from 0 to 3;
m is an integer ranging from 0 to 2; and
x is the integer 0 or 1.

5. The method of claim 4, wherein Ar₂ is a phenyl group.

6. The method of claim 5, wherein m is 0.

7. The method of claim 5, wherein m is 1 and $R_3$ is a methyl group.

8. The method of claim 1, wherein the pain is headache pain or arthritis pain.

9. The method of claim 4, wherein the pain is headache pain or arthritis pain.

10. The method of claim 1, wherein the pain is acute pain.

11. The method of claim 1, wherein the pain is inflammatory pain.

12. The method of claim 1, wherein the pain is neuropathic pain.

13. The method of claim 4, wherein the pain is acute pain.

14. The method of claim 4, wherein the pain is inflammatory pain.

15. The method of claim 4, wherein the pain is neuropathic pain.

16. The method of claim 2, wherein the $R_6$ phenyl is unsubstituted.

17. The method of claim 2, wherein the $R_6$ phenyl is substituted with an $R_8$ group at the para-position.

18. The method of claim 17, wherein the $R_8$ group is a —$(C_1$-$C_6)$alkyl group, -halo, —$CF_3$, or —$OCF_3$.

19. The method of claim 18, wherein the $R_8$—$(C_1$-$C_6)$alkyl group is a tert-butyl group or an iso-propyl group.

20. The method of claim 3, wherein the $R_6$ phenyl is unsubstituted.

21. The method of claim 3, wherein the $R_6$ phenyl is substituted with an $R_8$ group at the para-position.

22. The method of claim 21, wherein the $R_8$ group is a —$(C_1$-$C_6)$alkyl group, -halo, —$CF_3$, or —$OCF_3$.

23. The method of claim 22, wherein the $R_8$—$(C_1$-$C_6)$alkyl group is a tert-butyl group or an iso-propyl group.

24. The method of claim 1, wherein:
$R_1$ is -halo, —$CH_3$ or —$C(halo)_3$;
n is 1;
$R_2$ is —$(C_1$-$C_{10})$alkyl, —$(C_2$-$C_{10})$alkenyl, —$(C_2$-$C_{10})$alkynyl, —$(C_3$-$C_{10})$cycloalkyl, —$(C_8$-$C_{14})$bicycloalkyl, —$(C_8$-$C_{14})$tricycloalkyl, —$(C_5$-$C_{10})$cycloalkenyl, —$(C_8$-$C_{14})$bicycloalkenyl, —$(C_8$-$C_{14})$tricycloalkenyl, -(3- to 7-membered)heterocycle, or -(7- to 10-membered)bicycloheterocycle, each of which is unsubstituted or substituted with one or more $R_7$ groups;
m is 0; and
$R_6$ is phenyl.

25. The method of claim 24, wherein $R_2$ is —$(C_1$-$C_{10})$alkyl substituted with two independently selected $R_7$ groups.

26. The method of claim 24, wherein the $R_6$ phenyl is unsubstituted.

27. The method of claim 24, wherein the $R_6$ phenyl is substituted with an $R_8$ group at the para-position.

28. The method of claim 27, wherein the $R_8$ group is a —$(C_1$-$C_6)$alkyl group, -halo, —$CF_3$, or —$OCF_3$.

29. The method of claim 28, wherein the $R_8$—$(C_1$-$C_6)$alkyl group is a tert-butyl group or an iso-propyl group.

30. The method of claim 1, wherein:
$R_1$ is -halo, —$CH_3$ or —$C(halo)_3$;
n is 1;
$R_2$ is —$(C_1$-$C_{10})$alkyl, —$(C_2$-$C_{10})$alkenyl, —$(C_2$-$C_{10})$alkynyl, —$(C_3$-$C_{10})$cycloalkyl, —$(C_8$-$C_{14})$bicycloalkyl, —$(C_8$-$C_{14})$tricycloalkyl, —$(C_5$-$C_{10})$cycloalkenyl, —$(C_8$-$C_{14})$bicycloalkenyl, —$(C_8$-$C_{14})$tricycloalkenyl, -(3- to 7-membered)heterocycle, or -(7- to 10-membered)bicycloheterocycle, each of which is unsubstituted or substituted with one or more $R_7$ groups;
m is 1;
$R_3$ is methyl; and
$R_6$ is phenyl.

31. The method of claim 30, wherein $R_2$ is —$(C_1$-$C_{10})$alkyl substituted with two independently selected $R_7$ groups.

32. The method of claim 30, wherein the $R_6$ phenyl is unsubstituted.

33. The method of claim 30, wherein the $R_6$ phenyl is substituted with an $R_8$ group at the para-position.

34. The method of claim 33, wherein the $R_8$ group is a —$(C_1$-$C_6)$alkyl group, -halo, —$CF_3$, or —$OCF_3$.

35. The method of claim 34, wherein the $R_8$—$(C_1$-$C_6)$alkyl group is a tert-butyl group or an iso-propyl group.

36. The method of claim 6, wherein:
$R_1$ is -halo, —$CH_3$ or —$C(halo)_3$;
n is 1;
$R_2$ is —$(C_1$-$C_{10})$alkyl, —$(C_2$-$C_{10})$alkenyl, —$(C_2$-$C_{10})$alkynyl, —$(C_3$-$C_{10})$cycloalkyl, —$(C_8$-$C_{14})$bicycloalkyl, —$(C_8$-$C_{14})$tricycloalkyl, —$(C_5$-$C_{10})$cycloalkenyl, —$(C_8$-$C_{14})$bicycloalkenyl, —$(C_8$-$C_{14})$tricycloalkenyl, -(3- to 7-membered)heterocycle, or -(7- to 10-membered)bicycloheterocycle, each of which is unsubstituted or substituted with one or more $R_7$ groups; and
t is 0.

37. The method of claim 36, wherein $R_2$ is —$(C_1$-$C_{10})$alkyl substituted with two independently selected $R_7$ groups.

38. The method of claim 36, wherein the $Ar_2$ phenyl is unsubstituted.

39. The method of claim 36, wherein the $Ar_2$ phenyl is substituted with an $R_{11}$ group at the para-position.

40. The method of claim 39, wherein the $R_{11}$ group is a —$(C_1$-$C_6)$alkyl group, -halo, —$CF_3$, or —$OCF_3$.

41. The method of claim 40, wherein the $R_{11}$—$(C_1$-$C_6)$alkyl group is a tert-butyl group or an iso-propyl group.

42. The method of claim 7, wherein:
$R_1$ is -halo, —$CH_3$ or —$C(halo)_3$;
n is 1;
$R_2$ is —$(C_1$-$C_{10})$alkyl, —$(C_2$-$C_{10})$alkenyl, —$(C_2$-$C_{10})$alkynyl, —$(C_3$-$C_{10})$cycloalkyl, —$(C_8$-$C_{14})$bicycloalkyl, —$(C_8$-$C_{14})$tricycloalkyl, —$(C_5$-$C_{10})$cycloalkenyl, —$(C_8$-$C_{14})$bicycloalkenyl, —$(C_8$-$C_{14})$tricycloalkenyl, -(3- to 7-membered)heterocycle, or -(7- to 10-membered)bicycloheterocycle, each of which is unsubstituted or substituted with one or more $R_7$ groups; and
t is 0.

43. The method of claim 42, wherein $R_2$ is —$(C_1$-$C_{10})$alkyl substituted with two independently selected $R_7$ groups.

44. The method of claim 42, wherein the $Ar_2$ phenyl is unsubstituted.

45. The method of claim 42, wherein the $Ar_2$ phenyl is substituted with an $R_{11}$ group at the para-position.

46. The method of claim 45, wherein the $R_{11}$ group is a —$(C_1$-$C_6)$alkyl group, -halo, —$CF_3$, or —$OCF_3$.

47. The method of claim 46, wherein the $R_{11}$—$(C_1$-$C_6)$alkyl group is a tert-butyl group or an iso-propyl group.

48. A method of treating pain modulated by VR1 in an animal, comprising:
administering to an animal in need of treatment for pain a compound or a pharmaceutically acceptable salt of the compound of formula I:

wherein:
$R_1$ is -halo, —$CH_3$, —$NO_2$, —$CN$, —$OH$, —$OCH_3$, —$NH_2$, —$C(halo)_3$, —$CH(halo)_2$, or —$CH_2(halo)$;
each $R_2$ is independently:

(a) -halo, —CN, —OH, —NO$_2$, —O(C$_1$-C$_6$)alkyl, or —NH$_2$;
(b) —(C$_1$-C$_{10}$)alkyl, —(C$_2$-C$_{10}$)alkenyl, —(C$_2$-C$_{10}$)alkynyl, —(C$_3$-C$_{10}$)cycloalkyl, —(C$_8$-C$_{14}$)bicycloalkyl, —(C$_8$-C$_{14}$)tricycloalkyl, —(C$_5$-C$_{10}$)cycloalkenyl, —(C$_8$-C$_{14}$)bicycloalkenyl, —(C$_8$-C$_{14}$)tricycloalkenyl, -(3- to 7-membered)heterocycle, or -(7- to 10-membered)bicycloheterocycle, each of which is unsubstituted or substituted with one or more R$_7$ groups; or
(c) -phenyl, -naphthyl, —(C$_{14}$)aryl or -(5- to 10-membered)heteroaryl, each of which is unsubstituted or substituted with one or more R$_8$ groups;
each 1(3 is independently:
(a) -halo, —CN, —OH, —NO$_2$, —O(C$_1$-C$_6$)alkyl, or —NH$_2$;
(b) —(C$_1$-C$_{10}$)alkyl, —(C$_2$-C$_{10}$)alkenyl, —(C$_2$-C$_{10}$)alkynyl, —(C$_3$-C$_{10}$)cycloalkyl, —(C$_8$-C$_{14}$)bicycloalkyl, —(C$_8$-C$_{14}$)tricycloalkyl, —(C$_5$-C$_{10}$)cycloalkenyl, —(C$_8$-C$_{14}$)bicycloalkenyl, —(C$_8$-C$_{14}$)tricycloalkenyl, -(3- to 7-membered)heterocycle, or -(7- to 10-membered)bicycloheterocycle, each of which is unsubstituted or substituted with one or more R$_7$ groups; or
(c) -phenyl, -naphthyl, —(C$_{14}$)aryl or -(5- to 10-membered)heteroaryl, each of which is unsubstituted or substituted with one or more R$_8$ groups;
R$_4$ is —H, —(C$_1$-C$_{10}$)alkyl, —C(O)R$_9$, or —C(O)NHR$_9$;
R$_5$ is —H or —(C$_1$-C$_{10}$)alkyl;
R$_6$ is:
(a) —(C$_1$-C$_{10}$)alkyl, —(C$_2$-C$_{10}$)alkenyl, —(C$_2$-C$_{10}$)alkynyl, —(C$_3$-C$_{10}$)cycloalkyl, —(C$_8$-C$_{14}$)bicycloalkyl, —(C$_8$-C$_{14}$)tricycloalkyl, —(C$_5$-C$_{10}$)cycloalkenyl, —(C$_8$-C$_{14}$)bicycloalkenyl, —(C$_8$-C$_{14}$)tricycloalkenyl, -(3- to 7-membered)heterocycle, or -(7- to 10-membered)bicycloheterocycle, each of which is unsubstituted or substituted with one or more 1(7 groups; or
(b) -phenyl, -naphthyl, —(C$_{14}$)aryl, or -(5- to 10-membered)heteroaryl, each of which is unsubstituted or substituted with one or more 1(8 groups;
each 1(7 and R$_8$ is independently —(C$_1$-C$_6$)alkyl, —(C$_2$-C$_6$)alkenyl, —(C$_2$-C$_6$)alkynyl, —(C$_3$-C$_8$)cycloalkyl, —(C$_5$-C$_8$)cycloalkenyl, -phenyl, -(3- to 5-membered)heterocycle, —C(halo)$_3$, —CH(halo)$_2$, —CH$_2$(halo), —CN, —OH, -halo, —N$_3$, —NO$_2$, —N(R$_{10}$)$_2$, —CH=NR$_{10}$, —NR$_{10}$OH, —OR$_{10}$, —COR$_{10}$, —C(O)OR$_{10}$, —OC(O)R$_{10}$, —OC(O)OR$_{10}$, —SR$_{10}$, —S(O)R$_{10}$, or —S(O)$_2$R$_{10}$;
each R$_9$ is independently —H, —(C$_1$-C$_6$)alkyl, —(C$_2$-C$_6$)alkenyl, —(C$_2$-C$_6$)alkynyl, —(C$_3$-C$_8$)cycloalkyl, —(C$_5$-C$_8$)cycloalkenyl, -phenyl, -(3- to 5-membered)heterocycle, —C(halo)$_3$, —CH(halo)$_2$, —CH$_2$(halo), —OH, —N(R$_{10}$)$_2$, —CH=NR$_{10}$, —NR$_{10}$OH, —OR$_{10}$, or —SR$_{10}$;
each R$_{10}$ is independently —H, —(C$_1$-C$_6$)alkyl, —(C$_2$-C$_6$)alkenyl, —(C$_2$-C$_6$)alkynyl, —(C$_3$-C$_8$)cycloalkyl, —(C$_5$-C$_8$)cycloalkenyl, -phenyl, -(3- to 5-membered)heterocycle, —C(halo)$_3$, —CH(halo)$_2$, or —CH$_2$(halo);
each halo is independently —F, —Cl, —Br, or —I;
n is an integer ranging from 0 to 2; and
m is an integer ranging from 0 to 2;
in an amount ranging from 0.01 mg/kg body weight to 2500 mg/kg body weight;
wherein the compound or a pharmaceutically acceptable salt of the compound is capable of reducing pain as or more effectively than a similar dose of the positive control analgesic indomethacin as measured by one or more of the in vivo pain tests consisting of an acute pain test, an inflammatory pain test, a neuropathic pain test, a mechanical stimuli pain test, a thermal stimuli pain test, or a tactile allodynia test.

49. A method of treating pain modulated by VR1 in an animal, comprising:
administering to an animal in need of treatment for pain a compound or a pharmaceutically acceptable salt of the compound of formula VIIa:

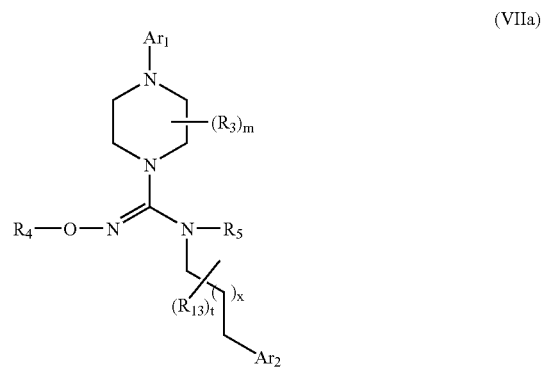

(VIIa)

wherein:
Ar$_1$ is

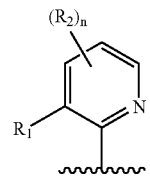

Ar$_2$ is

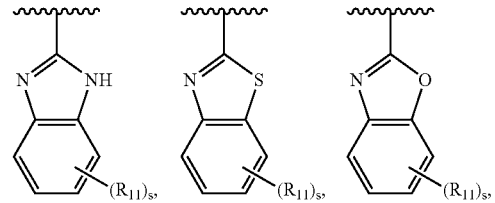

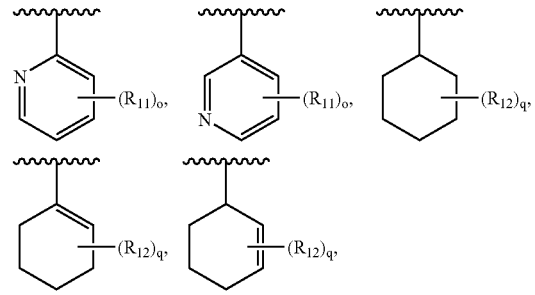

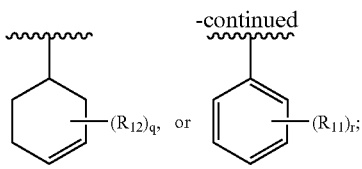

$R_1$ is —H, -halo, —$CH_3$, —$NO_2$, —CN, —OH, —$OCH_3$, —$NH_2$, —C(halo)$_3$, —CH(halo)$_2$, or —$CH_2$(halo);

each $R_2$ is independently:
(a) -halo, —CN, —OH, —$NO_2$, —O($C_1$-$C_6$)alkyl, or —$NH_2$;
(b) —($C_1$-$C_{10}$)alkyl, —($C_2$-$C_{10}$)alkenyl, —($C_2$-$C_{10}$)alkynyl, —($C_3$-$C_{10}$)cycloalkyl, —($C_8$-$C_{14}$)bicycloalkyl, —($C_8$-$C_{14}$)tricycloalkyl, —($C_5$-$C_{10}$)cycloalkenyl, —($C_8$-$C_{14}$)bicycloalkenyl, —($C_8$-$C_{14}$)tricycloalkenyl, -(3- to 7-membered)heterocycle, or -(7- to 10-membered)bicycloheterocycle, each of which is unsubstituted or substituted with one or more $R_7$ groups; or
(c) -phenyl, -naphthyl, —($C_{14}$)aryl, or -(5- to 10-membered)heteroaryl, each of which is unsubstituted or substituted with one or more $R_8$ groups;

each $R_3$ is independently:
(a) -halo, —CN, —OH, —$NO_2$, —O($C_1$-$C_6$)alkyl, or —$NH_2$;
(b) —($C_1$-$C_{10}$)alkyl, —($C_2$-$C_{10}$)alkenyl, —($C_2$-$C_{10}$)alkynyl, —($C_3$-$C_{10}$)cycloalkyl, —($C_8$-$C_{14}$)bicycloalkyl, —($C_8$-$C_{14}$)tricycloalkyl, —($C_5$-$C_{10}$)cycloalkenyl, —($C_8$-$C_{14}$)bicycloalkenyl, —($C_8$-$C_{14}$)tricycloalkenyl, -(3- to 7-membered)heterocycle, or -(7- to 10-membered)bicycloheterocycle, each of which is unsubstituted or substituted with one or more $R_7$ groups; or
(c) -phenyl, -naphthyl, —($C_{14}$)aryl, or -(5- to 10-membered)heteroaryl, each of which is unsubstituted or substituted with one or more $R_8$ groups;

$R_4$ is —H, —($C_1$-$C_{10}$)alkyl, —C(O)$R_9$, or —C(O)NHR$_9$;
$R_5$ is —H or —($C_1$-$C_{10}$)alkyl;

each $R_7$ and $R_8$ is independently —($C_1$-$C_6$)alkyl, —($C_2$-$C_6$)alkenyl, —($C_2$-$C_6$)alkynyl, —($C_3$-$C_8$)cycloalkyl, —($C_5$-$C_8$)cycloalkenyl, -phenyl, -(3- to 5-membered) heterocycle, —C(halo)$_3$, —CH(halo)$_2$, —$CH_2$(halo), —CN, —OH, -halo, —$N_3$, —$NO_2$, —N($R_{10}$)$_2$, —CH=$NR_{10}$, —$NR_{10}$OH, —OR$_{10}$, —COR$_{10}$, —C(O)OR$_{10}$, —OC(O)$R_{10}$, —OC(O)OR$_{10}$, —SR$_{10}$, —S(O)$R_{10}$, or —S(O)$_2$R$_{10}$;

each $R_9$ is independently —H, —($C_1$-$C_6$)alkyl, —($C_2$-$C_6$)alkenyl, —($C_2$-$C_6$)alkynyl, —($C_3$-$C_8$)cycloalkyl, —($C_5$-$C_8$)cycloalkenyl, -phenyl, -(3- to 5-membered)heterocycle, —C(halo)$_3$, —CH(halo)$_2$, —$CH_2$(halo), —OH, —N($R_{10}$)$_2$, —CH=$NR_{10}$, —$NR_{10}$OH, —OR$_{10}$, or —SR$_{10}$;

each $R_{10}$ is independently —H, —($C_1$-$C_6$)alkyl, —($C_2$-$C_6$)alkenyl, —($C_2$-$C_6$)alkynyl, —($C_3$-$C_8$)cycloalkyl, —($C_5$-$C_8$)cycloalkenyl, -phenyl, -(3- to 5-membered)heterocycle, —C(halo)$_3$, —CH(halo)$_2$, or —$CH_2$(halo);

each $R_{11}$ and $R_{12}$ is independently —($C_1$-$C_6$)alkyl, —($C_2$-$C_6$)alkenyl, —($C_2$-$C_6$)alkynyl, —($C_3$-$C_8$)cycloalkyl, —($C_5$-$C_8$)cycloalkenyl, -phenyl, —C(halo)$_3$, —CH(halo)$_2$, —$CH_2$(halo), —CN, —OH, -halo, —$N_3$, —$NO_2$, —N($R_7$)$_2$, —CH=$NR_7$, —$NR_7$OH, —OR$_7$, —COR$_7$, —C(O)OR$_7$, —OC(O)$R_7$, —OC(O)OR$_7$, —SR$_7$, —S(O)$R_7$, or —S(O)$_2$R$_7$;

each $R_{13}$ is independently —($C_1$-$C_6$)alkyl, —($C_2$-$C_6$)alkenyl, —($C_2$-$C_6$)alkynyl, —($C_3$-$C_8$)cycloalkyl, —($C_5$-$C_8$)cycloalkenyl, -phenyl, -(3- to 5-membered)heterocycle, —C(halo)$_3$, —CH(halo)$_2$, —$CH_2$(halo), or -halo;

each halo is independently —F, —Cl, —Br, or —I;
s is an integer ranging from 0 to 4;
o is an integer ranging from 0 to 4;
q is an integer ranging from 0 to 6;
r is an integer ranging from 0 to 5;
t is an integer ranging from 0 to 2;
n is an integer ranging from 0 to 3;
m is an integer ranging from 0 to 2; and
x is the integer 0 or 1;

in an amount ranging from 0.01 mg/kg body weight to 2500 mg/kg body weight;

wherein the compound or a pharmaceutically acceptable salt of the compound is capable of reducing pain as or more effectively than a similar dose of the positive control analgesic indomethacin as measured by one or more of the in vivo pain tests consisting of an acute pain test, an inflammatory pain test, a neuropathic pain test, a mechanical stimuli pain test, a thermal stimuli pain test, or a tactile allodynia test.

* * * * *